(12) United States Patent
Hackney et al.

(10) Patent No.: US 11,261,493 B2
(45) Date of Patent: *Mar. 1, 2022

(54) METHODS FOR DIAGNOSING AND TREATING INFLAMMATORY BOWEL DISEASE

(71) Applicant: GENENTECH, INC., South San Francisco, CA (US)

(72) Inventors: Jason A. Hackney, San Carlos, CA (US); Mary Keir, San Francisco, CA (US); Gaik Wei Tew, Belmont, CA (US)

(73) Assignee: GENENTECH, INC., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/845,575

(22) Filed: Apr. 10, 2020

(65) Prior Publication Data

US 2020/0325538 A1 Oct. 15, 2020

Related U.S. Application Data

(60) Division of application No. 16/295,536, filed on Mar. 7, 2019, now Pat. No. 10,669,587, which is a division of application No. 15/271,687, filed on Sep. 21, 2016, now Pat. No. 10,273,542, which is a continuation of application No. PCT/US2015/022762, filed on Mar. 26, 2015.

(60) Provisional application No. 61/971,379, filed on Mar. 27, 2014.

(51) Int. Cl.
  *C12Q 1/6883* (2018.01)
  *G01N 33/573* (2006.01)
  *G01N 33/53* (2006.01)
  *C07K 16/28* (2006.01)
  *A61K 39/00* (2006.01)

(52) U.S. Cl.
  CPC .......... *C12Q 1/6883* (2013.01); *G01N 33/53* (2013.01); *G01N 33/573* (2013.01); *A61K 2039/505* (2013.01); *C07K 16/2842* (2013.01); *C07K 2317/24* (2013.01); *C12Q 2600/106* (2013.01); *C12Q 2600/158* (2013.01)

(58) Field of Classification Search
  None
  See application file for complete search history.

(56) References Cited

U.S. PATENT DOCUMENTS

| | | |
|---|---|---|
| 4,816,567 A | 3/1989 | Cabilly et al. |
| 5,229,275 A | 7/1993 | Goroff |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,571,894 A | 11/1996 | Wels et al. |
| 5,573,905 A | 11/1996 | Lerner et al. |
| 5,587,458 A | 12/1996 | King et al. |
| 5,591,669 A | 1/1997 | Krimpenfort et al. |
| 5,641,870 A | 6/1997 | Rinderknecht et al. |
| 10,273,542 B2 | 4/2019 | Hackney et al. |
| 10,669,587 B2 * | 6/2020 | Hackney ............. A61P 1/04 |
| 2006/0093601 A1 | 5/2006 | Fong et al. |
| 2008/0089881 A1 | 4/2008 | Li et al. |
| 2008/0293582 A1 | 11/2008 | Li et al. |
| 2009/0269774 A1 | 10/2009 | Rothenberg et al. |
| 2010/0093552 A1 | 4/2010 | Panja |
| 2010/0255508 A1 | 10/2010 | Gelzleichter et al. |
| 2011/0033486 A1 | 2/2011 | Abbas |
| 2011/0045476 A1 | 2/2011 | Barken et al. |
| 2011/0177502 A1 | 7/2011 | Hakonarson et al. |
| 2011/0212104 A1 | 9/2011 | Beaumont et al. |
| 2012/0079611 A1 | 3/2012 | Shih et al. |
| 2013/0040835 A1 | 2/2013 | Harris |
| 2013/0287775 A1 | 10/2013 | Bowman et al. |

FOREIGN PATENT DOCUMENTS

| | | |
|---|---|---|
| JP | 2011-521236 A | 7/2011 |
| WO | WO 93/16185 A2 | 8/1993 |
| WO | WO 93/16185 A3 | 8/1993 |
| WO | WO 97/17852 A1 | 5/1997 |
| WO | WO 2005/009339 A2 | 2/2005 |
| WO | WO 2006/026759 A2 | 3/2006 |
| WO | WO 2006/026759 A3 | 3/2006 |
| WO | WO 2006/026759 A9 | 3/2006 |
| WO | WO 2009/062125 A1 | 5/2009 |

(Continued)

OTHER PUBLICATIONS

Lawrance et al Human Molecular Genetics. 2001. 19(5): 445-456 (Year: 2001).*

(Continued)

*Primary Examiner* — Carla J Myers

(74) *Attorney, Agent, or Firm* — Baker Botts L.L.P.

(57) ABSTRACT

Biomarkers predictive of responsiveness to integrin beta7 antagonists, including anti-beta7 integrin subunit antibodies, and methods of using such biomarkers are provided. In addition, methods of treating gastrointestinal inflammatory disorders such as inflammatory bowel diseases including ulcerative colitis and Crohn's disease are provided. Also provided are methods of using such predictive biomarkers for the treatment of inflammatory bowel diseases including ulcerative colitis and Crohn's disease.

27 Claims, 77 Drawing Sheets

Specification includes a Sequence Listing.

(56) References Cited

FOREIGN PATENT DOCUMENTS

| WO | WO 2009/140684 A2 | 11/2009 |
|---|---|---|
| WO | WO 2009/140684 A3 | 11/2009 |
| WO | WO 2012/101183 A2 | 8/2012 |
| WO | WO 2012/135589 A1 | 10/2012 |
| WO | WO 2014/055824 A1 | 4/2014 |
| WO | WO 2014/160753 A1 | 10/2014 |
| WO | WO 2015/148809 A1 | 10/2015 |

OTHER PUBLICATIONS

U.S. Appl. No. 16/295,536 (now U.S. Pat. No. 10,669,587), filed Mar. 7, 2019 (Jun. 2, 2020).
U.S. Appl. No. 15/271,687 (now U.S. Pat. No. 10,273,542), filed Sep. 21, 2016 (Apr. 30, 2019).
U.S. Appl. No. 16/295,536, Apr. 9, 2020 Issue Fee Payment.
U.S. Appl. No. 16/295,536, Jan. 10, 2020 Notice of Allowance.
U.S. Appl. No. 16/295,536, Dec. 3, 2019 Response to Non-Final Office Action.
U.S. Appl. No. 16/295,536, Jun. 5, 2019 Non-Final Office Action.
U.S. Appl. No. 15/271,687, Mar. 7, 2019 Issue Fee Payment.
U.S. Appl. No. 15/271,687, Dec. 10, 2018 Notice of Allowance.
U.S. Appl. No. 15/271,687, Oct. 8, 2018 Response to Non-Final Office Action.
U.S. Appl. No. 15/271,687, Jul. 3, 2018 Non-Final Office Action.
U.S. Appl. No. 15/271,687, May 22, 2018 Response to Restriction Requirement.
U.S. Appl. No. 15/271,687, Feb. 23, 2018 Restriction Requirement.
Affymetrix Expression Probeset Details for HG-U133 Plus 2, available at URL: <Affymetrix.com>, printed on Jun. 25, 2018.
Andrew et al., "Distinct but overlapping epitopes are involved in a 4β7-mediated adhesion to vascular cell adhesion molecule-i, mucosal addressin-i, fibronectin, and lymphocyte Aggregation," J Immunol 153:3847-3861 (1994).
Barbas et al., "In Vitro Evolution of a Neutralizing Human Antibody to Human Immunodeficiency Virus Type i to Enhance Affinity and Broaden Strain Cross-Reactivity," P Natl Acad Sci USA 91(9):3809-3813 (Apr. 1994).
Berlin et al., "α4β7 Integrin mediates lymphocyte binding to the mucosal vascular addressin MAdCAM-1," Cell 74:185-195 (Jul. 16, 1993).
Boerner et al., "Production of antigen-specific human monoclonal antibodies from in vitro-primed human splenocytes," J Immunol 147(1):86-95 (Jul. 1, 1991).
Bovin et al., "Gene expression in autoimmune diseases: Chronic inflammation or disease specific patterns?" Autoimmunity 40(3): 191-201 (May 2007).
Brennan et al., "Preparation of bispecific antibodies by chemical recombination of monoclonal immunoglobulin G1 fragments," Science 229(4708):81-83 (Jul. 5, 1985).
Briskin et al., "Human mucosal addressin cell adhesion molecule-1 is preferentially expressed in intestinal tract and associated lymphoid tissue," Am J Pathol 151(1):97-110 (Jul. 1997).
Briskin et al., "MAdCAM-1 has homology to immunoglobulin and mucin-like adhesion receptors and to IgA1," Nature 363(6428):461-464 (Jun. 3, 1993).
Brodeur et al. Monoclonal Antibody Production Techniques and Applications New York: Marcel Dekker, Inc.:51-63 (1987).
Bruggermann et al., "Designer mice: The production of human antibody repertoires in transgenic animals," Year Immun 7:33-40 (1993).
Buri et al., "Cytotoxic T cells are preferentially activated in the duodenal epithelium from patients with florid coeliac disease," J Pathol 206:178-185 (2005).
Butcher et al., "Lymphocyte Homing and Homeostasis," Science 272:60-66 (1996).
Calvo, Modulation of ion transport in inflammatory bowel diseases: Regulatory targets, University of Granada PhD. Thesis. 2013.
Carter et al., "High level *Escherichia coli* expression and production of a bivalent humanized antibody fragment," Bio/Technol 10:163-167 (Feb. 1992).
Carter et al., "Humanization of an anti-p185HER2 antibody for human cancer therapy," P Natl Acad Sci USA 89:4285-4289 (May 1992).
Cepek et al., "Integrin αEβ7 mediates adhesion of T lymphocytes to epithelial cells[1]" J Immunol 150(8):3459-3470 (Apr. 15, 1993).
Chan et al., "Adhesion to vascular cell adhesion molecule I and fibronectin," J Biol Chem 267(12):8366-8370 (Apr. 25, 1992).
Chang and Lichtenstein, "Drug Insight: antagonists of tumor-necrosis factor-α in the treatment of inflammatory bowel disease," Nat Clin Pract Gastroenterol Hepatol 3:220-228 (2006).
Chothia et al., "Canonical structures for the hypervariable regions of immunoglobulins," J Mol Biol 196:901-917 (1987).
Clackson et al., "Making antibody fragments using phage display libraries," Nature 352(6336):624-628 (Aug. 15, 1991).
Extended European search report for European Application No. 15768557.9 dated Jan. 25, 2018.
International Search Report on patentability for PCT/US15/22762 dated Jul. 24, 2015.
Partial Supplementary European Search Report on patentability, Application No. 15768557.9-1412/3122377 dated Oct. 12, 2017.
Costello et al., "Dissection of the inflammatory bowel disease transcriptome using genome-wide cDNA microarrays," PLoS MED 2(8):0771-0787 (Aug. 2005).
Elewaut et al., "Altered expression of αEβ7 integrin on intra-epithelial and lamina propria lymphocytes in patients with Crohn's disease," Acta Gastro-Enterologica Belgica 61:288-294 (1998).
Elices et al., "VCAM-1 on activated endothelium interacts with the leukocyte integrin VLA-4 at a site distinct from the VLA-4/fibronectin binding site," Cell 60:577-584 (1990).
Erle et al., "Complete amino acid sequence of an integrin β subunit (β7) identified in leukocytes," J Biol Chem 266(17):11009-11016 (Jun. 15, 1991).
Feagan et al., "Treatment of ulcerative colitis with a humanized antibody to the α4β7 integrin," New Engl J Med 352(24):2499-2507 (Jun. 16, 2005).
Feagan et al., "Vedolizumab as induction and maintenance therapy for ulcerative colitis," N Engl J Med 369(8):699-710 (Aug. 22, 2013).
Griffiths et al., "Human anti-self antibodies with high specificity from phage display libraries," EMBO J 12(2):725-734 (1993).
Gurish et al., "Expression of murine β7, α4, and β1 integrin genes by rodent mast cells," J Immunol 149(6):1964-1972 (Sep. 15, 1992).
Hadley et al., "The epithelial cell-specific integrin, CD103 (Ae integrin), defines a novel subset of alloreactive CD8 + CTL 1," J Immunol 159:3748-3756 (1997).
Hanauer et al., "Maintenance infliximab for Crohn's disease: the ACCENT I randomised trial," Lancet:1541-1549 (2002).
Harris, "Production of humanized monoclonal antibodies for in vivo imaging and therapy," Biochem Soc Trans 23(4):1035-1038 (Nov. 1995).
Hawkins et al., "Selection of phage antibodies by binding affinity mimicking affinity maturation," J Mol Biol 226:889-896 (1992).
Hemler, "VLA proteins in the integrin family: structures, functions, and their role on leukocytes," Annu Rev Immunol 8:365-400 (1990).
Hirayasu et al., "A role of a lymphocyte tryptase, granzyme A, in experimental ulcerative colitis," Biosci Biotechnol Biochem 71(1):234-237 (2007).
Hoentjen et al., "Safety of anti-tumor necrosis factor therapy in inflammatory bowel disease," World J Gastroenterol 15(17):2067-2073 (2009).
Holzmann et al., "Identification of a Murine Peyer's Patch-specific lymphocyte homing receptor as an integrin molecule with an a chain homologous to human VLA-4α" Cell 56:37-46 (1989).
Hoogenboom et al., "Multi-subunit proteins on the surface of filamentous phage: methodologies for displaying antibody (Fab) heavy and light chains" Nucl Acids Res 19(15):4133-4137 (1991).

(56) References Cited

OTHER PUBLICATIONS

Hu et al., "Cloning and expression of mouse integrin βp (β7): A functional role in Peyer's patch-specific lymphocyte homing," P Natl Acad Sci USA 89:8254-8258 (Sep. 1992).
Hurle and Gross, "Protein engineering techniques for antibody humanization," Curr Opin Biotechnol 5:428-433 (1994).
Hynes, "Integrins: versatility, modulation, and signaling in cell adhesion," Cell 69(1): 11-25 (1992).
Jackson et al., "In vitro antibody maturation. Improvement of a high affinity, neutralizing antibody against IL-1 beta," J Immunol 154(7):3310-3319 (Apr. 1, 1995).
Jakobovits et al., "Analysis of Homozygous Mutant Chimeric Mice: Deletion of the Immunoglobulin Heavy-Chain Joining Region Blocks B-cell Development and Antibody Production," P Natl Acad Sci USA 90(6):2551-2555 (Mar. 15, 1993).
Jakobovits et al., "Germ-line transmission and expression of a human-derived yeast artificial chromosome," Nature 362:255-258 (Mar. 18, 1993).
Johnson et al., "Human Antibody Engineering," Curr Opin Struc Biol 3:564-571 (1993).
Jones et al., "Replacing the complementarity-determining regions in a human antibody with those from a mouse," Nature 321:522-525 (May 1986).
Kabat et al., Sequences of Proteins of Immunological Interest 5th edition, NIH:2 pages (1991).
Karecla et al., "Recognition of E-cadherin on epithelial cells by the mucosal T cell integrin αM290 (αEβ7)," Eur J Immunol 25:852-856 (1995).
Keir et al., "AlphaE integrin expression as a predictive biomarker for induction of clinical remission by etrolizumab: Analysis of a phase II trial in moderate-to-severely active ulcerative colitis," Journal of Crohn's and Colitis, Abstracts of the 9th Congress of ECCO, S7:OP010A (Feb. 1, 2014).
Kilger and Holzmann, "Molecular analysis of the physiological and pathophysiological role of α4-integrins," J Mol Med 73(7):347-354 (Jul. 1995).
Kilshaw and Murant, "Expression and regulation of β7(βp) integrins on mouse lymphocytes: relevance to the mucosal immune system," Eur J Immunol 21(10):2591-2597 (Oct. 1991).
Kozbor et al., "A human hybrid myeloma for production of human monoclonal antibodies," J Immunol 133(6):3001-3005 (Dec. 1984).
Ludviksson et al., "Administration of mAb against αEβ7 prevents and ameliorates immunization-induced colitis in IL-2 -/- mice," J Immunol 162:4975-4982 (1999).
Marks et al., "By-passing immunization, human antibodies from V-gene libraries displayed on phage," J Mol Biol 222:581-597 (1991).
Marks et al., "By-passing immunization: building high affinity human antibodies by chain shuffling," Bio/Technology 10:779-783 (Jul. 1992).
McCafferty et al., "Phage antibodies: filamentous phage displaying antibody variable domains," Nature 348:552-554 (Dec. 6, 1990).
Morimoto and Inouye, "Single-step purification of F(ab') 2 fragments of mouse monoclonal antibodies (immunoglobulins G1) by hydrophobic interaction high performance liquid chromatography using TSKgel phenyl-5PW," J Biochem Biophys Meth 24:107-117 (1992).
Morrison et al., "Chimeric human antibody molecules: Mouse antigen-binding domains with human constant region domains," P Natl Acad Sci USA 81:6851-6855 (Nov. 1984).
Muller et al., "Activated CD4 + and CD8 + cytotoxic cells are present in increased numbers in the intestinal mucosa from patients with active inflammatory bowel disease," Am J Pathol 152(1):261-268 (Jan. 1998).
Nakajima et al., "Role of vascular cell adhesion molecule 1/very late activation antigen 4 and intercellular adhesion molecule 1/lymphocyte function-associated antigen 1 interactions in antigen-induced eosinophil and T cell recruitment into the tissue," J Exp Med 179:1145-1154 (1994).

Oshitani et al., "Differential expression of homing receptor CD103 on lamina propria lymphocytes and association of CD103 with epithelial adhesion molecules in inflammatory bowel disease," International J Molecule Med 12:715-719 (2003).
Picornell et al., "TNFSF15 is an ethnic-specific IBD gene," Inflamm Bowel Dis 13(11):1333-1338 (Nov. 1, 2007).
Presta et al., "Humanization of an antibody directed against IgE," J Immunol 151(5):2623-2632 (Sep 1. 1993).
Presta L.G., "Antibody engineering," Curr Opin Struct Biol 2:593-596 (1992).
Rice et al., "Anti-α4 integrin therapy for multiple sclerosis," Neurology 64:1336-1342 (2005).
Riechmann et al., "Reshaping human antibodies for therapy," Nature 332:323-327 (Mar. 24, 1988).
Ruegg et al., "Role of integrin α4β7/α4βP in lymphocyte adherence to fibronectin and VCAM-1 and in homotypic cell clustering," J Cell Biol 117(1):179-189 (Apr. 1992).
Sandborn et al., "Natalizumab induction and maintenance therapy for Crohn's disease," New Engl J Med 353(18):1912-1925 (Nov. 3, 2005).
Sandborn et al., "Vedolizumab as induction and maintenance therapy for Crohn's disease," N Engl J Med 369(8):711-721 (2013).
Scaldaferri et al., "Mucosal biomarkers in inflammatory bowel disease: Key pathogenic players or disease predictors?" World J Gastroenterology 16(21):2616-2625 (Jun. 7, 2010).
Schier et al., "Identification of functional and structural amino-acid residues by parsimonious mutagenesis," Gene 169:147-155 (1996).
Shaw and Brenner, "The β7 integrins in mucosal homing and retention," Semin Immunol 7:335-342 (1995).
Shyjan et al., "Human mucosal addressin cell adhesion molecule-1 (MAdCAM-1) demonstrates structural and functional similarities to the α4β7-integrin binding domains of murine MAdCAM-1, but extreme divergence of mucin-like sequences," J Immunol 156(8):2851-2857 (Apr. 15, 1996).
Sims et al., "A Humanized CD 18 Antibody Can Block Function Without Cell Destruction," J Immunol 151(4):2296-2308 (Aug. 15, 1993).
Souza et al., "Expression of lymphocyte-endothelial receptor-ligand pairs, α4β7/MAdCAM-1 and OX40/OX40 ligand in the colon and jejunum of patients with inflammatory bowel disease," Gut 45:856-863 (1999).
Stefanich et al., "A humanized monoclonal antibody targeting the B7 integrin selectively blocks intestinal homing of T lymphocytes," Brit J Pharmacol 162:1855-1870 (2011).
Takedatsu et al., "TL1A (TNFSF15) regulates the development of chronic colitis by modulating both T-helper 1 and T-helper 17 activation," Gastroenterology 135(2):552-567 (Aug. 1, 2008).
Tew et al., "Association between response to etrolizumab and expression of integrin αE and granzyme A in colon biopsies of patients with ulcerative colitis," Gastroenterology 150:477-487 (2016).
Tew et al., "Increased expression of t-cell-associated genes in baseline biopsies from TNF antagonist-naive patients with moderately to severely active ulcerative colitis who undergo remission in response to Etrolizumab in a Phase 2 Trial," Poster United European Gastroenterology Week, Vienna, Austria, pp. P0343 (Oct. 18-22, 2014).
The Free Dictionary definition for 'measuring' available via url: <thefreedictionary.com/measuring>, printed on Sep. 20, 2017.
Vaswani and Hamilton et al., "Humanized antibodies as potential therapeutic drugs," Ann Allergy Asthma Immunol 81:105-115 (Nov. 1998).
Verhoeyen et al., "Reshaping human antibodies: Grafting an antilysozyme activity," Science 239:1534-1536 (Mar. 1988).
Von Andrian et al., "T-Cell function and migration," N Engl J Med 343:1020-1034 (Oct. 5, 2000).
Yednock et al., "Prevention of experimental autoimmune encephalomyelitis by antibodies against α4β1 integrin," Nature 356:63-66 (Mar. 5, 1992).

(56) References Cited

OTHER PUBLICATIONS

Yelton et al., "Affinity maturation of the BR96 anti-carcinoma antibody by codon-based mutagenesis," J Immunol 155:1994-2004 (1995).

* cited by examiner

FIG. 1A

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 |
|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | HVR1 | | | | | | | | | | | |
| hukI | D | I | Q | M | T | Q | S | P | S | S | L | S | A | S | V | G | D | R | V | T | I | T | C | R | A | S | Q | S | I | S | N | Y | L | A | W |
| Fib504 | D | V | V | M | T | Q | S | P | A | T | L | S | A | V | T | P | G | E | R | V | S | L | S | C | R | A | S | E | S | V | D | T | Y | L | H | W |
| 504K graft | D | I | Q | M | T | Q | S | P | S | S | L | S | A | S | V | G | D | R | V | T | I | T | C | R | A | S | E | S | V | D | T | Y | L | H | W |
| hu504-5 | | | | | | | | | | | | | | | | | | | | | | | | | | | | | | | S | | L | | |
| hu504-16 | | | | | | | | | | | | | | | | | | | | | | | | | | | | | | | S | | L | | |
| hu504-32 | | | | | | | | | | | | | | | | | | | | | | | | | | | | | | | D | | L | | |

| Kabat# | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | HVR2 | | | | | | | | | | | | | | | | | | | | | | | | | |
| hukI | Y | Q | Q | K | P | G | K | A | P | K | L | L | I | Y | A | A | S | S | L | E | S | G | V | P | S | R | F | S | G | S | G | S | G | T | D | F | T | L | T | I |
| Fib504 | Y | Q | Q | K | P | N | E | S | P | R | L | L | I | K | Y | A | S | Q | S | I | S | G | I | P | S | R | F | S | G | S | G | S | G | T | D | F | T | L | S | I |
| 504K graft | Y | Q | Q | K | P | G | K | A | P | K | L | L | I | K | Y | A | S | Q | S | I | S | G | V | P | S | R | F | S | G | S | G | S | G | T | D | F | T | L | T | I |

| Kabat# | 76 | 77 | 78 | 79 | 80 | 81 | 82 | 83 | 84 | 85 | 86 | 87 | 88 | 89 | 90 | 91 | 92 | 93 | 94 | 95 | a | 96 | 97 | 98 | 99 | 100 | 101 | 102 | 103 | 104 | 105 | 106 | 107 | 108 | |
|---|---|---|---|---|---|---|---|---|---|---|---|---|---|---|---|---|---|---|---|---|---|---|---|---|---|---|---|---|---|---|---|---|---|---|---|
| | | | | | | | | | | | | | | HVR3 | | | | | | | | | | | | | | | | | | | | | |
| hukI | S | S | L | Q | P | E | D | F | A | T | Y | Y | C | Q | Q | Y | N | S | L | P | W | T | F | G | Q | G | T | K | V | E | I | K | R | | (SEQ ID NO:12) |
| Fib504 | N | G | V | E | L | E | D | L | S | I | Y | Y | C | Q | Q | G | N | S | L | P | | F | G | G | A | G | T | K | L | E | L | K | R | | (SEQ ID NO:10) |
| 504K graft | S | S | L | Q | P | E | D | F | A | T | Y | Y | C | Q | Q | G | N | S | L | P | | F | G | Q | G | T | K | V | E | I | K | R | | | (SEQ ID NO:14) |

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
|  |  |  |  |  |  |  |  |  |  |  |  |  |  |  |  |  |  |  |  |  |  |  |  |  |  |  |  |  | HVR1 | | | | | | | | | | | | | |
| humIII | E | V | Q | L | V | E | S | G | G | G | L | V | Q | P | G | G | S | L | R | L | S | C | A | A | S | G | F | T | F | S | S | Y | A | M | S | W | V | R | Q | A | P | G |
| Fib504 | E | V | Q | L | Q | Q | S | G | P | G | L | V | K | P | S | Q | S | L | S | L | T | C | S | V | T | G | F | F | I | T | N | Y | W | I | G | W | I | R | K | F | G |
| 504K graft | E | V | Q | L | V | E | S | G | G | G | L | V | Q | P | G | G | S | L | R | L | S | C | A | A | S | G | F | F | I | T | N | N | Y | W | G | W | V | R | Q | A | P | G |

| Kabat# | 43 | 44 | 45 | 46 | 47 | 48 | 49 | 50 | 51 | 52 | a | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | a |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
|  |  |  |  |  | HVR2 | | | | | | | | | | | | | | | | | | | | | | | | | | | | | | | | | | | | | |
| humIII | K | G | L | E | W | V | S | V | I | S | G | D | G | G | S | T | Y | Y | A | D | S | V | K | G | R | F | T | I | S | R | D | N | S | K | N | T | L | Y | L | Q | M | N |
| Fib504 | N | K | M | E | W | M | G | Y | I | S | | Y | S | G | S | T | S | Y | N | P | S | L | K | S | R | I | S | I | T | R | D | T | S | K | N | Q | F | F | L | K | L | N |
| 504K graft | K | G | L | E | W | V | G | Y | I | S | | Y | S | G | S | T | S | Y | N | P | S | L | K | S | R | F | T | I | S | A | D | T | S | K | N | T | A | Y | L | Q | M | N |
| hu504-5 |  |  |  |  |  |  |  |  |  |  |  |  |  |  |  |  |  |  |  |  |  |  |  |  |  |  |  |  |  | R |  |  |  |  |  |  | F |  |  |  |  |  |
| hu504-16 |  |  |  |  |  |  |  |  |  |  |  |  |  |  |  |  |  |  |  |  |  |  |  |  |  |  |  |  |  | R |  |  |  |  |  |  | F |  |  |  |  |  |
| hu504-32 |  |  |  |  |  |  |  |  |  |  |  |  |  |  |  |  |  |  |  |  |  |  |  |  |  |  |  |  |  | R |  |  |  |  |  |  | F |  |  |  |  |  |

| Kabat# | b | c | 83 | 84 | 85 | 86 | 87 | 88 | 89 | 90 | 91 | 92 | 93 | 94 | 95 | 96 | 97 | 98 | 99 | 100 | a | k | 101 | 102 | 103 | 104 | 105 | 106 | 107 | 108 | 109 | 110 | 111 | 112 | 113 | |
|---|---|---|---|---|---|---|---|---|---|---|---|---|---|---|---|---|---|---|---|---|---|---|---|---|---|---|---|---|---|---|---|---|---|---|---|---|
|  |  |  |  |  |  |  |  |  |  |  |  |  |  | HVR3 | | | | | | | | | | | | | | | | | | | | | | |
| humIII | S | L | R | A | E | D | T | A | V | Y | Y | C | A | R | G |  |  |  |  |  |  |  | F | D | Y | W | G | Q | G | T | L | V | T | V | S | S (SEQ ID NO.:13) |
| Fib504 | S | V | T | T | E | D | T | A | T | Y | Y | C | A | M | T | G | S | S | G | Y |  |  | F | D | F | W | G | P | G | T | M | V | T | V | S | S (SEQ ID NO.:11) |
| 504K graft | S | L | R | A | E | D | T | A | V | Y | Y | C | A | M | T | G | S | S | G | Y |  |  | F | D | F | W | G | Q | G | T | L | V | T | V | S | S (SEQ ID NO.:15) |

*FIG. 1B*

```
1         10        20        30        40        50        60
|          |         |         |         |         |         |
DIQMTQSPSSLSASVGDRVTITCRASESVDDLLHWYQQKPGKAPKLLIKYASQSISGVPS 70        80        90       100
          |         |         |         |
RFSGSGSGTDFTLTISSLQPEDFATYYCQQGNSLPNTFGQGTKVEIKR  (SEQ ID NO.:31)
```

FIG. 2A

```
1         10        20        30        40        50        60
|          |         |         |         |         |         |
EVQLVESGGGLVQPGGSLRLSCAASGFFITNNYWGWVRQAPGKGLEWVGYISYSGSTSYN 70        80        90       100       110
          |         |         |         |         |
PSLKSRFTISRDTSKNTFYLQMNSLRAEDTAVYYCARTGSSGYFDFWGQGTLVTVSS
                                                   (SEQ ID NO.:32)
```

FIG. 2B

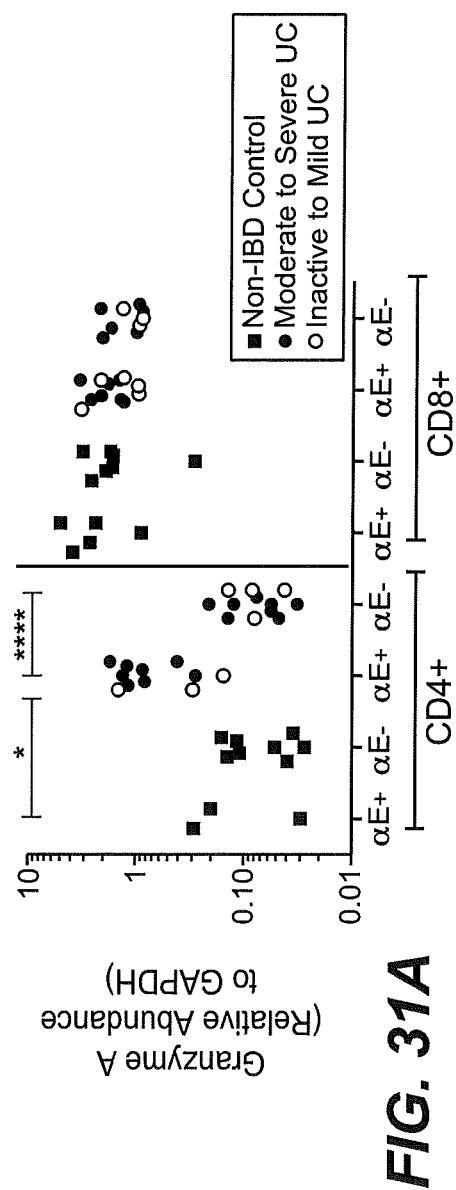
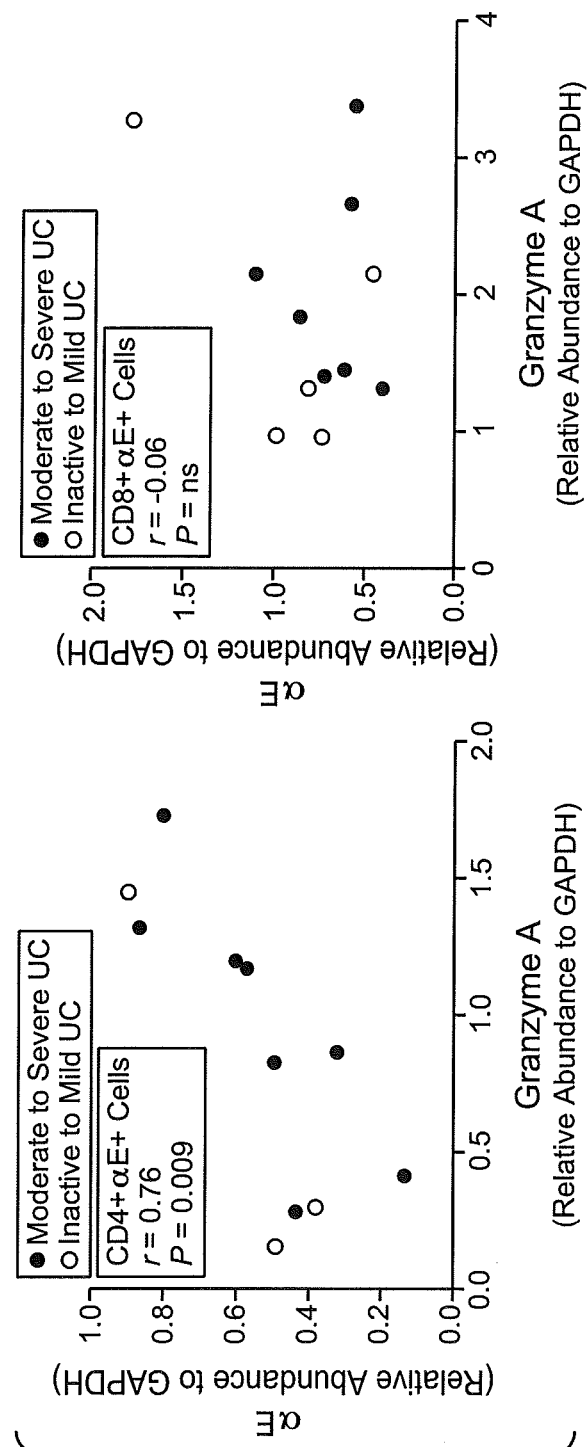
FIG. 31A
FIG. 31B

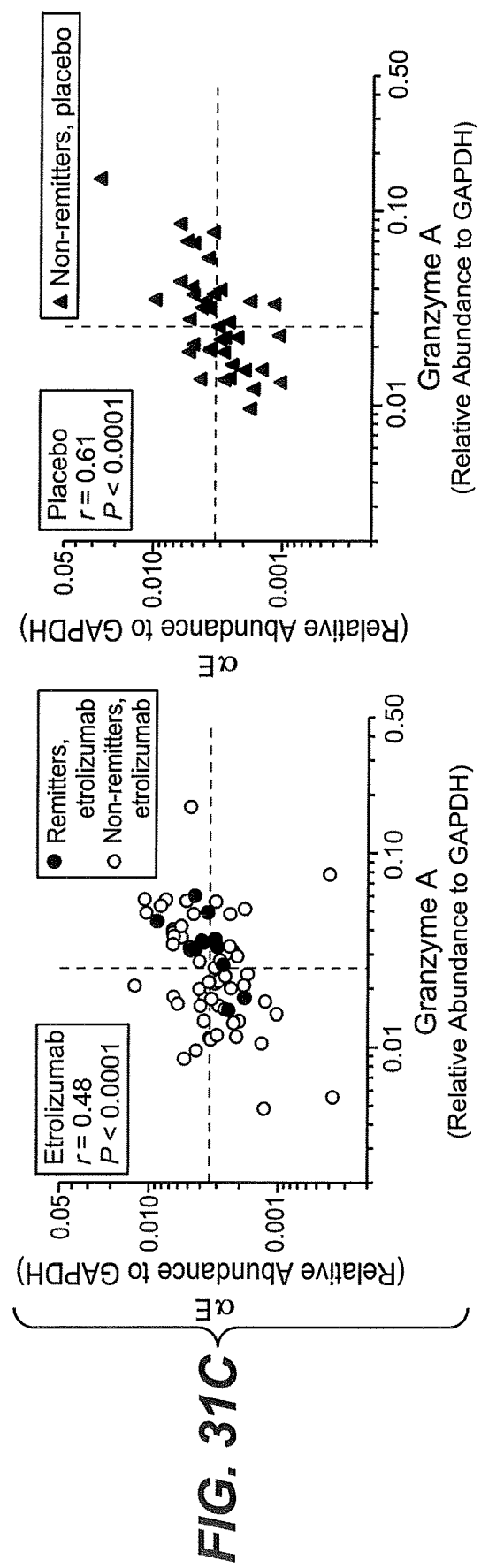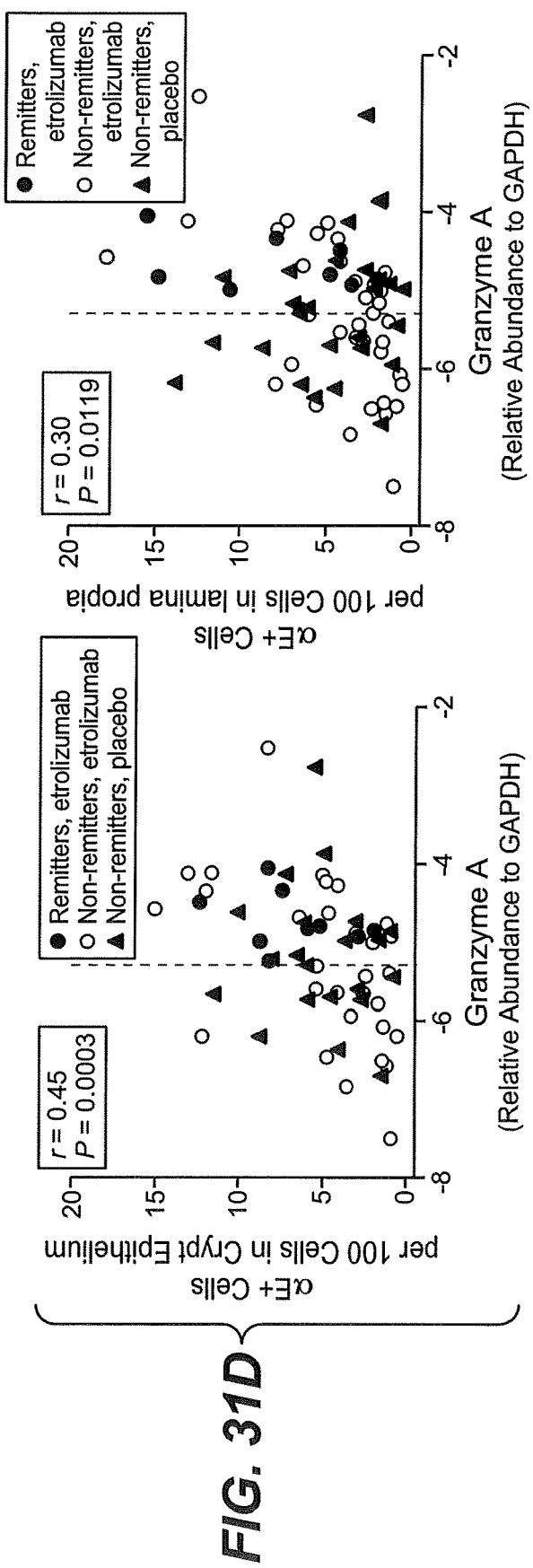
FIG. 31C
FIG. 31D

SEQUENCE LISTING

```
<160> NUMBER OF SEQ ID NOS: 32

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ala Ser Glu Ser Val Asp Thr Tyr Leu His
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Tyr Ala Ser Gln Ser Ile Ser
1               5

<210> SEQ ID NO 3
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 3

Gln Gln Gly Asn Ser Leu Pro Asn Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Phe Ile Thr Asn Asn Tyr Trp Gly
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Tyr Ile Ser Tyr Ser Gly Ser Thr Ser Tyr Asn Pro Ser Leu Lys
1               5                   10                  15

Ser

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Thr Gly Ser Ser Gly Tyr Phe Asp Phe
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ala Ser Glu Ser Val Asp Ser Leu Leu His
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8
```

Arg Ala Ser Glu Ser Val Asp Thr Leu Leu His
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ala Ser Glu Ser Val Asp Asp Leu Leu His
1               5                   10

<210> SEQ ID NO 10
<211> LENGTH: 108
<212> TYPE: PRT
<213> ORGANISM: Rattus sp.

<400> SEQUENCE: 10

Asp Val Val Met Thr Gln Ser Pro Ala Thr Leu Ser Val Thr Pro Gly
1               5                   10                  15

Glu Arg Ile Ser Leu Ser Cys Arg Ala Ser Glu Ser Val Asp Thr Tyr
            20                  25                  30

Leu His Trp Tyr Gln Gln Lys Pro Asn Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Gly Val Glu Leu
65                  70                  75                  80

Glu Asp Leu Ser Ile Tyr Tyr Cys Gln Gln Gly Asn Ser Leu Pro Asn
                85                  90                  95

Thr Phe Gly Ala Gly Thr Lys Leu Glu Leu Lys Arg
            100                 105

<210> SEQ ID NO 11
<211> LENGTH: 117
<212> TYPE: PRT
<213> ORGANISM: Rattus sp.

<400> SEQUENCE: 11

Glu Val Gln Leu Gln Glu Ser Gly Pro Gly Leu Val Lys Pro Ser Gln
1               5                   10                  15

Ser Leu Ser Leu Thr Cys Ser Val Thr Gly Phe Phe Ile Thr Asn Asn
            20                  25                  30

Tyr Trp Gly Trp Ile Arg Lys Phe Pro Gly Asn Lys Met Glu Trp Met
        35                  40                  45

Gly Tyr Ile Ser Tyr Ser Gly Ser Thr Ser Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu Asn Ser Val Thr Thr Glu Asp Thr Ala Thr Tyr Tyr Cys Ala
                85                  90                  95

Met Thr Gly Ser Ser Gly Tyr Phe Asp Phe Trp Gly Pro Gly Thr Met
            100                 105                 110

Val Thr Val Ser Ser
        115

```
<210> SEQ ID NO 12
<211> LENGTH: 108
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys Arg
            100                 105

<210> SEQ ID NO 13
<211> LENGTH: 113
<212> TYPE: PRT
<213> ORGANISM: Homo sapiens

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Phe Asp Tyr Trp Gly Gln Gly Thr Leu Val Thr Val Ser
            100                 105                 110

Ser

<210> SEQ ID NO 14
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Thr Tyr
            20                  25                  30

Leu His Trp Tyr Gln Gln Lys Pro Gly Lys Ala Pro Lys Leu Leu Ile
        35                  40                  45
```

```
Lys Tyr Ala Ser Gln Ser Ile Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Ser Leu Pro Asn
                85                  90                  95

Thr Phe Gly Gln Gly Thr Lys Val Glu Ile Lys Arg
            100                 105
```

<210> SEQ ID NO 15
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Phe Ile Thr Asn Asn
             20                  25                  30

Tyr Trp Gly Trp Val Arg Gln Ala Pro Gly Lys Gly Leu Glu Trp Val
         35                  40                  45

Gly Tyr Ile Ser Tyr Ser Gly Ser Thr Ser Tyr Asn Pro Ser Leu Lys
     50                  55                  60

Ser Arg Phe Thr Ile Ser Ala Asp Thr Ser Lys Asn Thr Ala Tyr Leu
 65                  70                  75                  80

Gln Met Asn Ser Leu Arg Ala Glu Asp Thr Ala Val Tyr Tyr Cys Ala
                85                  90                  95

Met Thr Gly Ser Ser Gly Tyr Phe Asp Phe Trp Gly Gln Gly Thr Leu
            100                 105                 110

Val Thr Val Ser Ser
        115
```

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Ala Met Thr Gly Ser Ser Gly Tyr Phe Asp Phe
  1               5                  10
```

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Ala Arg Thr Gly Ser Ser Gly Tyr Phe Asp Phe
  1               5                  10
```

<210> SEQ ID NO 18
<211> LENGTH: 11
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 18

Ala Gln Thr Gly Ser Ser Gly Tyr Phe Asp Phe
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Thr Gly Ser Ser Gly Tyr Phe Asp Phe
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Tyr Ala Ser Gln Ser Ile Ser
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 21

Xaa Tyr Ala Ser Gln Ser Ile Ser
1               5

<210> SEQ ID NO 22
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Leu
            20                  25                  30

Leu His Trp Tyr Gln Gln Lys Pro Gly Lys Ala Pro Lys Leu Leu Ile
        35                  40                  45

Lys Tyr Ala Ser Gln Ser Ile Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Ser Leu Pro Asn
                 85                  90                  95

Thr Phe Gly Gln Gly Thr Lys Val Glu Ile Lys Arg
                100                 105
```

<210> SEQ ID NO 23
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Glu Ser Val Asp Thr Leu
                 20                  25                  30

Leu His Trp Tyr Gln Gln Lys Pro Gly Lys Ala Pro Lys Leu Leu Ile
             35                  40                  45

Lys Tyr Ala Ser Gln Ser Ile Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Ser Leu Pro Asn
                 85                  90                  95

Thr Phe Gly Gln Gly Thr Lys Val Glu Ile Lys Arg
                100                 105
```

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Glu Ser Val Asp Asp Leu
                 20                  25                  30

Leu His Trp Tyr Gln Gln Lys Pro Gly Lys Ala Pro Lys Leu Leu Ile
             35                  40                  45

Lys Tyr Ala Ser Gln Ser Ile Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Ser Leu Pro Asn
                 85                  90                  95

Thr Phe Gly Gln Gly Thr Lys Val Glu Ile Lys Arg
                100                 105
```

<210> SEQ ID NO 25
<211> LENGTH: 117
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Phe Ile Thr Asn Asn
            20                  25                  30

Tyr Trp Gly Trp Val Arg Gln Ala Pro Gly Lys Gly Leu Glu Trp Val
        35                  40                  45

Gly Tyr Ile Ser Tyr Ser Gly Ser Thr Ser Tyr Asn Pro Ser Leu Lys
    50                  55                  60

Ser Arg Phe Thr Ile Ser Arg Asp Thr Ser Lys Asn Thr Phe Tyr Leu
65                  70                  75                  80

Gln Met Asn Ser Leu Arg Ala Glu Asp Thr Ala Val Tyr Tyr Cys Ala
                85                  90                  95

Met Thr Gly Ser Ser Gly Tyr Phe Asp Phe Trp Gly Gln Gly Thr Leu
            100                 105                 110

Val Thr Val Ser Ser
        115

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala, Gly, Ser, Thr or Val
<220> FEATURE:
<221> NAME/KEY: MOD_RES
<222> LOCATION: (3)..(3)
<223> OTHER INFORMATION: Ser, Gly, Ile, Lys, Asn, Pro, Gln, Arg or Thr
<220> FEATURE:
<221> NAME/KEY: MOD_RES
<222> LOCATION: (4)..(4)
<223> OTHER INFORMATION: Glu, Val, Gln, Ala, Asp, Gly, His, Ile, Lys,
      Leu, Asn or Arg
<220> FEATURE:
<221> NAME/KEY: MOD_RES
<222> LOCATION: (5)..(5)
<223> OTHER INFORMATION: Ser, Tyr, Ala, Asp, Gly, His, Ile, Lys, Asn,
      Pro, Arg, Thr or Val
<220> FEATURE:
<221> NAME/KEY: MOD_RES
<222> LOCATION: (6)..(6)
<223> OTHER INFORMATION: Val, Arg, Ile, Ala, Gly, Lys, Leu, Met or Gln
<220> FEATURE:
<221> NAME/KEY: MOD_RES
<222> LOCATION: (7)..(7)
<223> OTHER INFORMATION: Asp, Val, Ser, Ala, Glu, Gly, His, Ile, Lys,
      Leu, Asn, Pro, Ser or Thr
<220> FEATURE:
<221> NAME/KEY: MOD_RES
<222> LOCATION: (8)..(8)
<223> OTHER INFORMATION: Asp, Gly, Asn, Glu, Thr, Pro or Ser
<220> FEATURE:
<221> NAME/KEY: MOD_RES
<222> LOCATION: (9)..(9)
<223> OTHER INFORMATION: Leu, Tyr, Ile or Met
<220> FEATURE:
<221> NAME/KEY: MOD_RES
<222> LOCATION: (10)..(10)
<223> OTHER INFORMATION: Leu, Ala, Ile, Met or Val
<220> FEATURE:
<221> NAME/KEY: MOD_RES
<222> LOCATION: (11)..(11)

<223> OTHER INFORMATION: His, Tyr, Phe or Ser

<400> SEQUENCE: 26

Arg Xaa Xaa Xaa Xaa Xaa Xaa Xaa Xaa Xaa Xaa
1               5                   10

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Ser or Asp
<220> FEATURE:
<221> NAME/KEY: MOD_RES
<222> LOCATION: (5)..(5)
<223> OTHER INFORMATION: Gln or Ser
<220> FEATURE:
<221> NAME/KEY: MOD_RES
<222> LOCATION: (6)..(6)
<223> OTHER INFORMATION: Ser, Asp, Leu or Arg
<220> FEATURE:
<221> NAME/KEY: MOD_RES
<222> LOCATION: (7)..(7)
<223> OTHER INFORMATION: Ile, Val, Glu or Lys
<220> FEATURE:
<223> OTHER INFORMATION: See specification as filed for detailed
      description of substitutions and certain embodiments

<400> SEQUENCE: 27

Xaa Tyr Ala Xaa Xaa Xaa Xaa Ser
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Asn, Val, Trp, Tyr, Arg, Ser, Thr, Ala, Phe,
      His, Ile, Leu or Met

<400> SEQUENCE: 28

Gln Gln Gly Asn Ser Leu Pro Xaa Thr
1               5

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr, Phe, Val or Asp
<220> FEATURE:
<221> NAME/KEY: MOD_RES
<222> LOCATION: (6)..(6)
<223> OTHER INFORMATION: Ser or Gly

```
<220> FEATURE:
<221> NAME/KEY: MOD_RES
<222> LOCATION: (10)..(10)
<223> OTHER INFORMATION: Ser or Tyr
<220> FEATURE:
<221> NAME/KEY: MOD_RES
<222> LOCATION: (12)..(12)
<223> OTHER INFORMATION: Asn, Thr, Ala or Asp
<220> FEATURE:
<221> NAME/KEY: MOD_RES
<222> LOCATION: (13)..(13)
<223> OTHER INFORMATION: Pro, His, Asp or Ala
<220> FEATURE:
<221> NAME/KEY: MOD_RES
<222> LOCATION: (15)..(15)
<223> OTHER INFORMATION: Leu or Val
<220> FEATURE:
<221> NAME/KEY: MOD_RES
<222> LOCATION: (17)..(17)
<223> OTHER INFORMATION: Ser or Gly

<400> SEQUENCE: 29

Gly Xaa Ile Ser Tyr Xaa Gly Ser Thr Xaa Tyr Xaa Xaa Ser Xaa Lys
1               5                   10                  15

Xaa

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (2)..(2)
<223> OTHER INFORMATION: Arg, Met, Ala, Glu, Gly, Gln or Ser
<220> FEATURE:
<221> NAME/KEY: MOD_RES
<222> LOCATION: (11)..(11)
<223> OTHER INFORMATION: Phe or Tyr

<400> SEQUENCE: 30

Ala Xaa Thr Gly Ser Ser Gly Tyr Phe Asp Xaa
1               5                   10

<210> SEQ ID NO 31
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asp Leu
            20                  25                  30

Leu His Trp Tyr Gln Gln Lys Pro Gly Lys Ala Pro Lys Leu Leu Ile
        35                  40                  45

Lys Tyr Ala Ser Gln Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Gly Asn Ser Leu Pro Asn
                85                  90                  95

Thr Phe Gly Gln Gly Thr Lys Val Glu Ile Lys Arg
            100                 105

<210> SEQ ID NO 32
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Phe Ile Thr Asn Asn
                20                  25                  30

Tyr Trp Gly Trp Val Arg Gln Ala Pro Gly Lys Gly Leu Glu Trp Val
            35                  40                  45

Gly Tyr Ile Ser Tyr Ser Gly Ser Thr Ser Tyr Asn Pro Ser Leu Lys
    50                  55                  60

Ser Arg Phe Thr Ile Ser Arg Asp Thr Ser Lys Asn Thr Phe Tyr Leu
65                  70                  75                  80

Gln Met Asn Ser Leu Arg Ala Glu Asp Thr Ala Val Tyr Tyr Cys Ala
                85                  90                  95

Arg Thr Gly Ser Ser Gly Tyr Phe Asp Phe Trp Gly Gln Gly Thr Leu
            100                 105                 110

Val Thr Val Ser Ser
            115
```

METHODS FOR DIAGNOSING AND TREATING INFLAMMATORY BOWEL DISEASE

CROSS REFERENCE TO RELATED APPLICATIONS

This application is a Divisional of U.S. patent application Ser. No. 16/295,536 filed Mar. 7, 2019, which is a Divisional of U.S. patent application Ser. No. 15/271,687 filed Sep. 21, 2016, now issued as U.S. Pat. No. 10,273,542, which is a Continuation of International Application No. PCT/US2015/022762 filed Mar. 26, 2015, which claims priority to U.S. Provisional Application No. 61/971,379 filed Mar. 27, 2014, the contents of each of which are hereby incorporated by reference in their entirety, and to each of which priority is claimed.

SEQUENCE LISTING

The specification incorporates by reference the Sequence Listing submitted herewith via EFS on Apr. 10, 2020. Pursuant to 37 C.F.R. § 1.52(e)(5), the Sequence Listing text file, identified as 00B2060903_SL.txt, is 20,261 bytes and was created on Apr. 10, 2020. The Sequence Listing, electronically filed herewith, does not extend beyond the scope of the specification and thus does not contain new matter.

FIELD

Biomarkers predictive of responsiveness to integrin beta7 antagonists, including anti-beta7 integrin subunit antibodies, and methods of using such biomarkers are provided. In addition, methods of treating gastrointestinal inflammatory disorders such as inflammatory bowel diseases including ulcerative colitis and Crohn's disease are provided. Also provided are methods of using such predictive biomarkers for the treatment of inflammatory bowel diseases including ulcerative colitis and Crohn's disease.

BACKGROUND

Inflammatory bowel disease (IBD) is a chronic inflammatory autoimmune condition of the gastrointestinal (GI) tract, which presents clinically as either ulcerative colitis (UC) or Crohn's disease (CD). CD is a chronic transmural inflammatory disease with the potential to affect any part of the entire GI tract, and UC is a mucosal inflammation of the colon. Both conditions are characterized clinically by frequent bowel motions, malnutrition, and dehydration, with disruption in the activities of daily living. CD is frequently complicated by the development of malabsorption, strictures, and fistulae and may require repeated surgery. UC, less frequently, may be complicated by severe bloody diarrhea and toxic megacolon, also requiring surgery. Both IBD conditions are associated with an increased risk for malignancy of the GI tract. The etiology of IBD is complex, and many aspects of the pathogenesis remain unclear.

The treatment of moderate to severe IBD poses significant challenges to treating physicians, because conventional therapy with corticosteroids and immunomodulator therapy (e.g., azathioprine, 6 mercaptopurine, and methotrexate) is associated with side effects and intolerance and has not shown proven benefit in maintenance therapy (steroids). Monoclonal antibodies targeting tumor necrosis factor alpha (TNF-.alpha.), such as infliximab (a chimeric antibody) and adalimumab (a fully human antibody), are currently used in the management of CD. Infliximab has also shown efficacy and has been approved for use in UC. However, approximately 10%-20% of patients with CD are primary nonresponders to anti TNF therapy, and another ~20%-30% of CD patients lose response over time (Schnitzler et al., Gut 58:492-500 (2009)). Other adverse events (AEs) associated with anti TNFs include elevated rates of bacterial infection, including tuberculosis, and, more rarely, lymphoma and demyelination (Chang et al., Nat Clin Pract Gastroenterol Hepatology 3:220 (2006); Hoentjen et al., World J. Gastroenterol. 15(17):2067 (2009)). No currently available therapy achieves sustained remission in more than 20%-30% of IBD patients with chronic disease (Hanauer et al., Lancet 359: 1541-49 (2002); Sandborn et al., N Engl J Med 353:1912-25 (2005)). In addition, most patients do not achieve sustained steroid-free remission and mucosal healing, clinical outcomes that correlate with true disease modification. Therefore, there is a need to develop more targeted therapy in IBD that is optimized for chronic use: an improved safety profile with sustained remission, particularly steroid-free remission and prevention of long-term complications in a greater proportion of patients, including those patients who either never respond to an anti TNF therapeutic agent or lose response over time (TNF inadequate responder patients or TNF-IR patients).

The integrins are alpha/beta heterodimeric cell surface glycoprotein receptors that play a role in numerous cellular processes including leukocyte adhesion, signaling, proliferation, and migration, as well as in gene regulation (Hynes, R. O., Cell, 1992, 69:11-25; and Hemler, M. E., Annu. Rev. Immunol., 1990, 8:365-368). They are composed of two heterodimeric, non-covalently interacting .alpha. and .beta. transmembrane subunits that bind specifically to distinct cell adhesion molecules (CAMs) on endothelia, epithelia, and extracellular matrix proteins. In this manner, integrins can function as tissue-specific cell adhesion receptors aiding in the recruitment of leukocytes from blood into nearly all tissue sites in a highly regulated manner, playing a role in the homing of leukocytes to normal tissue and to sites of inflammation (von Andrian et al., N Engl J Med 343:1020-34 (2000)). In the immune system, integrins are involved in leukocyte trafficking, adhesion and infiltration during inflammatory processes (Nakajima, H. et al., J. Exp. Med., 1994, 179:1145-1154). Differential expression of integrins regulates the adhesive properties of cells and different integrins are involved in different inflammatory responses. (Butcher, E. C. et al., Science, 1996, 272:60-66). The beta7 containing integrins (i.e., alpha4beta7 and alphaEbeta7) are expressed primarily on monocytes, lymphocytes, eosinophils, basophils, and macrophages but not on neutrophils (Elices, M. J. et al., Cell, 1990, 60:577-584).

The α4β7 integrin is a leukocyte-homing receptor that is important in the migration of cells to the intestinal mucosa and associated lymphoid tissues, such as Peyer's patches in the small intestine, lymphoid follicles in the large intestine, and mesenteric lymph nodes. In the gut, leukocyte rolling and firm adhesion to the mucosal endothelium is initiated by signals from chemokines and is mediated via mucosal addressin cell adhesion molecule (MAdCAM)-1-associated sialyl Lewis X. Chemokine signaling induces the α4β7 integrin to undergo a change from low to high MAdCAM-1 binding affinity. The leukocyte then arrests and begins the process of extravasation through the vascular endothelium to underlying tissue. This extravasation process is believed to occur in both the normal immune cell recirculation state and in inflammatory conditions (von Andrian et al., supra). The numbers of α4β7$^+$ cells in infiltrates and the expression of the ligand MAdCAM-1 are higher at sites of chronic inflammation such as in the intestinal tract of patients with UC or CD (Briskin et al., Am J Pathol 151:97-110 (1997); Souza et al., Gut 45:856-63 (1999)). α4β7 binds preferentially to high endothelial venules expressing MAdCAM-1 and vascular cell adhesion molecule (VCAM)-1, as well as to the extracellular matrix molecule fibronectin fragment CS-1 (Chan et al., J Biol Chem 267:8366-70 (1992); Ruegg et al., J Cell Biol 17:179-89 (1992); Berlin et al., Cell 74:185-95 (1993)). Together with constitutively expressed MAdCAM-1 in gut mucosal vessels, the α4β7 integrin plays a selective role in leukocyte gut tropism but does not seem to contribute to homing of leukocytes to the peripheral tissue or the CNS. Instead, peripheral lymphoid trafficking has been associated with α4β1 interaction with VCAM-1 (Yednock et al., Nature 356:63-6 (1992); Rice et al., Neurology 64:1336-42 (2005)).

Another member of the β7 integrin family, expressed exclusively on T lymphocytes and associated with mucosal tissues, is the αEβ7 integrin, otherwise known as CD103. The αEβ7 integrin binds selectively to E-cadherin on epithelial cells and has been proposed to play a role in the retention of T cells in the mucosal tissue in the intraepithelial lymphocyte compartment (Cepek et al., J Immunol 150: 3459-70 (1993); Karecla et al. Eur J Immunol 25:852-6 (1995)). The αEβ7+ cells in the lamina propria have been reported to exhibit cytotoxicity against stressed or infected epithelial cells (Hadley et al., J Immunol 159:3748-56 (1997); Buri et al., J Pathol 206:178-85 (2005)). The expression of αEβ7 is increased in CD (Elewaut et al., Acta Gastroenterol Belg 61:288-94 (1998); Oshitani et al., Int J Mol Med 12:715-9 (2003)), and anti-αEβ7 antibody treatment has been reported to attenuate experimental colitis in mice, implicating a role for αEβ7+ lymphocytes in experimental models of IBD (Ludviksson et al., J Immunol 162: 4975-82 (1999)).

Administration of monoclonal antibodies against alphaE beta7 reportedly prevents and ameliorates immunization induced colitis in IL-2$^{-/-}$ mice, suggesting that the onset and maintenance of inflammatory bowel disease depends on colonic localization of lamina propria CD4+ lymphocytes expressing alphaEbeta7 (Ludviksson et al., J Immunol. 1999, 162(8):4975-82). An anti-α4 antibody (natalizumab) reportedly has efficacy in treatment of patients with CD (Sandborn et al., N Engl J Med 2005; 353:1912-25) and an anti-α4β7 antibody (MLN-02, MLN0002, vedolizumab) reportedly is effective in patients with UC (Feagan et al., N Engl J Med 2005; 352:2499-507). A second anti-alpha4/beta7 antibody (AMG 181) is also in development and clinical trials have recently begun (clinicaltrials(dot)gov identifier, NCT01164904, September 2012). These studies and findings validate α4β7 as a therapeutic target and support the idea that the interaction between α4β7 and MAdCAM-1 mediates the pathogenesis of IBD. Thus, antagonists of beta7 integrin are of great potential as a therapeutic agent in treating IBD.

Humanized monoclonal antibodies targeted against the β7 integrin subunit have been described previously. See, e.g., Intn'l Patent Pub. No. WO2006/026759. One such antibody, rhuMAb Beta7 (etrolizumab) is derived from the rat anti-mouse/human monoclonal antibody FIB504 (Andrew et al. 1994). It was engineered to include human IgG1-heavy chain and κ1-light chain frameworks. Intn'l Patent Pub. No. WO2006/026759. Administration of etrolizumab to human patients according to certain dosing regimens has been described previously. See, e.g., Intn'l Patent Pub. No. WO/2012/135589.

RhuMAb Beta7 (etrolizumab) binds α4β7 (Holzmann et al., Cell 56:37-46 (1989); Hu et al., Proc Natl Acad Sci USA 89:8254-8 (1992)) and αEβ7 (Cepek et al., J Immunol 150:3459-70 (1993)), which regulate trafficking and retention of lymphocyte subsets, respectively, in the intestinal mucosa. Clinical studies have demonstrated the efficacy of an anti α4 antibody (natalizumab) for the treatment of CD (Sandborn et al., N Engl J Med 353:1912-25 (2005)), and encouraging results have been reported for anti α4β7 antibody (LDP02/MLN02/MLN0002/vedolizumab) in the treatment of UC (Feagan et al., N Engl J Med 352:2499-507 (2005), Feagan et al., N Engl J Med 369(8):699-710 (2013)) and also CD (Sandborn et al., N Engl J Med 369(8):711-721 (2013)) These findings help to validate α4β7 as a potential therapeutic target and support the hypothesis that the interaction between α4β7 and mucosal addressin cell adhesion molecule 1 (MAdCAM 1) contributes to the pathogenesis of inflammatory bowel disease (IBD).

Unlike natalizumab, which binds α4 and thus binds both α4β1 and α4β7, rhuMAb Beta7 binds specifically to the β7 subunit of α4β7 and αEβ7 and does not bind to α4 or β1 integrin individual subunits. This was demonstrated by the inability of the antibody to inhibit adhesion of α4β1+ α4β7—Ramos cells to vascular cell adhesion molecule 1 (VCAM 1) at concentrations as high as 100 nM. Importantly, this characteristic of rhuMAb Beta7 indicates selectivity: T cell subsets expressing α4β1 but not β7 should not be directly affected by rhuMAb Beta7.

Support for the gut-specific effects of rhuMAb Beta7 on leukocyte homing comes from several in vivo nonclinical studies. In severe combined immunodeficient (SCID) mice reconstituted with CD45RB$^{high}$CD4+ T cells (an animal model of colitis), rhuMAb Beta7 blocked radiolabeled lymphocyte homing to the inflamed colon but did not block homing to the spleen, a peripheral lymphoid organ. See, e.g., Intn'l Patent Pub. No. WO2006/026759. In addition, the rat-mouse chimeric anti-murine β7 (anti β7, muFIB504) was unable to reduce the histologic degree of central nervous system (CNS) inflammation or improve disease survival in myelin basic protein T cell receptor (MBP-TCR) transgenic mice with experimental autoimmune encephalitis (EAE), an animal model of multiple sclerosis. Id. Furthermore, in two safety studies in cynomolgus monkeys, rhuMAb Beta7 induced a moderate increase in peripheral blood lymphocyte numbers that was largely due to a marked (approximately three- to sixfold) increase in CD45RA$^-$β7$^{high}$ peripheral blood T cells, a subset that is phenotypically similar to gut-homing memory/effector T cells in humans. See, e.g., Intn'l Patent Pub. No. WO2009/140684; Stefanich et al., Br. J. Pharmacol. 162:1855-1870 (2011). In contrast, rhuMAb Beta7 had minimal to no effect on the number of CD45RA+ β7 intermediate peripheral blood T cells, a subset that is phenotypically similar to naïve T cells in humans, and no effect on the number of CD45RA$^-$β7$^{low}$ peripheral blood T cells, a subset that is phenotypically similar to peripheral homing memory/effector T cells in humans, confirming the specificity of rhuMAb Beta7 for the gut homing lymphocyte subpopulation. Intn'l Patent Pub. No. WO2009/140684; Stefanich et al., Br. J. Pharmacol. 162:1855-1870 (2011).

While clinical studies have demonstrated the efficacy of an anti-α,4 antibody (natalizumab) for the treatment of CD (Sandborn et al., N Engl J Med 353:1912-25 (2005)), and encouraging results have been reported for anti-α4β7 antibody (LDP02/MLN02/MLN0002/vedolizumab) in the treatment of UC, there remains a need for further improvements in the treatment of these disorders. For example, natalizumab treatment has been associated with confirmed cases of progressive multifocal leukoencephalopathy (PML) in patients with Crohn's disease (and separately, multiple sclerosis) who received concomitant treatment with natalizumab and immunosupressives. PML is a potentially fatal neurological condition linked to reactivation of a polyomavirus (JC virus) and active viral replication in the brain. No known interventions can reliably prevent PML or adequately treat PML, if it occurs. One limitation of vedolizumab treatment is that it is administered intravenously which can be inconvenient for the patient and can also be associated with undesirable or adverse events, e.g., infusion site reactions. Accordingly, there is a need for improved therapeutic approaches to the treatment of gastrointestinal inflammatory disorders such as IBD, e.g., ulcerative colitis and Crohn's disease, as well as more desirable dosing regimens.

It is often unknown, prior to treatment, whether a patient will respond to a particular therapeutic agent or class of therapeutic agents. Accordingly, as IBD patients in general, and UC and CD patients in particular, seek treatment, there is considerable trial and error involved in the search for therapeutic agent(s) effective for a particular patient. Such trial and error often involves considerable risk and discomfort for the patient in order to find the most effective therapy. Thus, there is a need for more effective means for determining which patients will respond to which treatment and for incorporating such determinations into more effective treatment regimens for IBD patients.

It would therefore be highly advantageous to have additional diagnostic methods, including predictive diagnostic methods, that can be used to objectively identify patients most likely to respond to treatment with various IBD therapeutic agents, including anti-beta7 integrin subunit antibodies. Thus, there is a continuing need to identify new biomarkers associated with ulcerative colitis, Crohn's disease as well as other inflammatory bowel disorders and that are predictive of response to treatment with anti-beta7 integrin subunit antibodies. In addition, statistically and biologically significant and reproducible information regarding such associations could be utilized as an integral component in efforts to identify specific subsets of UC or CD patients, such as TNF-IR patients, who would be expected to significantly benefit from treatment with anti-beta7 integrin subunit antibodies, for example where the therapeutic agent is or has been shown in clinical studies to be of therapeutic benefit in such specific UC or CD patient subpopulation.

The invention described herein meets certain of the above-described needs and provides other benefits.

All references cited herein, including patent applications and publications, are incorporated by reference in their entirety for any purpose.

SUMMARY

The methods of the invention are based, at least in part, on the discovery that mRNA expression levels of certain genes in biological samples obtained from patients, e.g., intestinal biopsies or blood, are predictive of responsiveness of patients suffering from a gastrointestinal inflammatory disorder to treatment with integrin beta7 antagonists.

Accordingly, in one aspect, methods of predicting the response of a patient suffering from a gastrointestinal inflammatory disorder, or predicting responsiveness of a gastrointestinal inflammatory disorder patient, to a therapy comprising an integrin beta7 antagonist are provided. In certain embodiments, a biological sample is obtained from the patient and levels of mRNA expression are measured. In some embodiments, expression of at least one, at least two, at least three, or at least four High Expression Predictive Genes ("HEPG") in the sample selected from GZMA, KLRB1, FOXM1, CCDC90A, CCL4, CPA2, CXCR6, DDO, ECH1, FAM125B, FASLG, FGF9, GPR15, GZMB, KCNMA1, PHF14, TIFAB, TMEM200A, TMIGD2, and SLC8A3 are measured. In some embodiments, the at least one, at least two, at least three, or at least four HEPG are selected from GZMA, KLRB1, FOXM1, SLC8A3, and ECH1. In some embodiments, a further HEPG in addition to those identified above is measured, which further HEPG is ITGAE. In one embodiment, the biological sample is a tissue biopsy sample. In one embodiment, the biopsy is obtained from intestinal tissue. In certain such embodiments comprising a tissue biopsy sample or intestinal tissue, the HEPG does not include SLC8A3. In one embodiment, the biological sample is peripheral whole blood. In certain such embodiments comprising peripheral blood, the HEPG includes SLC8A3. In one embodiment, the peripheral whole blood is collected in a PAXgene tube. In certain embodiments, the mRNA expression level is measured by an RNA sequencing method, microarray or PCR method. In one embodiment, the PCR method is qPCR. In certain embodiments, the measuring comprises amplifying one or more of GZMA, KLRB1, FOXM1, CCDC90A, CCL4L1.2, CPA2, CXCR6, DDO, ECH1, FAM125B, FASLG, FGF9, GPR15, GZMB, KCNMA1, PHF14, TIFAB, TMEM200A, TMIGD2, and SLC8A3 mRNA, and optionally further comprises amplifying ITGAE mRNA, and detecting the amplified mRNA, thereby measuring the level of amplified mRNA. In certain embodiments, the mRNA expression level is compared to a reference level. In some embodiments, the mRNA expression level is compared to a reference level for each of the HEPG measured. In certain embodiments, each of the reference levels is a median value. In some embodiments, the patient is predicted to respond to therapy comprising the integrin beta7 antagonist when the mRNA expression level of at least one, at least two, at least three, or at least four HEPG in the sample selected from GZMA, KLRB1, FOXM1, CCDC90A, CCL4, CPA2, CXCR6, DDO, ECH1, FAM125B, FASLG, FGF9, GPR15, GZMB, KCNMA1, PHF14, TIFAB, TMEM200A, TMIGD2, and SLC8A3 is elevated compared to a reference value for each of the HEPG measured, which in certain embodiments is a median value for each reference value. In one embodiment, the response is clinical remission. In one embodiment, the response is mucosal healing. In one embodiment, the response is clinical response. In certain embodiments, remission in the patient is determined to be induced when the absolute Mayo Clinic Score ≤2 and no individual subscore >1, which is also referred to as clinical remission. In certain embodiments, mucosal healing is determined to have occurred when the patient is determined to have an endoscopy subscore of 0 or 1 as assessed by flexible sigmoidoscopy. In certain such embodiments, patients who experience mucosal healing are determined to have an endoscopy subscore of 0. In certain embodiments, clinical response is determined to have occurred when the patient experiences a 3-point decrease and 30% reduction from baseline in MCS and ≥1-point decrease in rectal bleeding subscore or absolute rectal bleeding score of 0 or 1.

In another aspect, methods of identifying a patient suffering from a gastrointestinal inflammatory disorder as likely to respond to a therapy comprising an integrin beta7 antagonist are provided. In certain embodiments, the methods comprise: (a) measuring the level of mRNA expression of at least one, at least two, at least three, or at least four HEPG selected from GZMA, KLRB1, FOXM1, CCDC90A, CCL4, CPA2, CXCR6, DDO, ECH1, FAM125B, FASLG, FGF9, GPR15, GZMB, KCNMA1, PHF14, TIFAB, TMEM200A, TMIGD2, and SLC8A3 in a biological sample from the patient; (b) comparing the level of mRNA expression measured in (a) to a reference level for each of the HEPG measured; and (c) identifying the patient as more likely to respond to the therapy comprising an integrin beta7 antagonist when the level of mRNA expression of each HEPG measured in (a) is above the reference level for each of the HEPG measured. In some embodiments, the at least one, at least two, at least three, or at least four HEPG are selected from GZMA, KLRB1, FOXM1, SLC8A3, and ECH1. In some embodiments, a further HEPG in addition to those identified above is measured, which further HEPG is ITGAE. In one embodiment, the patient is a human. In one embodiment, the patient is not previously treated with an anti-TNF therapeutic agent. In one embodiment, the gastrointestinal inflammatory disorder is an inflammatory bowel disease. In one embodiment, the inflammatory bowel disease is ulcerative colitis or Crohn's disease. In one embodiment, the inflammatory bowel disease is ulcerative colitis and the response is selected from clinical response, mucosal healing and remission. In certain embodiments, remission in the patient is determined to be induced when the absolute Mayo Clinic Score ≤2 and no individual subscore >1, which is also referred to as clinical remission. In certain embodiments, mucosal healing is determined to have occurred when the patient is determined to have an endoscopy subscore of 0 or 1 as assessed by flexible sigmoidoscopy. In certain such embodiments, patients who experience mucosal healing are determined to have an endoscopy subscore of 0. In certain embodiments, clinical response is determined to have occurred when the patient experiences a 3-point decrease and 30% reduction from baseline in MCS and ≥1-point decrease in rectal bleeding subscore or absolute rectal bleeding score of 0 or 1.

In a further aspect, methods of treating a patient having a gastrointestinal inflammatory disorder are provided. In certain embodiments, the methods comprise: (a) measuring the level of mRNA expression of at least one, at least two, at least three, or at least four HEPG selected from GZMA, KLRB1, FOXM1, CCDC90A, CCL4, CPA2, CXCR6, DDO, ECH1, FAM125B, FASLG, FGF9, GPR15, GZMB, KCNMA1, PHF14, TIFAB, TMEM200A, TMIGD2, and SLC8A3 in a biological sample from the patient; (b) comparing the level of mRNA expression of each HEPG measured in (a) to a reference level for each of the HEPG measured; (c) identifying the patient as more likely to respond a therapy comprising an integrin beta7 antagonist when the level of mRNA expression of each HEPG measured in (a) is above the respective reference level for each of the HEPG measured; and (d) administering the therapy when the level of mRNA expression of each HEPG measured in (a) is above the respective reference level for each of the HEPG measured, thereby treating the gastrointestinal inflammatory disorder. In some embodiments, the at least one, at least two, at least three, or at least four HEPG are selected from GZMA, KLRB1, FOXM1, SLC8A3, and ECH1. In some embodiments, a further HEPG in addition to those identified above is measured, which further HEPG is ITGAE. In one embodiment, 105 mg of the integrin beta7 antagonist is administered subcutaneously once every four weeks. In one embodiment, an initial dose of 210 mg of the integrin beta7 antagonist is administered subcutaneously followed by subsequent doses, each subsequent dose of 210 mg of the integrin beta7 antagonist administered subcutaneously, administered at each of weeks 2, 4, 8 and 12 after the initial dose. In one embodiment, the patient is a human. In one embodiment, the patient is not previously treated with an anti-TNF therapeutic agent. In one embodiment, the gastrointestinal inflammatory disorder is an inflammatory bowel disease. In one embodiment, the inflammatory bowel disease is ulcerative colitis or Crohn's disease. In one embodiment, the inflammatory bowel disease is ulcerative colitis and the response is selected from clinical response, mucosal healing and remission. In certain embodiments, remission in the patient is determined to be induced when the absolute Mayo Clinic Score ≤2 and no individual subscore >1, which is also referred to as clinical remission. In certain embodiments, mucosal healing is determined to have occurred when the patient is determined to have an endoscopy subscore of 0 or 1 as assessed by flexible sigmoidoscopy. In certain such embodiments, patients who experience mucosal healing are determined to have an endoscopy subscore of 0. In certain embodiments, clinical response is determined to have occurred when the patient experiences a 3-point decrease and 30% reduction from baseline in MCS and ≥1-point decrease in rectal bleeding subscore or absolute rectal bleeding score of 0 or 1.

In yet another aspect, methods of predicting the response of a patient suffering from a gastrointestinal inflammatory disorder, or predicting responsiveness of a gastrointestinal inflammatory disorder patient, to a therapy comprising an integrin beta7 antagonist are provided in which expression of at least one, at least two, or at least three Low Expression Predictive Genes ("LEPG") in the sample selected from SLC8A3, TNFSF15, BEST2, CCL2, CCL3, CCL3L1/3, CPA3, FGF7, HAMP, IL1A, IL18RAP, INHBA, LIF, LMO4, LRRC4, MLK7.AS1, MT1M, MUCL1, MX1, PMCH, REM2, SSTR2, TM4SF4, TMEM154, UROS, VNN2, and VNN3 are measured. In some embodiments, the at least one, at least two, or at least three LEPG are selected from SLC8A3, TNFSF15, BEST2, VNN2, and CCL2. In some embodiments, at least one, at least two, or at least three LEPG are selected from SLC8A3, VNN2, and TNFSF15. In one embodiment, the biological sample is a tissue biopsy sample. In one embodiment, the biopsy is obtained from intestinal tissue. In certain such embodiments comprising a tissue biopsy sample or intestinal tissue, the LEPG includes SLC8A3. In one embodiment, the biological sample is peripheral whole blood. In certain such embodiments comprising peripheral whole blood, the LEPG does not include SLC8A3. In one embodiment, the peripheral whole blood is collected in a PAXgene tube. In certain embodiments, the mRNA expression level is measured by an RNA sequencing method, microarray, or PCR method. In one embodiment, the PCR method is qPCR. In certain embodiments, the measuring comprises amplifying one or more of SLC8A3, TNFSF15, BEST2, CCL2, CCL3, CCL3L1/3, CPA3, FGF7, HAMP, IL1A, IL18RAP, INHBA, LIF, LMO4, LRRC4, MLK7.AS1, MT1M, MUCL1, MX1, PMCH, REM2, SSTR2, TM4SF4, TMEM154, UROS, VNN2, VNN3 mRNA, and detecting the amplified mRNA, thereby measuring the level of amplified mRNA. In certain embodiments, the mRNA expression level is compared to a reference level. In some embodiments, the mRNA expression level is compared to a reference level for each of the LEPG measured. In certain embodiments, the reference level for each LEPG measured is a median value. In some embodiments, the patient is predicted to respond to therapy comprising the integrin beta7 antagonist when the mRNA expression level of at least one, at least two, or at least three LEPG in the sample selected from SLC8A3, TNFSF15, BEST2, CCL2, CCL3, CCL3L1/3, CPA3, FGF7, HAMP, IL1A, IL18RAP, INHBA, LIF, LMO4, LRRC4, MLK7.AS1, MT1M, MUCL1, MX1, PMCH, REM2, SSTR2, TM4SF4, TMEM154, UROS, VNN2, and VNN3 are reduced compared to a reference value for each of the LEPG measured, which in certain embodiments is a median value for each reference value. In one embodiment, the response is clinical remission. In one embodiment, the response is mucosal healing. In one embodiment, the response is clinical response. In certain embodiments, remission in the patient is determined to be induced when the absolute Mayo Clinic Score ≤2 and no individual subscore >1, which is also referred to as clinical remission. In certain embodiments, mucosal healing is determined to have occurred when the patient is determined to have an endoscopy subscore of 0 or 1 as assessed by flexible sigmoidoscopy. In certain such embodiments, patients who experience mucosal healing are determined to have an endoscopy subscore of 0. In certain embodiments, clinical response is determined to have occurred when the patient experiences a 3-point decrease and 30% reduction from baseline in MCS and ≥1-point decrease in rectal bleeding subscore or absolute rectal bleeding score of 0 or 1.

In still another aspect, methods of identifying a patient suffering from a gastrointestinal inflammatory disorder as likely to respond to a therapy comprising an integrin beta7 antagonist are provided. In certain embodiments, the methods comprise: (a) measuring the level of mRNA expression of at least one, at least two, or at least three LEPG in the sample selected from SLC8A3, TNFSF15, BEST2, CCL2, CCL3, CCL3L1/3, CPA3, FGF7, HAMP, IL1A, IL18RAP, INHBA, LIF, LMO4, LRRC4, MLK7.AS1, MT1M, MUCL1, MX1, PMCH, REM2, SSTR2, TM4SF4, TMEM154, UROS, VNN2, and VNN3 in a biological sample from the patient; (b) comparing the level of mRNA expression measured in (a) to a reference level for each of the LEPG measured; and (c) identifying the patient as more likely to respond to the therapy comprising an integrin beta7 antagonist when the level of mRNA expression of each LEPG measured in (a) is below the reference level for each of the LEPG measured. In some embodiments, the at least one, at least two, or at least three LEPG are selected from SLC8A3, TNFSF15, BEST2, VNN2, and CCL2. In some embodiments, at least one, at least two, or at least three LEPG are selected from SLC8A3, VNN2, and TNFSF15. In one embodiment, the patient is a human. In one embodiment, the patient is not previously treated with an anti-TNF therapeutic agent. In one embodiment, the gastrointestinal inflammatory disorder is an inflammatory bowel disease. In one embodiment, the inflammatory bowel disease is ulcerative colitis or Crohn's disease. In one embodiment, the inflammatory bowel disease is ulcerative colitis and the response is selected from clinical response, mucosal healing and remission. In certain embodiments, remission in the patient is determined to be induced when the absolute Mayo Clinic Score ≤2 and no individual subscore >1, which is also referred to as clinical remission. In certain embodiments, mucosal healing is determined to have occurred when the patient is determined to have an endoscopy subscore of 0 or 1 as assessed by flexible sigmoidoscopy. In certain such embodiments, patients who experience mucosal healing are determined to have an endoscopy subscore of 0. In certain embodiments, clinical response is determined to have occurred when the patient experiences a 3-point decrease and 30% reduction from baseline in MCS and ≥1-point decrease in rectal bleeding subscore or absolute rectal bleeding score of 0 or 1.

In a further aspect, methods of treating a patient having a gastrointestinal inflammatory disorder are provided. In certain embodiments, the methods comprise: (a) measuring the level of mRNA expression of at least one, at least two, or at least three LEPG in the sample selected from SLC8A3, TNFSF15, BEST2, CCL2, CCL3, CCL3L1/3, CPA3, FGF7, HAMP, IL1A, IL18RAP, INHBA, LIF, LMO4, LRRC4, MLK7.AS1, MT1M, MUCL1, MX1, PMCH, REM2, SSTR2, TM4SF4, TMEM154, UROS, VNN2, and VNN3 in a biological sample from the patient; (b) comparing the level of mRNA expression of each LEPG measured in (a) to a reference level for each of the LEPG measured; (c) identifying the patient as more likely to respond a therapy comprising an integrin beta7 antagonist when the level of mRNA expression of each LEPG measured in (a) is below the respective reference level for each of the LEPG measured; and (d) administering the therapy when the level of mRNA expression of each LEPG measured in (a) is below the respective reference level for each of the LEPG measured, thereby treating the gastrointestinal inflammatory disorder. In some embodiments, the at least one, at least two, or at least three LEPG are selected from SLC8A3, TNFSF15, BEST2, VNN2, and CCL2. In some embodiments, at least one, at least two, or at least three LEPG are selected from SLC8A3, VNN2, and TNFSF15. In one embodiment, 105 mg of the integrin beta7 antagonist is administered subcutaneously once every four weeks. In one embodiment, an initial dose of 210 mg of the integrin beta7 antagonist is administered subcutaneously followed by subsequent doses, each subsequent dose of 210 mg of the integrin beta7 antagonist administered subcutaneously, administered at each of weeks 2, 4, 8 and 12 after the initial dose. In one embodiment, the patient is a human. In one embodiment, the patient is not previously treated with an anti-TNF therapeutic agent. In one embodiment, the gastrointestinal inflammatory disorder is an inflammatory bowel disease. In one embodiment, the inflammatory bowel disease is ulcerative colitis or Crohn's disease. In one embodiment, the inflammatory bowel disease is ulcerative colitis and the response is selected from clinical response, mucosal healing and remission. In certain embodiments, remission in the patient is determined to be induced when the absolute Mayo Clinic Score ≤2 and no individual subscore >1, which is also referred to as clinical remission. In certain embodiments, mucosal healing is determined to have occurred when the patient is determined to have an endoscopy subscore of 0 or 1 as assessed by flexible sigmoidoscopy. In certain such embodiments, patients who experience mucosal healing are determined to have an endoscopy subscore of 0. In certain embodiments, clinical response is determined to have occurred when the patient experiences a 3-point decrease and 30% reduction from baseline in MCS and ≥1-point decrease in rectal bleeding subscore or absolute rectal bleeding score of 0 or 1.

In yet still another aspect, methods of predicting the response of a patient suffering from a gastrointestinal inflammatory disorder, or predicting responsiveness of a gastrointestinal inflammatory disorder patient, to a therapy comprising an integrin beta7 antagonist are provided in which expression of at least one, at least two, at least three, or at least four HEPG in a biological sample selected from GZMA, KLRB1, FOXM1, CCDC90A, CCL4, CPA2, CXCR6, DDO, ECH1, FAM125B, FASLG, FGF9, GPR15, GZMB, KCNMA1, PHF14, TIFAB, TMEM200A, TMIGD2, and SLC8A3 are measured and in which expression of of at least one, at least two, or at least three LEPG in the sample selected from SLC8A3, TNFSF15, BEST2, CCL2, CCL3, CCL3L1/3, CPA3, FGF7, HAMP, IL1A, IL18RAP, INHBA, LIF, LMO4, LRRC4, MLK7.AS1, MT1M, MUCL1, MX1, PMCH, REM2, SSTR2, TM4SF4, TMEM154, UROS, VNN2, and VNN3 are measured. In some embodiments, the at least one, at least two, at least three, or at least four HEPG are selected from GZMA, KLRB1, FOXM1, SLC8A3, and ECH1 and the at least one, at least two, or at least three LEPG are selected from SLC8A3, TNFSF15, BEST2, VNN2, and CCL2. In some embodiments, at least one, at least two, or at least three LEPG are selected from SLC8A3, VNN2, and TNFSF15. In some embodiments, the level of mRNA expression of each HEPG is compared to a reference level for each of the HEPG measured and the level of mRNA expression of each LEPG is compared to a reference level for each of the LEPG measured. In some embodiments, the patient is predicted to respond to the therapy when the level of mRNA expression of each of the HEPG measured is elevated compared to the respective reference level for each of the HEPG measured and when the level of mRNA expression of each of the LEPG measured is reduced compared to the respective reference level for each of the LEPG measured. In one embodiment, the biological sample is a tissue biopsy sample. In one embodiment, the biopsy is obtained from intestinal tissue. In certain such embodiments comprising a tissue biopsy sample or intestinal tissue, the HEPG does not include SLC8A3 and the LEPG includes SLC8A3. In one embodiment, the biological sample is peripheral whole blood. In certain such embodiments comprising peripheral blood, the HEPG includes SLC8A3 and the LEPG does not include SLC8A3. In one embodiment, the peripheral whole blood is collected in a PAXgene tube. In certain embodiments, the mRNA expression level is measured by an RNA sequencing method, microarray, or PCR method. In one embodiment, the PCR method is qPCR. In certain embodiments, the measuring comprises amplifying one or more of GZMA, KLRB1, FOXM1, CCDC90A, CCL4L1.2, CPA2, CXCR6, DDO, ECH1, FAM125B, FASLG, FGF9, GPR15, GZMB, KCNMA1, PHF14, TIFAB, TMEM200A, TMIGD2, and SLC8A3 mRNA, and optionally further comprising amplifying ITGAE mRNA, and comprising amplifying one or more of SLC8A3, TNFSF15, BEST2, CCL2, CCL3, CCL3L1/3, CPA3, FGF7, HAMP, IL1A, IL18RAP, INHBA, LIF, LMO4, LRRC4, MLK7.AS1, MT1M, MUCL1, MX1, PMCH, REM2, SSTR2, TM4SF4, TMEM154, UROS, VNN2, VNN3 mRNA, and detecting the amplified mRNA, thereby measuring the level of amplified mRNA. In certain embodiments, the mRNA expression level for each gene measured is compared to a reference level for the measured gene, which in some embodiments, is a median level. In one embodiment, the response is clinical remission. In one embodiment, the response is mucosal healing. In one embodiment, the response is clinical response. In certain embodiments, remission in the patient is determined to be induced when the absolute Mayo Clinic Score ≤2 and no individual subscore >1, which is also referred to as clinical remission. In certain embodiments, mucosal healing is determined to have occurred when the patient is determined to have an endoscopy subscore of 0 or 1 as assessed by flexible sigmoidoscopy. In certain such embodiments, patients who experience mucosal healing are determined to have an endoscopy subscore of 0. In certain embodiments, clinical response is determined to have occurred when the patient experiences a 3-point decrease and 30% reduction from baseline in MCS and ≥1-point decrease in rectal bleeding subscore or absolute rectal bleeding score of 0 or 1.

In another aspect, methods of identifying a patient suffering from a gastrointestinal inflammatory disorder as likely to respond to a therapy comprising an integrin beta7 antagonist are provided which comprise: (a) measuring the level of mRNA expression of at least one, at least two, at least three, or at least four HEPG selected from GZMA, KLRB1, FOXM1, CCDC90A, CCL4, CPA2, CXCR6, DDO, ECH1, FAM125B, FASLG, FGF9, GPR15, GZMB, KCNMA1, PHF14, TIFAB, TMEM200A, TMIGD2, and SLC8A3 in a biological sample from the patient; (b) comparing the level of mRNA expression measured in (a) to a reference level for each of the HEPG measured; and which methods further comprise (c) measuring the level of mRNA expression of at least one, at least two, or at least three LEPG selected from SLC8A3, TNFSF15, BEST2, CCL2, CCL3, CCL3L1/3, CPA3, FGF7, HAMP, IL1A, IL18RAP, INHBA, LIF, LMO4, LRRC4, MLK7.AS1, MT1M, MUCL1, MX1, PMCH, REM2, SSTR2, TM4SF4, TMEM154, UROS, VNN2, and VNN3 in the biological sample from the patient; (d) comparing the level of mRNA expression measured in (c) to a reference level for each of the LEPG measured and (e) identifying the patient as more likely to respond to the therapy comprising an integrin beta7 antagonist when the level of mRNA expression of each HEPG measured in (a) is above the respective reference level for each of the HEPG measured and when the level of mRNA expression of each LEPG measured in (c) is below the respective reference level for each of the LEPG measured. In some embodiments, the at least one, at least two, at least three, or at least four HEPG are selected from GZMA, KLRB1, FOXM1, SLC8A3, and ECH1 and the at least one, at least two, or at least three LEPG are selected from SLC8A3, TNFSF15, BEST2, VNN2, and CCL2. In some embodiments, at least one, at least two, or at least three LEPG are selected from SLC8A3, VNN2, and TNFSF15. In some embodiments, a further HEPG in addition to those identified above is measured, which further HEPG is ITGAE. In one embodiment, the patient is a human. In one embodiment, the patient is not previously treated with an anti-TNF therapeutic agent. In one embodiment, the gastrointestinal inflammatory disorder is an inflammatory bowel disease. In one embodiment, the inflammatory bowel disease is ulcerative colitis or Crohn's disease. In one embodiment, the inflammatory bowel disease is ulcerative colitis and the response is selected from clinical response, mucosal healing and remission. In certain embodiments, remission in the patient is determined to be induced when the absolute Mayo Clinic Score ≤2 and no individual subscore >1, which is also referred to as clinical remission. In certain embodiments, mucosal healing is determined to have occurred when the patient is determined to have an endoscopy subscore of 0 or 1 as assessed by flexible sigmoidoscopy. In certain such embodiments, patients who experience mucosal healing are determined to have an endoscopy subscore of 0. In certain embodiments, clinical response is determined to have occurred when the patient experiences a 3-point decrease and 30% reduction from baseline in MCS and ≥1-point decrease in rectal bleeding subscore or absolute rectal bleeding score of 0 or 1.

In yet still another aspect, methods of treating a patient having a gastrointestinal inflammatory disorder are provided in which the methods comprise: (a) measuring the level of mRNA expression of at least one, at least two, at least three, or at least four HEPG selected from GZMA, KLRB1, FOXM1, CCDC90A, CCL4, CPA2, CXCR6, DDO, ECH1, FAM125B, FASLG, FGF9, GPR15, GZMB, KCNMA1, PHF14, TIFAB, TMEM200A, TMIGD2, and SLC8A3 in a biological sample from the patient; (b) comparing the level of mRNA expression of each HEPG measured in (a) to a reference level for each of the HEPG measured ("HEPG reference level") and which methods further comprise (c) measuring the level of mRNA expression of at least one, at least two, or at least three LEPG in the sample selected from SLC8A3, TNFSF15, BEST2, CCL2, CCL3, CCL3L1/3, CPA3, FGF7, HAMP, IL1A, IL18RAP, INHBA, LIF, LMO4, LRRC4, MLK7.AS1, MT1M, MUCL1, MX1, PMCH, REM2, SSTR2, TM4SF4, TMEM154, UROS, VNN2, and VNN3 in a biological sample from the patient; (d) comparing the level of mRNA expression of each LEPG measured in (c) to a reference level for each of the LEPG measured ("LEPG reference level"); (e) identifying the patient as more likely to respond a therapy comprising an integrin beta7 antagonist when the level of mRNA expression of each of the HEPG measured in (a) is above the HEPG reference level and the level of mRNA expression of each of the LEPG measured in (c) is below the LEPG reference level; and (f) administering the therapy when the level of mRNA expression of each of the HEPG measured in (a) is above the HEPG reference level and the level of mRNA expression of each of the LEPG measured in (c) is below the LEPG reference level, thereby treating the gastrointestinal inflammatory disorder. In some embodiments, the at least one, at least two, at least three, or at least four HEPG are selected from GZMA, KLRB1, FOXM1, SLC8A3, and ECH1 and the at least one, at least two, or at least three LEPG are selected from SLC8A3, TNFSF15, BEST2, VNN2, and CCL2. In some embodiments, at least one, at least two, or at least three LEPG are selected from SLC8A3, VNN2, and TNFSF15. In some embodiments, a further HEPG in addition to those identified above is measured, which further HEPG is ITGAE. In one embodiment, 105 mg of the integrin beta7 antagonist is administered subcutaneously once every four weeks. In one embodiment, an initial dose of 210 mg of the integrin beta7 antagonist is administered subcutaneously followed by subsequent doses, each of 210 mg of the integrin beta7 antagonist administered subcutaneously, administered at each of weeks 2, 4, 8 and 12 after the initial dose. In one embodiment, the patient is a human. In one embodiment, the patient is not previously treated with an anti-TNF therapeutic agent. In one embodiment, the gastrointestinal inflammatory disorder is an inflammatory bowel disease. In one embodiment, the inflammatory bowel disease is ulcerative colitis or Crohn's disease. In one embodiment, the inflammatory bowel disease is ulcerative colitis and the response is selected from clinical response, mucosal healing and remission. In certain embodiments, remission in the patient is determined to be induced when the absolute Mayo Clinic Score ≤2 and no individual subscore >1, which is also referred to as clinical remission. In certain embodiments, mucosal healing is determined to have occurred when the patient is determined to have an endoscopy subscore of 0 or 1 as assessed by flexible sigmoidoscopy. In certain such embodiments, patients who experience mucosal healing are determined to have an endoscopy subscore of 0. In certain embodiments, clinical response is determined to have occurred when the patient experiences a 3-point decrease and 30% reduction from baseline in MCS and ≥1-point decrease in rectal bleeding subscore or absolute rectal bleeding score of 0 or 1.

In still yet another aspect, an integrin beta7 antagonist for use in treating a patient having a gastrointestinal inflammatory disorder is provided. In certain embodiments, the patient is treated or selected for treatment when the level of mRNA expression of at least one gene selected from GZMA, KLRB1, FOXM1, CCDC90A, CCL4L1.2, CPA2, CXCR6, DDO, ECH1, FAM125B, FASLG, FGF9, GPR15, GZMB, KCNMA1, PHF14, TIFAB, TMEM200A, TMIGD2, and SLC8A3 is above a reference level. In one embodiment, a further gene in addition to those identified above is measured, which further gene is ITGAE. In certain embodiments, the patient is treated or selected for treatment when the level of mRNA expression of at least one gene selected from SLC8A3, TNFSF15, BEST2, CCL2, CCL3, CCL3L1/3, CPA3, FGF7, HAMP, IL1A, IL18RAP, INHBA, LIF, LMO4, LRRC4, MLK7.AS1, MT1M, MUCL1, MX1, PMCH, REM2, SSTR2, TM4SF4, TMEM154, UROS, VNN2, and VNN3 is below a reference level. In one embodiment, the reference level for each gene measured is a median value. In one embodiment, the integrin beta7 antagonist is for use in treating the patient wherein 105 mg is administered subcutaneously once every four weeks. In one embodiment, an initial dose of 210 mg of the integrin beta7 antagonist is administered subcutaneously followed by subsequent doses, each of 210 mg of the integrin beta7 antagonist administered subcutaneously, administered at each of weeks 2, 4, 8 and 12 after the initial dose.

In a further aspect, in vitro use of at least one agent that specifically binds to a biomarker selected from GZMA, KLRB1, FOXM1, CCDC90A, CCL4L1.2, CPA2, CXCR6, DDO, ECH1, FAM125B, FASLG, FGF9, GPR15, GZMB, KCNMA1, PHF14, TIFAB, TMEM200A, TMIGD2, and SLC8A3 is provided. In one embodiment, an agent that binds to a further biomarker in addition to those identified above is measured, which further biomarker is ITGAE. In certain embodiments, the at least one agent is used for identifying or selecting a patient having a gastroinflammatory disorder as likely to respond to a therapy comprising an integrin beta7 antagonist, wherein a level of mRNA expression above a reference level identifies or selects that the patient is more likely to respond to the therapy. In one embodiment, the reference level is a median value. In certain embodiments, the in vitro use comprises a kit.

In yet still another aspect, in vitro use of at least one agent that specifically binds to a biomarker selected from SLC8A3, TNFSF15, BEST2, CCL2, CCL3, CCL3L1/3, CPA3, FGF7, HAMP, IL1A, IL18RAP, INHBA, LIF, LMO4, LRRC4, MLK7.AS1, MT1M, MUCL1, MX1, PMCH, REM2, SSTR2, TM4SF4, TMEM154, UROS, VNN2, and VNN3 is provided. In certain embodiments, the at least one agent is used for identifying or selecting a patient having a gastroinflammatory disorder as likely to respond to a therapy comprising an integrin beta7 antagonist, wherein a level of mRNA expression below a reference level identifies or selects that the patient is more likely to respond to the therapy. In one embodiment, the reference level is a median value. In certain embodiments, the in vitro use comprises a kit.

In still another aspect, methods of treating a gastrointestinal inflammatory disorder in a patient are provided. In certain embodiments, a therapeutically effective amount of an integrin beta7 antagonist is administered to a patient when a biological sample obtained from the patient has been determined to express elevated mRNA expression levels of one or more of certain genes. In some embodiments, the sample has been determined to express elevated GZMA, KLRB1, FOXM1, CCDC90A, CCL4L1.2, CPA2, CXCR6, DDO, ECH1, FAM125B, FASLG, FGF9, GPR15, GZMB, KCNMA1, PHF14, TIFAB, TMEM200A, TMIGD2, or SLC8A3 compared to the median value. In some embodiments, the sample has been determined to express elevated mRNA levels of two or three or four of GZMA, KLRB1, FOXM1, CCDC90A, CCL4L1.2, CPA2, CXCR6, DDO, ECH1, FAM125B, FASLG, FGF9, GPR15, GZMB, KCNMA1, PHF14, TIFAB, TMEM200A, TMIGD2, and SLC8A3 compared to the median levels of the same mRNAs. In some embodiments, the sample has been determined to express elevated mRNA levels of a further gene in addition to those identified above, which further gene is ITGAE. In certain embodiments, the patient has been selected for treatment based on elevated mRNA expression levels of certain genes in the biological sample compared to a median value of the same gene or genes. In one embodiment, the biological sample is a tissue biopsy sample. In certain such embodiments comprising a tissue biopsy, expression of SLC8A3 has not been determined. In one embodiment, the biological sample is peripheral whole blood. In certain such embodiments comprising peripheral blood, elevated expression of SLC8A3 has been determined. In one embodiment, the peripheral whole blood is collected in a PAXgene tube. In certain embodiments, the mRNA expression level is measured by an RNA sequencing method, microarray, or PCR method. In one embodiment, the PCR method is qPCR. In certain embodiments, the measuring comprises amplifying one or more of GZMA, KLRB1, FOXM1, CCDC90A, CCL4L1.2, CPA2, CXCR6, DDO, ECH1, FAM125B, FASLG, FGF9, GPR15, GZMB, KCNMA1, PHF14, TIFAB, TMEM200A, TMIGD2, and SLC8A3 mRNA, and optionally further comprising amplifying ITGAE mRNA, and detecting the amplified mRNA, thereby measuring the level of amplified mRNA. In certain embodiments administration of the integrin beta7 antagonist results in one or more of the following: (1) a 3-point decrease and 30% reduction from baseline in MCS and ≥1-point decrease in rectal bleeding subscore or absolute rectal bleeding score of 0 or 1, (2) an endoscopic subscore of 0 or 1, (3) MCS ≤2 with no individual subscore >1. In one embodiment, 105 mg of the integrin beta7 antagonist is administered subcutaneously once every four weeks. In one embodiment, an initial dose of 210 mg of the integrin beta7 antagonist is administered subcutaneously followed by subsequent doses, each of 210 mg of the integrin beta7 antagonist administered subcutaneously, administered at each of weeks 2, 4, 8 and 12 after the initial dose.

In still another aspect, methods of treating a gastrointestinal inflammatory disorder in a patient are provided. In certain embodiments, a therapeutically effective amount of an integrin beta7 antagonist is administered to a patient when a biological sample obtained from the patient has been determined to express reduced mRNA expression levels of one or more of certain genes. In some embodiments, the sample has been determined to express reduced SLC8A3, TNFSF15, BEST2, CCL2, CCL3, CCL3L1/3, CPA3, FGF7, HAMP, IL1A, IL18RAP, INHBA, LIF, LMO4, LRRC4, MLK7.AS1, MT1M, MUCL1, MX1, PMCH, REM2, SSTR2, TM4SF4, TMEM154, UROS, VNN2, or VNN3 compared to the median value. In some embodiments, the sample has been determined to express reduced mRNA levels of two or three of SLC8A3, TNFSF15, BEST2, CCL2, CCL3, CCL3L1/3, CPA3, FGF7, HAMP, IL1A, IL18RAP, INHBA, LIF, LMO4, LRRC4, MLK7.AS1, MT1M, MUCL1, MX1, PMCH, REM2, SSTR2, TM4SF4, TMEM154, UROS, VNN2, and VNN3 compared to the median levels of the same mRNAs. In certain embodiments, the patient has been selected for treatment based on reduced mRNA expression levels of certain genes in the biological sample compared to a median value of the same gene or genes. In some embodiments, the patient has been selected for treatment based on reduced SLC8A3, TNFSF15, BEST2, CCL2, CCL3, CCL3L1/3, CPA3, FGF7, HAMP, IL1A, IL18RAP, INHBA, LIF, LMO4, LRRC4, MLK7.AS1, MT1M, MUCL1, MX1, PMCH, REM2, SSTR2, TM4SF4, TMEM154, UROS, VNN2, or VNN3 expression compared to the median value. In some embodiments, the patient has been selected for treatment based on reduced mRNA expression of two or three of SLC8A3, TNFSF15, BEST2, CCL2, CCL3, CCL3L1/3, CPA3, FGF7, HAMP, IL1A, IL18RAP, INHBA, LIF, LMO4, LRRC4, MLK7.AS1, MT1M, MUCL1, MX1, PMCH, REM2, SSTR2, TM4SF4, TMEM154, UROS, VNN2, and VNN3 compared to the median values for the same mRNAs. In one embodiment, the biological sample is a tissue biopsy sample. In certain such embodiments comprising a tissue biopsy sample, the method comprises reduced SLC8A3 expression compared to a reference or median value. In one embodiment, the biological sample is peripheral whole blood. In certain such embodiments comprising peripheral blood, SLC8A3 expression is not reduced compared to a reference or median value. In one embodiment, the peripheral whole blood is collected in a PAXgene tube. In certain embodiments, the mRNA expression level is measured by an RNA sequencing method, microarray, or PCR method. In one embodiment, the PCR method is qPCR. In certain embodiments, the measuring comprises amplifying one or more of SLC8A3, TNFSF15, BEST2, CCL2, CCL3, CCL3L1/3, CPA3, FGF7, HAMP, IL1A, IL18RAP, INHBA, LIF, LMO4, LRRC4, MLK7.AS1, MT1M, MUCL1, MX1, PMCH, REM2, SSTR2, TM4SF4, TMEM154, UROS, VNN2, and VNN3 mRNA, and detecting the amplified mRNA, thereby measuring the level of amplified mRNA. In certain embodiments administration of the integrin beta7 antagonist results in one or more of the following: (1) a 3-point decrease and 30% reduction from baseline in MCS and ≥1-point decrease in rectal bleeding subscore or absolute rectal bleeding score of 0 or 1, (2) an endoscopic subscore of 0 or 1, (3) MCS ≤2 with no individual subscore >1. In one embodiment, 105 mg of the integrin beta7 antagonist is administered subcutaneously once every four weeks. In one embodiment, an initial dose of 210 mg of the integrin beta7 antagonist is administered subcutaneously followed by subsequent doses, each of 210 mg of the integrin beta7 antagonist administered subcutaneously, administered at each of weeks 2, 4, 8 and 12 after the initial dose.

In certain of the above embodiments, the gastrointestinal inflammatory disorder is an inflammatory bowel disease, and in certain such embodiments, the inflammatory bowel disease is ulcerative colitis (UC) or Crohn's disease (CD), and in certain such embodiments, the integrin beta7 antagonist is a monoclonal anti-beta7 antibody. In certain such embodiments, the anti-beta7 antibody is selected from a chimeric antibody, a human antibody, and a humanized antibody. In certain embodiments, the anti-beta7 antibody is an antibody fragment. In certain embodiments, the anti-beta7 antibody comprises six hypervariable regions (HVRs), wherein:

(i) HVR-L1 comprises amino acid sequence A1-A11, wherein A1-A11 is RASESVDTYLH (SEQ ID NO:1); RASESVDSLLH (SEQ ID NO:7), RASESVDTLLH (SEQ ID NO:8), or RASESVDDLLH (SEQ ID NO:9) or a variant of SEQ ID NOs:1, 7, 8 or 9 (SEQ ID NO:26) wherein amino acid A2 is selected from the group consisting of A, G, S, T, and V and/or amino acid A3 is selected from the group consisting of S, G, I, K, N, P, Q, R, and T, and/or A4 is selected from the group consisting of E, V, Q, A, D, G, H, I, K, L, N, and R, and/or amino acid A5 is selected from the group consisting of S, Y, A, D, G, H, I, K, N, P, R, T, and V, and/or amino acid A6 is selected from the group consisting of V, R, I, A, G, K, L, M, and Q, and/or amino acid A7 is selected from the group consisting of D, V, S, A, E, G, H, I, K, L, N, P, S, and T, and/or amino acid A8 is selected from the group consisting of D, G, N, E, T, P and S, and/or amino acid A9 is selected from the group consisting of L, Y, I and M, and/or amino acid A10 is selected from the group consisting of L, A, I, M, and V and/or amino acid A11 is selected from the group consisting of H, Y, F, and S;

(ii) HVR-L2 comprises amino acid sequence B1-B8, wherein B1-B8 is KYASQSIS (SEQ ID NO:2), RYASQSIS (SEQ ID NO:20), or XaaYASQSIS (SEQ ID NO:21, where Xaa represents any amino acid) or a variant of SEQ ID NOs:2, 20 or 21 (SEQ ID NO:27) wherein amino acid B1 is selected from the group consisting of K, R, N, V, A, F, Q, H, P, I, L, Y and Xaa (where Xaa represents any amino acid), and/or amino acid B4 is selected from the group consisting of S and D, and/or amino acid B5 is selected from the group consisting of Q and S, and/or amino acid B6 is selected from the group consisting of S, D, L, and R, and/or amino acid B7 is selected from the group consisting of I, V, E, and K;

(iii) HVR-L3 comprises amino acid sequence C1-C9, wherein C1-C9 is QQGNSLPNT (SEQ ID NO:3) or a variant of SEQ ID NO:3 (SEQ ID NO:28) wherein amino acid C8 is selected from the group consisting of N, V, W, Y, R, S, T, A, F, H, I L, and M;

(iv) HVR-H1 comprises amino acid sequence D1-D10 wherein D1-D10 is GFFITNNYWG (SEQ ID NO:4);

(v) HVR-H2 comprises amino acid sequence E1-E17 wherein E1-E17 is GYISYSGSTSYNPSLKS (SEQ ID NO:5), or a variant of SEQ ID NO:5 (SEQ ID NO:29) wherein amino acid E2 is selected from the group consisting of Y, F, V, and D, and/or amino acid E6 is selected from the group consisting of S and G, and/or amino acid E10 is selected from the group consisting of S and Y, and/or amino acid E12 is selected from the group consisting of N, T, A, and D, and/or amino acid 13 is selected from the group consisting of P, H, D, and A, and/or amino acid E15 is selected from the group consisting of L and V, and/or amino acid E17 is selected from the group consisting of S and G; and (vi) HVR-H3 comprises amino acid sequence F2-F11 wherein F2-F11 is MTGSSGYFDF (SEQ ID NO:6) or RTGSSGYFDF (SEQ ID NO:19); or comprises amino acid sequence F1-F11, wherein F1-F11 is AMTGSSGYFDF (SEQ ID NO:16), ARTGSSGYFDF (SEQ ID NO:17), or AQTGSSGYFDF (SEQ ID NO:18), or a variant of SEQ ID NOs:6, 16, 17, 18, or 19 (SEQ ID NO:30) wherein amino acid F2 is R, M, A, E, G, Q, S, and/or amino acid F11 is selected from the group consisting of F and Y.

In certain embodiments, the anti-beta7 antibody comprises three heavy chain hypervariable region (HVR-H1-H3) sequences and three light chain hypervariable region (HVR-L1-L3) sequences, wherein:
(i) HVR-L1 comprises SEQ ID NO:7, SEQ ID NO:8 or SEQ ID NO:9;
(ii) HVR-L2 comprises SEQ ID NO:2;
(iii) HVR-L3 comprises SEQ ID NO:3;
(iv) HVR-H1 comprises SEQ ID NO:4;
(v) HVR-H2 comprises SEQ ID NO:5; and
(vi) HVR-H3 comprises SEQ ID NO:6 or SEQ ID NO:16 or SEQ ID NO:17 or SEQ ID NO:19.

In certain embodiments, the anti-beta7 antibody comprises three heavy chain hypervariable region (HVR-H1-H3) sequences and three light chain hypervariable region (HVR-L1-L3) sequences, wherein:
(i) HVR-L1 comprises SEQ ID NO:9;
(ii) HVR-L2 comprises SEQ ID NO:2;
(iii) HVR-L3 comprises SEQ ID NO:3;
(iv) HVR-H1 comprises SEQ ID NO:4;
(v) HVR-H2 comprises SEQ ID NO:5; and
(vi) HVR-H3 comprises SEQ ID NO:19. In certain embodiments, the anti-beta7 antibody comprises a variable light chain comprising the amino acid sequence of SEQ ID NO:31 and a variable heavy chain comprising the amino acid sequence of SEQ ID NO:32.

In certain embodiments the anti-beta7 antibody is etrolizumab, also referred to as rhuMAb Beta7.

BRIEF DESCRIPTION OF THE DRAWINGS

FIGS. 1A and 1B show alignment of sequences of the variable light and heavy chains for the following consensus sequences and anti-beta7 subunit antibody sequences: light chain human subgroup kappa I consensus sequence (FIG. 1A, SEQ ID NO:12), heavy chain human subgroup III consensus sequence (FIG. 1B, SEQ ID NO:13), rat anti-mouse beta7 antibody (Fib504) variable light chain (FIG. 1A, SEQ ID NO:10), rat anti-mouse beta7 antibody (Fib504) variable heavy chain (FIG. 1B, SEQ ID NO:11), and humanized antibody variants: Humanized hu504Kgraft variable light chain (FIG. 1A, SEQ ID NO:14), humanized hu504K graft variable heavy chain (FIG. 1B, SEQ ID NO:15), variants hu504-5, hu504-16, and hu504-32 (amino acid variations from humanized hu504K graft are indicated in FIG. 1A) (light chain) (SEQ ID NOS:22-24, respectively, in order of appearance) and FIG. 1B (heavy chain) for variants hu504-5, hu504-16, and hu504-32 (SEQ ID NO:25).

FIGS. 2A and 2B show the variable light chain region (FIG. 2A) (SEQ ID NO:31) and the variable heavy chain region (FIG. 2B) (SEQ ID NO:32) of etrolizumab.

(FIG. 8A) Proportion of patients stratified by granzyme A (GZMA) gene expression; (FIG. 8B) proportion of patients stratified by KLRB1 gene expression; (FIG. 8C) proportion of patients stratified by FOXM1 gene expression; (FIG. 8D) proportion of patients stratified by integrin alphaE (ITGAE) gene expression. Left side of panel, all patients;

Figure 3:
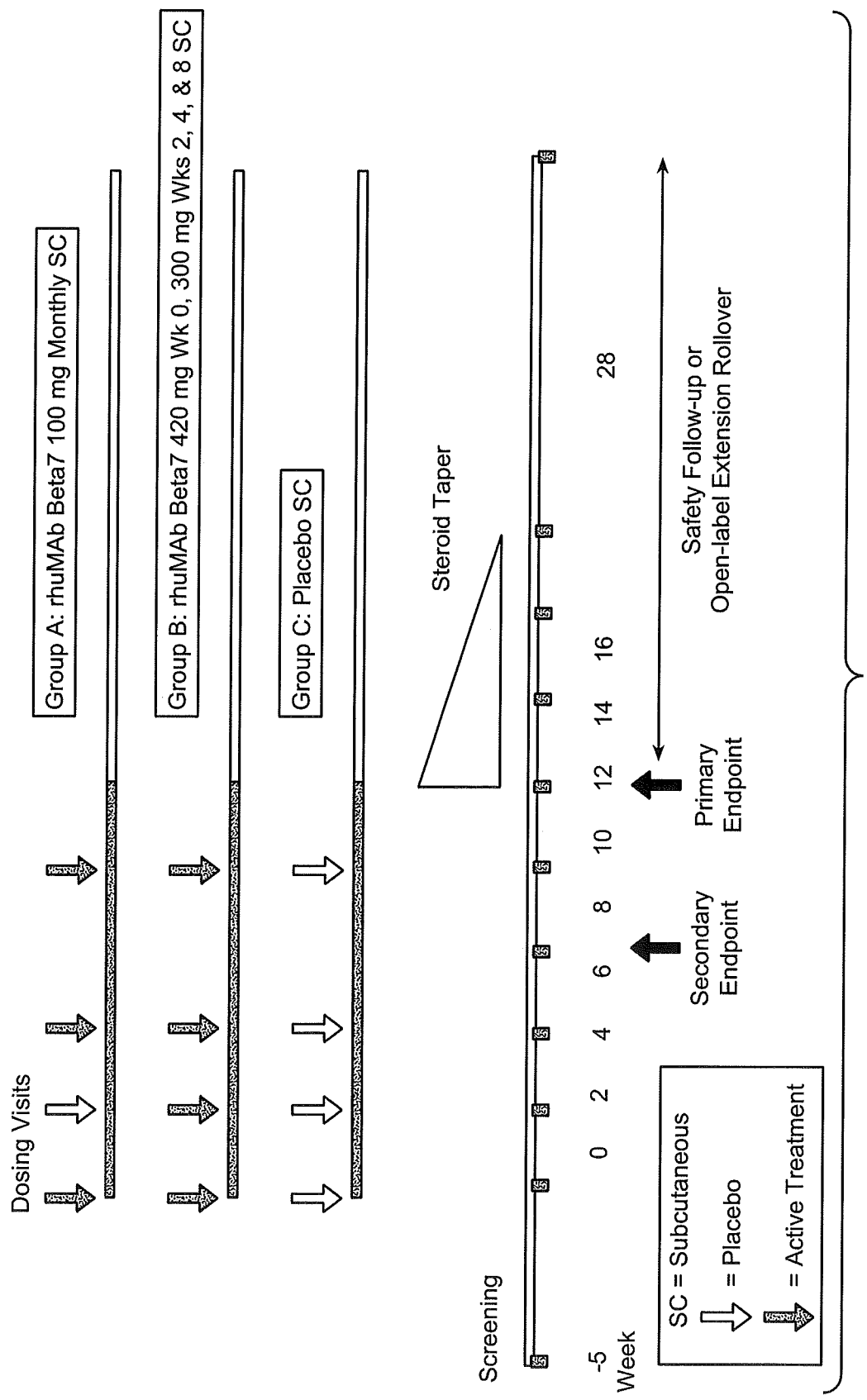
FIG. 3 shows the study schema for the Phase II clinical study as described in Example 1.
Figure 4:
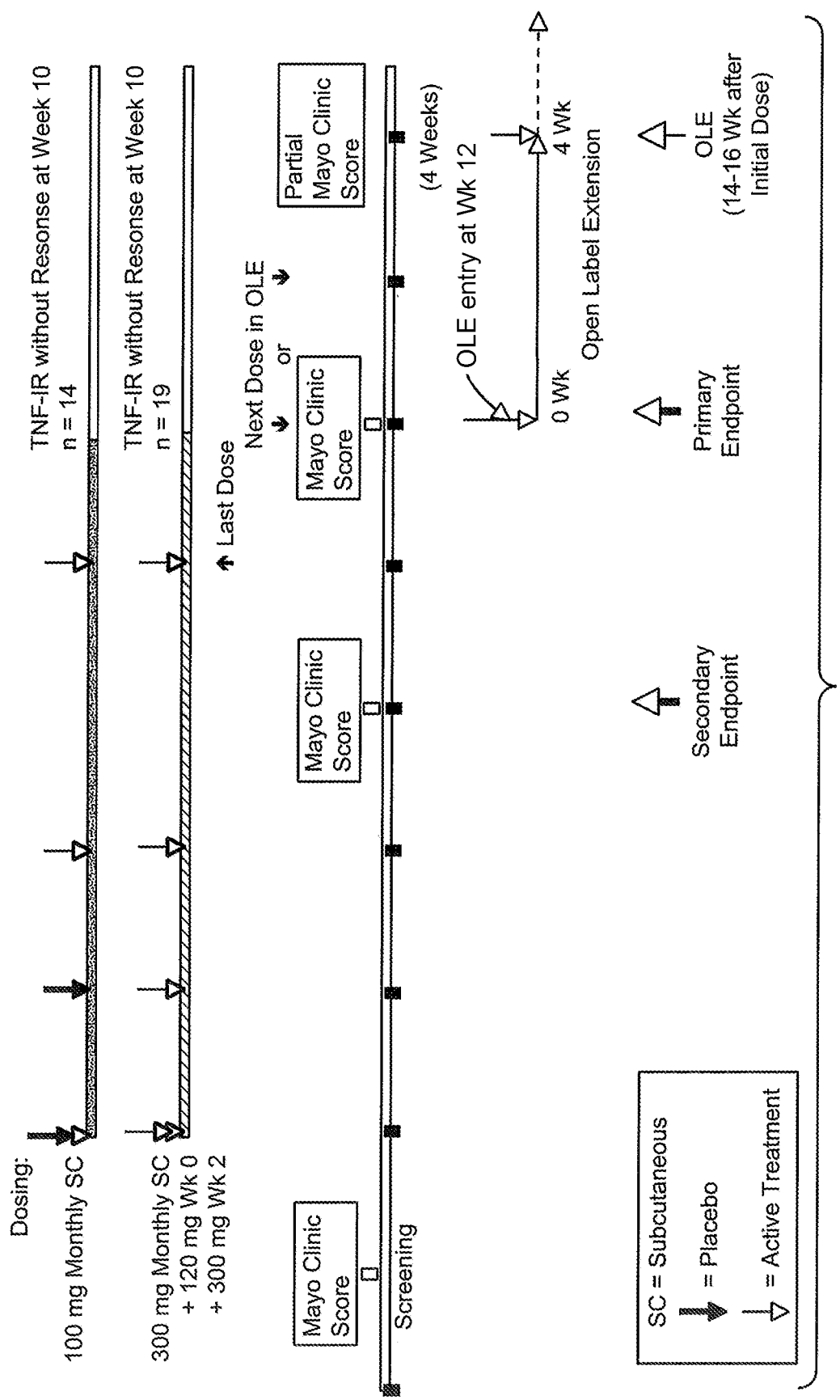
FIG. 4 shows the study schema for the Phase II open label extension clinical study as described in Example 1.

right side of panel, patients that had not previously been treated with any antagonist of tumor necrosis factor (TNF) activity (anti-TNF naïve).

FIGS. 9A-9D show that higher than median levels of baseline expression of granzyme A (GZMA) enriched for responsiveness to etrolizumab treatment as described in Example 2. (FIG. 9A) The proportion of TNF antagonist naïve patients (percentage) stratified by baseline GZMA gene expression levels (low, below the median vs. high, at or above the median) in intestinal biopsies and treated with placebo (black bars), 100 mg/dose etrolizumab (stippled bars), or 300 mg/dose etrolizumab (striped bars) that were in remission at week 10, showed mucosal healing at week 10, or showed clinical response at week 10. (FIG. 9B) The percentage of patients that had previously failed or had an inadequate response to treatment with an antagonist of TNF activity (TNF-IR) from the open label extension study stratified by baseline GZMA gene expression (low, below the median vs. high, at or above the median) in intestinal biopsies that were in clinical remission (left side) or showing clinical response (right side) at 4-6 weeks following continued treatment with etrolizumab. (FIG. 9C) GZMA gene expression relative to GAPDH expression in baseline biopsy tissue obtained from patients enrolled in the Phase II etrolizumab trial and identified as TNF antagonist naïve (anti-TNF naïve) or TNF-IR (anti-TNF failure), black filled circles: non-remitters at week 10, open circles: remitters at week 10, dotted line indicates median. (FIG. 9D) GZMA variability is shown in TNF antagonist naïve patients (left panel) and TNF-IR patients (right panel) in the placebo group at baseline, day 43 and day 71. Each line represents a single patient at each time point tested.

FIGS. 10A-10D show that higher than median levels of baseline expression of KLRB1 enriched for responsiveness to etrolizumab treatment as described in Example 2. (FIG. 10A) The proportion of TNF antagonist naïve patients (percentage) stratified by baseline KLRB1 gene expression levels (low, below the median vs. high, at or above the median) in intestinal biopsies and treated with placebo (black bars), 100 mg/dose etrolizumab (stippled bars), or 300 mg/dose etrolizumab (striped bars) that were in remission at week 10, showed mucosal healing at week 10, or showed clinical response at week 10. (FIG. 10B) The percentage of TNF-IR patients from the open label extension study stratified by baseline KLRB1 gene expression (low, below the median vs. high, at or above the median) in intestinal biopsies that were in clinical remission (left side) or showing clinical response (right side) at 4-6 weeks following continued treatment with etrolizumab. (FIG. 10C) KLRB1 gene expression relative to GAPDH expression in baseline biopsy tissue obtained from patients enrolled in the Phase II etrolizumab trial and identified as TNF antagonist naïve (anti-TNF naïve) or TNF-IR (anti-TNF failure), black filled circles: non-remitters at week 10, open circles: remitters at week 10, dotted line indicates median. (FIG. 10D) KLRB1 variability is shown in TNF antagonist naïve patients (left panel) and TNF-IR patients (right panel) in the placebo group at baseline, day 43 and day 71. Each line represents a single patient at each time point tested.

FIGS. 11A-11D show that higher than median levels of baseline expression of FOXM1 enriched for responsiveness to etrolizumab treatment as described in Example 2. (FIG. 11A) The proportion of TNF antagonist naïve patients (percentage) stratified by baseline FOXM1 gene expression levels (low, below the median vs. high, at or above the median) in intestinal biopsies and treated with placebo (black bars), 100 mg/dose etrolizumab (stippled bars), or 300 mg/dose etrolizumab (striped bars) that were in remission at week 10, showed mucosal healing at week 10, or showed clinical response at week 10. (FIG. 11B) The percentage of TNF-IR patients from the open label extension study stratified by baseline FOXM1 gene expression (low, below the median vs. high, at or above the median) in intestinal biopsies that were in clinical remission (left side) or showing clinical response (right side) at 4-6 weeks following continued treatment with etrolizumab. (FIG. 11C) FOXM1 gene expression relative to GAPDH expression in baseline biopsy tissue obtained from patients enrolled in the Phase II etrolizumab trial and identified as TNF antagonist naïve (anti-TNF naïve) or TNF-IR (anti-TNF failure), black filled circles: non-remitters at week 10, open circles: remitters at week 10, dotted line indicates median. (FIG. 11D) FOXM1 variability is shown in TNF antagonist naïve patients (left panel) and TNF-IR patients (right panel) in the placebo group at baseline, day 43 and day 71. Each line represents a single patient at each time point tested.

FIGS. 12A-12D show that higher than median levels of baseline expression of ITGAE enriched for responsiveness to etrolizumab treatment as described in Example 2. (FIG. 12A) The proportion of TNF antagonist naïve patients (percentage) stratified by baseline ITGAE gene expression levels (low, below the median vs. high, at or above the median) in intestinal biopsies and treated with placebo (black bars), 100 mg/dose etrolizumab (stippled bars), or 300 mg/dose etrolizumab (striped bars) that were in remission at week 10, showed mucosal healing at week 10, or showed clinical response at week 10. (FIG. 12B) The percentage of TNF-IR patients from the open label extension study stratified by baseline ITGAE gene expression (low, below the median vs. high, at or above the median) in intestinal biopsies that were in clinical remission (left side) or showing clinical response (right side) at 4-6 weeks following continued treatment with etrolizumab. (FIG. 12C) ITGAE gene expression relative to GAPDH expression in baseline biopsy tissue obtained from patients enrolled in the Phase II etrolizumab trial and identified as TNF antagonist naïve (anti-TNF naïve) or TNF-IR (anti-TNF failure), black filled circles: non-remitters at week 10, open circles: remitters at week 10, dotted line indicates median. (FIG. 12D) ITGAE variability is shown in TNF antagonist naïve patients (left panel) and TNF-IR patients (right panel) in the placebo group at baseline, day 43 and day 71. Each line represents a single patient at each time point tested.

FIGS. 13A-13D show the proportion of patients (percentage) stratified by baseline gene expression levels (low, below the median vs. high, at or above the median) in intestinal biopsies and treated with placebo (black bars), 100 mg/dose etrolizumab (stippled bars) or 300 mg/dose etrolizumab+LD (striped bars) as described in Example 2. (FIG. 13A) Proportion of patients stratified by SLC8A3 gene expression; (FIG. 13B) proportion of patients stratified by TNFSF15 gene expression; (FIG. 13C) proportion of patients stratified by CCL2 gene expression; (FIG. 13D) proportion of patients stratified by BEST2 gene expression.

FIGS. 14A-14D show that lower than median levels of baseline expression of SLC8A3 in screening biopsy tissue enriched for responsiveness to etrolizumab treatment as described in Example 2. (FIG. 14A) The proportion of TNF antagonist naïve patients (percentage) stratified by baseline SLC8A3 gene expression levels (low, below the median vs. high, at or above the median) in intestinal biopsies and treated with placebo (black bars), 100 mg/dose etrolizumab (stippled bars), or 300 mg/dose etrolizumab (striped bars) that were in remission at week 10, showed mucosal healing at week 10, or showed clinical response at week 10. (FIG. 14B) The percentage of TNF-IR patients from the open label extension study stratified by baseline SLC8A3 gene expression (low, below the median vs. high, at or above the median) in intestinal biopsies that were in clinical remission (left side) or showing clinical response (right side) at 4-6 weeks following continued treatment with etrolizumab. (FIG. 14C) SLC8A3 gene expression relative to GAPDH expression in baseline biopsy tissue obtained from patients enrolled in the Phase II etrolizumab trial and identified as TNF antagonist naïve (anti-TNF naïve) or TNF-IR (anti-TNF failure), black filled circles: non-remitters at week 10, open circles: remitters at week 10, dotted line indicates median. (FIG. 14D) SLC8A3 variability is shown in TNF antagonist naïve patients (left panel) and TNF-IR patients (right panel) in the placebo group at baseline, day 43 and day 71. Each line represents a single patient at each time point tested.

FIGS. 15A-15D show that lower than median levels of baseline expression of TNFSF15 enriched for responsiveness to etrolizumab treatment as described in Example 2. (FIG. 15A) The proportion of TNF antagonist naïve patients (percentage) stratified by baseline TNFSF15 gene expression levels (low, below the median vs. high, at or above the median) in intestinal biopsies and treated with placebo (black bars), 100 mg/dose etrolizumab (stippled bars), or 300 mg/dose etrolizumab (striped bars) that were in remission at week 10, showed mucosal healing at week 10, or showed clinical response at week 10. (FIG. 15B) The percentage of TNF-IR patients from the open label extension study stratified by baseline TNFSF15 gene expression (low, below the median vs. high, at or above the median) in intestinal biopsies that were in clinical remission (left side) or showing clinical response (right side) at 4-6 weeks following continued treatment with etrolizumab. (FIG. 15C) TNFSF15 gene expression relative to GAPDH expression in baseline biopsy tissue obtained from patients enrolled in the Phase II etrolizumab trial and identified as TNF antagonist naïve (anti-TNF naïve) or TNF-IR (anti-TNF failure), black filled circles: non-remitters at week 10, open circles: remitters at week 10, dotted line indicates median. (FIG. 15D) TNFSF15 variability is shown in TNF antagonist naïve patients (left panel) and TNF-IR patients (right panel) in the placebo group at baseline, day 43 and day 71. Each line represents a single patient at each time point tested.

FIGS. 16A-16D show that lower than median levels of baseline expression of CCL2 enriched for responsiveness to etrolizumab treatment as described in Example 2. (FIG. 16A) The proportion of TNF antagonist naïve patients (percentage) stratified by baseline CCL2 gene expression levels (low, below the median vs. high, at or above the median) in intestinal biopsies and treated with placebo (black bars), 100 mg/dose etrolizumab (stippled bars), or 300 mg/dose etrolizumab (striped bars) that were in remission at week 10, showed mucosal healing at week 10, or showed clinical response at week 10. (FIG. 16B) The percentage of TNF-IR patients from the open label extension study stratified by baseline CCL2 gene expression (low, below the median vs. high, at or above the median) in intestinal biopsies that were in clinical remission (left side) or showing clinical response (right side) at 4-6 weeks following continued treatment with etrolizumab. (FIG. 16C) CCL2 gene expression relative to GAPDH expression in baseline biopsy tissue obtained from patients enrolled in the Phase II etrolizumab trial and identified as TNF antagonist naïve (anti-TNF naïve) or TNF-IR (anti-TNF failure), black filled circles: non-remitters at week 10, open circles: remitters at week 10, dotted line indicates median. (FIG. 16D) CCL2 variability is shown in TNF antagonist naïve patients (left panel) and TNF-IR patients (right panel) in the placebo group at baseline, day 43 and day 71. Each line represents a single patient at each time point tested.

FIGS. 17A-17D show that lower than median levels of baseline expression of BEST2 enriched for responsiveness to etrolizumab treatment as described in Example 2. (FIG. 17A) The proportion of TNF antagonist naïve patients (percentage) stratified by baseline BEST2 gene expression levels (low, below the median vs. high, at or above the median) in intestinal biopsies and treated with placebo (black bars), 100 mg/dose etrolizumab (stippled bars), or 300 mg/dose etrolizumab (striped bars) that were in remission at week 10, showed mucosal healing at week 10, or showed clinical response at week 10. (FIG. 17B) The percentage of TNF-IR patients from the open label extension study stratified by baseline BEST2 gene expression (low, below the median vs. high, at or above the median) in intestinal biopsies that were in clinical remission (left side) or showing clinical response (right side) at 4-6 weeks following continued treatment with etrolizumab. (FIG. 17C) BEST2 gene expression relative to GAPDH expression in baseline biopsy tissue obtained from patients enrolled in the Phase II etrolizumab trial and identified as TNF antagonist naïve (anti-TNF naïve) or TNF-IR (anti-TNF failure), black filled circles: non-remitters at week 10, open circles: remitters at week 10, dotted line indicates median. (FIG. 17D) BEST2 variability is shown in TNF antagonist naïve patients (left panel) and TNF-IR patients (right panel) in the placebo group at baseline, day 43 and day 71. Each line represents a single patient at each time point tested.

FIGS. 18A-18D show (FIG. 18A) the proportion of TNF antagonist naïve patients (percentage) stratified by baseline ECH1 gene expression levels (low, below the median vs. high, at or above the median) in intestinal biopsies and treated with placebo (black bars), 100 mg/dose etrolizumab (stippled bars), or 300 mg/dose etrolizumab (striped bars) that were in remission at week 10, showed mucosal healing at week 10, or showed clinical response at week 10 as described in Example 2. (FIG. 18B) The percentage of TNF-IR patients from the open label extension study stratified by baseline ECH1 gene expression (low, below the median vs. high, at or above the median) in intestinal biopsies that were in clinical remission (left side) or showing clinical response (right side) at 4-6 weeks following continued treatment with etrolizumab. (FIG. 18C) ECH1 gene expression relative to GAPDH expression in baseline biopsy tissue obtained from patients enrolled in the Phase II etrolizumab trial and identified as TNF antagonist naïve (anti-TNF naïve) or TNF-IR (anti-TNF failure), black filled circles: non-remitters at week 10, open circles: remitters at week 10, dotted line indicates median. (FIG. 18D) ECH1 variability is shown in TNF antagonist naïve patients (left panel) and TNF-IR patients (right panel) in the placebo group at baseline, day 43 and day 71. Each line represents a single patient at each time point tested.

FIGS. 19A-19D show (FIG. 19A) the proportion of TNF antagonist naïve patients (percentage) stratified by baseline VNN2 gene expression levels (low, below the median vs. high, at or above the median) in intestinal biopsies and treated with placebo (black bars), 100 mg/dose etrolizumab (stippled bars), or 300 mg/dose etrolizumab (striped bars) that were in remission at week 10, showed mucosal healing at week 10, or showed clinical response at week 10 as described in Example 2. (FIG. 19B) The percentage of TNF-IR patients from the open label extension study stratified by baseline VNN2 gene expression (low, below the median vs. high, at or above the median) in intestinal biopsies that were in clinical remission (left side) or showing clinical response (right side) at 4-6 weeks following continued treatment with etrolizumab. (FIG. 19C) VNN2 gene expression relative to GAPDH expression in baseline biopsy tissue obtained from patients enrolled in the Phase II etrolizumab trial and identified as TNF antagonist naïve (anti-TNF naïve) or TNF-IR (anti-TNF failure), black filled circles: non-remitters at week 10, open circles: remitters at week 10, dotted line indicates median. (FIG. 19D) VNN2 variability is shown in TNF antagonist naïve patients (left panel) and TNF-IR patients (right panel) in the placebo group at baseline, day 43 and day 71. Each line represents a single patient at each time point tested.

FIGS. 20A-20D show that higher than median levels of baseline peripheral blood gene expression (baseline in this context means the mean of the value at screen and the value at day 1) of ITGAE enriched for responsiveness to etrolizumab treatment as described in Example 2. (FIG. 20A) The proportion of TNF antagonist naïve patients (percentage) stratified by baseline peripheral blood ITGAE gene expression levels (low, below the median vs. high, at or above the median) and treated with placebo (black bars), 100 mg/dose etrolizumab (stippled bars), or 300 mg/dose etrolizumab (striped bars) that were in remission at week 10, showed mucosal healing at week 10, or showed clinical response at week 10. (FIG. 20B) The percentage of TNF-IR patients from the open label extension study stratified by baseline peripheral blood ITGAE gene expression (low, below the median vs. high, at or above the median) that were in clinical remission (left side) or showing clinical response (right side) at 4-6 weeks following continued treatment with etrolizumab. (FIG. 20C) ITGAE gene expression relative to GAPDH expression in peripheral blood from patients enrolled in the Phase II etrolizumab trial and identified as TNF antagonist naïve (anti-TNF naïve) or TNF-IR (anti-TNF failure), black filled circles: non-remitters at week 10, open circles: remitters at week 10, dotted line indicates median. (FIG. 20D) ITGAE gene expression variability in the peripheral blood is shown in TNF antagonist naïve patients (left panel) and TNF-IR patients (right panel) in the placebo group at baseline, day 43 and day 71. Each line represents a single patient at each time point tested.

FIGS. 21A-21D show that higher than median levels of baseline peripheral blood gene expression of ECH1 enriched for responsiveness to etrolizumab treatment as described in Example 2. (FIG. 21A) The proportion of TNF antagonist naïve patients (percentage) stratified by baseline peripheral blood ECH1 gene expression levels (low, below the median vs. high, at or above the median) and treated with placebo (black bars), 100 mg/dose etrolizumab (stippled bars), or 300 mg/dose etrolizumab (striped bars) that were in remission at week 10, showed mucosal healing at week 10, or showed clinical response at week 10. (FIG. 21B) The percentage of TNF-IR patients from the open label extension study stratified by baseline ECH1 peripheral blood gene expression (low, below the median vs. high, at or above the median) that were in clinical remission (left side) or showing clinical response (right side) at 4-6 weeks following continued treatment with etrolizumab. (FIG. 21C) ECH1 gene expression relative to GAPDH expression in baseline biopsy tissue obtained from patients enrolled in the Phase II etrolizumab trial and identified as TNF antagonist naïve (anti-TNF naïve) or TNF-IR (anti-TNF failure), black filled circles: non-remitters at week 10, open circles: remitters at week 10, dotted line indicates median. (FIG. 21D) ECH1 gene expression variability in the peripheral blood is shown in TNF antagonist naïve patients (left panel) and TNF-IR patients (right panel) in the placebo group at baseline, day 43 and day 71. Each line represents a single patient at each time point tested.

FIGS. 22A-22D show (FIG. 22A) the proportion of TNF antagonist naïve patients (percentage) stratified by baseline peripheral blood FOXM1 gene expression levels (low, below the median vs. high, at or above the median) and treated with placebo (black bars), 100 mg/dose etrolizumab (stippled bars), or 300 mg/dose etrolizumab (striped bars) that were in remission at week 10, showed mucosal healing at week 10, or showed clinical response at week 10 as described in Example 2. (FIG. 22B) The percentage of TNF-IR patients from the open label extension study stratified by baseline FOXM1 gene expression (low, below the median vs. high, at or above the median) in peripheral blood that were in clinical remission (left side) or showing clinical response (right side) at 4-6 weeks following continued treatment with etrolizumab. (FIG. 22C) FOXM1 gene expression relative to GAPDH expression in baseline peripheral blood obtained from patients enrolled in the Phase II etrolizumab trial and identified as TNF antagonist naïve (anti-TNF naïve) or TNF-IR (anti-TNF failure), black filled circles: non-remitters at week 10, open circles: remitters at week 10, dotted line indicates median. (FIG. 22D) FOXM1 gene expression variability in the peripheral blood is shown in TNF antagonist naïve patients (left panel) and TNF-IR patients (right panel) in the placebo group at baseline, day 43 and day 71. Each line represents a single patient at each time point tested.

FIGS. 23A-23D show (FIG. 23A) the proportion of TNF antagonist naïve patients (percentage) stratified by baseline peripheral blood GZMA gene expression levels (low, below the median vs. high, at or above the median) and treated with placebo (black bars), 100 mg/dose etrolizumab (stippled bars), or 300 mg/dose etrolizumab (striped bars) that were in remission at week 10, showed mucosal healing at week 10, or showed clinical response at week 10 as described in Example 2. (FIG. 23B) The percentage of TNF-IR patients from the open label extension study stratified by baseline GZMA gene expression (low, below the median vs. high, at or above the median) in peripheral blood that were in clinical remission (left side) or showing clinical response (right side) at 4-6 weeks following continued treatment with etrolizumab. (FIG. 23C) GZMA gene expression relative to GAPDH expression in baseline peripheral blood samples obtained from patients enrolled in the Phase II etrolizumab trial and identified as TNF antagonist naïve (anti-TNF naïve) or TNF-IR (anti-TNF failure), black filled circles: non-remitters at week 10, open circles: remitters at week 10, dotted line indicates median. (FIG. 23D) GZMA gene expression variability in peripheral blood is shown in TNF antagonist naïve patients (left panel) and TNF-IR patients (right panel) in the placebo group at baseline, day 43 and day 71. Each line represents a single patient at each time point tested.

FIGS. 24A-24D show (FIG. 24A) The proportion of TNF antagonist naïve patients (percentage) stratified by baseline peripheral blood KLRB1 gene expression levels (low, below the median vs. high, at or above the median) and treated with placebo (black bars), 100 mg/dose etrolizumab (stippled bars), or 300 mg/dose etrolizumab (striped bars) that were in remission at week 10, showed mucosal healing at week 10, or showed clinical response at week 10 as described in Example 2. (FIG. 24B) The percentage of TNF-IR patients from the open label extension study stratified by baseline KLRB1 gene expression (low, below the median vs. high, at or above the median) in peripheral blood samples that were in clinical remission (left side) or showing clinical response (right side) at 4-6 weeks following continued treatment with etrolizumab. (FIG. 24C) KLRB1 gene expression relative to GAPDH expression in baseline peripheral blood samples obtained from patients enrolled in the Phase II etrolizumab trial and identified as TNF antagonist naïve (anti-TNF naïve) or TNF-IR (anti-TNF failure), black filled circles: non-remitters at week 10, open circles: remitters at week 10, dotted line indicates median. (FIG. 24D) KLRB1 gene expression variability in peripheral blood is shown in TNF antagonist naïve patients (left panel) and TNF-IR patients (right panel) in the placebo group at baseline, day 43 and day 71. Each line represents a single patient at each time point tested.

FIGS. 25A-25D show that higher than median levels of peripheral blood gene expression of SLC8A3 enriched for responsiveness to etrolizumab treatment as described in Example 2. (FIG. 25A) The proportion of TNF antagonist naïve patients (percentage) stratified by baseline SLC8A3 gene expression levels (low, below the median vs. high, at or above the median) in peripheral blood and treated with placebo (black bars), 100 mg/dose etrolizumab (stippled bars), or 300 mg/dose etrolizumab (striped bars) that were in remission at week 10, showed mucosal healing at week 10, or showed clinical response at week 10. (FIG. 25B) The percentage of TNF-IR patients from the open label extension study stratified by baseline SLC8A3 gene expression (low, below the median vs. high, at or above the median) in peripheral blood that were in clinical remission (left side) or showing clinical response (right side) at 4-6 weeks following continued treatment with etrolizumab. (FIG. 25C) SLC8A3 peripheral blood gene expression relative to GAPDH expression in patients enrolled in the Phase II etrolizumab trial and identified as TNF antagonist naïve (anti-TNF naïve) or TNF-IR (anti-TNF failure), black filled circles: non-remitters at week 10, open circles: remitters at week 10, dotted line indicates median. (FIG. 25D) SLC8A3 gene expression variability in peripheral blood is shown in TNF antagonist naïve patients (left panel) and TNF-IR patients (right panel) in the placebo group at baseline, day 43 and day 71. Each line represents a single patient at each time point tested.

FIGS. 26A-26D show that lower than median levels of baseline peripheral blood expression of TNFSF15 enriched for responsiveness to etrolizumab treatment as described in Example 2. (FIG. 26A) The proportion of TNF antagonist naïve patients (percentage) stratified by baseline TNFSF15 gene expression levels (low, below the median vs. high, at or above the median) in peripheral blood and treated with placebo (black bars), 100 mg/dose etrolizumab (stippled bars), or 300 mg/dose etrolizumab (striped bars) that were in remission at week 10, showed mucosal healing at week 10, or showed clinical response at week 10. (FIG. 26B) The percentage of TNF-IR patients from the open label extension study stratified by baseline peripheral blood TNFSF15 gene expression (low, below the median vs. high, at or above the median) that were in clinical remission (left side) or showing clinical response (right side) at 4-6 weeks following continued treatment with etrolizumab. (FIG. 26C) TNFSF15 peripheral blood gene expression relative to GAPDH expression in patients enrolled in the Phase II etrolizumab trial and identified as TNF antagonist naïve (anti-TNF naïve) or TNF-IR (anti-TNF failure), black filled circles: non-remitters at week 10, open circles: remitters at week 10, dotted line indicates median. (FIG. 26D) TNFSF15 gene expression variability in peripheral blood is shown in TNF antagonist naïve patients (left panel) and TNF-IR patients (right panel) in the placebo group at baseline, day 43 and day 71. Each line represents a single patient at each time point tested.

FIGS. 27A-27D show that lower than median levels of baseline peripheral blood gene expression of VNN2 enriches for responsiveness to etrolizumab treatment as described in Example 2. (FIG. 27A) The proportion of TNF antagonist naïve patients (percentage) stratified by baseline VNN2 gene expression levels (low, below the median vs. high, at or above the median) in peripheral blood and treated with placebo (black bars), 100 mg/dose etrolizumab (stippled bars), or 300 mg/dose etrolizumab (striped bars) that were in remission at week 10, showed mucosal healing at week 10, or showed clinical response at week 10. (FIG. 27B) The percentage of TNF-IR patients from the open label extension study stratified by baseline peripheral blood VNN2 gene expression (low, below the median vs. high, at or above the median) that were in clinical remission (left side) or showing clinical response (right side) at 4-6 weeks following continued treatment with etrolizumab. (FIG. 27C) Peripheral blood VNN2 gene expression relative to GAPDH expression in patients enrolled in the Phase II etrolizumab trial and identified as TNF antagonist naïve (anti-TNF naïve) or TNF-IR (anti-TNF failure), black filled circles: non-remitters at week 10, open circles: remitters at week 10, dotted line indicates median. (FIG. 27D) VNN2 gene expression variability in peripheral blood is shown in TNF antagonist naïve patients (left panel) and TNF-IR patients (right panel) in the placebo group at baseline, day 43 and day 71. Each line represents a single patient at each time point tested.

FIGS. 28A-28H show gene expression levels in biopsy samples from untreated patient samples, cohort 1, comprised of healthy controls (HC) (n=14), ulcerative colitis patients (UC) (n=30) and Crohn's disease patients (CD) (n=60) as described in Example 2. In this observational cohort, uninflamed biopsy samples were collected from the sigmoid colon from healthy control and UC patients, from the ascending or descending colon and ileum for healthy control and CD patients. In UC and CD patients with active lesional disease and adjacent uninflamed areas, paired inflamed and uninflamed biopsies were taken. Gene expression relative to GAPDH for ITGAE (FIG. 28A), GZMA (FIG. 28B), VNN2 (FIG. 28C), ECH1 (FIG. 28D), KLRB1 (FIG. 28E), SLC8A3 (FIG. 28F), TNFSF15 (FIG. 28G) and FOXM1 (FIG. 28H) is shown. Statistical differences are not shown on these figures.

FIGS. 29A-29H show gene expression levels in peripheral blood from untreated patient samples, cohort 2, comprised of healthy controls (n=10) and patients undergoing resection for ulcerative colitis (UC) (n=32) or Crohn's disease (CD) (n=32) as described in Example 2. Gene expression relative to GAPDH was measured for ITGAE (FIG. 29A), GZMA (FIG. 29B), VNN2 (FIG. 29C), ECH1 (FIG. 29D), KLRB1 (FIG. 29E), SLC8A3 (FIG. 29F), TNFSF15 (FIG. 29G) and FOXM1 (FIG. 29H) is shown. Using Mann Whitney, *=$p<0.05$, =$p<0.01$, **=$p<0.0001$.

FIGS. 30A-30D show the effect of etrolizumab on integrin alphaE-positive (αE+) cells in the intestinal crypt epithelium by biomarker stratification in the etrolizumab Phase II study as described in Example 2. αE+ cells associated with the intestinal crypt epithelium were counted before and after treatment with etrolizumab or placebo in patients enrolled in the etrolizumab Phase II study. Baseline colonic biopsy qPCR median value was used as cutoff to categorize patients as granzyme A$^{high}$ (GZMA) or αE$^{high}$ (in each case, high, at or above the median) or granzyme A$^{low}$ (GZMA) or αE$^{low}$ (in each case, low, below the median). Baseline distribution of αE+ cells in the intestinal crypt epithelium by baseline colonic biopsy granzyme A (FIG. 30A) and αE (FIG. 30B) gene expression status. Change in αE+ cells in the intestinal crypt epithelium before and after treatment with etrolizumab (open circles) or placebo (black filled triangles) by baseline biopsy granzyme A (FIG. 30C) and αE gene (FIG. 30D) expression levels. **p<0.01. Scr=screening.

FIGS. 31A-31E show increased granzyme A (GZMA) gene expression in αE+ T cells in UC patients as described in Example 2. (FIG. 31A) T cells were isolated from colonic biopsies from untreated patient samples, cohort 3, and sort purified by surface expression of CD4, CD8 and integrin αE. CD4+αE+ T cells from UC patients had increased granzyme A gene expression compared to sort purified CD4+αE− T cells from UC patients and CD4+αE+ T cells from non-IBD control subjects. (FIG. 31B) Gene expression of granzyme A and integrin αE was significantly correlated in sort purified CD4+αE+ T cells, but not sort purified CD8+αE+ T cells from UC patients. (FIG. 31C) Baseline colonic tissue gene expression of granzyme A and αE was significantly correlated in the etrolizumab Phase II study. The dotted lines indicate qPCR median cutoff. (FIG. 31D) Gene expression of granzyme A was significantly correlated with the number of αE+ cells in the epithelium and lamina propria in baseline colonic biopsies from the etrolizumab Phase II study. (FIG. 31E) Representative image showing co-immunofluorescence staining of granzyme A and αE in a colonic biopsy sample from a UC patient in untreated patient samples, cohort 3. *P<0.05. ****P<0.0001.

DETAILED DESCRIPTION

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

Certain Definitions

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

As used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like.

Ranges provided in the specification and appended claims include both end points and all points between the end points. Thus, for example, a range of 2.0 to 3.0 includes 2.0, 3.0, and all points between 2.0 and 3.0.

"Treatment," "treating," and grammatical variations thereof refer to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis.

"Treatment regimen" refers to a combination of dosage, frequency of administration, or duration of treatment, with or without addition of a second medication.

"Effective treatment regimen" refers to a treatment regimen that will offer beneficial response to a patient receiving the treatment.

"Modifying a treatment" refers to changing the treatment regimen including, changing dosage, frequency of administration, or duration of treatment, and/or addition of a second medication.

"Patient response" or "patient responsiveness" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e., reduction, slowing down or complete stopping) of disease spread; (6) decrease of auto-immune, immune, or inflammatory response, which may, but does not have to, result in the regression or ablation of the disease lesion; (7) relief, to some extent, of one or more symptoms associated with the disorder; (8) increase in the length of disease-free presentation following treatment; and/or (9) decreased mortality at a given point of time following treatment. The term "responsiveness" refers to a measurable response, including complete response (CR) and partial response (PR).

By "complete response" or "CR" is intended the disappearance of all signs of inflammation or remission in response to treatment. This does not always mean the disease has been cured.

"Partial response" or "PR" refers to a decrease of at least 50% in the severity of inflammation, in response to treatment.

A "beneficial response" of a patient to treatment with an integrin beta7 antagonist and similar wording refers to the clinical or therapeutic benefit imparted to a patient at risk for or suffering from a gastrointestinal inflammatory disorder from or as a result of the treatment with the antagonist, such as an anti-beta7 integrin antibody. Such benefit includes cellular or biological responses, a complete response, a partial response, a stable disease (without progression or relapse), or a response with a later relapse of the patient from or as a result of the treatment with the antagonist.

"A patient maintains responsiveness to a treatment" when the patient' responsiveness does not decrease with time during the course of a treatment.

As used herein, "non-response" or "lack of response" or similar wording means an absence of a complete response, a partial response, or a beneficial response to treatment with an integrin beta7 antagonist.

The term "sample" or "test sample", as used herein, refers to a composition that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. The sample can be obtained from a tissue for the subject of interest or from peripheral blood of the subject. For example, the sample may be obtained from blood and other liquid samples of biological origin and tissue samples such as a biopsy specimen or tissue cultures or cells derived therefrom. The source of the tissue sample may be solid tissue as from a fresh, frozen and/or preserved organ or tissue sample or biopsy or aspirate; blood or any blood constituents; bodily fluids; and cells from any time in gestation or development of the subject or plasma. The term "sample," or "test sample" includes biological samples that have been manipulated in any way after their procurement, such as by treatment with reagents, solubilization, or enrichment for certain components, such as proteins or polynucleotides, or embedding in a semi-solid or solid matrix for sectioning purposes. For the purposes herein a "section" of a tissue sample is meant a single part or piece of a tissue sample, e.g. a thin slice of tissue or cells cut from a tissue sample. Samples include, but are not limited to, whole blood, blood-derived cells, serum, plasma, lypmph fluid, synovial fluid, cellular extracts, and combinations thereof.

A "reference sample," as used herein, refers to any sample, standard, or level that is used for comparison purposes. In one embodiment, a reference sample is obtained from a healthy and/or non-diseased part of the body (e.g., tissue or cells) of the same subject or patient. In another embodiment, a reference sample is obtained from an untreated tissue and/or cell of the body of the same subject or patient. In yet another embodiment, a reference sample is obtained from a healthy and/or non-diseased part of the body (e.g., tissues or cells) of an individual who is not the subject or patient. In even another embodiment, a reference sample is obtained from an untreated tissue and/or cell part of the body of an individual who is not the subject or patient.

"A beta7 integrin antagonist" or "beta7 antagonist" refers to any molecule that inhibits one or more biological activities or blocking binding of beta7 integrin with one or more of its associated molecules. Antagonists of the invention can be used to modulate one or more aspects of beta7 associated effects, including but not limited to association with alpha4 integrin subunit, association with alphaE integrin subunit, binding of alpha4beta7 integrin to MAdCAM, VCAM-1 or fibronectin and binding of alphaEbeta7 integrin to E-cadherin. These effects can be modulated by any biologically relevant mechanism, including disruption of ligand binding to beta7 subunit or to the alpha4beta7 or alphaEbeta7 dimeric integrin, and/or by disrupting association between the alpha and beta integrin subunits such that formation of the dimeric integrin is inhibited. In one embodiment of the invention, the beta7 antagonist is an anti-beta7 integrin antibody (or anti-beta7 antibody). In one embodiment, the anti-beta7 integrin antibody is a humanized anti-beta7 integrin antibody and more particularly a recombinant humanized monoclonal anti-beta7 antibody, for example, rhuMAb beta7, also referred to as etrolizumab. In some embodiments, the anti-beta7 antibodies of the present invention are anti-integrin beta7 antagonistic antibodies that inhibit or block the binding of beta7 subunit with alpha4 integrin subunit, association with alphaE integrin subunit, binding of alpha4beta7 integrin to MAdCAM, VCAM-1 or fibronectin and binding of alphaEbeta7 integrin to E-cadherin.

By "beta7 subunit" or "β7 subunit" is meant the human β7 integrin subunit (Erle et al., (1991) J. Biol. Chem. 266: 11009-11016). The beta7 subunit associates with alpha4 integrin subunit, such as the human .alpha.4 subunit (Kilger and Holzmann (1995) J. Mol. Biol. 73:347-354). The alpha4beta7 integrin is reportedly expressed on a majority of mature lymphocytes, as well as a small population of thymocytes, bone marrow cells and mast cells. (Kilshaw and Murant (1991) Eur. J. Immunol. 21:2591-2597; Gurish et al., (1992) 149: 1964-1972; and Shaw, S. K. and Brenner, M. B. (1995) Semin. Immunol. 7:335). The beta7 subunit also associates with the alphaE subunit, such as the human alphaE integrin subunit (Cepek, K. L, et al. (1993) J. Immunol. 150:3459). The alphaEbeta7 integrin is expressed on intra-intestinal epithelial lymphocytes (iIELs) (Cepek, K. L. (1993) supra).

By "alphaE subunit" or "alphaE integrin subunit" or "αE subunit" or "αE integrin subunit" or "CD103" is meant an integrin subunit found to be associated with beta7 integrin on intra-epithelial lymphocytes, which alphaEbeta7 integrin mediates binding of the iELs to intestinal epithelium expressing E-cadherin (Cepek, K. L. et al. (1993) J. Immunol. 150:3459; Shaw, S. K. and Brenner, M. B. (1995) Semin. Immunol. 7:335).

"MAdCAM" or "MAdCAM-1" are used interchangeably in the context of the present invention and refer to the protein mucosal addressin cell adhesion molecule-1, which is a single chain polypeptide comprising a short cytoplasmic tail, a transmembrane region and an extracellular sequence composed of three immunoglobulin-like domains. The cDNAs for murine, human and macaque MAdCAM-1 have been cloned (Briskin, et al., (1993) Nature, 363:461-464; Shyjan et al., (1996) J. Immunol. 156:2851-2857).

"VCAM-1" or "vascular cell adhesion molecule-1" "CD106" refers to a ligand of alpha4beta7 and alpha4beta1, expressed on activated endothelium and important in endothelial-leukocyte interactions such as binding and transmigration of leukocytes during inflammation.

"CD45" refers to a protein of the protein tyrosine phosphatase (PTP) family. PTPs are known to be signaling molecules that regulate a variety of cellular processes including cell growth, differentiation, mitotic cycle, and oncogenic transformation. This PTP contains an extracellular domain, a single transmembrane segment and two tandem intracytoplasmic catalytic domains, and thus belongs to receptor type PTP. This gene is specifically expressed in hematopoietic cells. This PTP has been shown to be an essential regulator of T- and B-cell antigen receptor signaling. It functions through either direct interaction with components of the antigen receptor complexes, or by activating various Src family kinases required for the antigen receptor signaling. This PTP also suppresses JAK kinases, and thus functions as a regulator of cytokine receptor signaling. Four alternatively spliced transcripts variants of this gene, which encode distinct isoforms, have been reported. (Tchilian E Z, Beverley P C (2002). "CD45 in memory and disease." *Arch. Immunol. Ther. Exp.* (Warsz.) 50 (2): 85-93. Ishikawa H, Tsuyama N, Abroun S, et al. (2004). "Interleukin-6, CD45 and the src-kinases in myeloma cell proliferation." *Leuk. Lymphoma* 44 (9):1477-81.

Various isoforms of CD45 exist: CD45RA, CD45RB, CD45RC, CD45RAB, CD45RAC, CD45RBC, CD45RO, CD45R (ABC). CD45 is also highly glycosylated. CD45R is the longest protein and migrates at 200 kDa when isolated from T cells. B cells also express CD45R with heavier glycosylation, bringing the molecular weight to 220 kDa, hence the name B220; B cell isoform of 220 kDa. B220 expression is not restricted to B cells and can also be expressed on activated T cells, on a subset of dendritic cells and other antigen presenting cells. Stanton T, Boxall S, Bennett A, et al. (2004). "CD45 variant alleles: possibly increased frequency of a novel exon 4 CD45 polymorphism in HIV seropositive Ugandans." *Immunogenetics* 56 (2): 107-10.

"Gut-homing lymphocytes" refer to a subgroup of lymphocytes having the characteristic of selectively homing to intestinal lymph nodes and tissues but not homing to peripheral lymph nodes and tissues. This subgroup of lymphocytes are characterized by an unique expression pattern of a combination of multiples cell surface molecules, including, but not limited to, the combination of CD4, CD45RA and Beta7. Typically, at least two subsets of peripheral blood CD4$^+$ lymphocytes can be subdivided based on the markers of CD45RA and Beta7, CD45RA$^-$β7$^{high}$, and CD45RA$^-$β7$^{low}$ CD4$^+$ cells. CD45RA$^-$β7$^{high}$ CD4$^+$ cells home preferentially to intestinal lymph nodes and tissues, whereas CD45RA$^-$β7$^{low}$ CD4$^+$ cells home preferentially to peripheral lymph nodes and tissues (Rott et al. 1996; Rott et al. 1997; Williams et al. 1998; Rosé et al. 1998; Williams and Butcher 1997; Butcher et al. 1999). Gut-homing lymphocytes are therefore a distinctive subgroup of lymphocytes identified as CD45RA$^-$β7$^{high}$ CD4$^+$ in a flow cytometry assay. The methods of identifying this group of lymphocytes are well-known in the art.

As used herein with respect to a cell surface marker, the symbol "+" indicates a positive expression of a cell surface marker. For instance, CD4$^+$ lymphocytes are a group of lymphocytes having CD4 expressed on their cell surfaces.

As used herein with respect to a cell surface marker, the symbol "−" indicates a negative expression of a cell surface marker. For instance, CD45RA$^-$ lymphocytes are a group of lymphocytes having no CD45RA expressed on their cell surfaces.

An "amount" or "level" of biomarker can be determined using methods known in the art and disclosed herein, such as flow cytometry analysis or qPCR.

A "change in the amount or level of a biomarker" is as compared to a reference/comparator amount of the biomarker. In certain embodiments, the change is greater than about 10%, or greater than about 30%, or greater than about 50%, or greater than about 100%, or greater than about 300% as a function of the value for the reference or comparator amount. For example, a reference or comparator amount can be the amount of a biomarker before treatment and more particularly, can be the baseline or pre-dose amount.

The phrase "essentially the same as" as used herein, denotes an insignificant degree of change such that one of skill in the art would not consider the change to be of statistical significance or a biologically meaningful change within the context of the biological characteristic measured by said values (e.g., the drug serum level needed to saturate the drug target receptors). For example, serum drug concentrations needed to saturate receptors that are less than about two fold different, or less than about three fold different, or less than about four fold different from each other are considered essentially the same.

"Gastrointestinal inflammatory disorders" are a group of chronic disorders that cause inflammation and/or ulceration in the mucous membrane. These disorders include, for example, inflammatory bowel disease (e.g., Crohn's disease, ulcerative colitis, indeterminate colitis and infectious colitis), mucositis (e.g., oral mucositis, gastrointestinal mucositis, nasal mucositis and proctitis), necrotizing enterocolitis and esophagitis.

"Inflammatory Bowel Disease" or "IBD" is used interchangeably herein to refer to diseases of the bowel that cause inflammation and/or ulceration and includes without limitation Crohn's disease and ulcerative colitis.

"Crohn's disease (CD)" and "ulcerative colitis (UC)" are chronic inflammatory bowel diseases of unknown etiology. Crohn's disease, unlike ulcerative colitis, can affect any part of the bowel. The most prominent feature Crohn's disease is the granular, reddish-purple edematous thickening of the bowel wall. With the development of inflammation, these granulomas often lose their circumscribed borders and integrate with the surrounding tissue. Diarrhea and obstruction of the bowel are the predominant clinical features. As with ulcerative colitis, the course of Crohn's disease may be continuous or relapsing, mild or severe, but unlike ulcerative colitis, Crohn's disease is not curable by resection of the involved segment of bowel. Most patients with Crohn's disease require surgery at some point, but subsequent relapse is common and continuous medical treatment is usual.

Crohn's disease may involve any part of the alimentary tract from the mouth to the anus, although typically it appears in the ileocolic, small-intestinal or colonic-anorectal regions. Histopathologically, the disease manifests by discontinuous granulomatomas, crypt abscesses, fissures and aphthous ulcers. The inflammatory infiltrate is mixed, consisting of lymphocytes (both T and B cells), plasma cells, macrophages, and neutrophils. There is a disproportionate increase in IgM- and IgG-secreting plasma cells, macrophages and neutrophils.

Anti-inflammatory drugs sulfasalazine and 5-aminosalisylic acid (5-ASA) are used for treating mildly active colonic Crohn's disease and are commonly prescribed in an attempt to maintain remission of the disease. Metroidazole and ciprofloxacin are similar in efficacy to sulfasalazine and are particularly prescribed for treating perianal disease. In more severe cases, corticosteroids are prescribed to treat active exacerbations and can sometimes maintain remission. Azathioprine and 6-mercaptopurine have also been used in patients who require chronic administration of corticosteroids. It has been suggested that these drugs may play a role in the long-term prophylaxis. Unfortunately, there can be a very long delay (up to six months) before onset of action in some patients. Antidiarrheal drugs can also provide symptomatic relief in some patients. Nutritional therapy or elemental diet can improve the nutritional status of patients and induce symptomatic improvement of acute disease, but it does not induce sustained clinical remissions. Antibiotics are used in treating secondary small bowel bacterial overgrowth and in treatment of pyogenic complications.

"Ulcerative colitis (UC)" afflicts the large intestine. The course of the disease may be continuous or relapsing, mild or severe. The earliest lesion is an inflammatory infiltration with abscess formation at the base of the crypts of Lieberkuhn. Coalescence of these distended and ruptured crypts tends to separate the overlying mucosa from its blood supply, leading to ulceration. Symptoms of the disease include cramping, lower abdominal pain, rectal bleeding, and frequent, loose discharges consisting mainly of blood, pus and mucus with scanty fecal particles. A total colectomy may be required for acute, severe or chronic, unremitting ulcerative colitis.

The clinical features of UC are highly variable, and the onset may be insidious or abrupt, and may include diarrhea, tenesmus and relapsing rectal bleeding. With fulminant involvement of the entire colon, toxic megacolon, a life-threatening emergency, may occur. Extraintestinal manifestations include arthritis, pyoderma gangrenoum, uveitis, and erythema nodosum.

Treatment for UC includes sulfasalazine and related salicylate-containing drugs for mild cases and corticosteroid drugs in severe cases. Topical administration of either salicylates or corticosteroids is sometimes effective, particularly when the disease is limited to the distal bowel, and is associated with decreased side effects compared with systemic use. Supportive measures such as administration of iron and antidiarrheal agents are sometimes indicated. Azathioprine, 6-mercaptopurine and methotrexate are sometimes also prescribed for use in refractory corticosteroid-dependent cases.

An "effective dosage" refers to an amount effective, at dosages and for periods of time necessary, to achieve the desired therapeutic or prophylactic result.

As used herein, the term "patient" refers to any single subject for which treatment is desired. In certain embodiments, the patient herein is a human.

A "subject" herein is typically a human. In certain embodiments, a subject is a non-human mammal. Exemplary non-human mammals include laboratory, domestic, pet, sport, and stock animals, e.g., mice, cats, dogs, horses, and cows. Typically, the subject is eligible for treatment, e.g., treatment of a gastrointestinal inflammatory disorder.

The terms "antibody" and "immunoglobulin" are used interchangeably in the broadest sense and include monoclonal antibodies (for example, full length or intact monoclonal antibodies), polyclonal antibodies, multivalent antibodies, multi specific antibodies (e.g., bispecific antibodies so long as they exhibit the desired biological activity) and may also include certain antibody fragments (as described in greater detail herein). An antibody can be human, humanized and/or affinity matured.

"Antibody fragments" comprise only a portion of an intact antibody, wherein the portion preferably retains at least one, and typically most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin lo sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1: 105-115 (1998); Harris, Biochem. Soc. Transactions 23:1035-1038 (1995); Hurle and Gross, Curr. Op. Biotech. 5:428-433 (1994).

A "human antibody" is one which comprises an amino acid sequence corresponding to that of an antibody produced by a human and/or has been made using any of the techniques for making human antibodies as disclosed herein. Such techniques include screening human-derived combinatorial libraries, such as phage display libraries (see, e.g., Marks et al., *J. Mol. Biol.,* 222: 581-597 (1991) and Hoogenboom et al., *Nucl. Acids Res.,* 19: 4133-4137 (1991)); using human myeloma and mouse-human heteromyeloma cell lines for the production of human monoclonal antibodies (see, e.g., Kozbor *J. Immunol.,* 133: 3001 (1984); Brodeur et al., *Monoclonal Antibody Production Techniques and Applications,* pp. 55-93 (Marcel Dekker, Inc., New York, 1987); and Boerner et al., *J. Immunol.,* 147: 86 (1991)); and generating monoclonal antibodies in transgenic animals (e.g., mice) that are capable of producing a full repertoire of human antibodies in the absence of endogenous immunoglobulin production (see, e.g., Jakobovits et al., *Proc. Natl. Acad. Sci USA,* 90: 2551 (1993); Jakobovits et al., *Nature,* 362: 255 (1993); Bruggermann et al., *Year in Immunol,* 7: 33 (1993)). This definition of a human antibody specifically excludes a humanized antibody comprising antigen-binding residues from a non-human animal.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In certain embodiments, the antibody will be purified (1) to greater than 95% by weight of antibody as determined by the Lowry method, and often more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

The term "hypervariable region," "HVR," or "HV," when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these HVRs are noted below.

compared to a parent antibody which does not possess those alteration(s). In certain embodiments, affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci, USA 91:3809-3813 (1994); Schier et al. Gene 169:147-155 (1996); Yelton et al. J. Immunol. 155:1994-2004 (1995); Jackson et al., J. Immunol. 154(7):3310-9 (1995); and Hawkins et al. J. Mol. Biol. 226:889-896 (1992).

The phrase "substantially similar," or "substantially the same," as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

Hypervariable regions may comprise "extended hypervariable regions" as follows: 24-36 or 24-34 (L1), 46-56 or 49-56 or 50-56 or 52-56 (L2) and 89-97 (L3) in the VL and 26-35 (H1), 50-65 or 49-65 (H2) and 93-102, 94-102 or 95-102 (H3) in the VH. The variable domain residues are numbered according to Kabat et al., supra for each of these definitions.

"Framework" or "FR" residues are those variable domain residues other than the hypervariable region residues as herein defined.

A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. In one embodiment, for the VL, the subgroup is subgroup kappa I as in Kabat et al. In one embodiment, for the VH, the subgroup is subgroup III as in Kabat et al.

An "affinity matured" antibody is one with one or more alterations in one or more CDRs thereof which result in an improvement in the affinity of the antibody for antigen, antigen slowly and tend to dissociate readily, whereas high-affinity antibodies generally bind antigen faster and tend to remain bound longer. A variety of methods of measuring binding affinity are known in the art, any of which can be used for purposes of the present invention.

The term "variable" in connection with antibodies or immunoglobulins refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy-chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. *Cellular and Mol. Immunology*, 4th ed. (W. B. Saunders, Co., 2000). An antibody may be part of a larger fusion molecule, formed by covalent or non-covalent association of the antibody with one or more other proteins or peptides.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

Unless indicated otherwise, herein the numbering of the residues in an immunoglobulin heavy chain is that of the EU index as in Kabat et al., *Sequences of Proteins of Immunological Interest*, 5th Ed. Public Health Service, National Institutes of Health, Bethesda, Md. (1991), expressly incorporated herein by reference. The "EU index as in Kabat" refers to the residue numbering of the human IgG1 EU antibody.

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding domain (e.g., an antibody variable domain) and can be assessed using various assays as herein disclosed, for example.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification. In certain embodiments, the variant Fc region has at least one amino acid substitution compared to a native sequence Fc region or to the Fc region of a parent polypeptide, e.g., from about one to about ten amino acid substitutions, and in certain embodiments from about one to about five amino acid substitutions in a native sequence Fc region or in the Fc region of the parent polypeptide. In certain embodiments, the variant Fc region herein will possess at least about 80% homology with a native sequence Fc region and/or with an Fc region of a parent polypeptide, or at least about 90% homology therewith, or at least about 95% homology therewith.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. In certain embodiments, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils. The effector cells may be isolated from a native source thereof, e.g., from blood or PBMCs as described herein.

The terms "Fc receptor" or "FcR" are used to describe a receptor that binds to the Fc region of an antibody. In certain embodiments, FcR is a native sequence human FcR. Moreover, FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, *Annu. Rev. Immunol*. 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)), and regulates homeostasis of immunoglobulins. Antibodies with improved binding to the neonatal Fc receptor (FcRn), and increased half-lives, are described in WO00/42072 (Presta, L.) and US2005/0014934A1 (Hinton et al.). These antibodies comprise an Fc region with one or more substitutions therein which improve binding of the Fc region to FcRn. For example, the Fc region may have substitutions at one or more of positions 238, 250, 256, 265, 272, 286, 303, 305, 307, 311, 312, 314, 317, 340, 356, 360, 362, 376, 378, 380, 382, 413, 424, 428 or 434 (Eu numbering of residues). In certain embodiments, the Fc region-comprising antibody variant with improved FcRn binding comprises amino acid substitutions at one, two or three of positions 307, 380 and 434 of the Fc region thereof (Eu numbering of residues).

"Single-chain Fv" or "scFv" antibody fragments comprise the $V_H$ and $V_L$ domains of antibody, wherein these domains are present in a single polypeptide chain. In certain embodiments, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

An "affinity matured" antibody is one with one or more alterations in one or more hypervariable regions thereof which result an improvement in the affinity of the antibody for antigen, compared to a parent antibody which does not possess those alteration(s). In certain embodiments, affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al *J. Immunol.* 155:1994-2004 (1995); Jackson et al., *J. Immunol.* 154(7):3310-9 (1995); and Hawkins et al., *J. Mol. Biol.* 226:889-896 (1992).

An "amino acid sequence variant" antibody herein is an antibody with an amino acid sequence which differs from a main species antibody. In certain embodiments, amino acid sequence variants will possess at least about 70% homology with the main species antibody, or they will be at least about 80%, or at least about 90% homologous with the main species antibody. The amino acid sequence variants possess substitutions, deletions, and/or additions at certain positions within or adjacent to the amino acid sequence of the main species antibody. Examples of amino acid sequence variants herein include an acidic variant (e.g., deamidated antibody variant), a basic variant, an antibody with an amino-terminal leader extension (e.g. VHS-) on one or two light chains thereof, an antibody with a C-terminal lysine residue on one or two heavy chains thereof, etc, and includes combinations of variations to the amino acid sequences of heavy and/or light chains. The antibody variant of particular interest herein is the antibody comprising an amino-terminal leader extension on one or two light chains thereof, optionally further comprising other amino acid sequence and/or glycosylation differences relative to the main species antibody.

A "glycosylation variant" antibody herein is an antibody with one or more carbohydrate moieties attached thereto which differ from one or more carbohydrate moieties attached to a main species antibody. Examples of glycosylation variants herein include antibody with a G1 or G2 oligosaccharide structure, instead a G0 oligosaccharide structure, attached to an Fc region thereof, antibody with one or two carbohydrate moieties attached to one or two light chains thereof, antibody with no carbohydrate attached to one or two heavy chains of the antibody, etc, and combinations of glycosylation alterations. Where the antibody has an Fc region, an oligosaccharide structure may be attached to one or two heavy chains of the antibody, e.g. at residue 299 (298, Eu numbering of residues).

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF), granulocyte-macrophage-CSF (GM-CSF), and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "immunosuppressive agent" as used herein for adjunct therapy refers to substances that act to suppress or mask the immune system of the subject being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); non-steroidal anti-inflammatory drugs (NSAIDs); ganciclovir; tacrolimus; glucocorticoids such as cortisol or aldosterone; anti-inflammatory agents such as a cyclooxygenase inhibitor; a 5-lipoxygenase inhibitor; or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporine; 6 mercaptopurine; steroids such as corticosteroids or glucocorticosteroids or glucocorticoid analogs, e.g., prednisone, methylprednisolone, including SOLU-MEDROL® methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies or antagonists including anti-interferon-alpha, -beta, or -gamma antibodies, anti-tumor necrosis factor (TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists; anti-LFA-1 antibodies, including anti-CD11a and anti-CD18 antibodies; anti-L3T4 antibodies; heterologous anti-lymphocyte globulin; pan-T antibodies, anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodomase; RNA or DNA from the host; FK506; RS-61443; chlorambucil; deoxyspergualin; rapamycin; T-cell receptor (Cohen et al., U.S. Pat. No. 5,114,721); T-cell receptor fragments (Offner et al., Science, 251: 430-432 (1991); WO 90/11294; Ianeway, Nature, 341: 482 (1989); and WO 91/01133); BAFF antagonists such as BAFF or BR3 antibodies or immunoadhesins and zTNF4 antagonists (for review, see Mackay and Mackay, Trends Immunol., 23:113-5 (2002) and see also definition below); biologic agents that interfere with T cell helper signals, such as anti-CD40 receptor or anti-CD40 ligand (CD154), including blocking antibodies to CD40-CD40 ligand. (e.g., Dune et al., Science, 261: 1328-30 (1993); Mohan et al., J. Immunol., 154: 1470-80 (1995)) and CTLA4-Ig (Finck et al., Science, 265: 1225-7 (1994)); and T-cell receptor antibodies (EP 340,109) such as T10B9.

The term "ameliorates" or "amelioration" as used herein refers to a decrease, reduction or elimination of a condition, disease, disorder, or phenotype, including an abnormality or symptom.

A "symptom" of a disease or disorder (e.g., inflammatory bowel disease, e.g., ulcerative colitis or Crohn's disease) is any morbid phenomenon or departure from the normal in structure, function, or sensation, experienced by a subject and indicative of disease.

The expression "therapeutically effective amount" refers to an amount that is effective for preventing, ameliorating, or treating a disease or disorder (e.g., inflammatory bowel disease, e.g., ulcerative colitis or Crohn's disease). For example, a "therapeutically effective amount" of an antibody refers to an amount of the antibody that is effective for preventing, ameliorating, or treating the specified disease or disorder. Similarly, a "therapeutically effective amount" of a combination of an antibody and a second compound refers to an amount of the antibody and an amount of the second compound that, in combination, is effective for preventing, ameliorating, or treating the specified disease or disorder.

It is to be understood that the terminology "a combination of" two compounds does not mean that the compounds have to be administered in admixture with each other. Thus, treatment with or use of such a combination encompasses a mixture of the compounds or separate administration of the compounds, and includes administration on the same day or different days. Thus the terminology "combination" means two or more compounds are used for the treatment, either individually or in admixture with each other. When an antibody and a second compound, for example, are administered in combination to a subject, the antibody is present in the subject at a time when the second compound is also present in the subject, whether the antibody and second compound are administered individually or in admixture to the subject. In certain embodiments, a compound other than the antibody is administered prior to the antibody. In certain embodiments, a compound other than the antibody is administered after the antibody.

For the purposes herein, "tumor necrosis factor-alpha (TNF-alpha)" refers to a human TNF-alpha molecule comprising the amino acid sequence as described in Pennica et al., Nature, 312:721 (1984) or Aggarwal et al., JBC, 260: 2345 (1985).

The term "TNF-alpha inhibitor" is used interchangeably herein with "anti-TNF therapeutic agent" and refers to an agent that inhibits, to some extent, a biological function of TNF-alpha, generally through binding to TNF-alpha and neutralizing its activity. Examples of TNF inhibitors specifically contemplated herein are etanercept (ENBREL®), infliximab (REMICADE®), adalimumab (HUMIRA®), golimumab (SIMPONI™), and certolizumab pegol (CIMZIA®).

"Corticosteroid" refers to any one of several synthetic or naturally occurring substances with the general chemical structure of steroids that mimic or augment the effects of the naturally occurring corticosteroids. Examples of synthetic corticosteroids include prednisone, prednisolone (including methylprednisolone), dexamethasone triamcinolone, and betamethasone.

An "antagonist" refers to a molecule capable of neutralizing, blocking, inhibiting, abrogating, reducing or interfering with the activities of a particular or specified protein, including its binding to one or more receptors in the case of a ligand or binding to one or more ligands in case of a receptor. Antagonists include antibodies and antigen-binding fragments thereof, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Antagonists also include small molecule inhibitors of the protein, and fusion proteins, receptor molecules and derivatives which bind specifically to the protein thereby sequestering its binding to its target, antagonist variants of the protein, anti sense molecules directed to the protein, RNA aptamers, and ribozymes against the protein.

A "self-inject device" refers to a medical device for self-administration, e.g., by a patient or in-home caregiver, of a therapeutic agent. Self-inject devices include autoinjector devices and other devices designed for self-administration.

"Oligonucleotide," as used herein, refers to short, single stranded polynucleotides that are at least about seven nucleotides in length and less than about 250 nucleotides in length. Oligonucleotides may be synthetic. The terms "oligonucleotide" and "polynucleotide" are not mutually exclusive. The description above for polynucleotides is equally and fully applicable to oligonucleotides.

The term "primer" refers to a single stranded polynucleotide that is capable of hybridizing to a nucleic acid and allowing the polymerization of a complementary nucleic acid, generally by providing a free 3'-OH group.

The term "amplification" refers to the process of producing one or more copies of a reference nucleic acid sequence or its complement. Amplification may be linear or exponential (e.g., PCR). A "copy" does not necessarily mean perfect sequence complementarity or identity relative to the template sequence. For example, copies can include nucleotide analogs such as deoxyinosine, intentional sequence alterations (such as sequence alterations introduced through a primer comprising a sequence that is hybridizable, but not fully complementary, to the template), and/or sequence errors that occur during amplification.

The term "detection" includes any means of detecting, including direct and indirect detection.

"Elevated expression" or "elevated levels" refers to an increased expression of a mRNA or a protein in a patient relative to a control or to a reference level, such as an individual or individuals who are not suffering from an autoimmune disease, e.g., TBD, or relative to a pre-established threshold or cut-off value, or relative to the median for a population of patients and/or subjects.

"Low expression" or "low expression levels" or "reduced expression" refers to a decreased expression of a mRNA or a protein in a patient relative to a control or to a reference level, such as an individual or individuals who are not suffering from an autoimmune disease, e.g., IBD, or relative to a pre-established threshold or cut-off value, or relative to the median for a population of patients and/or subjects.

The term "multiplex-PCR" refers to a single PCR reaction carried out on nucleic acid obtained from a single source (e.g., a patient) using more than one primer set for the purpose of amplifying two or more DNA sequences in a single reaction.

The term "biomarker" as used herein refers to an indicator of a phenotype of a patient, e.g., a pathological state or likely responsiveness to a therapeutic agent, which can be detected in a biological sample of the patient. Biomarkers include, but are not limited to, DNA, RNA, protein, carbohydrate, or glycolipid-based molecular markers.

The term "diagnosis" is used herein to refer to the identification or classification of a molecular or pathological state, disease or condition. For example, "diagnosis" may refer to identification of a particular type of gastrointestinal inflammatory disorder, or the classification of a particular sub-type of gastrointestinal inflammatory disorder, by tissue/organ involvement (e.g., inflammatory bowel disease), or by other features (e.g., a patient subpopulation characterized by responsiveness to a treatment, such as to a treatment with an integrin beta7 antagonist), or by molecular features (e.g., a subtype characterized by expression of one or a combination of particular genes or proteins encoded by said genes).

The term "aiding diagnosis" is used herein to refer to methods that assist in making a clinical determination regarding the presence, or nature, of a particular type of symptom or condition. For example, a method of aiding diagnosis of IBD can comprise measuring the expression of certain genes in a biological sample from an individual.

The term "prognosis" is used herein to refer to the prediction of the likelihood of disease symptoms, including, for example, recurrence, flaring, and drug resistance, of a gastrointestinal inflammatory disorder.

The term "prediction" is used herein to refer to the likelihood that a patient will respond either favorably or unfavorably to a drug (therapeutic agent) or set of drugs or a therapeutic regimen. In one embodiment, the prediction relates to the extent of those responses. In one embodiment, the prediction relates to whether and/or the probability that a patient will survive or improve following treatment, for example treatment with a particular therapeutic agent, or for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, steroid treatment, etc., or whether long-term survival of the patient or remission or sustained remission, following a therapeutic regimen is likely.

A "control subject" refers to a healthy subject who has not been diagnosed as having a particular disease, e.g., IBD, and who does not suffer from any sign or symptom associated with that disease.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of gene expression analysis or protocol, one may use the results of the gene expression analysis or protocol to determine whether a specific therapeutic regimen should be performed.

The term "comparing" as used herein refers to comparing the level of the biomarker in the sample from the individual or patient with the reference level of the biomarker specified elsewhere in this description. It is to be understood that comparing as used herein usually refers to a comparison of corresponding parameters or values, e.g., an absolute amount is compared to an absolute reference amount while a concentration is compared to a reference concentration or an intensity signal obtained from the biomarker in a sample is compared to the same type of intensity signal obtained from a reference sample. The comparison may be carried out manually or computer assisted. Thus, the comparison may be carried out by a computing device (e.g., of a system disclosed herein). The value of the measured or detected level of the biomarker in the sample from the individual or patient and the reference level can be, e.g., compared to each other and the said comparison can be automatically carried out by a computer program executing an algorithm for the comparison. The computer program carrying out the said evaluation will provide the desired assessment in a suitable output format. For a computer assisted comparison, the value of the determined amount may be compared to values corresponding to suitable references which are stored in a database by a computer program. The computer program may further evaluate the result of the comparison, i.e. automatically provide the desired assessment in a suitable output format. For a computer assisted comparison, the value of the determined amount may be compared to values corresponding to suitable references which are stored in a database by a computer program. The computer program may further evaluate the result of the comparison, i.e. automatically provides the desired assessment in a suitable output format.

The phrase "recommending a treatment" as used herein refers to using the information or data generated relating to the level or presence of one or more of GZMA, KLRB1, FOXM1, CCDC90A, CCL4L1.2, CPA2, CXCR6, DDO, ECH1, FAM125B, FASLG, FGF9, GPR15, GZMB, KCNMA1, PHF14, TIFAB, TMEM200A, TMIGD2, SLC8A3, TNFSF15, BEST2, CCL2, CCL3, CCL3L1/3, CPA3, FGF7, HAMP, IL1A, IL18RAP, INHBA, LIF, LMO4, LRRC4, MLK7.AS1, MT1M, MUCL1, MX1, PMCH, REM2, SSTR2, TM4SF4, TMEM154, UROS, VNN2, VNN3 mRNA in a sample of a patient, and optionally relating further to the level or presence of ITGAE mRNA, to identify the patient as suitably treated or not suitably treated with a therapy. In some embodiments, the therapy comprises an integrin beta7 antagonist, including an anti-integrin beta7 antibody such as etrolizumab. In some embodiments, the phrase "recommending a treatment/therapy" includes the identification of a patient who requires adaptation of an effective amount of the integrin beta7 antagonist being administered. In some embodiments, recommending a treatment includes recommending that the amount of integrin beta7 antagonist being administered is adapted. The phrase "recommending a treatment" as used herein also may refer to using the information or data generated for proposing or selecting a therapy comprising an integrin beta7 antagonist for a patient identified or selected as more or less likely to respond to the therapy comprising an integrin beta7 antagonist. The information or data used or generated may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the level of one or more of GZMA, KLRB1, FOXM1, CCDC90A, CCL4L1.2, CPA2, CXCR6, DDO, ECH1, FAM125B, FASLG, FGF9, GPR15, GZMB, KCNMA1, PHF14, TIFAB, TMEM200A, TMIGD2, SLC8A3, TNFSF15, BEST2, CCL2, CCL3, CCL3L1/3, CPA3, FGF7, HAMP, IL1A, IL18RAP, INHBA, LIF, LMO4, LRRC4, MLK7.AS1, MT1M, MUCL1, MX1, PMCH, REM2, SSTR2, TM4SF4, TMEM154, UROS, VNN2, VNN3 mRNA, and optionally further including ITGAE mRNA, to a reference level. In some embodiments, the information or data includes an indication that one or more of the mRNAs identified is present at elevated or reduced levels in the sample. In some embodiments, the information or data includes an indication that the patient is suitably treated or not suitably treated with a therapy comprising an integrin beta7 antagonist, including an anti-integrin beta7 antibody such as etrolizumab.

A "package insert" is used to refer to instructions customarily included in commercial packages of therapeutic products or medicaments, that contain information about the indications, usage, dosage, administration, contraindications, other therapeutic products to be combined with the packaged product, and/or warnings concerning the use of such therapeutic products or medicaments and the like.

A "kit" is any manufacture (e.g. a package or container) comprising at least one reagent, e.g., a medicament for treatment of an IBD, e.g., UC or Crohn's disease, or a probe for specifically detecting a biomarker gene or protein of the invention. In certain embodiments, the manufacture is promoted, distributed, or sold as a unit for performing the methods of the present invention.

A "target audience" is a group of people or an institution to whom or to which a particular medicament is being promoted or intended to be promoted, as by marketing or advertising, especially for particular uses, treatments, or indications, such as individual patients, patient populations, readers of newspapers, medical literature, and magazines, television or internet viewers, radio or internet listeners, physicians, drug companies, etc.

The term "serum sample" refers to any serum sample obtained from an individual. Methods for obtaining sera from mammals are well known in the art.

The term "whole blood" refers to any whole blood sample obtained from an individual. Typically, whole blood contains all of the blood components, e.g., cellular components and plasma. Methods for obtaining whole blood from mammals are well known in the art.

The expression "not responsive to," "non-response" and grammatical variants thereof, as it relates to the reaction of subjects or patients to one or more of the medicaments (therapeutic agents) that were previously administered to them, describes those subjects or patients who, upon administration of such medicament(s), did not exhibit any or adequate signs of treatment of the disorder for which they were being treated, or they exhibited a clinically unacceptably high degree of toxicity to the medicament(s), or they did not maintain the signs of treatment after first being administered such medicament(s), with the word treatment being used in this context as defined herein. The phrase "not responsive" includes a description of those subjects who are resistant and/or refractory to the previously administered medication(s), and includes the situations in which a subject or patient has progressed while receiving the medicament(s) that he or she is being given, and in which a subject or patient has progressed within 12 months (for example, within six months) after completing a regimen involving the medicament(s) to which he or she is no longer responsive. The non-responsiveness to one or more medicaments thus includes subjects who continue to have active disease following previous or current treatment therewith. For instance, a patient may have active disease activity after about one to three months, or three to six months, or six to 12 months, of therapy with the medicament(s) to which they are non-responsive. Such responsiveness may be assessed by a clinician skilled in treating the disorder in question.

For purposes of non-response to medicament(s), a subject who experiences "a clinically unacceptably high level of toxicity" from previous or current treatment with one or more medicaments experiences one or more negative side-effects or adverse events associated therewith that are considered by an experienced clinician to be significant, such as, for example, serious infections, congestive heart failure, demyelination (leading to multiple sclerosis), significant hypersensitivity, neuropathological events, high degrees of autoimmunity, a cancer such as endometrial cancer, non-Hodgkin's lymphoma, breast cancer, prostate cancer, lung cancer, ovarian cancer, or melanoma, tuberculosis (TB), and the like.

The "amount" or "level" of a biomarker associated with an increased clinical benefit to a patient suffering from a certain disease or disorder, or predictive of response to a particular therapeutic agent or treatment regimen, is a detectable level in a biological sample. These can be measured by methods known to one skilled in the art and also disclosed herein. The expression level or amount of biomarker assessed can be used to determine the response or the predicted response to a treatment or therapeutic agent.

The terms "level of expression" or "expression level" in general are used interchangeably and generally refer to the amount of a polynucleotide or an amino acid product or protein in a biological sample. "Expression" generally refers to the process by which gene-encoded information is converted into the structures present and operating in the cell. Therefore, as used herein, "expression" of a gene may refer to transcription into a polynucleotide, translation into a protein, or even posttranslational modification of the protein. Fragments of the transcribed polynucleotide, the translated protein, or the post-translationally modified protein shall also be regarded as expressed whether they originate from a transcript generated by alternative splicing or a degraded transcript, or from a posttranslational processing of the protein, e.g., by proteolysis. "Expressed genes" include those that are transcribed into a polynucleotide as mRNA and then translated into a protein, and also those that are transcribed into RNA but not translated into a protein (for example, transfer and ribosomal RNAs).

A variety of additional terms are defined or otherwise characterized herein.

Compositions and Methods

A. Beta7 Integrin Antagonists

Methods of treating a gastrointestinal inflammatory disorder in a subject, e.g., a human, by administering beta7 integrin antagonists are provided. Examples of potential antagonists include an oligonucleotide that binds to the fusions of immunoglobulin with beta7 integrin, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the beta7 integrin that recognizes the ligand but imparts no effect, thereby competitively inhibiting the action of the beta7 integrin.

Another potential beta7 integrin antagonist is an anti sense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the beta7 integrin herein, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al., Science, 241: 456 (1988); Dervan et al., Science, 251:1360 (1991)), thereby preventing transcription and the production of the beta7 integrin. The antisense RNA oligonucleotide hybridizes to the mRNA in vivo and blocks translation of the mRNA molecule into beta7 integrin protein (antisense—Okano, Neurochem., 56:560 (1991); Oligodeoxynucleotides as Antisense Inhibitors of Gene Expression (CRC Press: Boca Raton, Fla., 1988). The oligonucleotides described above can also be delivered to cells such that the antisense RNA or DNA may be expressed in vivo to inhibit production of the PRO polypeptide. When antisense DNA is used, oligodeoxyribonucleotides derived from the translation-initiation site, e.g., between about −10 and +10 positions of the target gene nucleotide sequence, are typical.

Other potential antagonists include small molecules that bind to the active site, the ligand or binding molecule binding site, thereby blocking the normal biological activity of the beta7 integrin. Examples of small molecules include, but are not limited to, small peptides or peptide-like molecules, typically soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can-be identified by known techniques. For further details see, e.g., Rossi, Current Biology, 4:469-471 (1994), and PCT Publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT Publication No. WO 97/33551. These small molecules can be identified by any one or more of the screening assays discussed hereinabove and/or by any other screening techniques well known for those skilled in the art.

Screening assays for antagonists are designed to identify compounds that bind or complex with the beta7 integrin encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

B. Anti-Beta7 Integrin Antibodies

In one embodiment, the beta7 integrin antagonists are anti-beta7 antibodies. Exemplary antibodies include polyclonal, monoclonal, humanized, human, bispecific, and heteroconjugate antibodies, etc., as described below.

1. Polyclonal Antibodies

Polyclonal antibodies can be raised in animals by multiple subcutaneous (SC) or intraperitoneal (IP) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. In certain embodiments, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

2. Monoclonal Antibodies'

Monoclonal antibodies may be made using the hybridoma method first described by Kohler et al., Nature, 256:495 (1975), or may be made by recombinant DNA methods (see, e.g., U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium which medium may contain one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

In certain embodiments, fusion partner myeloma cells are those that fuse efficiently, support stable high-level production of antibody by the selected antibody-producing cells, and are sensitive to a selective medium that selects against the unfused parental cells. In certain embodiments, myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. In certain embodiments, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980). Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice. The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pluckthun, Immunol. Revs. 130:151-188 (1992).

In a further embodiment, monoclonal antibodies or antibody fragments can be isolated from antibody phage libraries generated using e.g., the techniques described in McCafferty et al., Nature, 348:552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res. 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain (CH and CL) sequences for the homologous murine sequences (U.S. Pat. No. 4,816,567; and Morrison, et al., Proc. Natl. Acad. Sci. USA, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Exemplary anti-beta7 antibodies are Fib504, Fib 21, 22, 27, 30 (Tidswell, M. J Immunol. 1997 Aug. 1; 159(3):1497-505) or humanized derivatives thereof. Humanized antibodies of Fib504 was disclosed in detail in U.S. Patent Publication No. 20060093601 (issued as U.S. Pat. No. 7,528, 236), the content of which is incorporated by reference in its entirety (also see discussion below).

3. Human and Humanized Antibodies

The anti-beta7 integrin antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol. 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol. 151:2623 (1993)). It is further important that antibodies be humanized with retention of high binding affinity for the antigen and other favorable biological properties. To achieve this goal, according to certain embodiments, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized Anti-beta7 integrin antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

Exemplary humanized anti-beta7 antibodies include, but are not limited to rhuMAb Beta7, which is a humanized monoclonal antibody against the integrin subunit β7 and was derived from the rat anti-mouse/human monoclonal antibody FIB504 (Andrew et al., 1994 J Immunol 1994; 153: 3847-61). It has been engineered to include human immunoglobulin IgG1 heavy chain and κ1 light chain frameworks and is produced by Chinese hamster ovary cells. This antibody binds to two integrins, α4β7 (Holzmann et al. 1989 Cell, 1989; 56:37-46; Hu et al., 1992, Proc Natl Acad Sci USA 1992; 89:8254-8) and αEβ7 (Cepek et al., 1993 J Immunol 1993; 150:3459-70), which regulate trafficking and retention of lymphocyte subsets in the gastrointestinal tract and are involved in inflammatory bowel diseases (IBD) such as ulcerative colitis (UC) and Crohn's disease (CD). rhuMAb Beta7 is a potent in vitro blocker of the cellular interaction between α4β7 and its ligands (mucosal addressin cell adhesion molecule-1 [MAdCAM]-1, vascular cell adhesion molecule [VCAM]-1, and fibronectin) as well as the interaction between αEβ7 and its ligand (E-cadherin). rhuMAb Beta7 binds reversibly, with similar high affinity, to β7 on lymphocytes from rabbits, cynomolgus monkeys, and humans. It also binds to mouse β7 with high affinity. The amino acid sequence as well as the making and using of rhuMAb Beta7 and its variants are disclosed in detail in e.g., U.S. Patent Application Publication No. 20060093601 (issued as U.S. Pat. No. 7,528,236), the content of which is incorporated in its entirety.

FIGS. 1A and 1B depict alignment of sequences of the variable light and heavy chains for the following: light chain human subgroup kappa I consensus sequence (FIG. 1A, SEQ ID NO:12), heavy chain human subgroup III consensus sequence (FIG. 1B, SEQ ID NO:13), rat anti-mouse beta7 antibody (Fib504) variable light chain (FIG. 1A, SEQ ID NO:10), rat anti-mouse beta7 antibody (Fib504) variable heavy chain (FIG. 1B, SEQ ID NO:11), and humanized antibody variants: Humanized hu504Kgraft variable light chain (FIG. 1A, SEQ ID NO:14), humanized hu504K graft variable heavy chain (FIG. 1B, SEQ ID NO:15), variants hu504-5, hu504-16, and hu504-32 (amino acid variations from humanized hu504K graft are indicated in FIG. 1A (light chain) (SEQ ID NOS:22-24, respectively, in order of appearance) and FIG. 1B (heavy chain) for variants hu504-5, hu504-16, and 504-32 (SEQ ID NO:25).

4. Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno. 7:33 (1993); U.S. Pat. Nos. 5,545,806, 5,569,825, 5,591,669 (all of GenPharm); U.S. Pat. No. 5,545,807; and WO 97/17852.

Alternatively, phage display technology (McCafferty et al., Nature 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Current Opinion in Structural Biology 3:564-571 (1993). Several sources of V-gene segments can be used for phage display. Clackson et al., Nature, 352:624-628(1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

5. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a "linear antibody," e.g., as described in U.S. Pat. No. 5,641,870 for example. Such linear antibody fragments may be monospecific or bispecific.

6. Bispecific Antibodies

Bispecific antibodies are antibodies that have binding specificities for at least two different epitopes. Exemplary bispecific antibodies may bind to two different epitopes of beta7 integrin as described herein. Other such antibodies may combine a TAT binding site with a binding site for another protein. Alternatively, an anti-Beta7 integrin arm may be combined with an arm which binds to a triggering molecule on a leukocyte such as a T-cell receptor molecule (e.g., CD3), or Fc receptors for IgG (Fc.γ.R), such as Fc.γRI (CD64), Fc.γRII (CD32) and Fc. γ.RIII (CD16), so as to focus and localize cellular defense mechanisms to the TAT-expressing cell. Bispecific antibodies may also be used to localize cytotoxic agents to cells which express TAT. These antibodies possess a TAT-binding arm and an arm which binds the cytotoxic agent (e.g., saporin, anti-interferon-.alpha., vinca alkaloid, ricin A chain, methotrexate or radioactive isotope hapten). Bispecific antibodies can be prepared as full length antibodies or antibody fragments (e.g., F(ab')$_2$ bispecific antibodies).

Methods for making bispecific antibodies are known in the art. Traditional production of full length bispecific antibodies is based on the co-expression of two immunoglobulin heavy chain-light chain pairs, where the two chains have different specificities (Millstein et al., Nature 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J. 10:3655-3659 (1991).

According to a different approach, antibody variable domains with the desired binding specificities (antibody-antigen combining sites) are fused to immunoglobulin constant domain sequences. In certain embodiments, the fusion is with an Ig heavy chain constant domain, comprising at least part of the hinge, $C_{H2}$, and $C_{H3}$ regions. In certain embodiments, the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In certain embodiments, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology 121:210 (1986).

According to another approach described in U.S. Pat. No. 5,731,168, the interface between a pair of antibody molecules can be engineered to maximize the percentage of heterodimers which are recovered from recombinant cell culture. In certain embodiments, the interface comprises at least a part of the $C_{H3}$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science 229:81 (1985) describe a procedure wherein intact antibodies are proteolytically cleaved to generate F(ab').sub.2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives: One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med. 175: 217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets. Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a V.sub.H connected to a V.sub.L by a linker which is too short to allow pairing between the two domains on the same chain. Accordingly, the V.sub.H and V.sub.L domains of one fragment are forced to pair with the complementary V.sub.L and V.sub.H domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al., J. Immunol. 147:60 (1991).

7. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

8. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. In certain embodiments, the dimerization domain comprises (or consists of) an Fc region or a hinge region. In this scenario, the antibody will comprise an Fc region and three or more antigen binding sites amino-terminal to the Fc region. In certain embodiments, the multivalent antibody herein comprises (or consists of) three to about eight, but typically four, antigen binding sites. The multivalent antibody comprises at least one polypeptide chain (and typically two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (and typically four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

9. Effector Function Engineering

It may be desirable to modify the antibody of the invention with respect to effector function, e.g., so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

10. Immunoconjugates

The antagonist or antibody used in the methods herein is optionally conjugated to another agent, such as a cytotoxic agent, or cytokine.

Conjugation will ordinarily be achieved through a covalent linkage, the precise nature of which will be determined by the targeting molecule and the linking site on the integrin beta7 antagonist or antibody polypeptide. Typically, a non-peptidic agent is modified by the addition of a linker that allows conjugation to anti-beta7 integrin antibody through its amino acid side chains, carbohydrate chains, or reactive groups introduced on antibody by chemical modification. For example, a drug may be attached through the .epsilon.-amino group of a lysine residue, through a free .alpha.-amino group, by disulfide exchange to a cysteine residue, or by oxidation of the 1,2-diols in a carbohydrate chain with periodic acid to allow attachment of drugs containing various nucleophiles through a Schiff-base linkage. See, for example, U.S. Pat. No. 4,256,833. Protein modifying agents include amine-reactive reagents (e.g., reactive esters, isothiocyanates, aldehydes, and sulfonyl halides), thiol-reactive reagents (e.g., haloacetyl derivatives and maleimides), and carboxylic acid- and aldehyde-reactive reagents. Integrin beta7 antagonist or antibody polypeptides can be covalently joined to peptidic agents through the use of bifunctional cross-linking reagents. Heterobifunctional reagents are more commonly used and permit the controlled coupling of two different proteins through the use of two different reactive moieties (e.g., amine-reactive plus thiol, iodoacetamide, or maleimide). The use of such linking agents is well known in the art. See, for example, Brinkley, supra, and U.S. Pat. No. 4,671,958. Peptidic linkers can also be employed. In the alternative, an anti-beta7 integrin antibody polypeptide can be linked to a peptidic moiety through preparation of a fusion polypeptide.

Examples of further bifunctional protein coupling agents include N-succinimidyl-3-(2-pyridyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

11. Immunoliposomes

The anti-beta7 integrin antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA 82:3688 (1985); Hwang et al., Proc. Natl Acad. Sci. USA 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

Fab' fragments of the antibody of the present invention can be conjugated to the liposomes as described in Martin et al., J. Biol. Chem. 257:286-288 (1982) via a disulfide interchange reaction. A chemotherapeutic agent is optionally contained within the liposome. See Gabizon et al., J. National Cancer Inst. 81(19):1484 (1989).

12. Vectors, Host Cells and Recombinant Methods for Antibody Production

Also provided are isolated nucleic acids encoding the anti-beta7 antibodies or polypeptide agents described herein, vectors and host cells comprising the nucleic acids and recombinant techniques for the production of the antibodies.

For recombinant production of the antibody, the nucleic acid encoding it may be isolated and inserted into a replicable vector for further cloning (amplification of the DNA) or for expression. In another embodiment, the antibody may be produced by homologous recombination, e.g., as described in U.S. Pat. No. 5,204,244, specifically incorporated herein by reference. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence, e.g., as described in U.S. Pat. No. 5,534,615 issued Jul. 9, 1996 and specifically incorporated herein by reference.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-beta7 integrin antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated anti-Beta7 antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, *petunia*, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for anti-beta7 integrin antibody production and cultured in conventional nutrient media modified as appropriate for inducing promoters, selecting transformants, or amplifying the genes encoding the desired sequences.

The host cells used to produce the anti-beta7 integrin antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem.

1 02:255 (1980), U.S. Pat. Nos. 4,767,704; 4,657,866; 4,927,762; 4,560,655; or 5,122,469; WO 90/03430; WO 87/00195; or U.S. Patent Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology 10:163-167 (1992) describe a procedure for isolating antibodies which are secreted to the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the typical purification technique. The suitability of protein A as an affinity ligand depends on the species and isotype of any immunoglobulin Fc domain that is present in the antibody. Protein A can be used to purify antibodies that are based on human .gamma.1, .gamma.2, or .gamma.4 heavy chains (Lindmark et al., J. Immunol. Meth. 62:1-13 (1983)). Protein G is recommended for all mouse isotypes and for human .gamma.3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a C.sub.H3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered. Following any preliminary purification step(s), the mixture comprising the antibody of interest and contaminants may be subjected to low pH hydrophobic interaction chromatography using an elution buffer at a pH between about 2.5-4.5, typically performed at low salt concentrations (e.g., from about 0-0.25 M salt).

C. Pharmaceutical Formulations

Therapeutic formulations comprising the therapeutic agents, antagonists or antibodies of the invention are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, typically those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

D. Administration

The physician administering treatment will be able to determine the appropriate dose for the individual subject for weight-based dosing or, for flat dosing, will follow the instructions on the label. Preparation and dosing schedules for commercially available second therapeutic and other compounds administered in combination with the integrin beta7 antagonists may be used according to manufacturers' instructions or determined empirically by the skilled practitioner.

For the prevention or treatment of disease, the appropriate dosage of the integrin beta7 antagonist and any second therapeutic or other compound administered in combination with the non-depleting antibody will depend on the type of gastrointestinal inflammatory disorder to be treated, e.g., IBD, UC, CD, the severity and course of the disease, whether the integrin beta7 antagonist or combination is administered for preventive or therapeutic purposes, previous therapy, the patient's clinical history and response to the integrin beta7 antagonist or combination, and the discretion of the attending physician. The integrin beta7 antagonist or combination is suitably administered to the patient at one time or more typically over a series of treatments. In certain embodiments, the integrin beta7 antagonist is administered once every week, or once every two weeks, or once every four weeks, or once every six weeks, or once every eight weeks for a period of one month (4 weeks), or two months, three months, or six months, or 12 months, or 18 months, or 24 months, or chronically for the lifetime of the patient. In certain embodiments, the treatment is self-administered by the patient.

Depending on the type and severity of the disease, about 0.5 mg/kg to 4.0 mg/kg of anti-beta7 antibody is an initial candidate dosage for administration to the patient, whether, for example, by one or more separate administrations, or by continuous infusion. For repeated administrations over several days or longer, depending on the condition, the treatment is sustained until a desired suppression of disease symptoms occurs. However, other dosage regimens may be useful.

For example, in certain embodiments, a flat dose of anti-beta7 antibody is administered to the patient. A flat dose is a particular amount of anti-beta7 antibody that is administered to every patient regardless of weight. Depending on the type and severity of the disease, a flat dose of between about 50 mg and 450 mg of anti-beta7 antibody is administered to the patient, which may be one or more separate injections or infusions or administrations. Such flat dose can be administered intravenously or subcutaneously or by other routes as described herein. In certain embodiments, the flat dose is 50 mg, or 100 mg, or 105 mg, or 150 mg, or 200 mg, or 210 mg, or 300 mg, or 315 mg or 400 mg, or 420 mg, or 450 mg.

In certain embodiments, an initial flat loading dose of anti-beta7 antibody is followed by one or more flat maintenance doses of anti-beta7 antibody. The loading dose is a larger quantity of anti-beta7 antibody than the maintenance dose. In certain embodiments, the loading dose is between about 400 mg and 450 mg and the maintenance dose is between about 50 mg and 350 mg. In certain embodiments, the loading dose is 400 mg, or 420 mg, or 430 mg, or 450 mg. In certain embodiments, the maintenance dose is 50 mg, or 100 mg, or 105 mg, or 150 mg, or 200 mg, or 210 mg, or 300 mg, or 315 mg or 350 mg.

Typically, the clinician will administer an antibody (alone or in combination with a second compound) of the invention until a dosage(s) is reached that provides the required biological effect. The progress of the therapy of the invention is easily monitored by conventional techniques and assays.

The integrin beta7 antagonist can be administered by any suitable means, including parenteral, topical, intravenous, subcutaneous, intraperitoneal, intrapulmonary, intranasal, and/or intralesional administration. Parenteral infusions include intramuscular, intravenous, intraarterial, intraperitoneal, or subcutaneous administration. Intrathecal administration is also contemplated (see, e.g., U.S. Patent Publication No. 2002/0009444 by Grillo-Lopez). In addition, the integrin beta7 antagonist may suitably be administered by pulse infusion, e.g., with declining doses of the antibody. In certain embodiments, the dosing is given intravenously or subcutaneously. Each exposure may be provided using the same or a different administration means. In one embodiment, each exposure to anti-beta7 antibody is by subcutaneous administration. In one embodiment, the first exposure to anti-beta7 antibody, e.g., the loading dose, is by intravenous administration and each subsequent exposure is by subcutaneous administration.

In certain embodiments, an anti-beta7 antibody is administered using, for example, a self-inject device, autoinjector device, or other device designed for self-administration. Various self-inject devices, including autoinjector devices, are known in the art and are commercially available. Exemplary devices include, but are not limited to, prefilled syringes (such as BD HYPAK SCF®, READYFILL™, and STERIFILL SCF™ from Becton Dickinson; CLEAR-SHOT™ copolymer prefilled syringes from Baxter; and Daikyo Seiko CRYSTAL ZENITH® prefilled syringes available from West Pharmaceutical Services); disposable pen injection devices such as BD Pen from Becton Dickinson; ultra-sharp and microneedle devices (such as INJECT-EASE™ and microinfuser devices from Becton Dickinson; and H-PATCH™ available from Valeritas) as well as needle-free injection devices (such as BIOJECTOR® and IJECT® available from Bioject; and SOF-SERTER® and patch devices available from Medtronic). In certain embodiments, rhuMAb Beta7 is an article of manufacture comprising a prefilled syringe comprising 2 ML (150 mg) rhuMAb Beta7. In certain embodiments, rhuMAb Beta7 is an article of manufacture comprising a prefilled syringe comprising 1 ML (180 mg) rhuMAb Beta7.

As noted, the integrin beta7 antagonist can be administered alone or in combination with at least a second therapeutic compound. These second therapeutic compounds are generally used in the same dosages and with administration routes as used heretofore, or about from 1 to 99% of the heretofore-employed dosages. If such second compounds are used, they are used in certain embodiments in lower amounts than if the integrin beta7 antagonist were not present, so as to eliminate or reduce side effects caused thereby.

Also as noted (e.g., see below), a variety of suitable second therapeutic compounds for the treatment of IBD, e.g., ulcerative colitis and Crohn's disease are known in the art, and dosages and administration methods for such second therapeutic compounds have likewise been described.

Administration of the integrin beta7 antagonist and any second therapeutic compound can be done simultaneously, e.g., as a single composition or as two or more distinct compositions using the same or different administration routes. Alternatively, or additionally, the administration can be done sequentially, in any order. In certain embodiments, intervals ranging from minutes to days, to weeks to months, can be present between the administrations of the two or more compositions. For example, the integrin beta7 antagonist may be administered first, followed by the second therapeutic compound. However, simultaneous administration or administration of the second therapeutic compound prior to the integrin beta7 antagonist is also contemplated.

The standard of care for subjects with active moderate-severe active UC involves therapy with standard doses of: an aminosalicylate, an oral corticosteroid, 6-mercaptopurine (6-MP) and/or azathioprine. Therapy with an integrin beta7 antagonist, such as an anti-beta7 integrin antibody as disclosed herein will result in an improvement in disease remission (rapid control of disease and/or prolonged remission), and/or clinical response, superior to that achieved with the standard of care for such subjects.

In one embodiment, the treatment of the present invention for inflammatory bowel disease (IBD) in a human subject with 1BD comprises administering to the subject an effective amount of an therapeutic agent, such as an anti-beta7 integrin antibody, and further comprising administering to the subject an effective amount of a second medicament, that is an immunosuppressant, a pain-control agent, an antidiarrheal agent, an antibiotic, or a combination thereof.

In an exemplary embodiment, said secondary medicine is selected from the group consisting of an aminosalicylate, an oral corticosteroid, 6-mercaptopurine (6-MP) and azathioprine. In another exemplary embodiment, said secondary medicine is another integrin beta7 antagonist, such as another anti-beta7 integrin antibody or an antibody against a cytokine.

All these second medicaments may be used in combination with each other or by themselves with the first medicament, so that the expression "second medicament" as used herein does not mean it is the only medicament besides the first medicament, respectively. Thus, the second medicament need not be one medicament, but may constitute or comprise more than one such drug.

Combined administration herein includes co-administration, using separate formulations or a single pharmaceutical formulation, and consecutive administration in either order, wherein generally there is a time period while both (or all) active agents simultaneously exert their biological activities.

The combined administration of a second medicament includes co-administration (concurrent administration), using separate formulations or a single pharmaceutical formulation, and consecutive administration in either order, wherein generally there is a time period while both (or all) active agents (medicaments) simultaneously exert their biological activities.

E. Design Treatment Regimens

Drug development is a complex and expensive process. The cost of bringing a new drug to market is estimated to be between $800 million and $1 billion. Less than 10% of drugs in phase I clinical trials make it to the approval phase. Two key reasons why drugs fail at late stages are a lack of understanding of the relationship between dose-concentration response and unanticipated safety events. Given this scenario, it is important to have enabling tools that help predict how a drug will perform in vivo and assist in the success of a clinical therapeutic candidate (Lakshmi Kamath, Drug Discovery and Development; Modeling Success in PK/PD Testing Drug Discovery & Development (2006)).

Pharmacokinetics (PK) characterizes the absorption, distribution, metabolism, and elimination properties of a drug. Pharmacodynamics (PD) defines the physiological and biological response to the administered drug. PK/PD modeling establishes a mathematical and theoretical link between these two processes and helps better predict drug action. Integrated PK/PD modeling and computer-assisted trial design via simulation are being incorporated into many drug development programs and are having a growing impact (Lakshmi Kamath, Drug Discovery and Development; Modeling Success in PK/PD Testing Drug Discovery & Development (2006)).

PK/PD testing is typically performed at every stage of the drug development process. Because development is becoming increasingly complex, time consuming, and cost intensive, companies are looking to make better use of PK/PD data to eliminate flawed candidates at the beginning and identify those with the best chance of clinical success. (Lakshmi Kamath, supra).

PK/PD modeling approaches are proving useful in determining relationships between biomarker response, drug levels, and dosing regimens. The PK/PD profile of a drug candidate and the ability to predict a patient's response to it are critical to the success of clinical trials. Recent advances in molecular biology techniques and a better understanding of targets for various diseases have validated biomarkers as a good clinical indicator of a drug's therapeutic efficacy. Biomarker assays (including those described herein) and use of such biomarker assays help identify a biological response to a drug candidate. Once a biomarker is clinically validated, trial simulations can be effectively modeled. Biomarkers have the potential to achieve surrogate status that may someday substitute for clinical outcomes in drug development. (Lakshmi Kamath, supra).

The amount of biomarkers in the peripheral blood such as those described herein can be used in identifying the biological response to a treatment with integrin beta7 antagonists and can therefore function as a good clinical indicator for the therapeutic efficacy of a candidate treatment.

Traditional PK/PD modeling in drug development defines parameters such as drug dose concentration, drug exposure effects, drug half-life, drug concentrations against time, and drug effects against time. When used more broadly, quantitative techniques such as drug modeling, disease modeling, trial modeling, and market modeling can support the entire development process, which results in better decisions through explicit consideration of risk and better utilization of knowledge. A variety of PK/PD modeling tools are available to drug development researchers, for example, WinNonlin and the Knowledgebase Server (PKS) developed by Pharsight, Inc. Mountain View, Calif.

General Biomarker Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Primers, oligonucleotides and polynucleotides employed in the present invention can be generated using standard techniques known in the art.

Gene expression biomarkers associated with predicting responsiveness of IBD patients including patient suffering from UC or Crohn's disease to certain therapeutic agents are provided herein. These expression levels of the mRNA or individual proteins encoded by the genes constitute biomarkers for predicting responsiveness to IBD therapeutic agents, UC therapeutic agents, and/or Crohn's disease therapeutic agents. Accordingly, the invention disclosed herein is useful in a variety of settings, e.g., in methods and compositions related to diagnosis and therapy of inflammatory bowel diseases.

Detection of Gene Expression Levels

Nucleic acid, according to any of the methods described herein may be RNA transcribed from genomic DNA or cDNA generated from RNA or mRNA. Nucleic acid may be derived from a vertebrate, e.g., a mammal. A nucleic acid is said to be "derived from" a particular source if it is obtained directly from that source or if it is a copy of a nucleic acid found in that source.

Nucleic acid includes copies of the nucleic acid, e.g., copies that result from amplification. Amplification may be desirable in certain instances, e.g., in order to obtain a desired amount of material for detecting variations. The amplicons may then be subjected to a variation detection method, such as those described below, to determine expression of certain genes.

Levels of mRNA may be measured and quantified by various methods well-known to those skilled in the art, including use of commercially available kits and reagents. One such method is polymerase chain reaction (PCR). Another method, for quantitative use, is real-time quantitative PCR, or qPCR. See, e.g., "PCR Protocols, A Guide to Methods and Applications," (M. A. Innis et al., eds., Academic Press, Inc., 1990); "Current Protocols in Molecular Biology" (F. M. Ausubel et al., eds., 1987, and periodic updates); and "PCR: The Polymerase Chain Reaction", (Mullis et al., eds., 1994).

A microarray is a multiplex technology that typically uses an arrayed series of thousands of nucleic acid probes to hybridize with, e.g., a cDNA or cRNA sample under high-stringency conditions. Probe-target hybridization is typically detected and quantified by detection of fluorophore-, silver-, or chemiluminescence-labeled targets to determine relative abundance of nucleic acid sequences in the target. In typical microarrays, the probes are attached to a solid surface by a covalent bond to a chemical matrix (via epoxy-silane, amino-silane, lysine, polyacrylamide or others). The solid surface is for example, glass, a silicon chip, or microscopic beads. Various microarrays are commercially available, including those manufactured, for example, by Affymetrix, Inc. and Illumina, Inc.

A biological sample may be obtained using certain methods known to those skilled in the art. Biological samples may be obtained from vertebrate animals, and in particular, mammals. In certain instances, a biological sample is synovial tissue, serum or peripheral blood mononuclear cells (PBMC). By screening such body samples, a simple early diagnosis can be achieved for diseases such as ulcerative colitis and Crohn's disease. In addition, the progress of therapy can be monitored more easily by testing such body samples for variations in expression levels of target nucleic acids (or encoded polypeptides).

Subsequent to the determination that a subject, or the tissue or cell sample comprises a gene expression signature or relative levels of certain biomarkers disclosed herein, it is contemplated that an effective amount of an appropriate therapeutic agent may be administered to the subject to treat the particular disease in the subject, e.g., UC or Crohn's disease. Clinical diagnosis in mammals of the various pathological conditions described herein can be made by the skilled practitioner. Clinical diagnostic techniques are available in the art which allow, e.g., for the diagnosis or detection of inflammatory bowel diseases in a mammal, e.g., ulcerative colitis and Crohn's disease.

Kits

For use in the applications described or suggested herein, kits or articles of manufacture are also provided. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be a polynucleotide specific for a polynucleotide comprising one or more genes of a gene expression signature. Where the kit utilizes nucleic acid hybridization to detect the target nucleic acid, the kit may also have containers containing nucleotide(s) for amplification of the target nucleic acid sequence and/or a container comprising a reporter means, such as a biotin-binding protein, such as avidin or streptavidin, bound to a reporter molecule, such as an enzymatic, florescent, or radioisotope label.

Kits will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above. Other optional components in the kit include one or more buffers (e.g., block buffer, wash buffer, substrate buffer, and the like), other reagents such as substrate (e.g., chromogen) which is chemically altered by an enzymatic label, epitope retrieval solution, control samples (positive and/or negative controls), control slide(s) etc.

Methods of Marketing

The invention herein also encompasses a method for marketing a therapeutic agent or a pharmaceutically acceptable composition thereof comprising promoting to, instructing, and/or specifying to a target audience, the use of the agent or pharmaceutical composition thereof for treating a patient or patient population with a particular disease, e.g., UC or Crohn's disease, from which a sample has been obtained showing a gene expression signature or levels of serum biomarkers as disclosed herein.

Marketing is generally paid communication through a non-personal medium in which the sponsor is identified and the message is controlled. Marketing for purposes herein includes publicity, public relations, product placement, sponsorship, underwriting, and sales promotion. This term also includes sponsored informational public notices appearing in any of the print communications media designed to appeal to a mass audience to persuade, inform, promote, motivate, or otherwise modify behavior toward a favorable pattern of purchasing, supporting, or approving the invention herein.

The marketing of the diagnostic method herein may be accomplished by any means. Examples of marketing media used to deliver these messages include television, radio, movies, magazines, newspapers, the internet, and billboards, including commercials, which are messages appearing in the broadcast media.

The type of marketing used will depend on many factors, for example, on the nature of the target audience to be reached, e.g., hospitals, insurance companies, clinics, doctors, nurses, and patients, as well as cost considerations and the relevant jurisdictional laws and regulations governing marketing of medicaments and diagnostics. The marketing may be individualized or customized based on user characterizations defined by service interaction and/or other data such as user demographics and geographical location.

The foregoing written specification and following examples are considered to be sufficient to enable one skilled in the art to practice the invention. Various modifications of the invention in addition to those shown and described herein will become apparent to those skilled in the art from the foregoing description and following examples and fall within the scope of the appended claims.

It is understood that the application of the teachings of the present invention to a specific problem or situation will be within the capabilities of one having ordinary skill in the art in light of the teachings contained herein.

Further details of the invention are illustrated by the following non-limiting Examples. The disclosures of all citations in the specification are expressly incorporated herein by reference.

EXAMPLES

Example 1

Phase II Randomized Double-Blind Placebo-Controlled Study to Evaluate the Efficacy and Safety of RhuMAb Beta7 (Etrolizumab) in Patients with Moderate to Severe Ulcerative Colitis and Open Label Extension Study Description of the Clinical Study
Description of rhuMAb Beta7 (Etrolizumab)

RhuMAb Beta7 (etrolizumab) is a humanized monoclonal antibody based on the human IgG1 subgroup III $V_H$, κ subgroup-I $V_L$ consensus sequences and is directed specifically against the β7 subunit of the integrin heterodimer. See FIGS. 1A and B. It has been shown to bind with high affinity to α4β7 ($K_d$ of about 116 pM) and αEβ7 ($K_d$ of about 1800 pM).

This recombinant antibody has two heavy chains (446 residues) and two light chains (214 residues) that are covalently linked by interchain and intrachain disulfide bonds typical of IgG1 antibodies. For the work described herein, it was produced in Chinese hamster ovary (CHO) cells. The molecular mass of the intact, non glycosylated rhuMAb Beta7 molecule was approximately 144 kDa. Each heavy chain of rhuMAb Beta7 has one conserved N linked glycosylation site at Asn297. The oligosaccharides present at this site were typical of those observed in recombinant antibodies expressed in CHO cells, with the predominant glycoforms being the asialo, biantennary G0, and G1 glycans. The mass of the most prevalent rhuMAb Beta7 form containing two G0 glycans and no C terminal lysine residues was approximately 147 kDa.

RhuMAb Beta7 drug product and placebo were prepared by Genentech. They were clear to slightly opalescent, colorless to slightly yellow aqueous solutions. Both solutions were sterile and preservative-free liquid intended for IV and SC administration.

Study Design
Description of the Study

This Phase II study was a randomized, double-blind, placebo-controlled multicenter study to evaluate the efficacy and safety across two rhuMAb Beta7 dose levels compared with placebo in patients with moderate to severe UC. The primary efficacy endpoint was evaluated at Week 10 (2 weeks after the final dose of study drug was administered) with a secondary efficacy endpoint at Week 6.

Patients were randomized in a 1:1:1 ratio across a dose range of rhuMAb Beta7 100 mg SC (flat dose) at Weeks 0, 4, and 8 and 420 mg SC (flat loading dose) at Week 0 followed by 300 mg SC at Weeks 2, 4, and 8 or matching placebo SC. The study schema is shown in FIG. 2. The study was divided into a screening period of 0-35 days, a double-blind treatment period of 10 weeks, a safety follow-up period of 18 weeks, and a progressive multifocal leukoencephalopathy (PML) follow up period of 17 months (2 years after randomization).

The dose values provided in the preceding paragraph are nominal doses. The phase II dose administration used a vial and a syringe with a vial concentration of 150 mg/ml. To enable consistent accurate dose administration, 0.7 ml was the selected volume per subcutaneous (SC) injection. The actual drug amount therefore, for the nominal 100 mg dose arm was 105 mg (1×0.7 ml SC injection) and for the nominal 300 mg dose was 315 mg (3×0.7 ml SC injections). The actual loading dose of 420 mg was 420 mg (4×0.7 ml SC injections). All SC injections were administered into the abdomen. Accordingly, a dose of "100 mg" and a dose of "105 mg" are used interchangeably herein. In addition, a dose of "300 mg" and a dose of "315 mg" are used interchangeably herein. Finally, in certain instances herein, the arm of the trial in which patients received "300 mg plus loading dose (LD)" is referred to as "300 mg dose" as a short-hand and for convenience. Accordingly, unless it is clear from the context otherwise, "300 mg plus loading dose" is equivalent to "300 mg dose".

To be eligible, patients must have had a minimum of a 12-week duration of UC diagnosed according to the American College of Gastroenterology (ACG) practice guidelines; that is, clinical and endoscopic evidence corroborated by a histopathology report, with evidence of moderate to severe disease as evidenced by, in certain instances an MCS of ≥5, or in certain instances, an MCS of ≥6, including an endoscopy subscore of ≥2; a rectal bleeding subscore of ≥1 (see Table 1); and endoscopic evidence of disease activity a minimum of 25 cm from the anal verge. Additional inclusion and exclusion criteria for this study are provided in Intn'l Patent Pub. No. WO/2012/135589.

TABLE 1

Mayo Clinic Scoring System for Assessment of Ulcerative Colitis Activity.

| | Assessment Category | | | |
|---|---|---|---|---|
| Score | Stool frequency[a] | Rectal bleeding[b] | Findings on Endoscopy | Physician's global assessment[c] |
| 0 | normal no. of stools for this patient | no blood seen | normal or inactive disease | normal |
| 1 | 1 to 2 stools more than normal | streaks of blood with stool less than half the time | mild disease (erythema, decreased vascular pattern, mild friability) | mild disease |
| 2 | 3 to 4 stools more than normal | obvious blood with stool most of the time | moderate disease (marked erythema, lack of vascular pattern, friability, erosions) | moderate disease |
| 3 | 5 or more stools more than normal | blood alone passes | severe disease (spontaneous bleeding, ulceration) | severe disease |
| | sub score: 0 to 3 | sub score: 0 to 3 | sub score: 0 to 3 | sub score: 0 to 3 |

[a]Each patient serves as his or her own control to establish the degree of abnormality of the stool frequency.
[b]The daily bleeding score represents the most severe bleeding of the day.
[c]The physician's global assessment acknowledges the three other criteria, the patient's daily recollection of abdominal discomfort and general sense of well-being, and other observations, such as physical findings and the patient's performance status.

Prior to randomization, patients must have been on stable doses of concomitant medications for UC. Oral 5-aminosalicylic acid (5-ASA) and immunosuppressant (azathioprine [AZA], 6-mercaptopurine [6-MP], or methotrexate) doses must have been kept stable for at least 4 weeks prior to randomization on Day 1. Patients who were receiving topical 5-ASA or corticosteroids must have discontinued 2 weeks before randomization on Day 1. Oral corticosteroid doses must have been kept stable for 2 weeks prior to randomization on Day 1. Patients receiving high-dose steroids must have had the dose reduced to ≤20 mg/day for 2 weeks prior to randomization on Day 1. For patients receiving oral corticosteroids during the study treatment period, tapering of steroids must have been commenced at Week 10 at a rate of a 5-mg prednisone or prednisone equivalent per week for 2 weeks and then at a rate of 2.5 mg prednisone or prednisone equivalent per week to discontinuation. For patients receiving oral immunosuppressants (other than oral corticosteroids), tapering of immunosuppressants must have been commenced at Week 8, and patients must have completely discontinued immunosuppressants by Week 10. Patients who have previously received anti-TNF therapy must have discontinued therapy for a minimum of 8 weeks prior to randomization to receive study drug on Day 1. If patients experienced persisting or increasing disease activity at any time during the study, rescue therapy in the form of an increase in steroids and or immunosuppressant dose may be increased or initiated according to the investigator's clinical judgment. Patients who required rescue therapy were permitted to remain in the study but discontinued study treatment and, during data analysis, were classified as having experienced treatment failure.

Patients were assessed to determine whether they failed to respond to conventional therapy, including at least one anti-TNF agent. As used herein, loss of response and/or intolerance to anti-TNF agents and immunosuppressants means the following. With respect to anti-TNF agents, loss of response and/or intolerance means that symptoms of active disease persist despite previous treatment with one or more of (a) infliximab: 5 mg/kg IV, 3 doses over 6 weeks with assessment at 8 weeks; (b) adalimumab: one 160-mg SC does at week 0, followed by one 80-mg dose at week 2 and then 40 mg at 4 and 6 weeks, with assessment at 8 weeks; or recurrent active symptoms during regularly scheduled maintenance dosing following a previous response (elective discontinuation of treatment by patient who has responded and did not lose response does not qualify); or history of intolerance to at least one ant-TNF antibody (including but not exclusive of or limited to infusion-related reaction or injection-site reaction, infection, congestive heart failure, demyelination). With respect to immunosuppressant agents, loss of response and/or intolerance means that symptoms of active disease persist despite previous treatment with one or more of azathioprine (≥1.5 mg/kg) or equivalent dose of 6-mercaptopurine mg/kg (≥0.75 mg/kg) or methotrexate, 25 mg SC/intramuscular (or as indicated) per week for at least 8 weeks; or history of intolerance of at least one immunosuppressive (including, but not exclusive of pancreatitis, drug fever, rash, nausea/vomiting, liver function test elevation, thiopurine S-methyltransferase genetic mutation, infection).

Randomization to study treatment were stratified by concomitant treatment with corticosteroids (yes/no), concomitant treatment with immunosuppressants (yes/no), previous anti-TNF exposure (yes/no) (except for patients randomized in the United States), and study site.

UC disease activity was assessed using the MCS at Screening (and this was considered the baseline MCS), Week 6 (2 weeks after dosing at Week 4), and Week 10 (2 weeks after the final dose of study drug). Biopsies of the colon were obtained during the flexible sigmoidoscopy conducted at these same time points. Partial MCS was also collected throughout the study. Patient Reported Outcomes (PROs) were also assessed by using a Short Inflammatory Bowel Disease Questionnaire (SIBDQ) and MCS, which were to be completed by patients at Day 1 and at Weeks 6 and 10. In addition, disease activity, daily symptoms, and impact of UC were collected in a patient diary, to be completed daily by patients from screening (approximately 7 days prior to and up to Day 1) and at least 7 days prior to and up to the study visits at Weeks 6 and 10. Serum and fecal samples were also obtained for biomarker analysis. Stool was obtained at screening and Weeks 6, 10, and 28 for measurement of biomarkers. Exemplary biomarkers that were considered for measurement include, but are not limited to, lipocalin, calprotectin, and lactorferrin. Serum and plasma were obtained at screening, at Day 1, and at Weeks 4, 6, 10, 16, and 28 for measurement of exploratory biomarkers.

The primary efficacy endpoint for this study was the proportion of patients who achieved clinical remission, defined as an absolute reduction in MCS to ≤2 with no individual subscore exceeding 1 point, by Week 10. Additional secondary endpoints are listed in the study outcome measures as described below.

Outcome Measures

Primary Efficacy Outcome Measure

The primary efficacy outcome measure was clinical remission at Week 10. Clinical remission is defined by an MCS ≤2 with no individual subscore exceeding 1 point (see Table 1).

Secondary Efficacy Outcome Measures

The secondary efficacy outcome measures for this study were (1) Clinical response at Week 6 and Week 10 where clinical response was defined by at least a 3-point decrease and 30% reduction from baseline in MCS and a ≥1-point decrease in rectal bleeding subscore or absolute rectal bleeding score of 0 or 1; (2) Clinical remission (defined above) at Week 6; and (3) An indicator for endoscopic score and rectal bleeding score of 0 at Week 6 and Week 10.

Exploratory Outcome Measures

The exploratory outcome measure for this study were the time to flare of UC in patients who achieved response or remission. For this outcome measure, a flare is defined as a 2 point increase in partial MCS accompanied by 3 days of continuous rectal bleeding and an endoscopy score of 2 on flexible sigmoidoscopy.

Safety Outcome Measures

The safety and tolerability of rhuMAb Beta7 were assessed using the following measures: (1) Incidence of adverse events and serious adverse events graded according to National Cancer Institute Common Terminology Criteria for Adverse Events (NCI CTCAE) Version 4.0; (2) Clinically significant changes in vital signs and safety laboratory measures; (3) Discontinuation due to adverse event(s); (4) Incidence and nature of injection-site reactions and hypersensitivity; (5) Incidence of infectious complications; and (6) Immunogenicity as measured by the incidence of ATAs.

Pharmacokinetic Outcome Measures

The pharmacokinetic outcome measures included the following: (1) $C_{max}$ after the first and final doses; (2) Time to maximum concentration ($T_{max}$) after the first and final doses; (3) Area under the serum concentration-time curve (AUC) within a dose interval after the final dose; (4) AUC from time 0 to time of the last detectable observation ($AUC_{last}$) or to infinity ($AUC_{inf}$); (5) Apparent clearance (CL/F); (6) Apparent volume of distribution (V/F); and (7) Elimination half-life ($t_{1/2}$).

Example 2—Predictive Biomarker Studies and Analyses

Experimental Design for Selection of Predictive Biomarkers for Enrichment of Efficacy in Patients Treated with Etrolizumab To identify novel biomarkers predictive of response to etrolizumab treatment, we first used RNA sequencing methods to establish baseline gene expression profiles of colonic biopsies from all etrolizumab treated patients. Baseline biopsies from TNF antagonist naïve etrolizumab treated patients were used to identify differential gene expression profiles between etrolizumab-treated patients who underwent remission and etrolizumab-treated patients who did not undergo remission. Differentially expressed genes were further selected based on strength of signal, biological relevance, and expression in other IBD datasets and then further assessed using quantitative polymerase chain reaction in colonic biopsies from etrolizuamb-treated patients and placebo for subgroup analyses.

Collection and Processing of Intestinal Biopsy Tissue

Intestinal biopsies were collected from study participants during flexible sigmoidoscopy/full colonoscopy at the screening visit (up to 4 weeks prior to treatment) and at weeks 6 and 10 after start of etrolizumab treatment. Biopsies were taken from the most inflamed area of the colon within 10-40 cm of the anal verge. Biopsies within necrotic areas of ulcerated mucosa or at suture sites in patients with prior colonic resection were avoided. Biopsies were placed into a tissue RNA stabilizing buffer (RNAlater, Qiagen, Cat. No. 76104) and frozen for shipment or they were placed into formalin for storage and subsequent processing.

RNA Isolation and Sequencing

Upon receipt, the biopsy samples were thawed and homogenized with 3 mm steel beads using a TissueLyzer (Qiagen, Cat. No. 69989) and RNA was isolated using the RNeasy Mini kit (Qiagen, Cat. No. 74106) according to manufacturer's instructions. RNA integrity was assessed with the Agilent 2100 Bioanalyzer using the Agilent RNA 6000 Pico Kit (Agilent Technologies, Cat. No. 5067-1513). Samples with low RNA quality (RIN≤5) were excluded from analysis. RNA was quantitated using the Quant-iT™ RNA Assay Kit (Life Technologies Corporation, Carlsbad, Calif., USA).

High quality total RNA (250 ng) was input into the Illumina TruSeq RNA Sample Preparation Kit v2 protocol and run in conjunction with Beckman Coulter Life Sciences' Biomek liquid handling platforms. RNA libraries were evaluated using the Agilent 2200 TapeStation High Sensitivity D1K Tape and qPCR with the KAPA Library Quantification Kit for Illumina Sequencing. 2 nM of library (12 samples per lane) was loaded for cluster generation and sequenced on the Illumina HiSeq2000 Sequencing System at 2×50 bp read length plus index read. Passing filter reads were determined and fastq files generated by Illumina CASAVA v1.8.

Identification of Differentially Expressed Genes

Processing and analysis of the RNA-sequencing data was performed using the R programming language (http://www.r-project.org) along with packages from the Bioconductor project (http://bioconductor.org). Raw RNA-sequencing reads were processed using the HTSeqGenie Bioconductor package. Briefly, reads were aligned to the reference human genome sequence (NCBI build 37) using the GSNAP algorithm (Wu, T. D. et al., Bioinformatics (Oxford, England) 26, 873-881 (2010)). Uniquely aligned read pairs that fell within exons were counted to give an estimate of expression levels for individual genes.

To calculate differential expression, we used the DESeq2 Bioconductor package (Anders et al., Genome Biology (2010) vol. 11 (10) pp. R106), which fits a negative binomial generalized linear model to determine the log fold change and p-value for differences between groups. We used the default library size estimation method from this package to account for differences in sequencing depth between individuals. Our final analysis only included samples from TNF-naïve patients. The final generalized model included whether a patient was in remission at week 10, and covariates for technical aspects of the sequencing reactions (sequencing plate and lane), and the endoscopic sub score of the Mayo clinical score. For our statistical analysis, we used the nominal (non-multiple test corrected) p-values to rank candidate genes associated with remission.

Gene Expression Analysis by Quantitative Polymerase Chain Reaction

RNA isolated from RNAlater® biopsies as described above was reverse transcribed into complementary deoxyribonucleic acid using the High-Capacity cDNA Reverse Transcription Kit (Life Technologies Corporation, Carlsbad, Calif., USA). Gene expression levels were assessed by real-time polymerase chain reaction, also referred to as quantitative polymerase chain reaction. Real-time polymerase chain reactions were run on the BioMark™ HD System (Fluidigm Corporation, South San Francisco, Calif., USA) with TaqMan PreAmp Master Mix (Life Technologies Corporation, Carlsbad, Calif., USA) and reagents (Fluidigm) using Taqman Gene Expression assays of respective genes (all from Life Technologies Corporation, Carlsbad, Calif., USA) according to manufacturer's instructions. Target gene expression was normalized to GAPDH expression using the ΔCt method.

Statistical Analysis

Statistical testing was performed using the Wilcoxon rank-sum test or the Fisher exact test as appropriate. No adjustments for multiple comparisons were performed. Subgroup analyses using the sample median cutoff were performed for selected genes. The longitudinal stability of gene expression was evaluated in patients who received placebo, where concordance rate of biomarker-low or biomarker-high categorization was determined from samples measured from the same patient at baseline, week 6 and week 10. Intrapatient variability was also assessed by calculating the standard deviations of samples from the same patient at baseline, week 6 and week 10.

Results

Following the methods and analyses described above, RNA sequence reads were used to identify differentially expressed genes between patients who underwent remission following etrolizumab treatment compared to patients who did not undergo remission following etrolizumab treatment. These results are summarized in Tables 2 and 3 below. Table 2 shows differentially expressed genes with high baseline expression associated with non-remission following treatment with etrolizumab. Table 3 shows differentially expressed genes with high baseline expression associated with remission following treatment with etrolizumab. As stated above, differentially expressed genes were identified in baseline colonic biopsies obtained from TNF antagonist naïve patients. A generalized linear model that accounted for race/ethnicity, sex, technical batches and baseline endoscopy score was used to control for additional baseline variables.

TABLE 2

High Baseline Gene Expression Associated with Non-Remission Following Etrolizumab Treatment.

| Symbol | Gene Name | Log2 Fold Change | p-Value |
|---|---|---|---|
| VNN2 | vanin 2 | −0.922 | 1.96E−05 |
| SSTR2 | somatostatin receptor 2 | −0.89 | 3.93E−05 |
| VNN3 | vanin 3 | −0.802 | 2.81E−04 |
| LRRC4 | leucine rich repeat containing 4 | −0.786 | 2.33E−04 |
| REM2 | RAS (RAD and GEM)-like GTP binding 2 | −0.745 | 7.91E−04 |
| CCL4L1 | chemokine (C-C motif) ligand 4-like 1 | −0.739 | 8.28E−04 |
| TM4SF4 | transmembrane 4 L six family member 4 | −0.732 | 4.87E−04 |
| HTR1B | 5-hydroxytryptamine (serotonin) receptor 1B, G protein-coupled | −0.706 | 1.24E−03 |
| CCL4L2 | chemokine (C-C motif) ligand 4-like 2 | −0.673 | 1.31E−03 |
| SLC8A3 | solute carrier family 8 (sodium/calcium exchanger), member 3 | −0.669 | 2.44E−03 |
| CPA3 | carboxypeptidase A3 (mast cell) | −0.66 | 2.05E−03 |
| CCL3 | chemokine (C-C motif) ligand 3 | −0.657 | 2.88E−03 |
| IL1A | interleukin 1, alpha | −0.655 | 2.78E−03 |
| SIGLECP3 | sialic acid binding Ig-like lectin 17, pseudogene | −0.654 | 1.86E−03 |
| ALPK3 | alpha-kinase 3 | −0.652 | 3.13E−03 |
| MLK7-AS1 | MLK7 antisense RNA 1 (non-protein coding) | −0.649 | 2.43E−04 |
| NCF1B | neutrophil cytosolic factor 1B pseudogene | −0.649 | 3.39E−03 |
| MIR146A | microRNA 146a | −0.647 | 2.79E−03 |
| C17orf107 | chromosome 17 open reading frame 107 | −0.643 | 1.79E−03 |
| GALNTL6 | UDP-N-acetyl-alpha-D-galactosamine: polypeptide N-acetylgalactosaminyltransferase-like 6 | −0.642 | 2.40E−03 |
| LOC100506801 | uncharacterized LOC100506801 | −0.642 | 3.38E−03 |
| ERV3-1 | endogenous retrovirus group 3, member 1 | −0.64 | 1.94E−03 |
| CHRNE | cholinergic receptor, nicotinic, epsilon (muscle) | −0.637 | 1.96E−03 |
| TMEM154 | transmembrane protein 154 | −0.636 | 2.12E−03 |
| TNFSF15 | tumor necrosis factor (ligand) superfamily, member 15 | −0.635 | 2.15E−03 |
| C17orf103 | chromosome 17 open reading frame 103 | −0.635 | 2.96E−03 |
| QPCT | glutaminyl-peptide cyclotransferase | −0.633 | 1.65E−04 |
| LOC100507417 | uncharacterized LOC100507417 | −0.628 | 5.96E−03 |
| ZNF697 | zinc finger protein 697 | −0.622 | 7.64E−04 |
| DPEP2 | dipeptidase 2 | −0.622 | 1.94E−03 |
| ADCYAP1 | adenylate cyclase activating polypeptide 1 (pituitary) | −0.614 | 3.54E−03 |
| MUCL1 | mucin-like 1 | −0.582 | 3.22E−03 |

TABLE 2-continued

High Baseline Gene Expression Associated with Non-Remission Following Etrolizumab Treatment.

| Symbol | Gene Name | Log2 Fold Change | p-Value |
|---|---|---|---|
| HAMP | hepcidin antimicrobial peptide | −0.582 | 3.81E−03 |
| CCL3L3 | chemokine (C-C motif) ligand 3-like 3 | −0.576 | 1.97E−03 |
| NINL | ninein-like | −0.529 | 3.79E−03 |
| AGA | aspartylglucosaminidase | −0.472 | 9.12E−06 |
| CTBS | chitobiase, di-N-acetyl- | −0.444 | 3.20E−04 |
| EHD1 | EH-domain containing 1 | −0.442 | 3.69E−03 |
| LMO4 | LIM domain only 4 | −0.422 | 2.96E−03 |
| TMEM120B | transmembrane protein 120B | −0.389 | 2.30E−03 |
| NBEAL2 | neurobeachin-like 2 | −0.365 | 2.55E−03 |
| DNASE1L1 | deoxyribonuclease I-like 1 | −0.322 | 1.32E−04 |
| UROS | uroporphyrinogen III synthase | −0.321 | 1.32E−03 |

TABLE 3

High Baseline Gene Expression Associated with Remission Following Etrolizumab Treatment.

| Symbol | Gene Name | Log2 Fold Change | p-Value |
|---|---|---|---|
| TMEM200A | transmembrane protein 200A | 0.804 | 1.51E−04 |
| GZMA | granzyme A (granzyme 1, cytotoxic T-lymphocyte-associated serine esterase 3) | 0.789 | 1.11E−04 |
| LOC728643 | heterogeneous nuclear ribonucleoprotein A1 pseudogene | 0.747 | 6.18E−04 |
| LINC00514 | long intergenic non-protein coding RNA 514 | 0.696 | 1.07E−03 |
| CPA2 | carboxypeptidase A2 (pancreatic) | 0.67 | 4.81E−04 |
| MT1M | metallothionein 1M | 0.652 | 2.69E−03 |
| BEST2 | bestrophin 2 | 0.636 | 3.26E−03 |
| HIST1H1B | histone cluster 1, H1b | 0.626 | 3.49E−03 |
| C17orf53 | chromosome 17 open reading frame 53 | 0.611 | 5.63E−04 |
| ACTL8 | actin-like 8 | 0.596 | 3.49E−03 |
| SKA1 | spindle and kinetochore associated complex subunit 1 | 0.582 | 2.13E−03 |
| FOXM1 | forkhead box M1 | 0.578 | 2.13E−04 |
| ATP6V0E2 | ATPase, H+ transporting V0 subunit e2 | 0.573 | 3.32E−04 |
| TIFAB | TRAF-interacting protein with forkhead-associated domain, family member B | 0.555 | 1.84E−03 |
| KIF18B | kinesin family member 18B | 0.543 | 1.27E−03 |
| CENPM | centromere protein M | 0.543 | 2.33E−03 |
| KLRB1 | killer cell lectin-like receptor subfamily B, member 1 | 0.535 | 1.16E−03 |
| BUB1 | budding uninhibited by benzimidazoles 1 homolog (yeast) | 0.534 | 1.87E−03 |
| PLK1 | polo-like kinase 1 | 0.53 | 1.22E−03 |
| PMCH | pro-melanin-concentrating hormone | 0.528 | 1.47E−03 |
| CCNB2 | cyclin B2 | 0.519 | 2.92E−03 |
| ARHGAP11A | Rho GTPase activating protein 11A | 0.511 | 6.44E−04 |
| DIAPH3 | diaphanous homolog 3 (Drosophila) | 0.51 | 3.72E−03 |
| CDC20 | cell division cycle 20 homolog (S. cerevisiae) | 0.505 | 2.75E−03 |
| KIF4A | kinesin family member 4A | 0.486 | 3.40E−03 |
| LOC643733 | caspase 4, apoptosis-related cysteine peptidase pseudogene | 0.484 | 5.23E−04 |
| KIF23 | kinesin family member 23 | 0.482 | 2.48E−03 |
| RNASEH2A | ribonuclease H2, subunit A | 0.477 | 2.29E−04 |
| CDK1 | cyclin-dependent kinase 1 | 0.461 | 3.87E−03 |
| BUB1B | budding uninhibited by benzimidazoles 1 homolog beta (yeast) | 0.458 | 3.60E−03 |
| LOC100507424 | uncharacterized LOC100507424 | 0.456 | 2.69E−03 |
| CXCR6 | chemokine (C-X-C motif) receptor 6 | 0.455 | 9.94E−04 |
| PSRC1 | proline/serine-rich coiled-coil 1 | 0.451 | 2.59E−03 |
| LOC100507591 | uncharacterized LOC100507591 | 0.451 | 3.58E−03 |
| ECH1 | enoyl CoA hydratase 1, peroxisomal | 0.44 | 3.40E−03 |
| SUV39H1 | suppressor of variegation 3-9 homolog 1 (Drosophila) | 0.438 | 3.68E−03 |
| KCNMA1 | potassium large conductance calcium-activated channel, subfamily M, alpha member 1 | 0.437 | 1.31E−03 |
| NUDT1 | nudix (nucleoside diphosphate linked moiety X)-type motif 1 | 0.436 | 1.66E−03 |
| FAM54A | family with sequence similarity 54, member A | 0.433 | 2.09E−03 |
| WDR62 | WD repeat domain 62 | 0.433 | 3.39E−03 |
| DTYMK | deoxythymidylate kinase (thymidylate kinase) | 0.424 | 2.79E−03 |

TABLE 3-continued

High Baseline Gene Expression Associated with Remission Following Etrolizumab Treatment.

| Symbol | Gene Name | Log2 Fold Change | p-Value |
|---|---|---|---|
| CHAF1A | chromatin assembly factor 1, subunit A (p150) | 0.391 | 2.62E−03 |
| ITGAE | integrin, alpha E (antigen CD103, human mucosal lymphocyte antigen 1; alpha polypeptide) | 0.386 | 3.37E−04 |
| DBF4 | DBF4 homolog (S. cerevisiae) | 0.368 | 2.80E−03 |
| PPIH | peptidylprolyl isomerase H (cyclophilin H) | 0.36 | 2.78E−03 |
| POLD1 | polymerase (DNA directed), delta 1, catalytic subunit | 0.332 | 1.65E−03 |
| PDCL3 | phosducin-like 3 | 0.321 | 1.03E−03 |
| CCDC90A | coiled-coil domain containing 90A | 0.3 | 1.96E−03 |
| PHF14 | PHD finger protein 14 | 0.3 | 3.69E−03 |
| SAE1 | SUMO1 activating enzyme subunit 1 | 0.292 | 2.91E−04 |
| RUVBL2 | RuvB-like 2 (E. coli) | 0.291 | 4.30E−04 |
| RPP30 | ribonuclease P/MRP 30 kDa subunit | 0.281 | 3.74E−03 |
| MAD1L1 | MAD1 mitotic arrest deficient-like 1 (yeast) | 0.275 | 1.97E−03 |
| PTMA | prothymosin, alpha | 0.268 | 2.23E−03 |
| SNRPA | small nuclear ribonucleoprotein polypeptide A | 0.265 | 1.52E−03 |
| ERCC3 | excision repair cross-complementing rodent repair deficiency, complementation group 3 | 0.171 | 2.21E−03 |
| HNRNPUL1 | heterogeneous nuclear ribonucleoprotein U-like 1 | 0.162 | 1.66E−03 |

Figure 5:
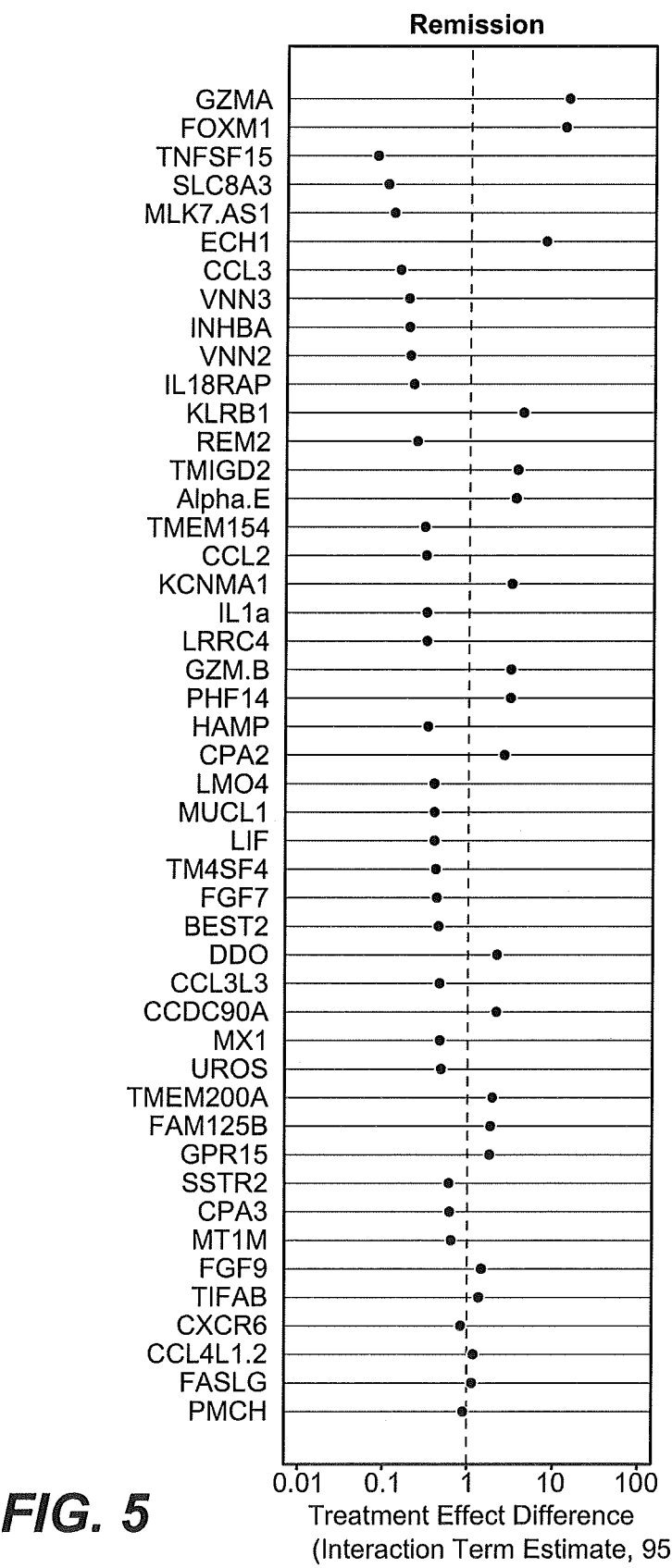
FIG. 5 shows odds ratios of the indicated differentially expressed genes as measured by qPCR adjusted for treatment effect difference estimates based on concomitant medications and previous anti-TNF exposure in all patients as described in Example 2. Shown is differential expression of genes that enriched for remission.

Following identification of candidate genes that were differentially expressed by RNA sequencing analysis, we selected a subset of these genes (n=46) for further analysis based on strength of signal, biological relevance and expression patterns in other datasets. For these genes, gene expression in bseline biopsies from all patients (n=106) was quantitated by quantitative polymerase chain reaction (qPCR) and enrichment was evaluated using a median cut-off approach. The two different etrolizumab dose groups described in Example 1 were combined for these analyses. FIG. 5 shows the odds ratios for treatment effect differences in all comers for the indicated genes with respect to remission. In FIG. 5, an odds ratio of 1 (no treatment effect) is shown as a dotted line in the middle of the box; positive treatment effects are indicated to the right of the median and negative treatment effects are indicated to the left of the median. Thus, for example, higher than median levels of granzyme A (GZMA) and FoxM1 expression and lower than medial levels of TNFSF15 and SLC8A3 tissue expression were associated with remission following etrolizumab treatment. Qualitative results of FIG. 5 and elsewhere are summarized in Table 4 and Table 5 below.

TABLE 4

Higher than median gene expression levels associated with etrolizumab responsiveness in all comers ("High Expression Predictive Genes" or "HEPG").

| GENE SYMBOL | CLINICAL ENDPOINT: REMISSION |
|---|---|
| GZMA | X |
| FOXM1 | X |
| ECH1 | X |
| KLRB1 | X |
| TMIGD2 | X |
| ITGAE | X |
| KCNMA1 | X |
| GZMB | X |
| PHF14 | X |
| CPA2 | X |
| DDO | X |
| CCDC90A | X |
| TMEM200A | X |
| FAM125B | X |
| GPR15 | X |

TABLE 4-continued

Higher than median gene expression levels associated with etrolizumab responsiveness in all comers ("High Expression Predictive Genes" or "HEPG").

| GENE SYMBOL | CLINICAL ENDPOINT: REMISSION |
|---|---|
| FGF9 | X |
| TIFAB | X |
| SLC8A3 (blood) | X |

TABLE 5

Lower than median gene expression levels associated with etrolizumab responsiveness in all comers ("Low Expression Predictive Genes" or "LEPG").

| GENE SYMBOL | CLINICAL ENDPOINT: REMISSION |
|---|---|
| TNFSF15 | X |
| SLC8A3 (tissue) | X |
| MLK7.AS1 | X |
| CCL3 | X |
| VNN3 | X |
| INHBA | X |
| VNN2 | X |
| IL18RAP | X |
| REM2 | X |
| TMEM154 | X |
| CCL2 | X |
| IL1A | X |
| LRRC4 | X |
| HAMP | X |
| LMO4 | X |
| MUCL1 | X |
| LIF | X |
| TM4SF4 | X |
| FGF7 | X |
| BEST2 | X |
| CCL3L3 | X |
| MX1 | X |
| UROS | X |
| SSTR2 | X |
| CPA3 | X |
| MT1M | X |

Figure 6:
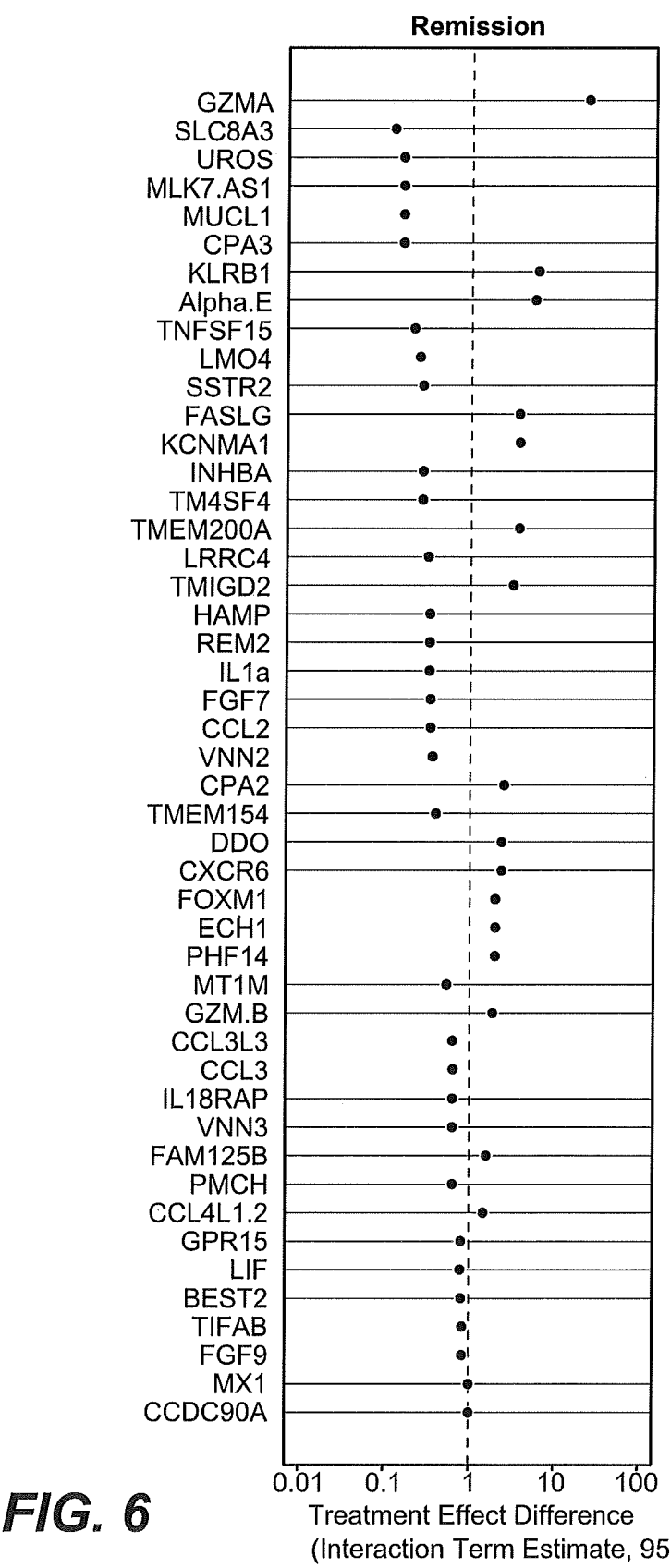
FIG. 6 shows odds ratios of the indicated differentially expressed genes as measured by qPCR adjusted for treatment effect difference estimates based on concomitant medications and previous anti-TNF exposure in anti-TNF naïve patients as described in Example 2. Shown is differential expression of genes that enriched for remission.

FIG. 6 shows the odds ratios for treatment effect differences in anti-TNF naïve patients for the indicated genes with respect to remission. In FIG. 6, an odds ratio of 1 (no treatment effect) is shown as a dotted line in the middle of the box; positive treatment effects are indicated to the right of the median and negative treatment effects are indicated to the left of the median. Thus, for example, higher than median levels of granzyme A (GZMA) expression and lower than medial levels of SLC8A3 expression were associated with remission following etrolizumab treatment. Qualitative results of FIG. 6 and elsewhere are summarized in Table 6 and Table 7 below.

TABLE 6

Higher than median gene expression levels associated with etrolizumab responsiveness in TNF-naive patients ("High Expression Predictive Genes" or "HEPG").

| GENE SYMBOL | CLINICAL ENDPOINT: REMISSION |
|---|---|
| FASLG | X |
| CCL4 | X |
| GZMA | X |
| FOXM1 | X |
| ECH1 | X |
| KLRB1 | X |
| TMIGD2 | X |
| ITGAE | X |
| KCNMA1 | X |
| GZMB | X |
| PHF14 | X |
| CPA2 | X |
| DDO | X |
| TMEM200A | X |
| FAM125B | X |
| CXCR6 | X |
| SLC8A3 (blood) | X |

TABLE 7

Lower than median gene expression levels associated with etrolizumab responsiveness in TNF-naive patients ("Low Expression Predictive Genes" or "LEPG").

| GENE SYMBOL | CLINICAL ENDPOINT: REMISSION |
|---|---|
| PMCH | X |
| TNFSF15 | X |
| SLC8A3 (tissue) | X |
| MLK7.AS1 | X |
| CCL3 | X |
| VNN3 | X |
| INHBA | X |
| VNN2 | X |
| IL18RAP | X |
| REM2 | X |
| TMEM154 | X |
| CCL2 | X |
| IL1A | X |
| LRRC4 | X |
| HAMP | X |
| LMO4 | X |
| MUCL1 | X |
| LIF | X |
| TM4SF4 | X |
| FGF7 | X |
| BEST2 | X |
| CCL3L1/3 | X |
| UROS | X |
| SSTR2 | X |
| CPA3 | X |
| MT1M | X |

Figure 7A:
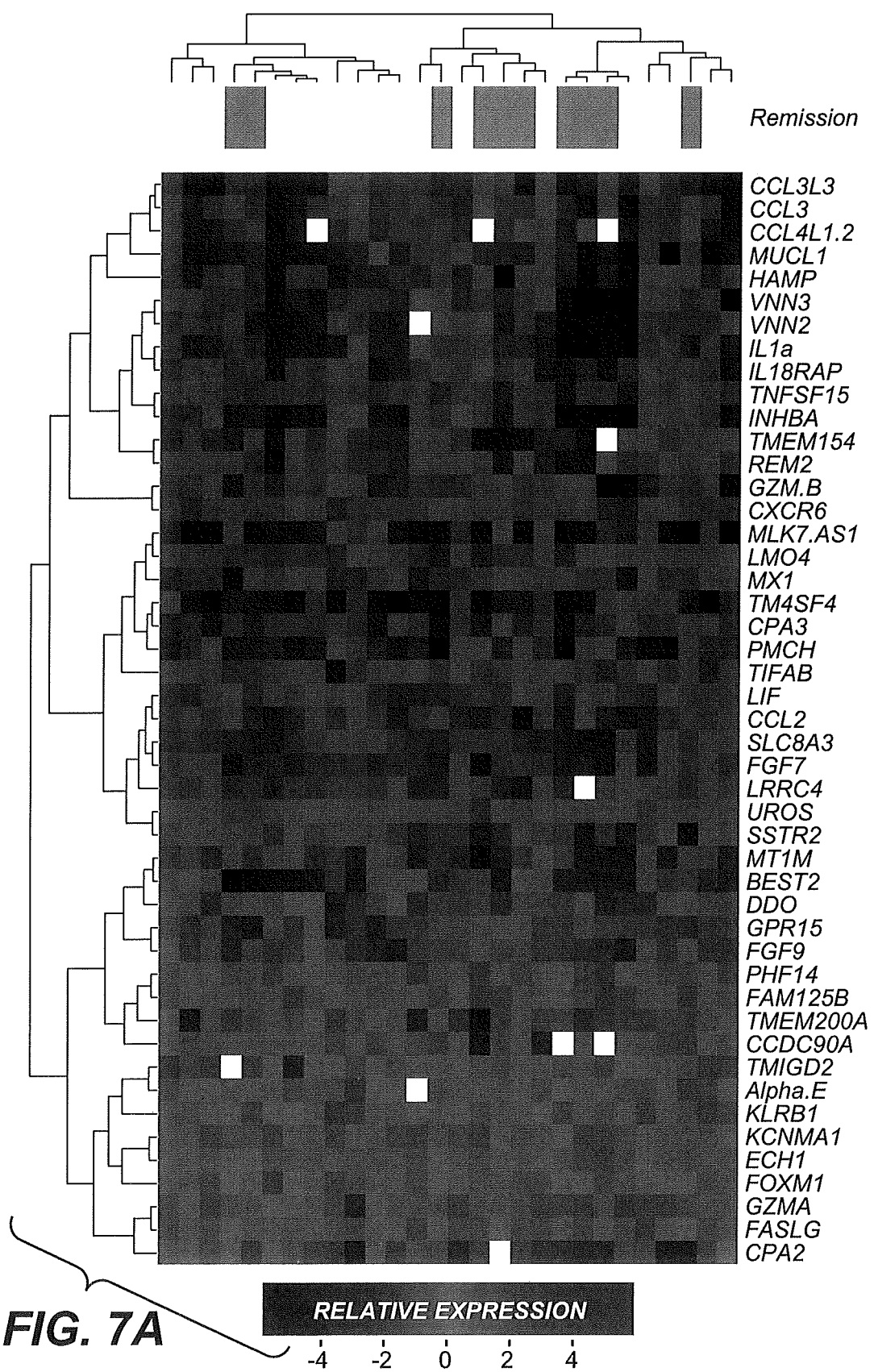
FIGS. 7A and 7B show a heatmap showing two-way clustering (FIG. 7A) and correlation (FIG. 7B) of selected genes as described in Example 2.
Figure 7B:
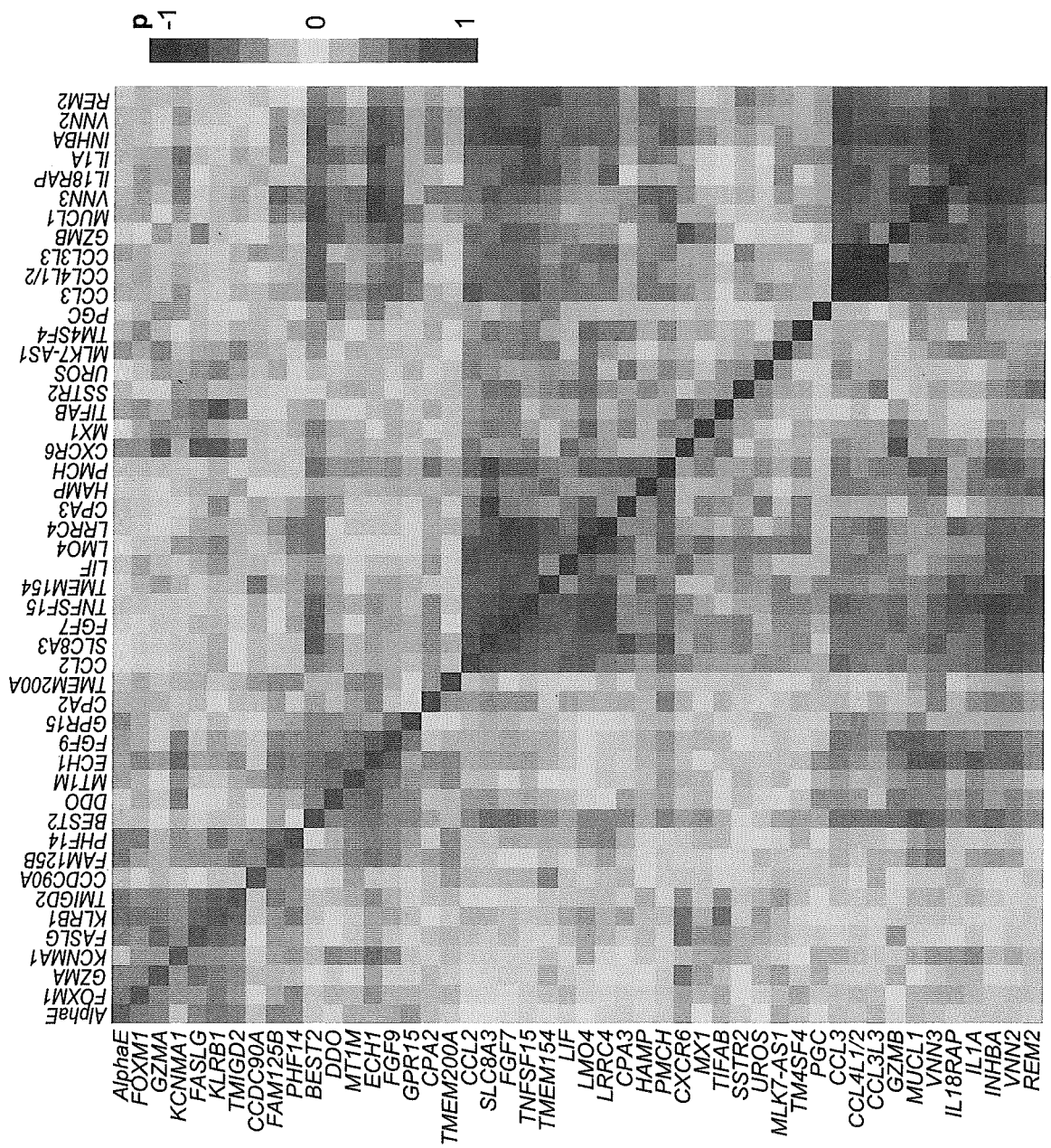
Figure 8A:
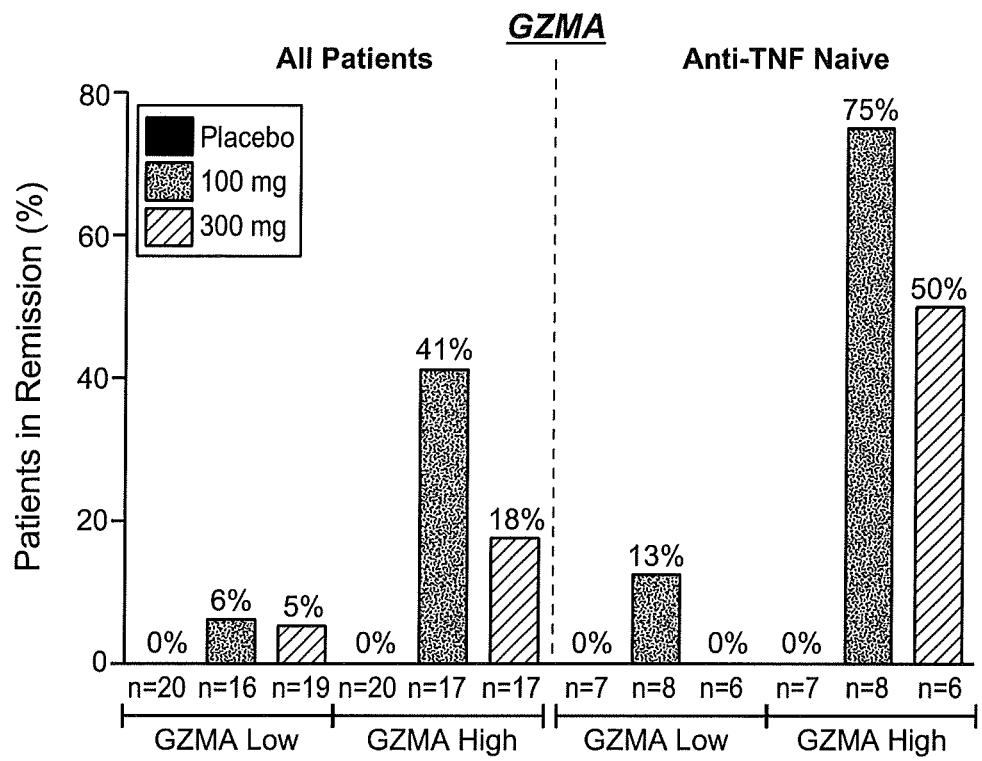
FIGS. 8A-8D show the proportion of patients (percentage) stratified by baseline gene expression levels (low, below the median vs. high, at or above the median) in intestinal biopsies and treated with placebo (black bars), 100 mg/dose etrolizumab (stippled bars) or 300 mg/dose etrolizumab+loading dose (LD) (striped bars) as described in Example 2.
Figure 8B:
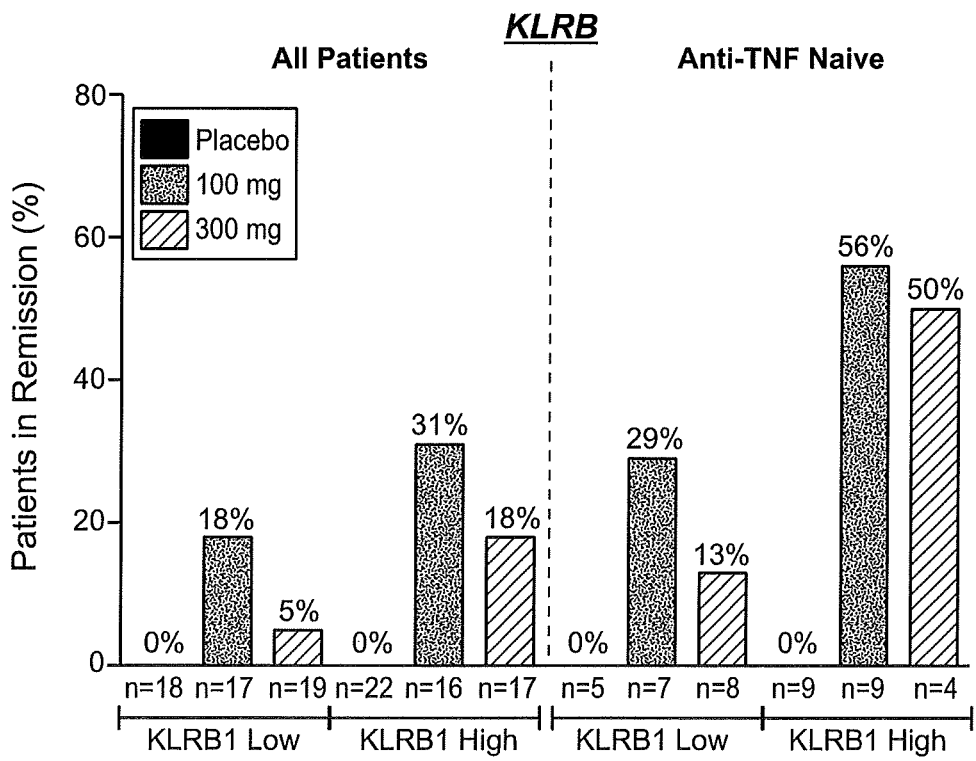
Figure 8C:
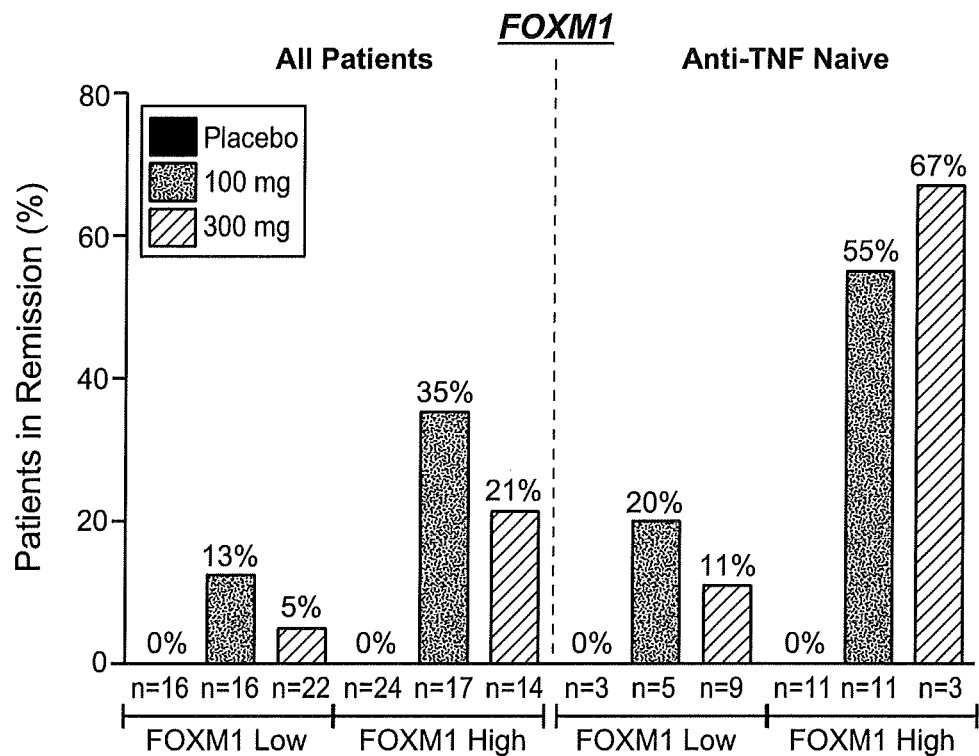
Figure 8D:
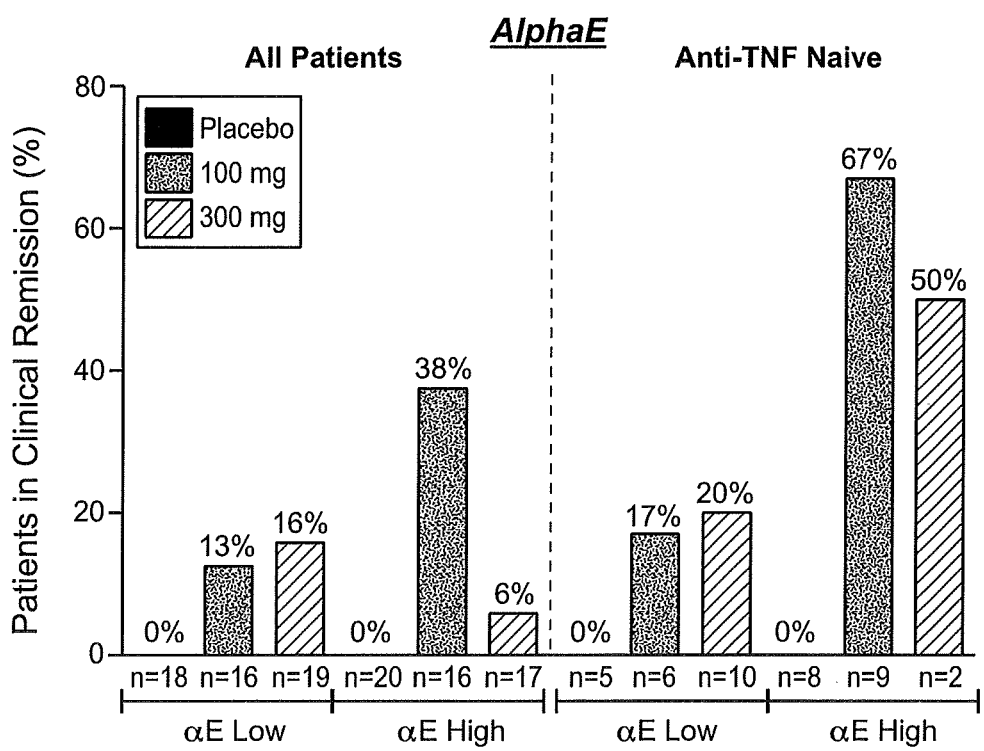
Figure 9A:
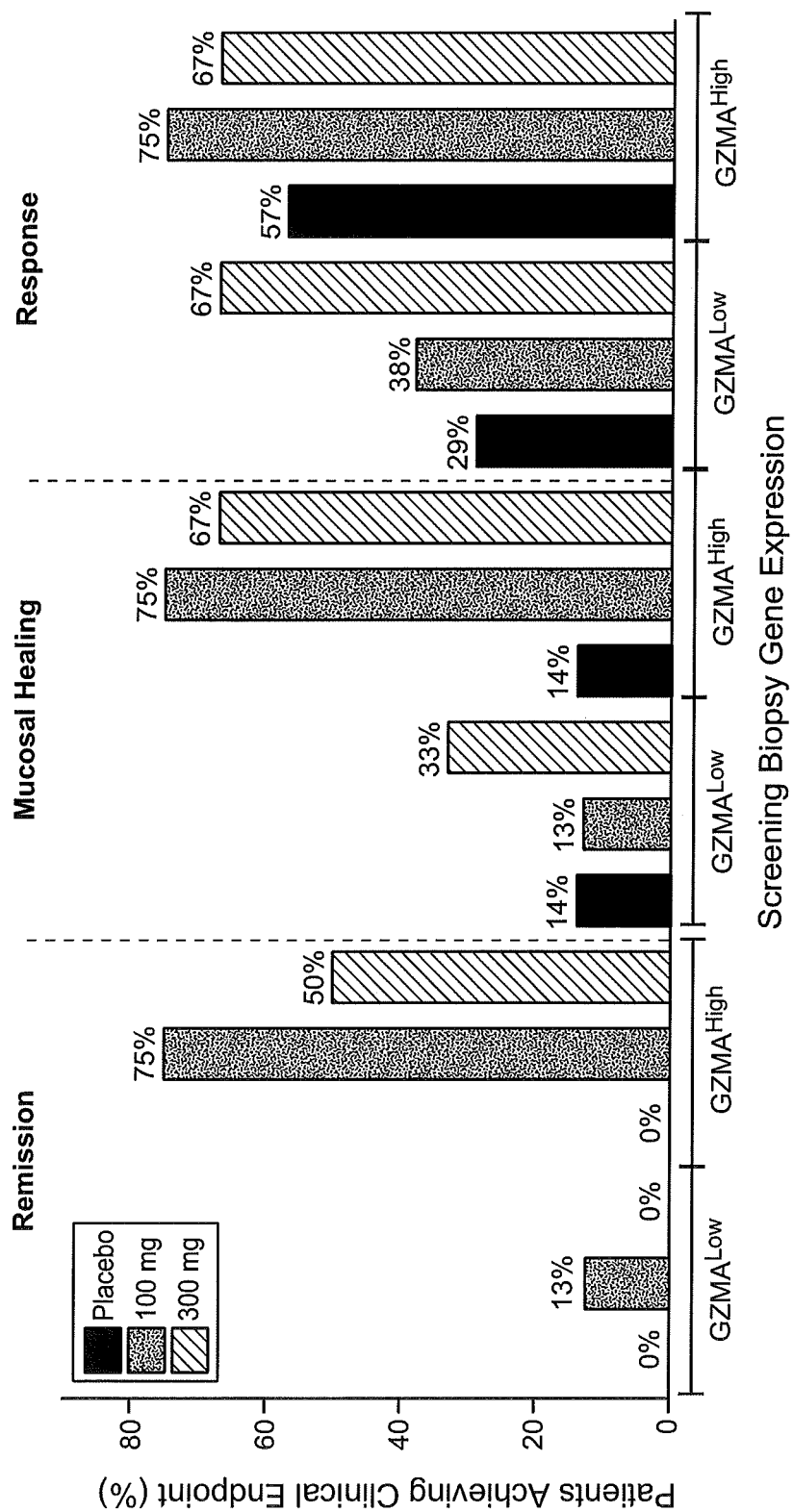
Figure 9B:
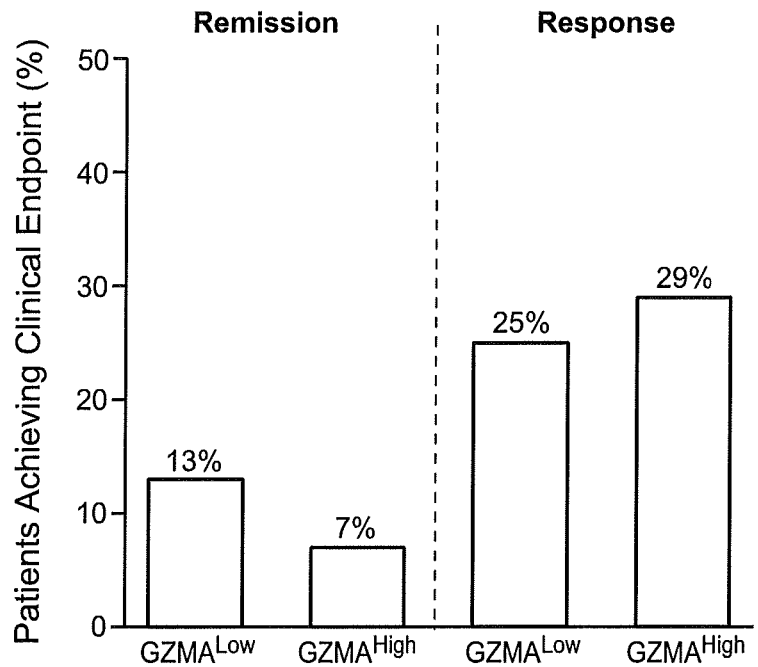
Figure 9C:
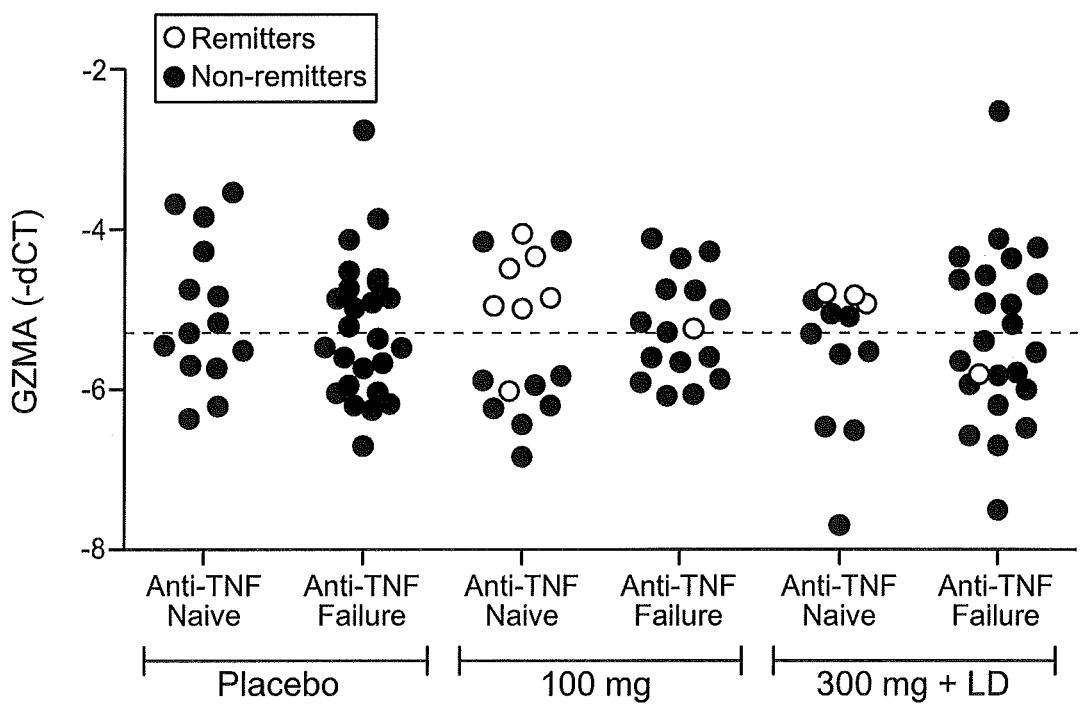
Figure 9D:
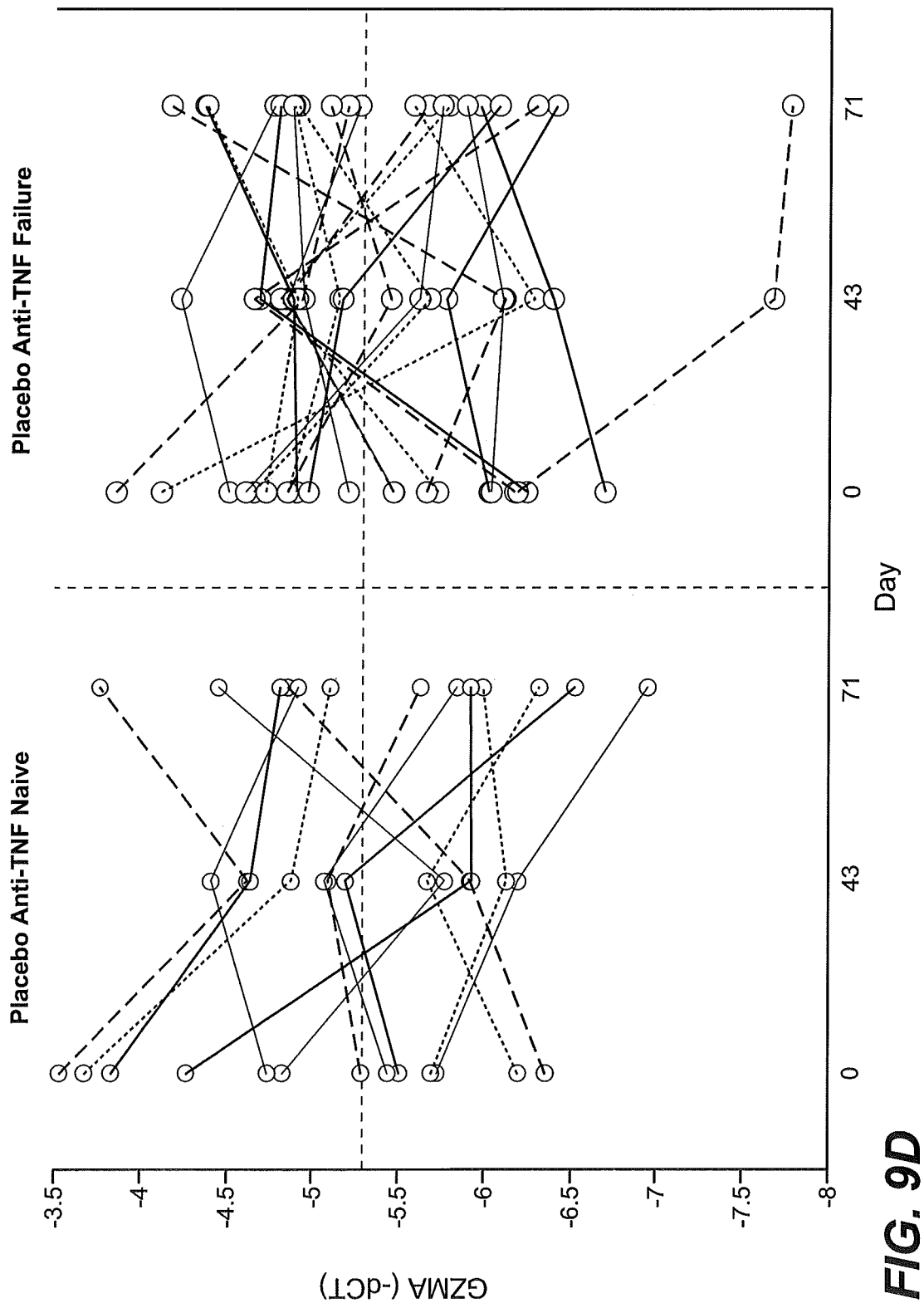
Figure 10A:
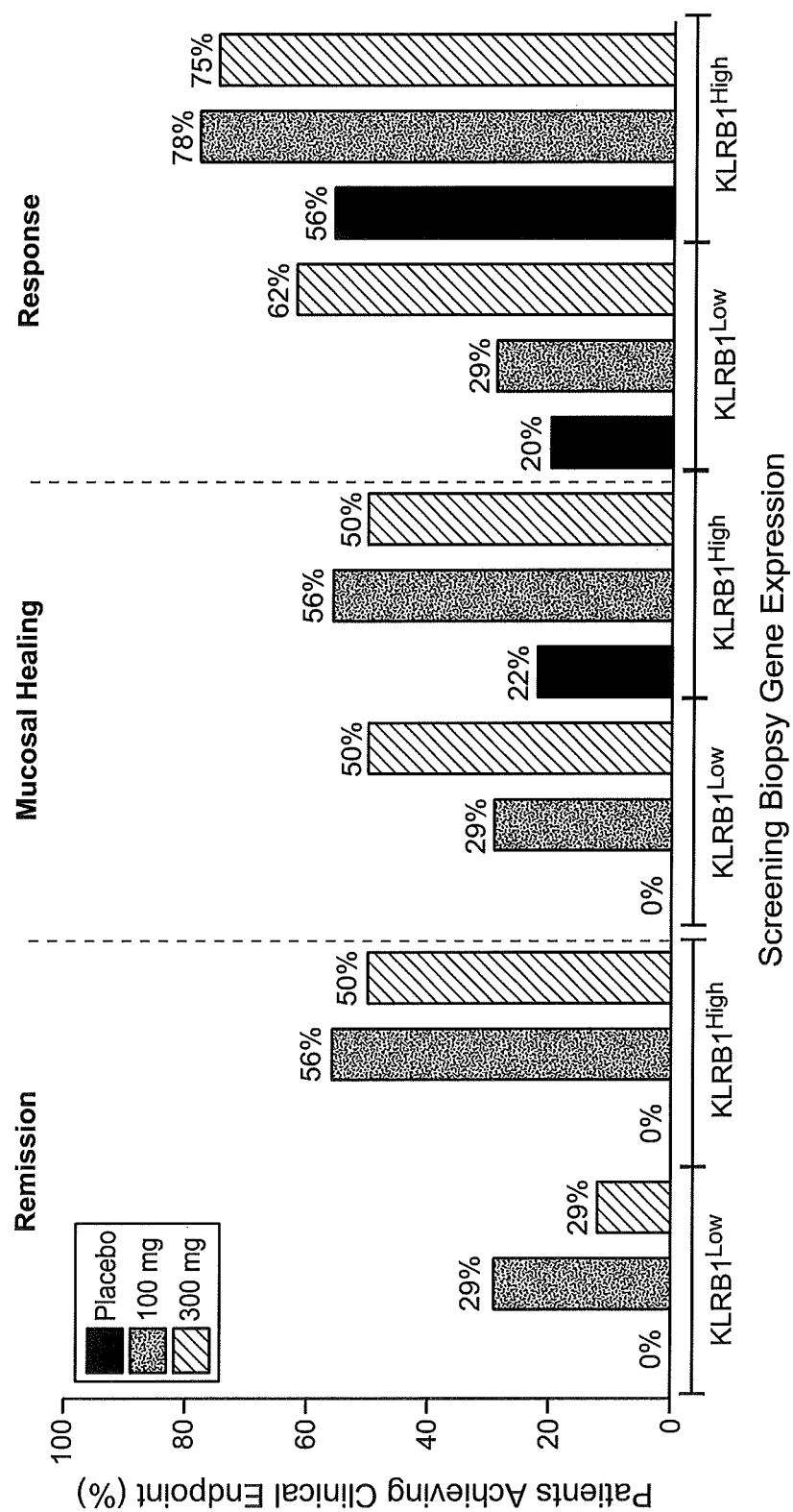
Figure 10B:
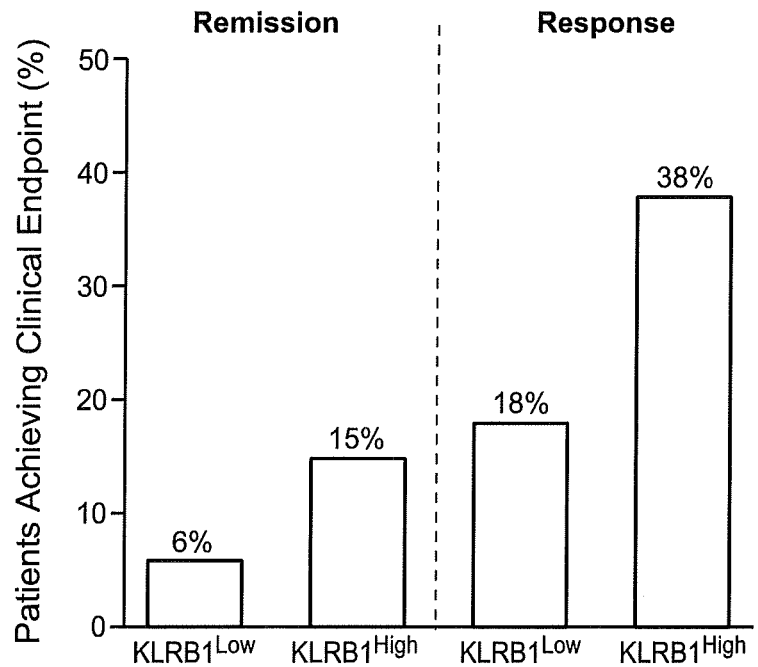
Figure 10C:
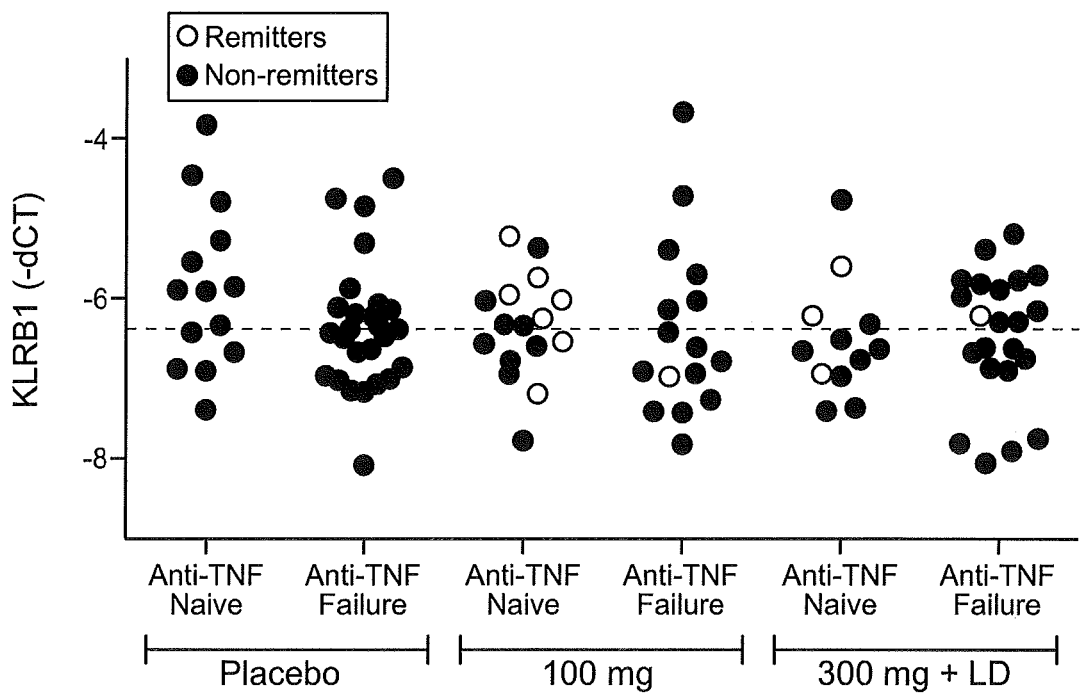
Figure 10D:
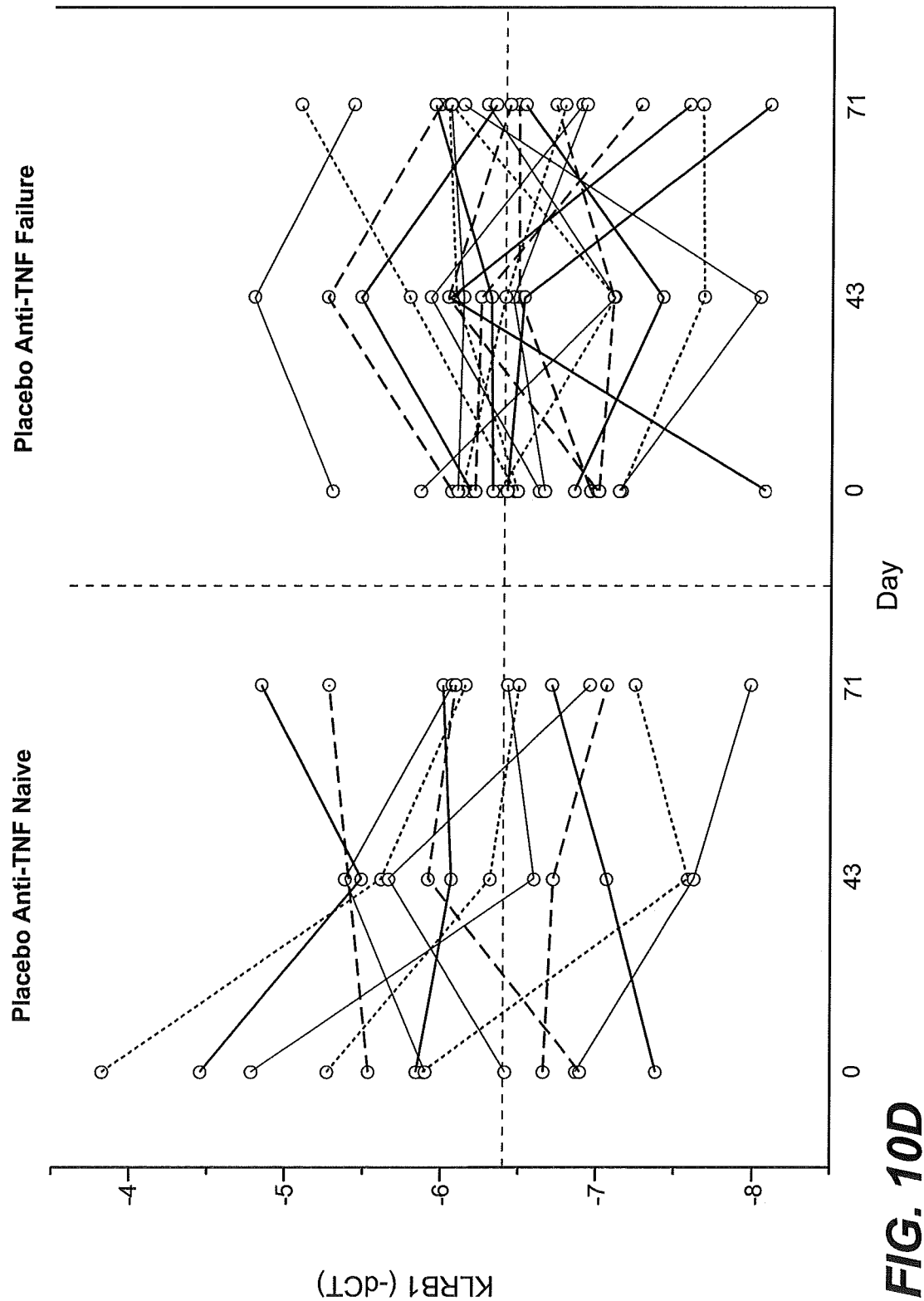
Figure 11A:
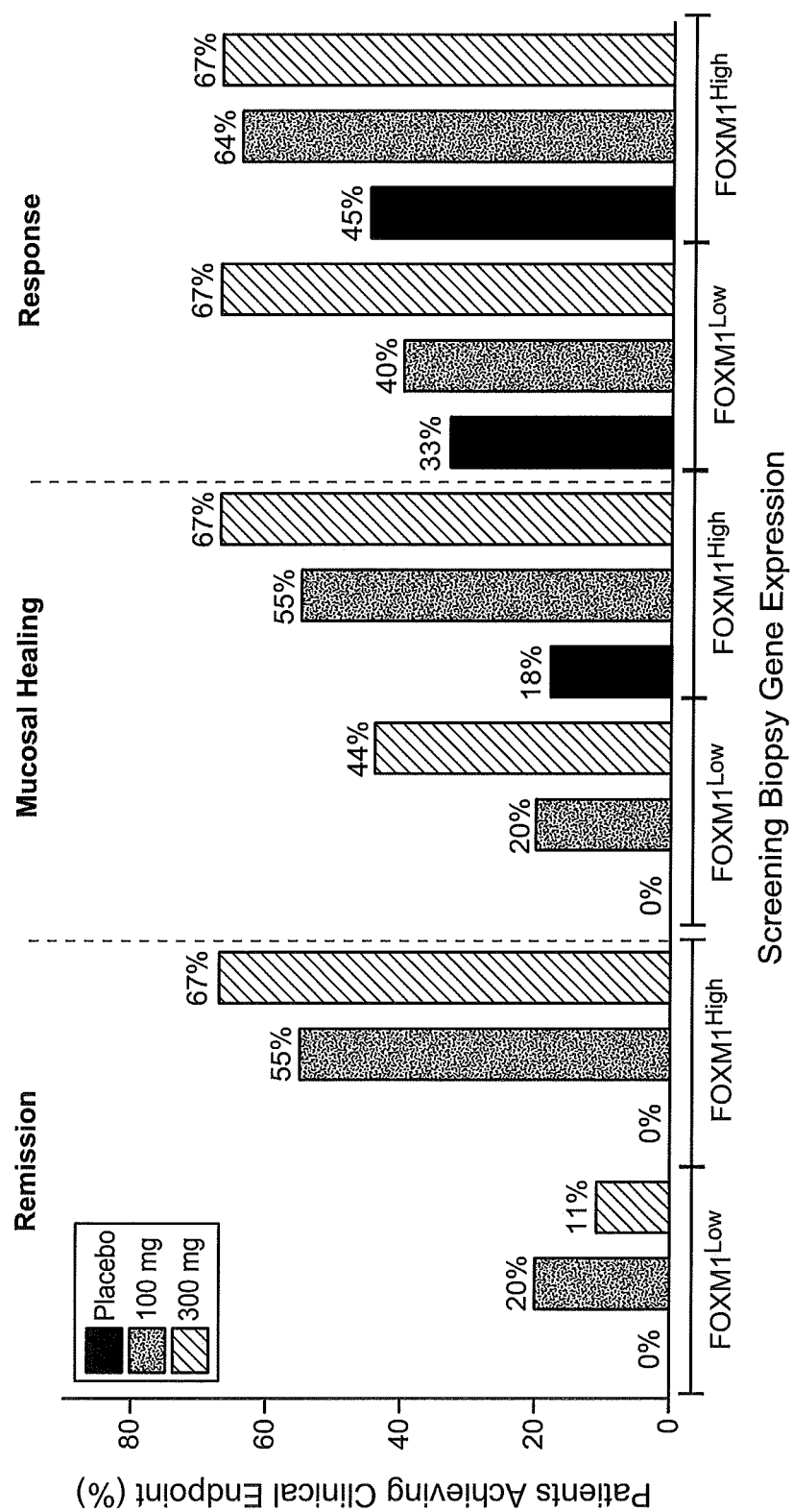
Figure 11B:
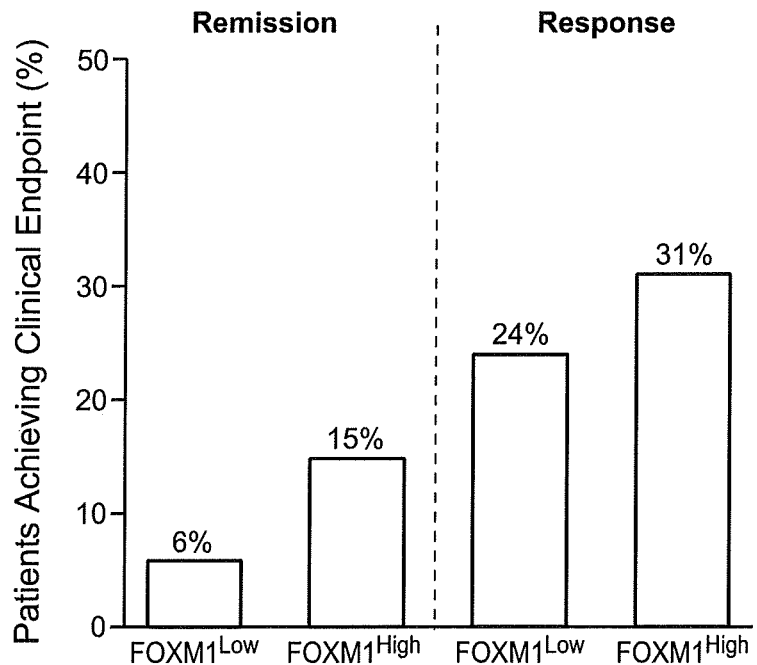
Figure 11C:
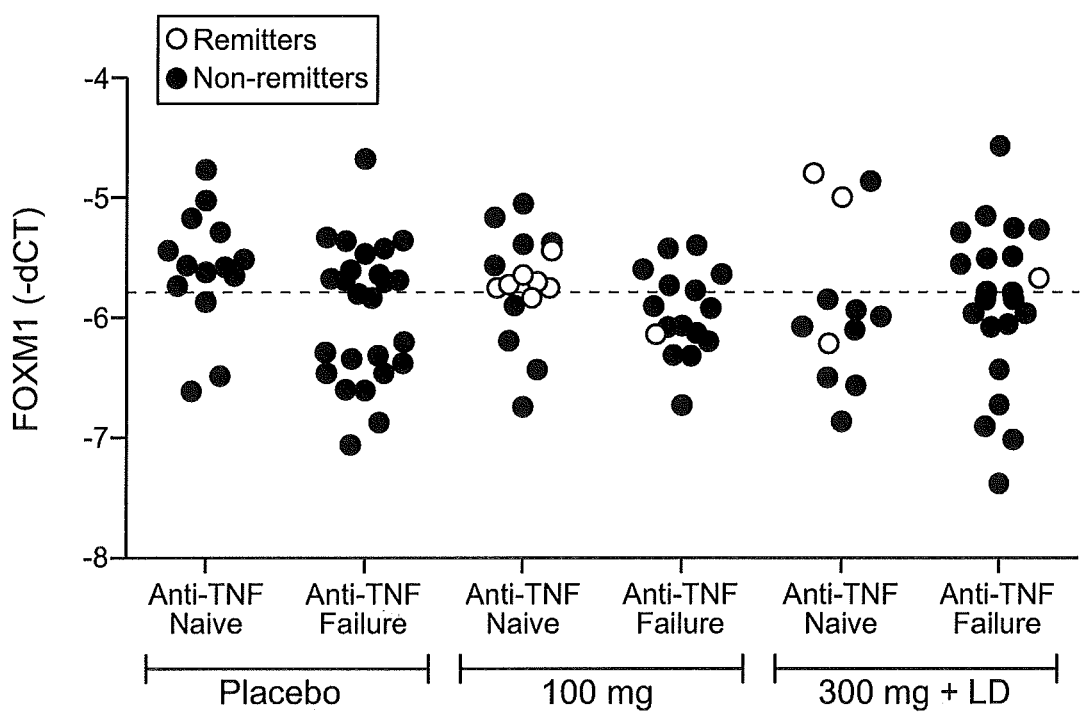
Figure 11D:
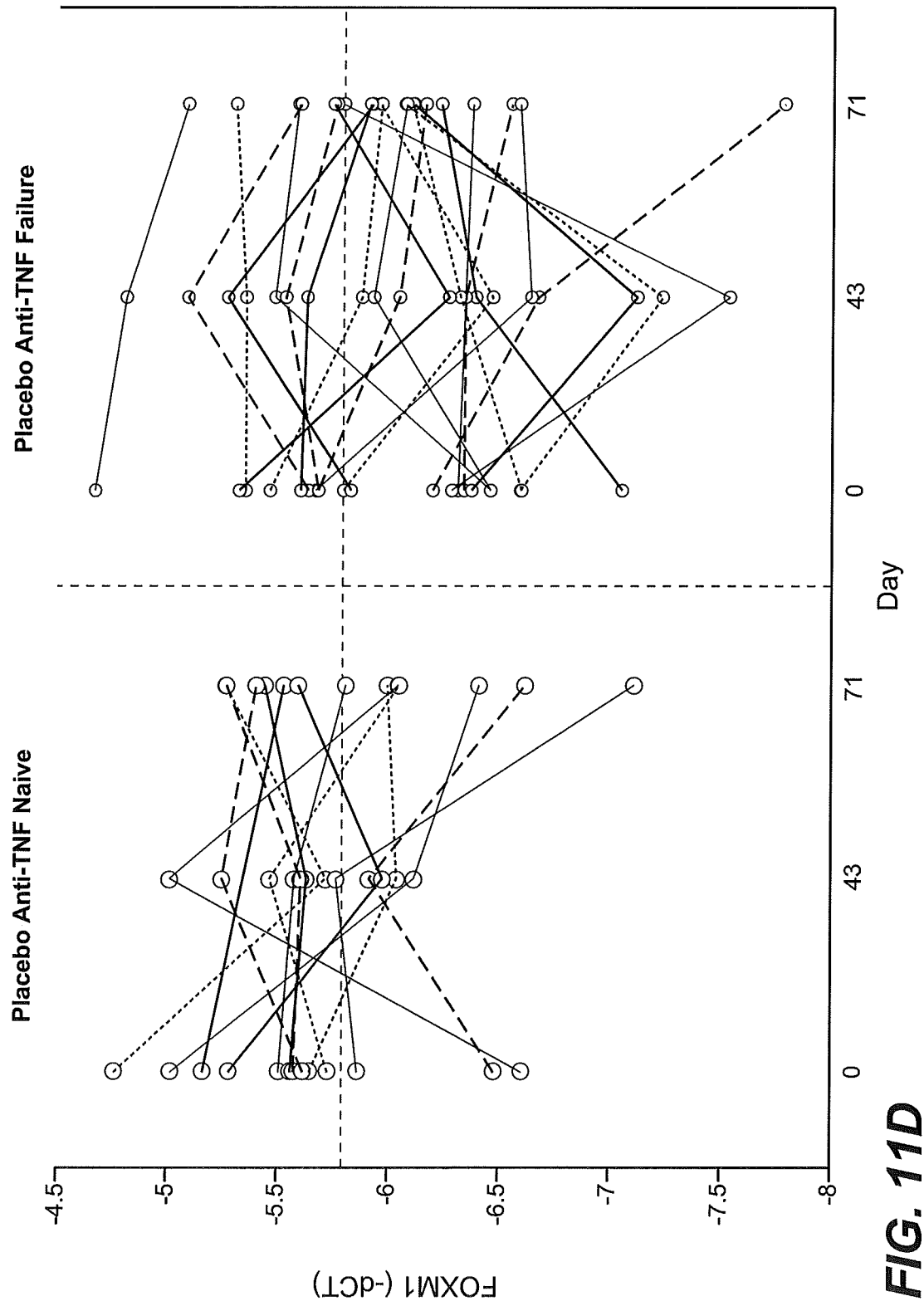
Figure 12A:
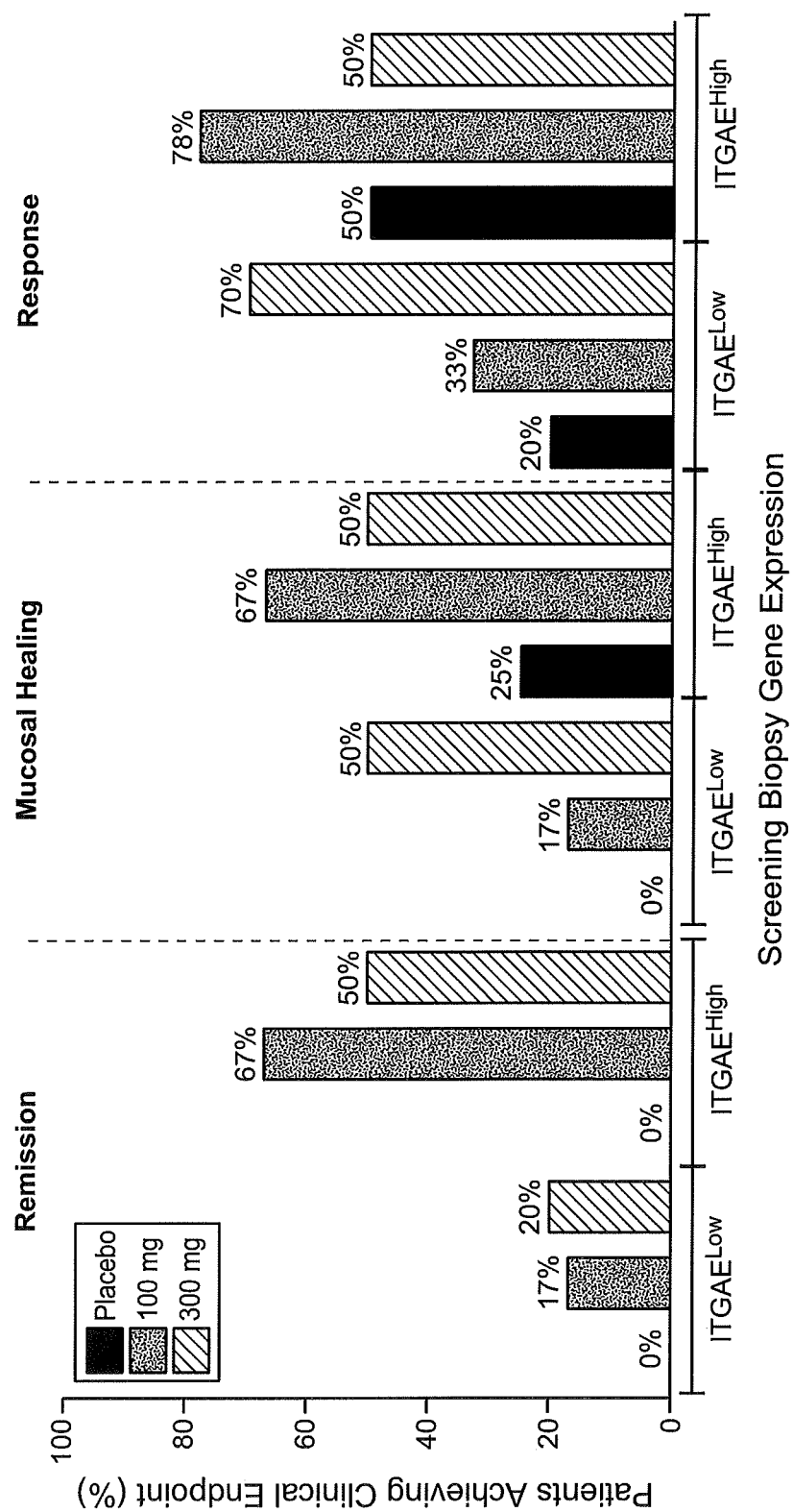
Figure 12B:
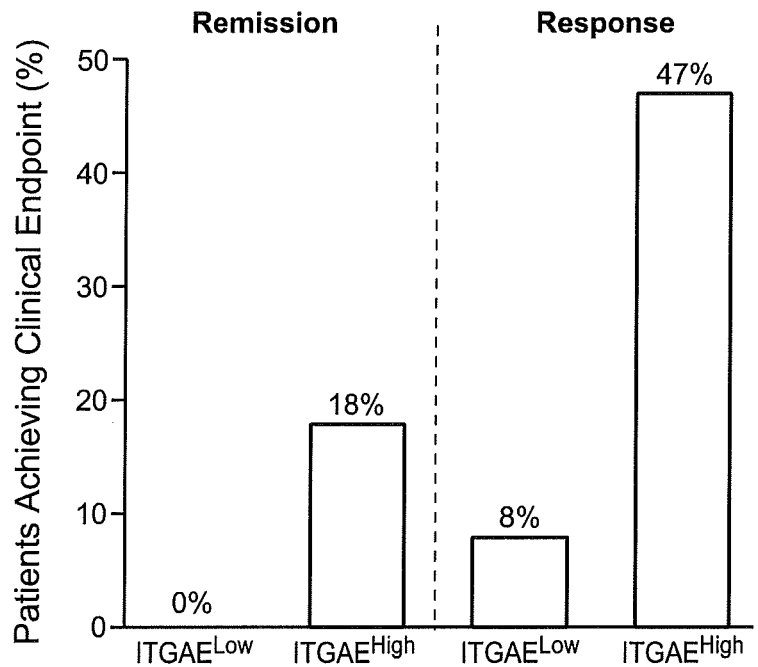
Figure 12C:
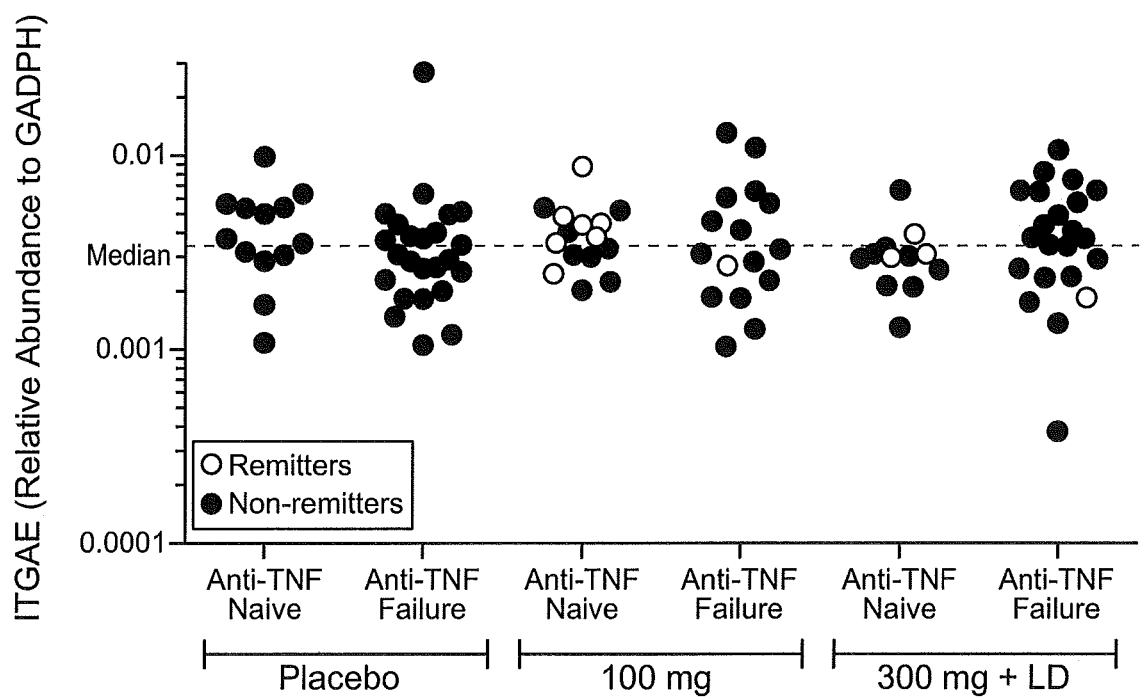
Figure 12D:
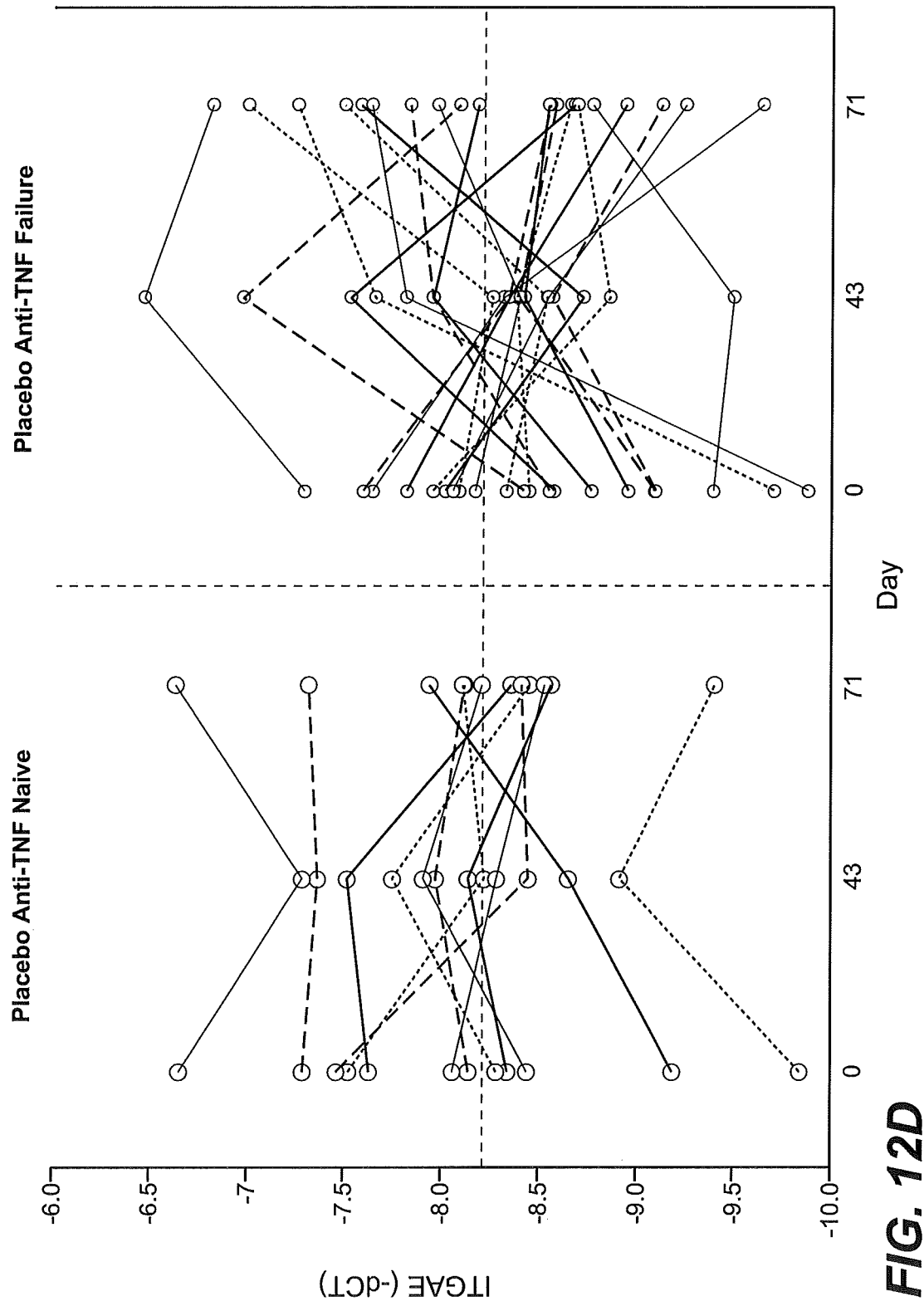

Two-way clustering using baseline gene expression for selected enrichment genes allowed us to identify two distinct patient clusters. As shown in FIG. 7A, patients with high expression of T-cell associated genes (integrin alphaE, KLRB1, FOXM1, GZMA, TMEM200A) and low expression of myeloid/neutrophil genes (IL1A, VNN2, VNN3) were more likely to undergo remission. In addition, FIG. 7B shows that genes that were higher at baseline in remitters tend to be correlated, while genes that were higher at baseline in non-remitters tend to be correlated.

Next we analyzed the percentage of patients achieving remission, mucosal healing and response for certain selected genes. FIGS. 8A-8D show that higher than median levels of gene expression in all patients (left half of each graph) and in anti-TNF naïve patients (right half of graph) of the indicated genes enriched for remission in patients treated with etrolizumab. The genes whose high expression enriched for remission as shown in FIGS. 8A-8D are (FIG. 8A) granzyme A, (FIG. 8B) KLRB1, (FIG. 8C) FOXM1, and (FIG. 8D) integrin alpha E. For the results shown in FIGS. 8A-8D, we also assessed qualitatively (i.e., gene expression higher than median, at median, or lower than median) the longitudinal stability of the gene expression levels in samples from the placebo arm of the study by measuring the gene expression levels of each of granzyme A, KLRB1, FOXM1 and alphaE in biopsies obtained from individual patients at screen, day 43 and day 71. These samples were compared pairwise for concordance and the mean concordance was calculated. The mean concordance in placebo samples for granzyme A was 67%, for KLRB1, the mean concordance was 71%, for FOXM1, the mean concordance was 70% and for alphaE, the mean concordance was 57%. Without being bound by theory, it is believed that genes with higher mean concordance reflect more stable aspects of the underlying biology than genes with lower mean concordance and thus such concordant genes may ultimately prove more robust for use as biomarkers for enriching for anti-integrin beta7 antagonist responsiveness.

Additional results for each of granzyme A (FIGS. 9A-9D), KLRB1 (FIGS. 10A-10D), FOXM1 (FIGS. 11A-11D), and alphaE (FIGS. 12A-12D) are shown. As shown in each of FIGS. 9A-9D, FIGS. 10A-10D, FIGS. 11A-11D, and FIGS. 12A-12D, and consistent with the results presented above, high baseline expression of each of the identified genes enriched for etrolizumab responsiveness as assessed by remission. Furthermore, the data in FIGS. 9A-9D, FIGS. 10A-10D, FIGS. 11A-11D, and FIGS. 12A-12D show that high baseline expression of each of GZMA, KLRB1, FOXM1 and ITGAE enriched for etrolizumab responsiveness as assessed by mucosal healing and clinical response, although the enrichment was less pronounced. Data for an additional gene, ECH1, examining baseline expression in screening biopsies and assessing etrolizumab responsiveness by remission, mucosal healing, and clinical response is shown in FIGS. 18A-18D.

Figure 13A:
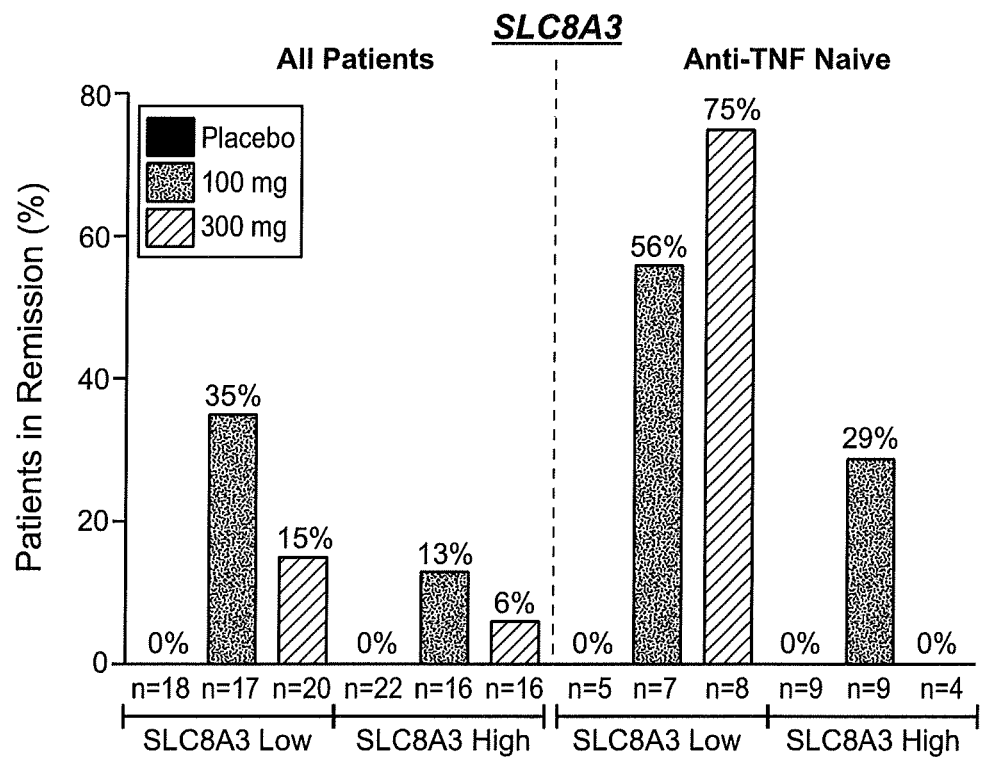
Figure 13B:
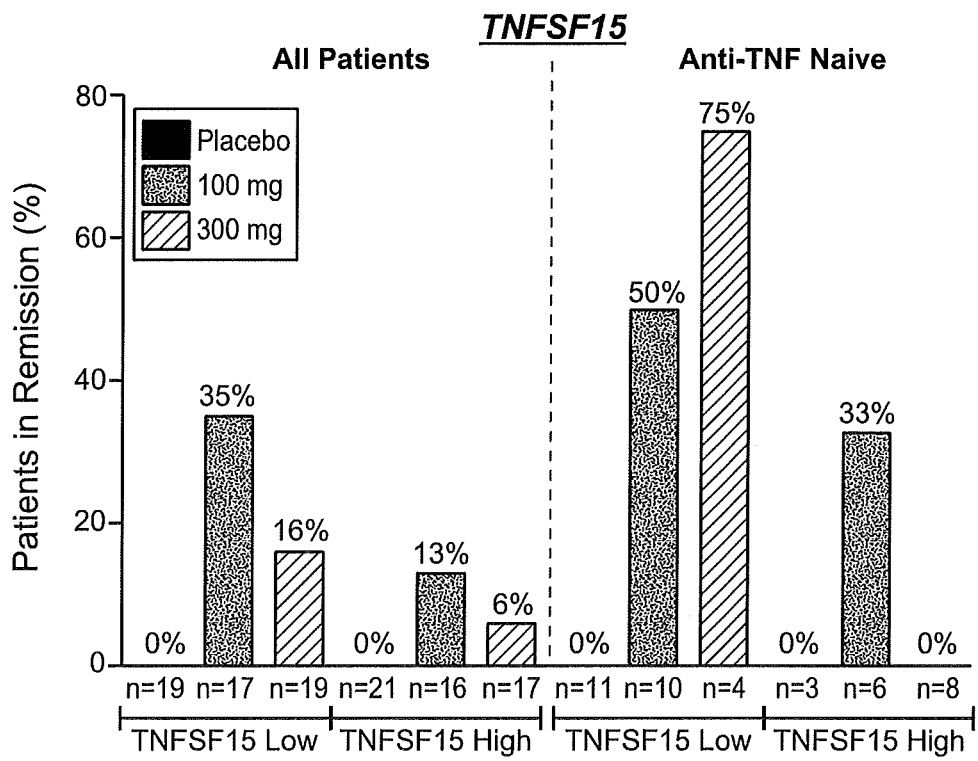
Figure 13C:
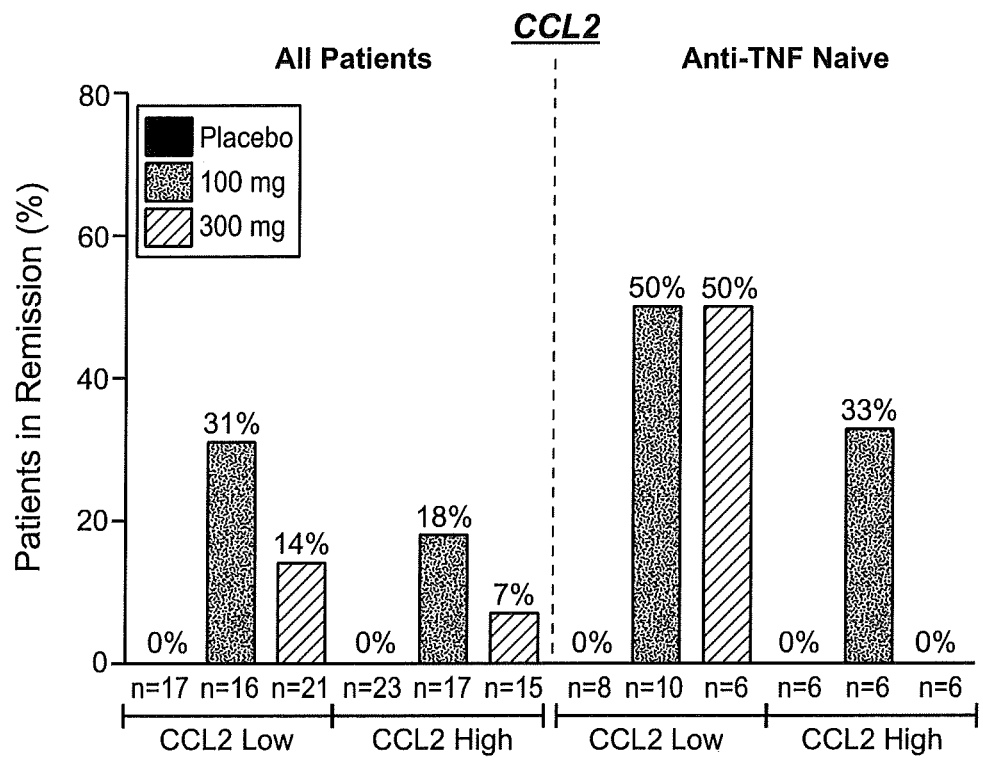
Figure 13D:
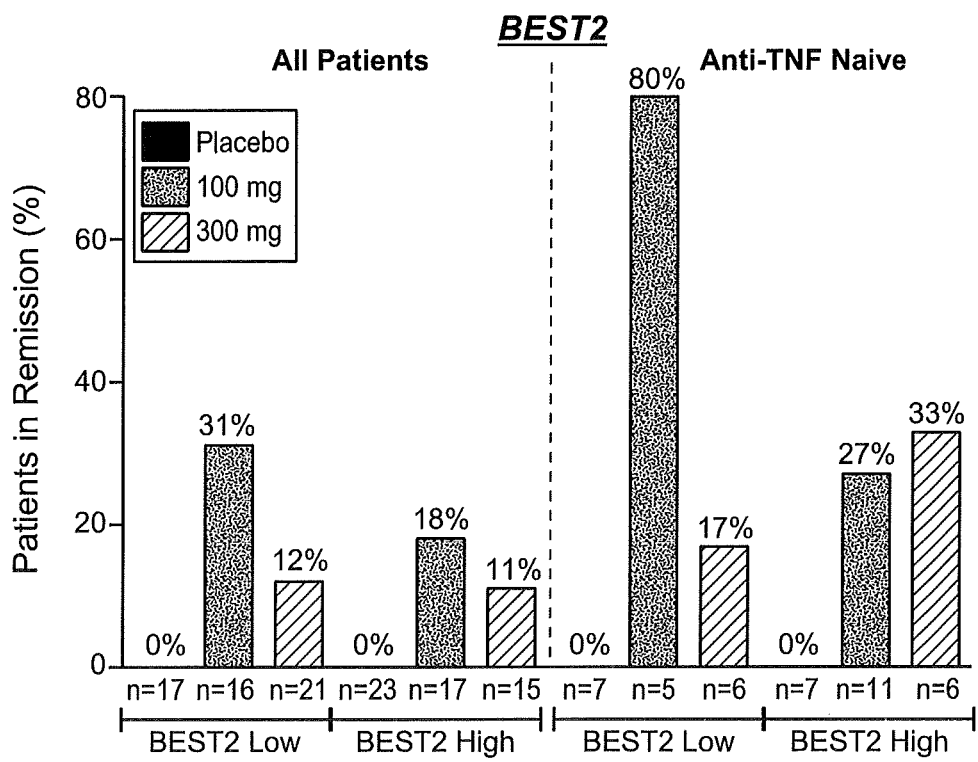
Figure 14A:
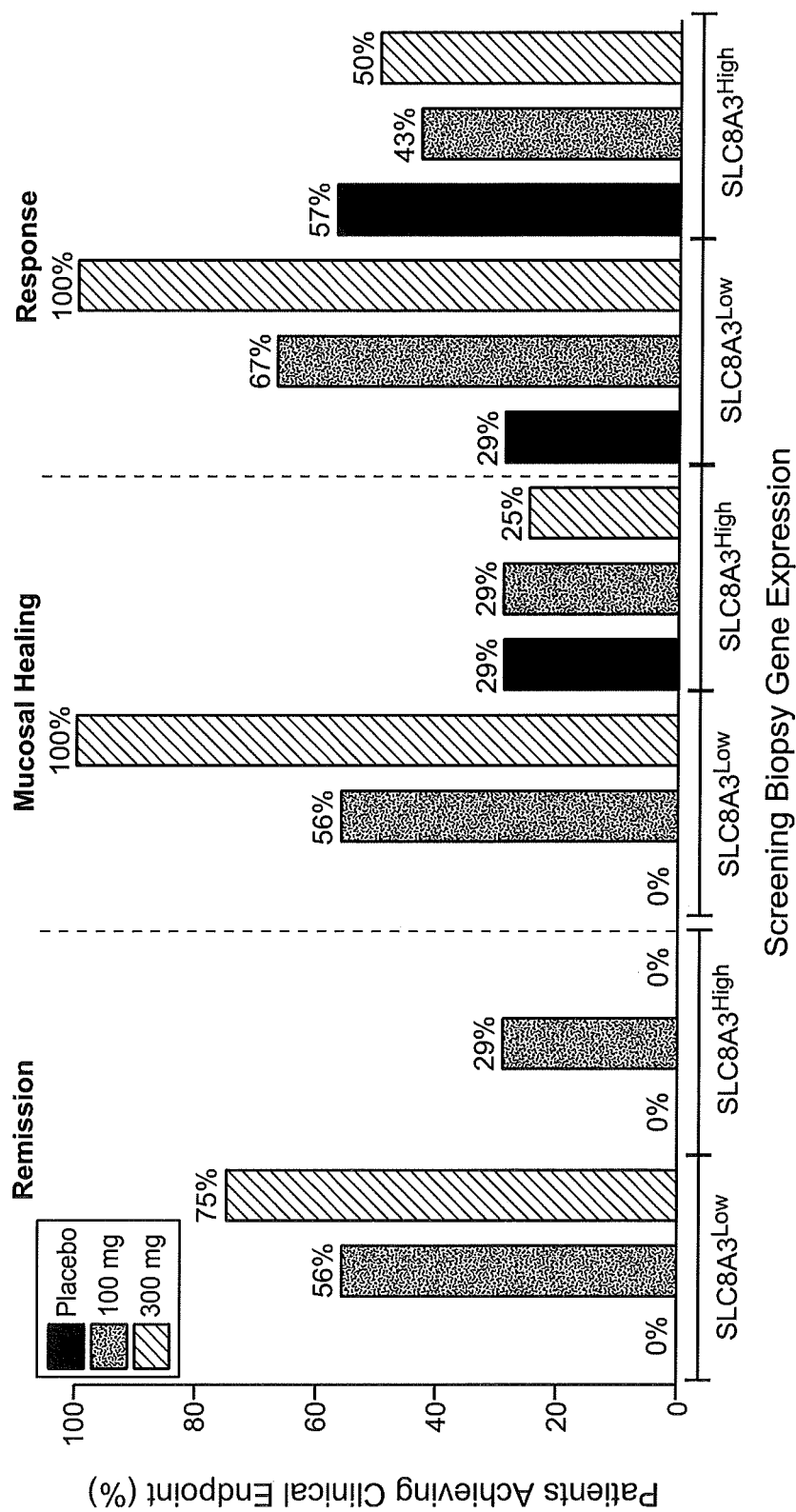
Figure 14B:
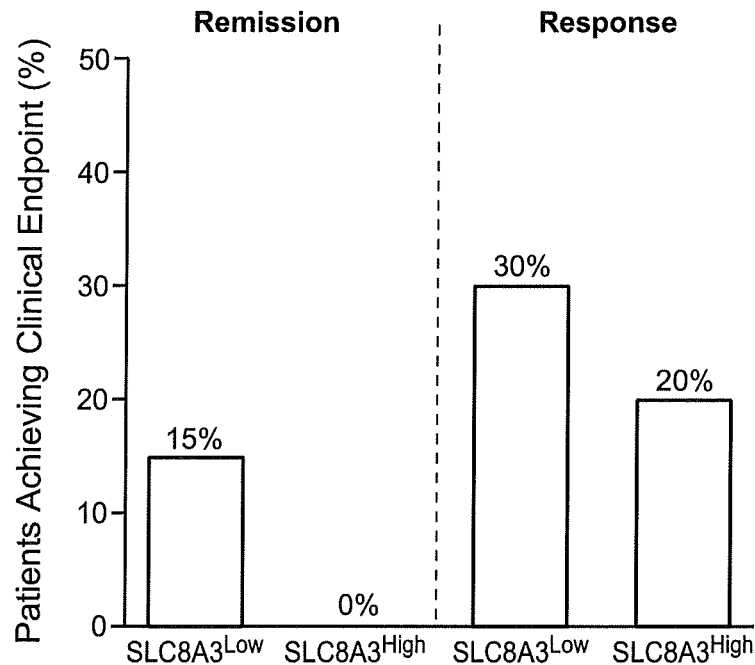
Figure 14C:
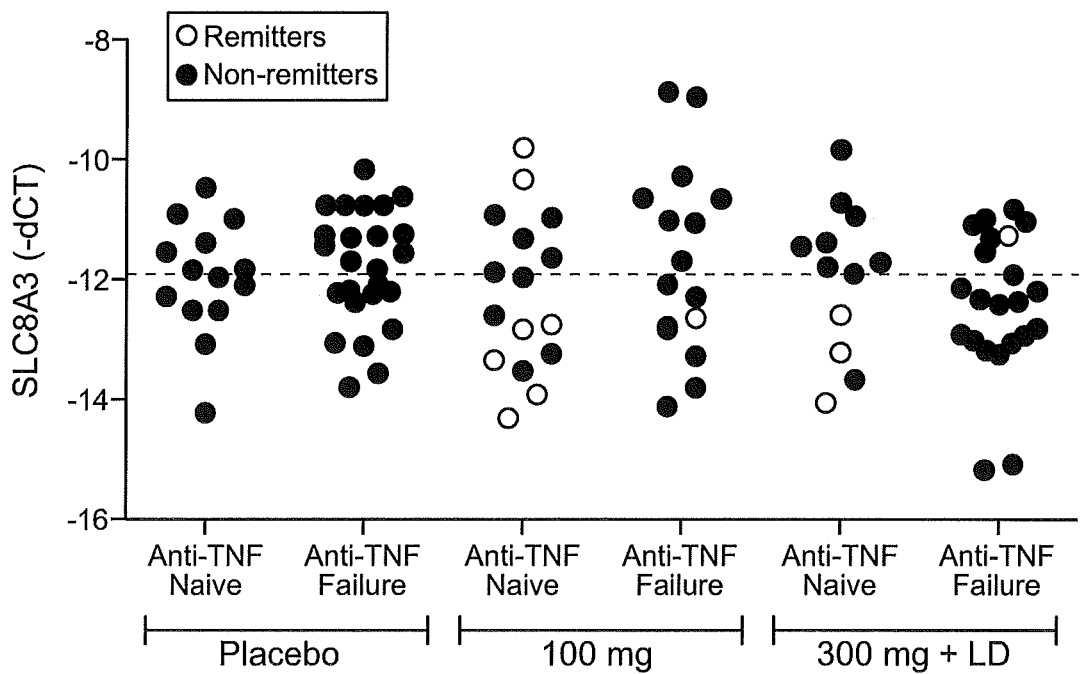
Figure 14D:
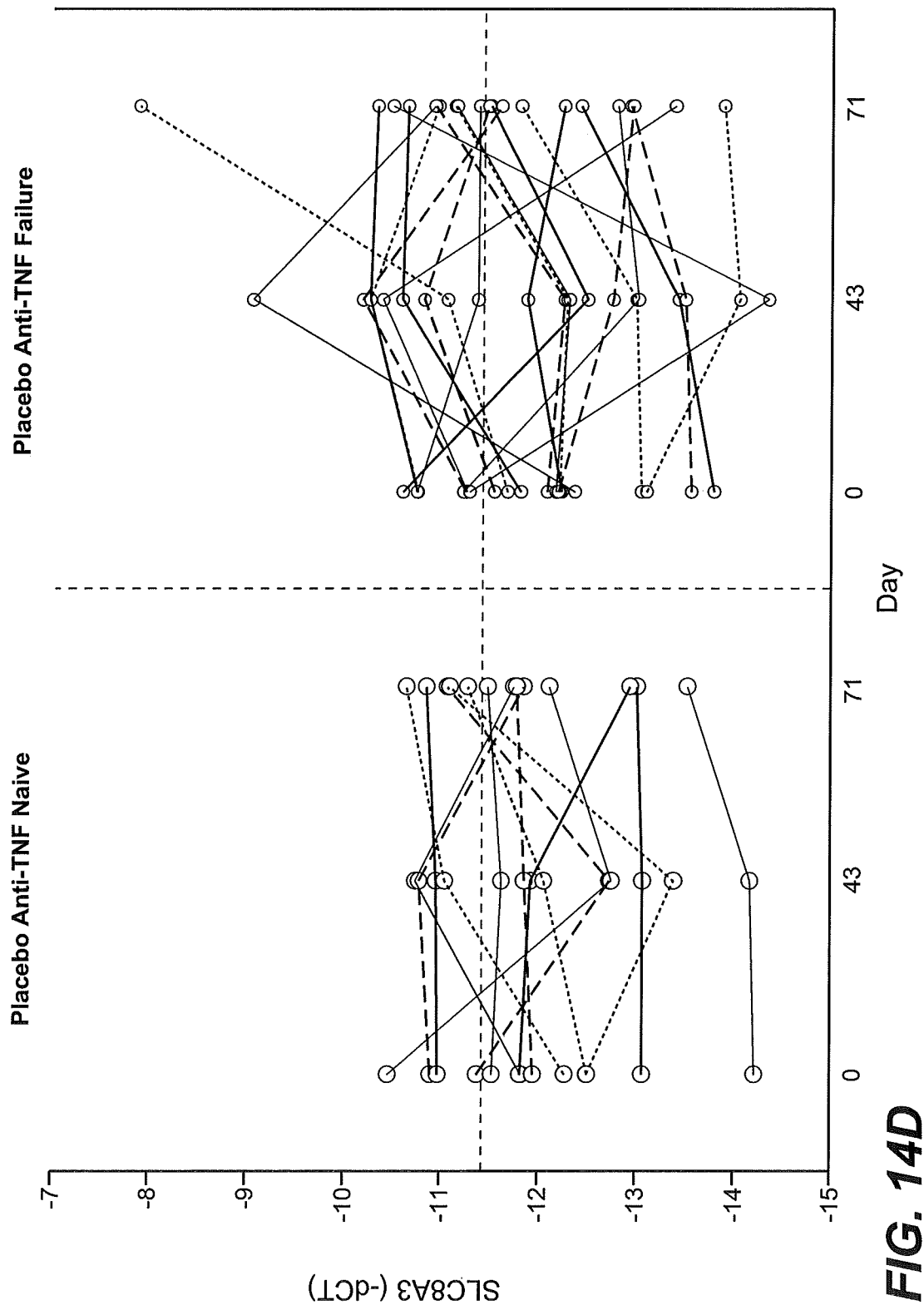
Figure 15A:
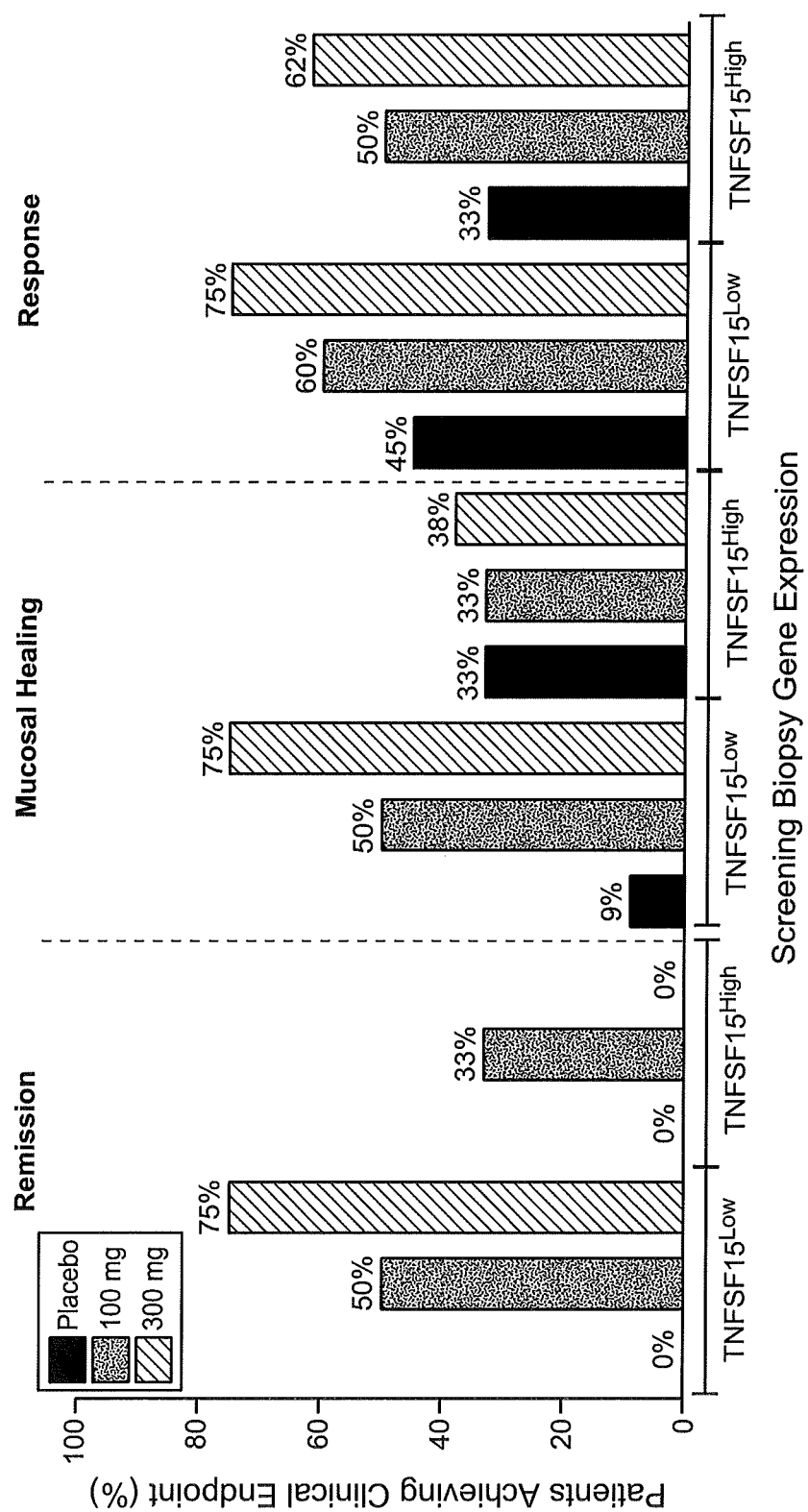
Figure 15B:
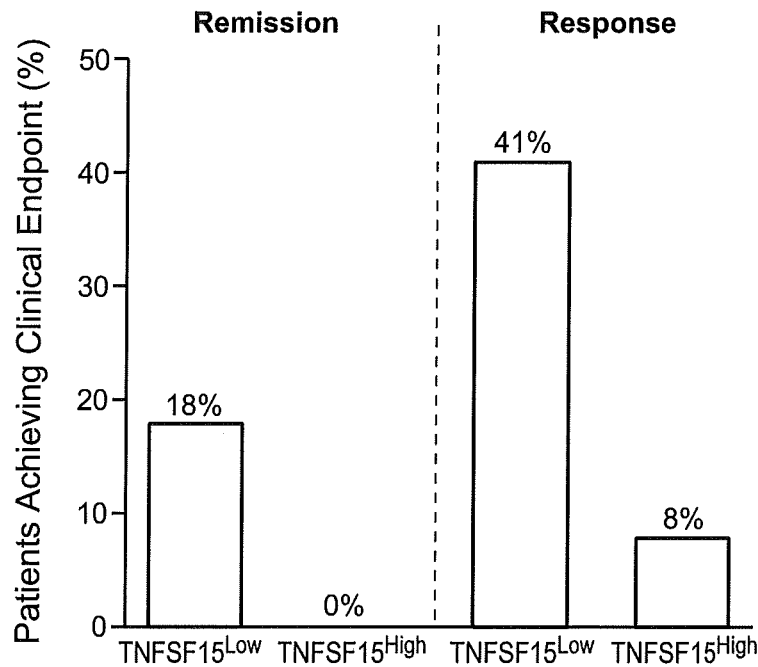
Figure 15C:
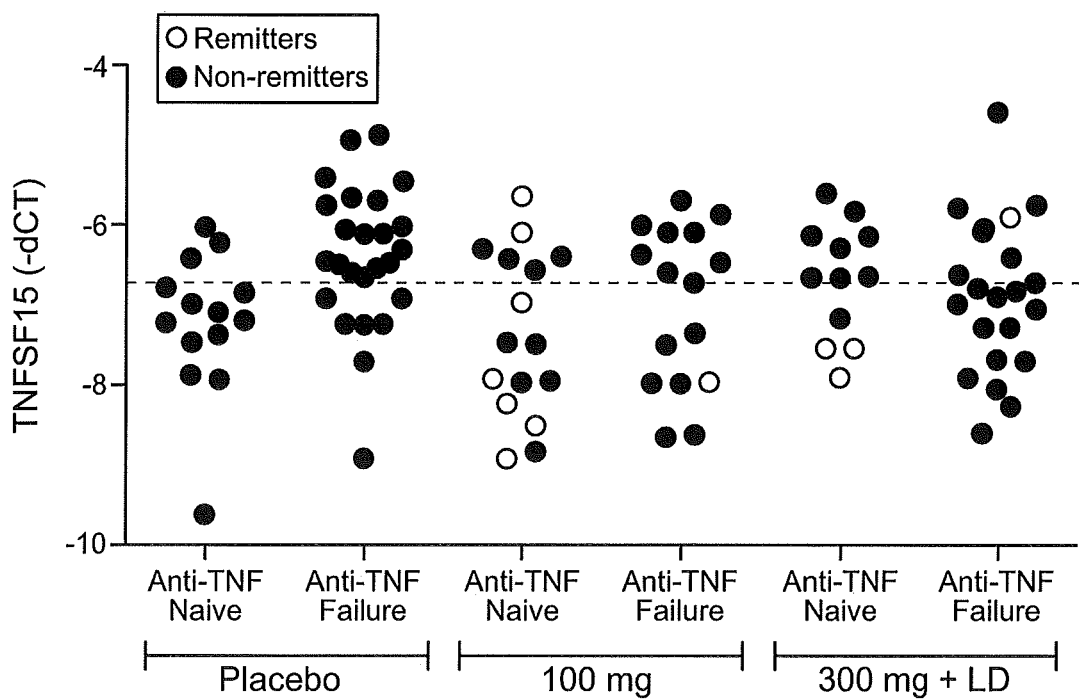
Figure 15D:
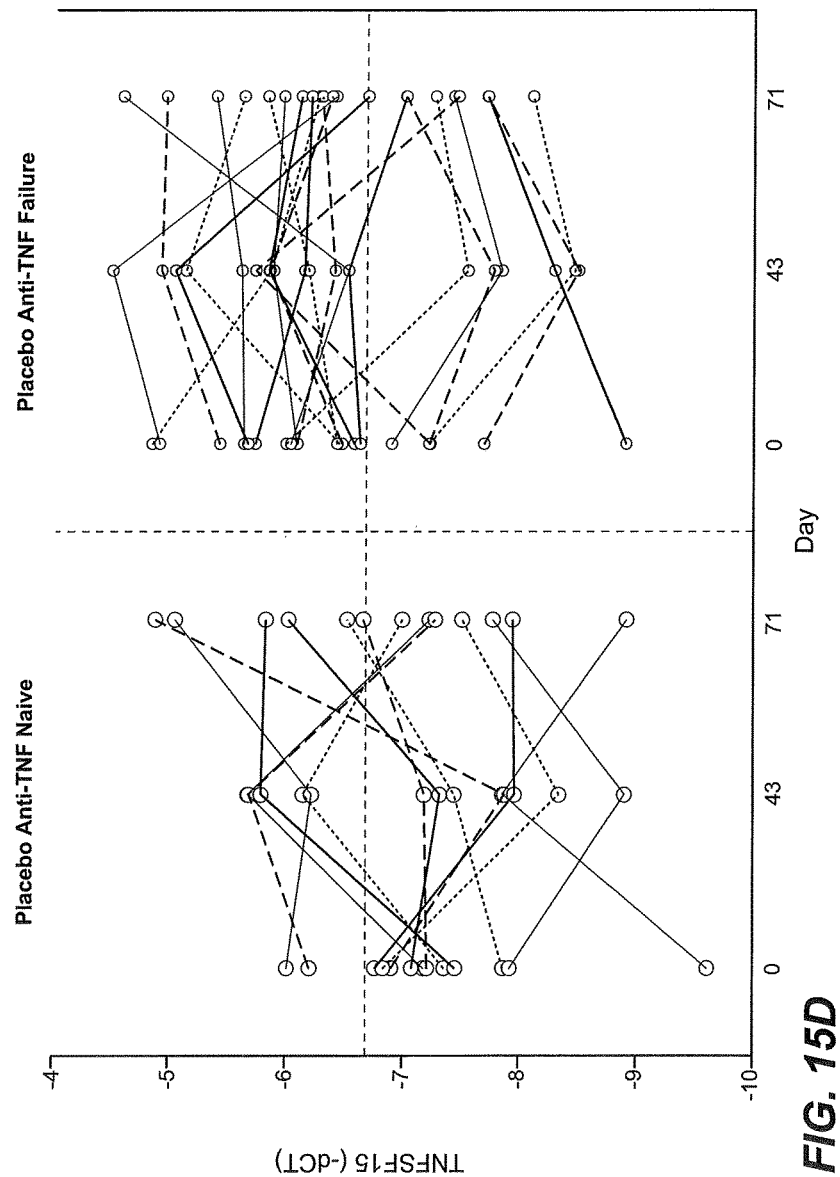
Figure 16A:
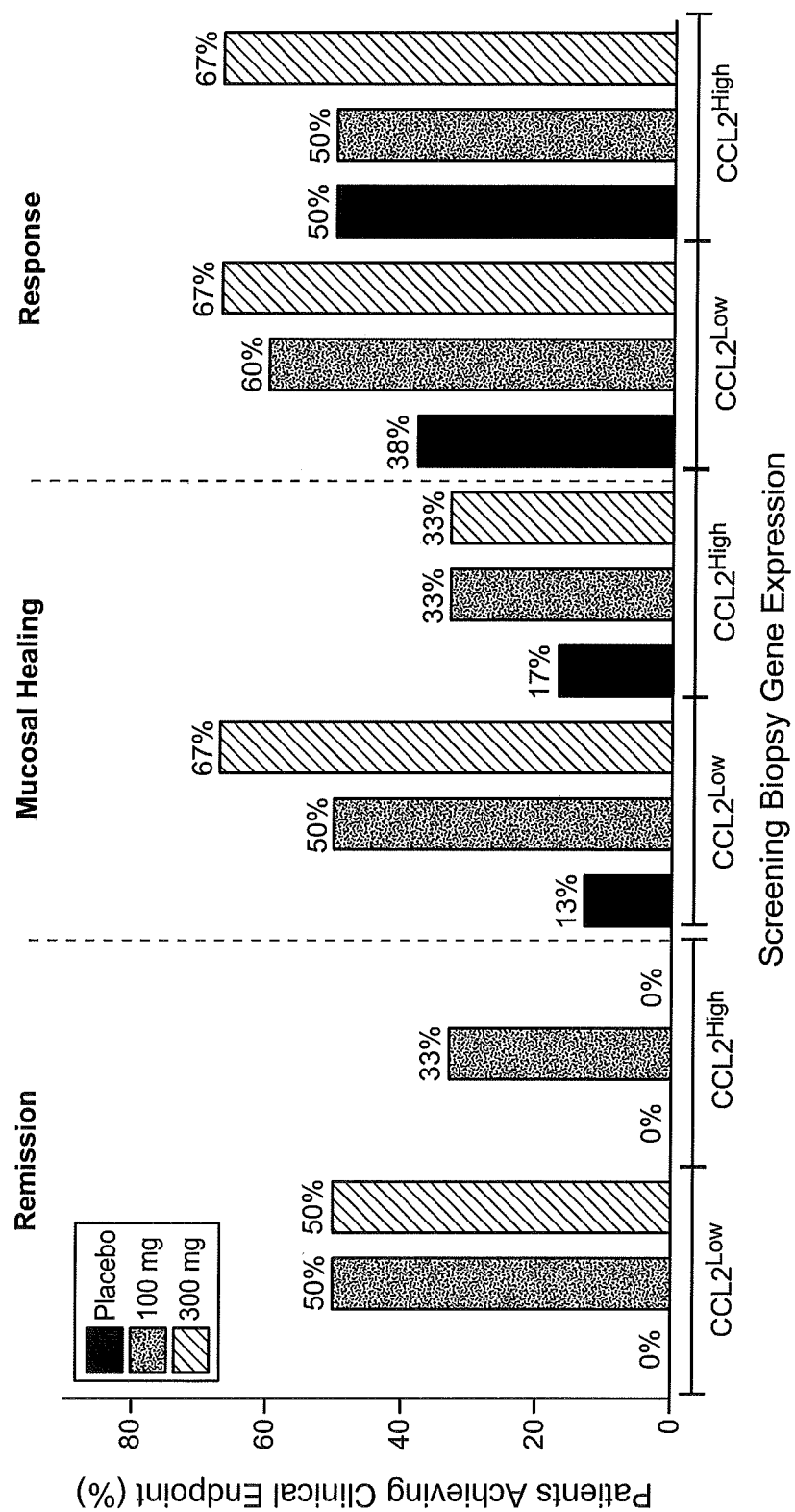
Figure 16B:
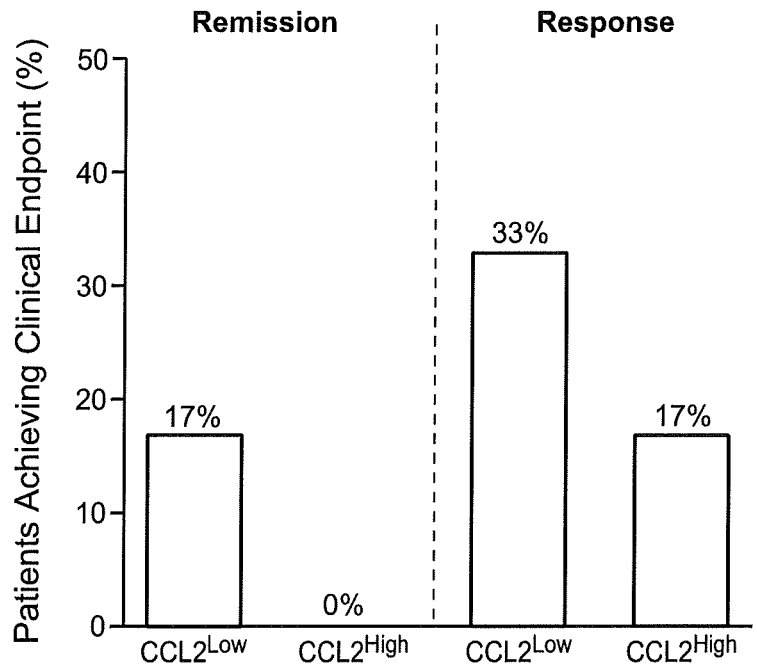
Figure 16C:
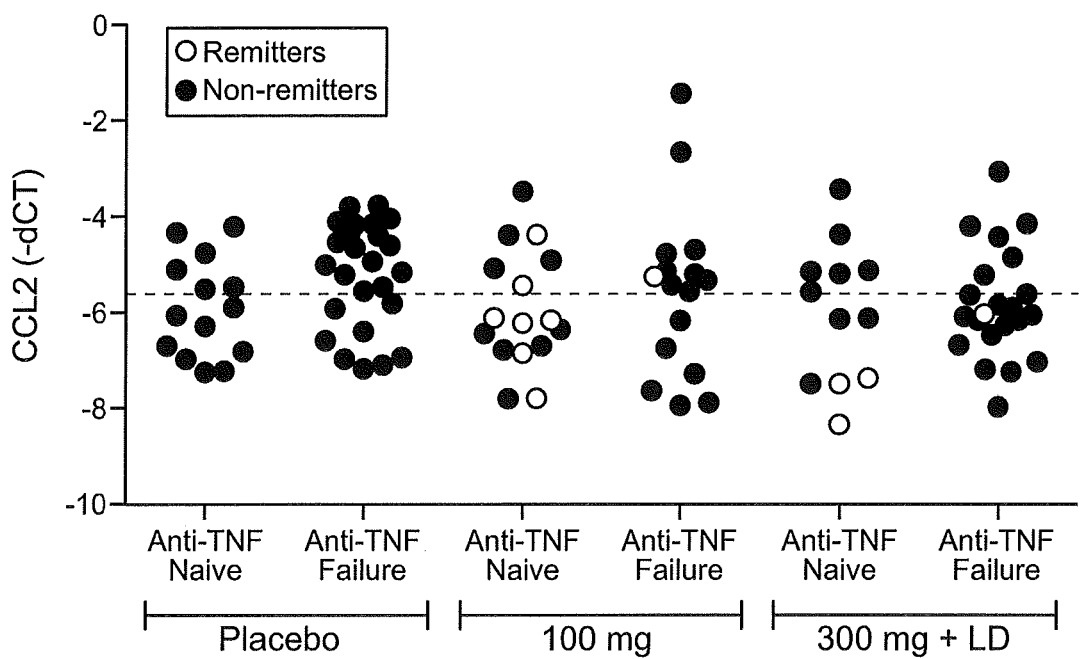
Figure 16D:
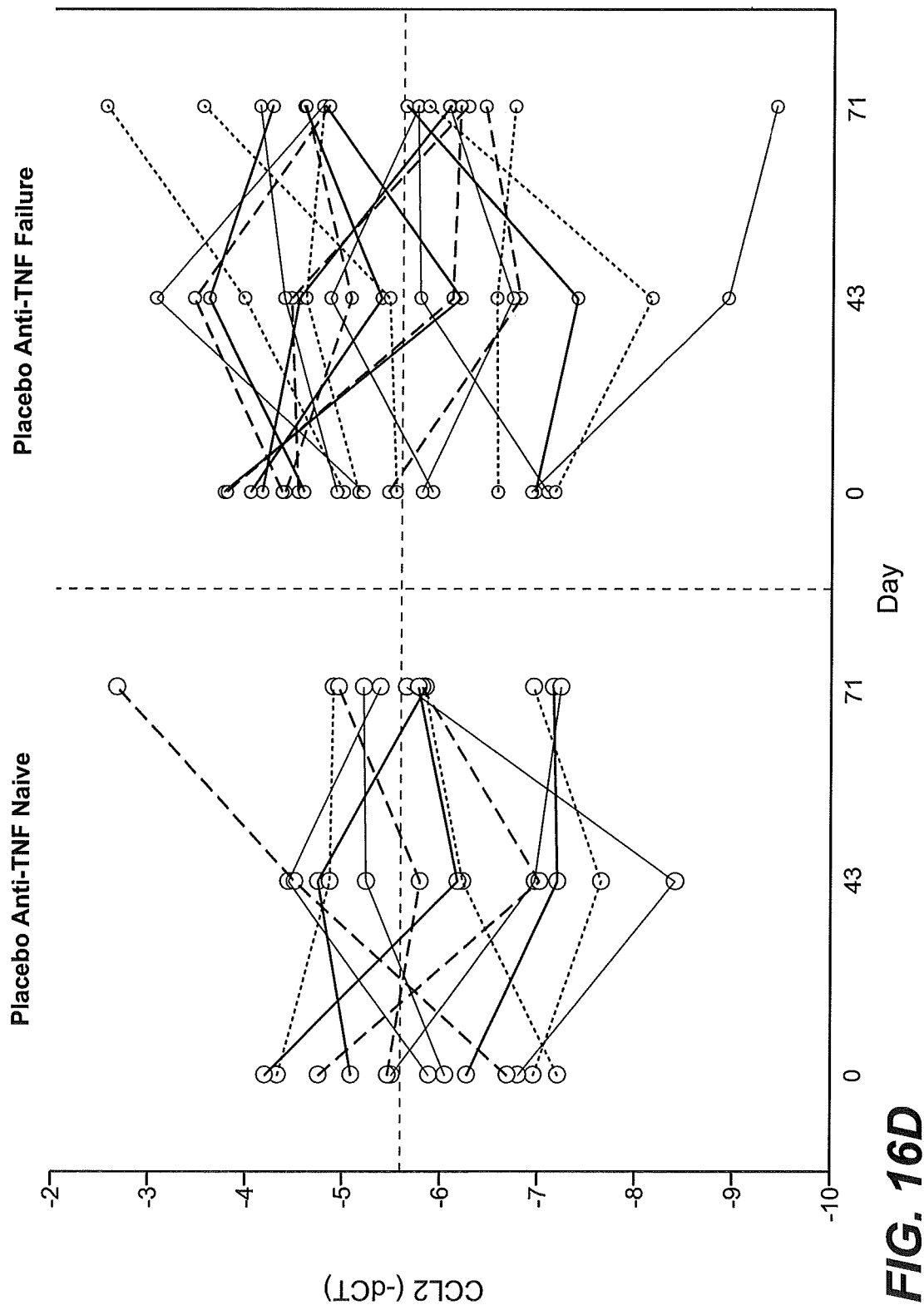
Figure 17A:
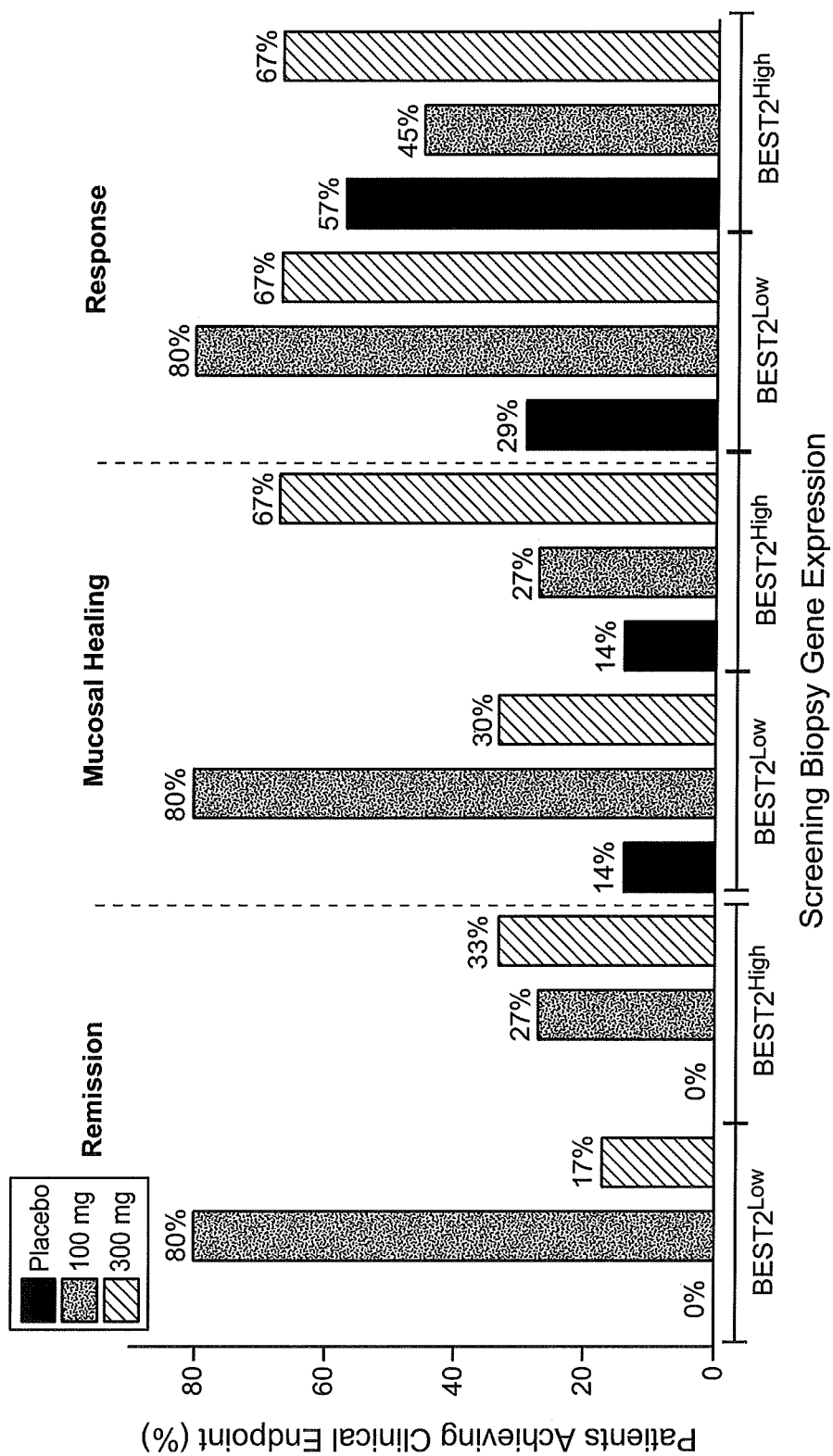
Figure 17B:
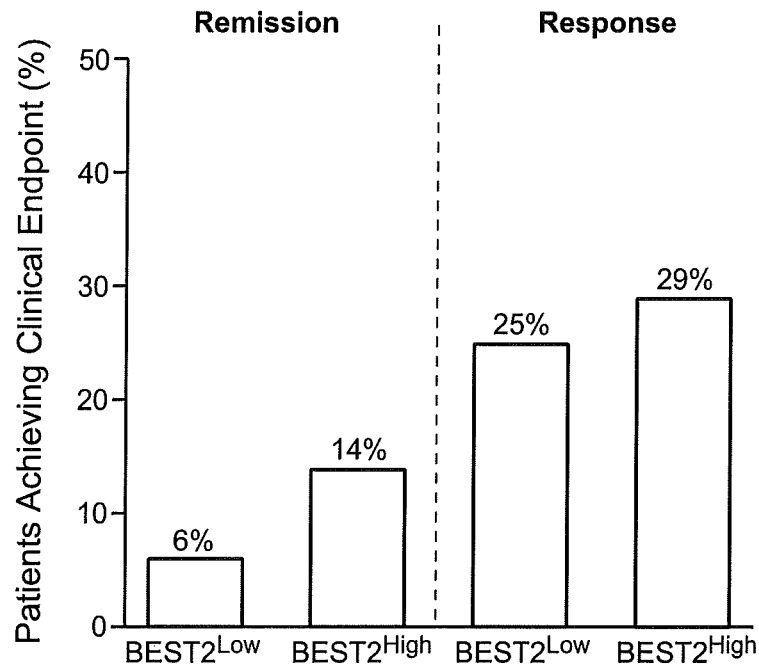
Figure 17C:
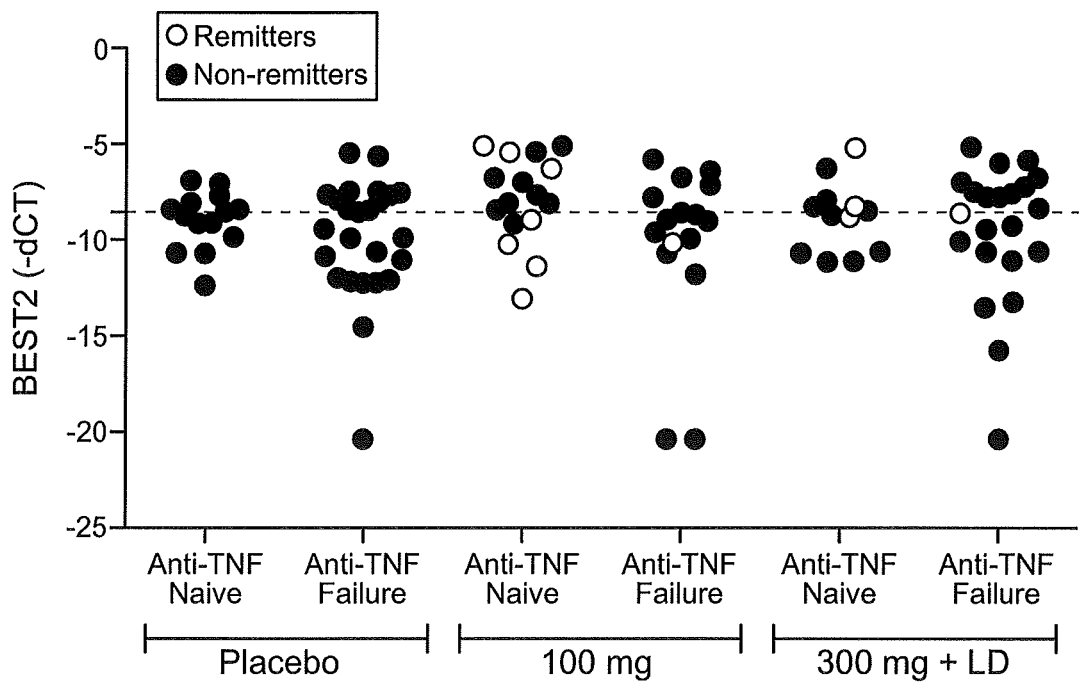
Figure 17D:
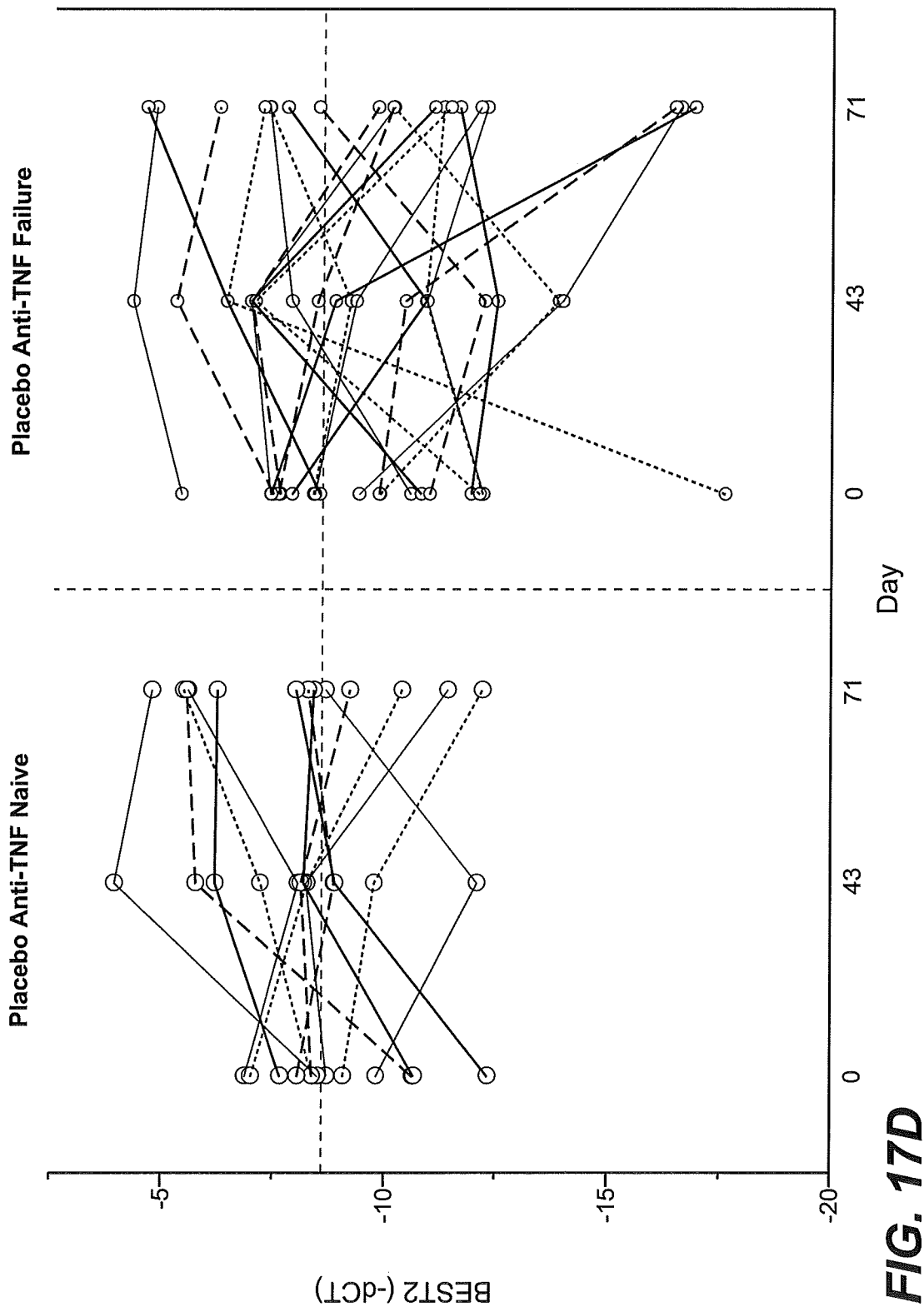
Figure 18A:
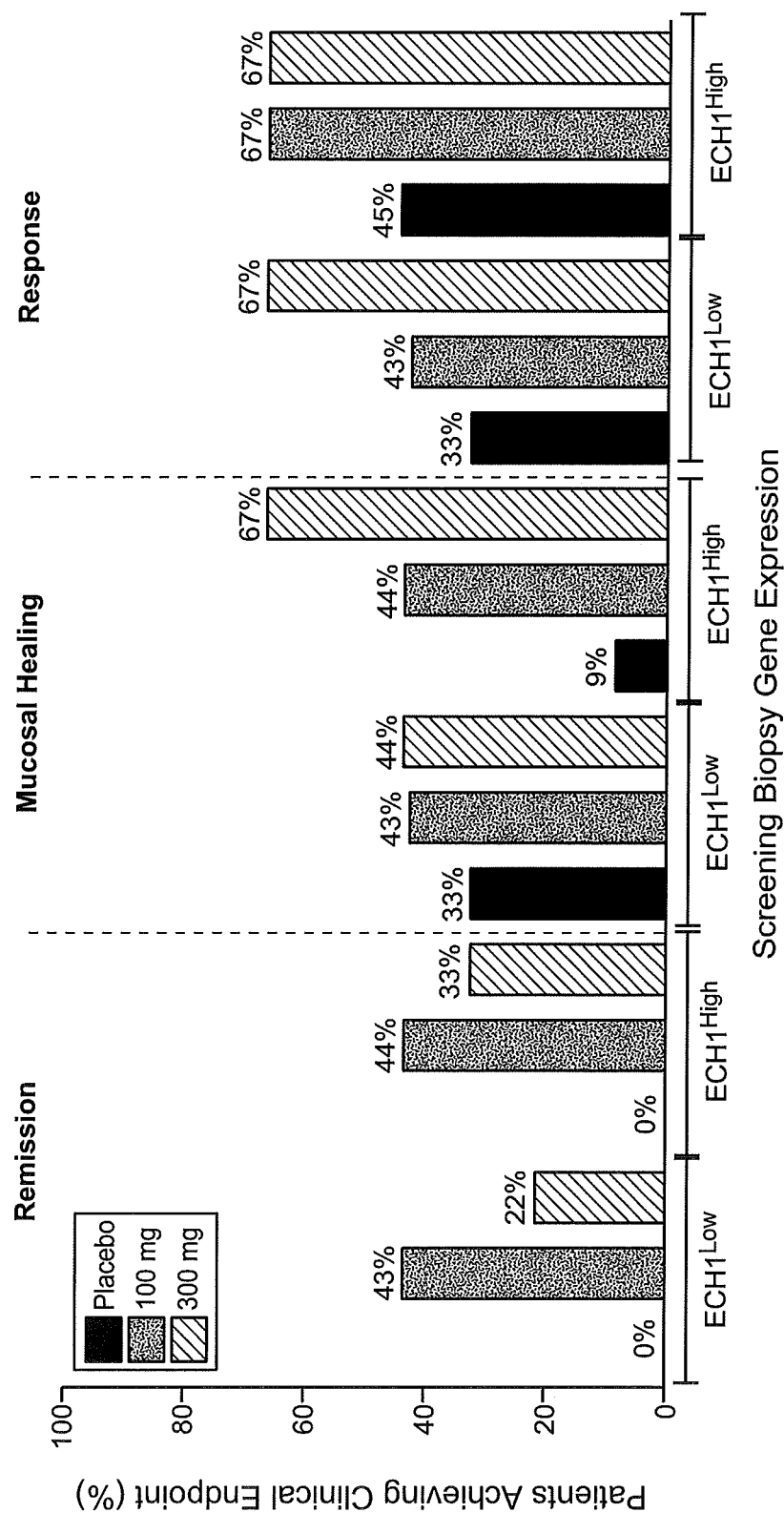
Figure 18B:
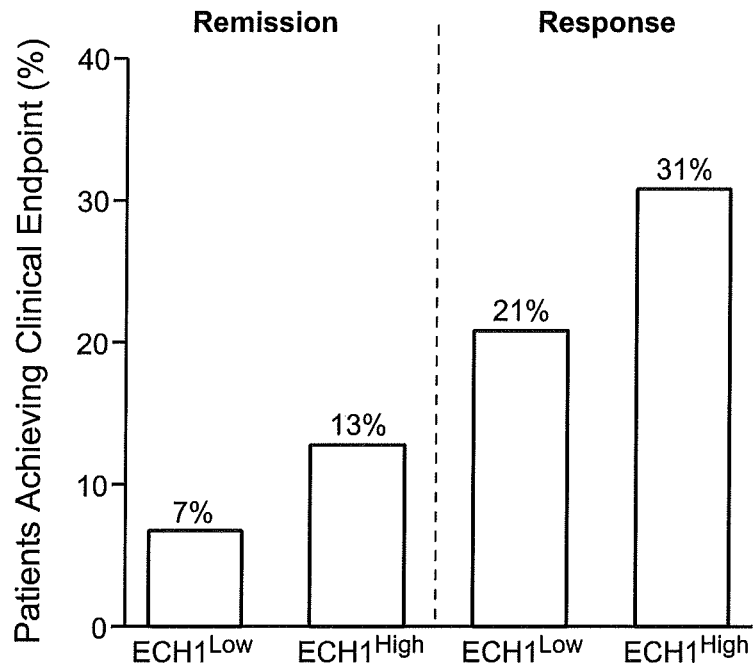
Figure 18C:
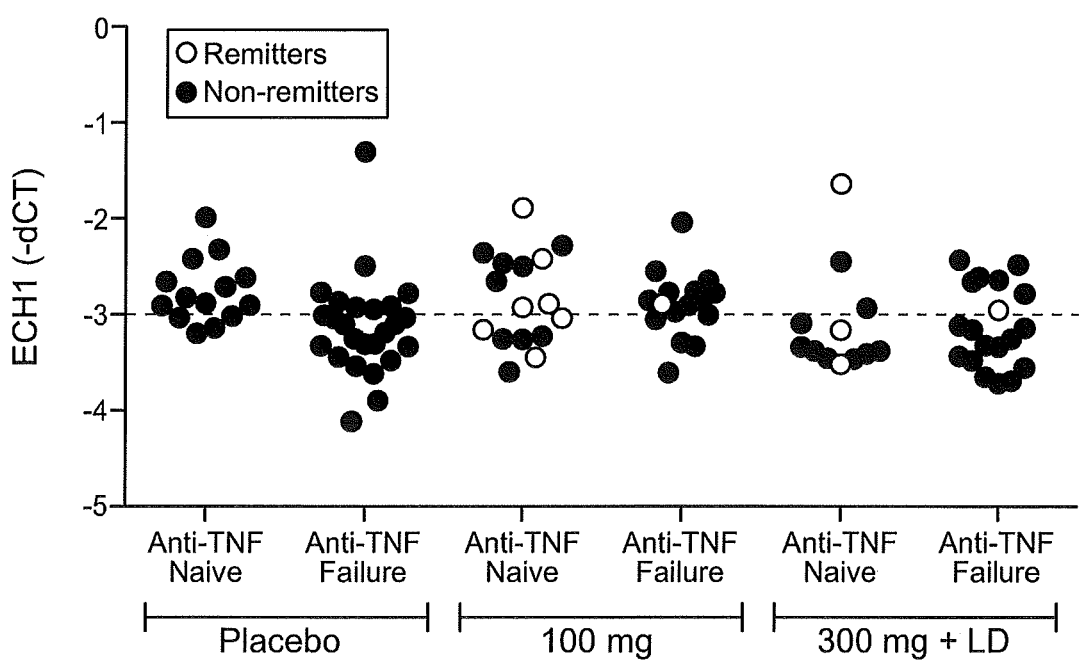
Figure 18D:
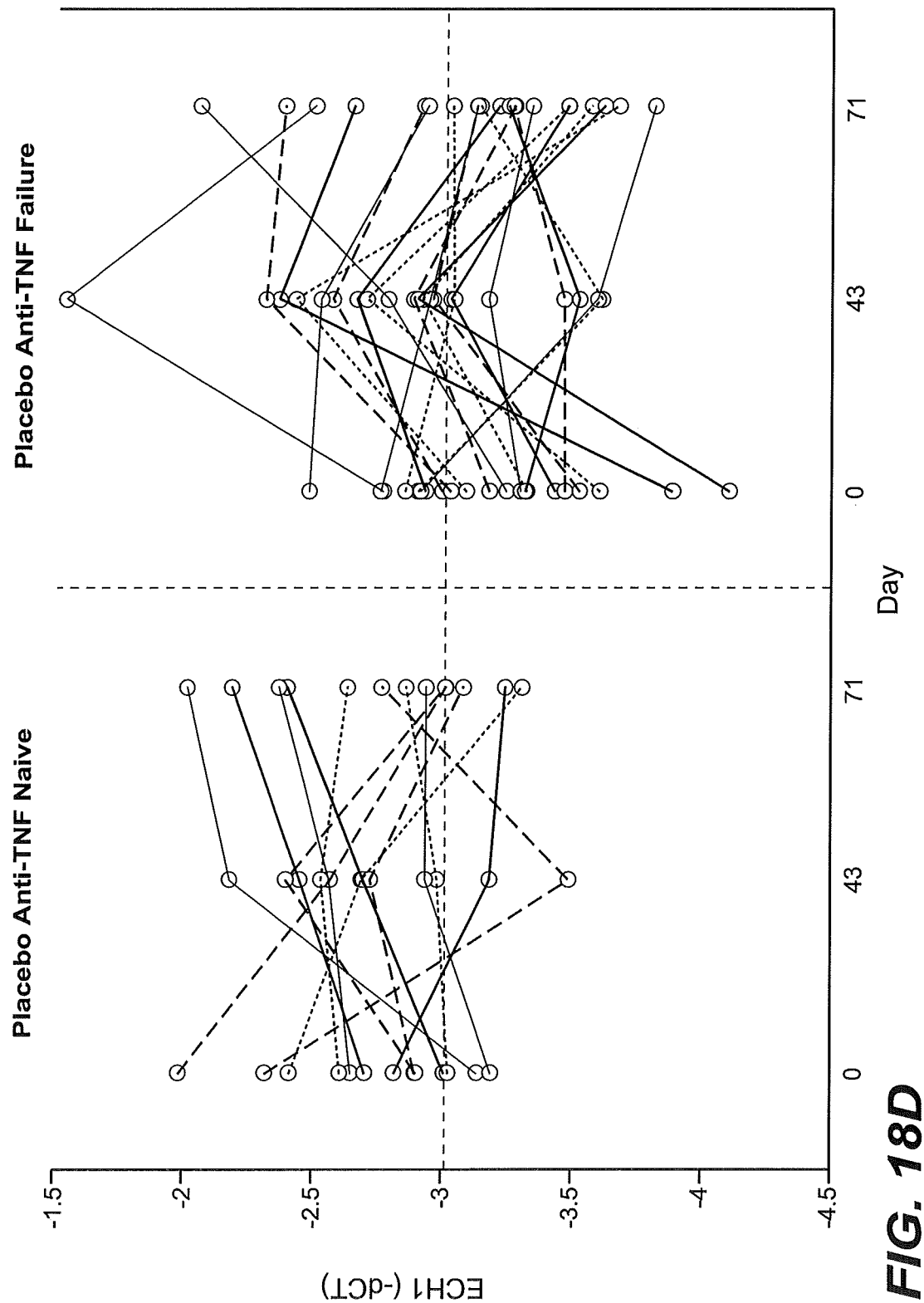
Figure 19A:
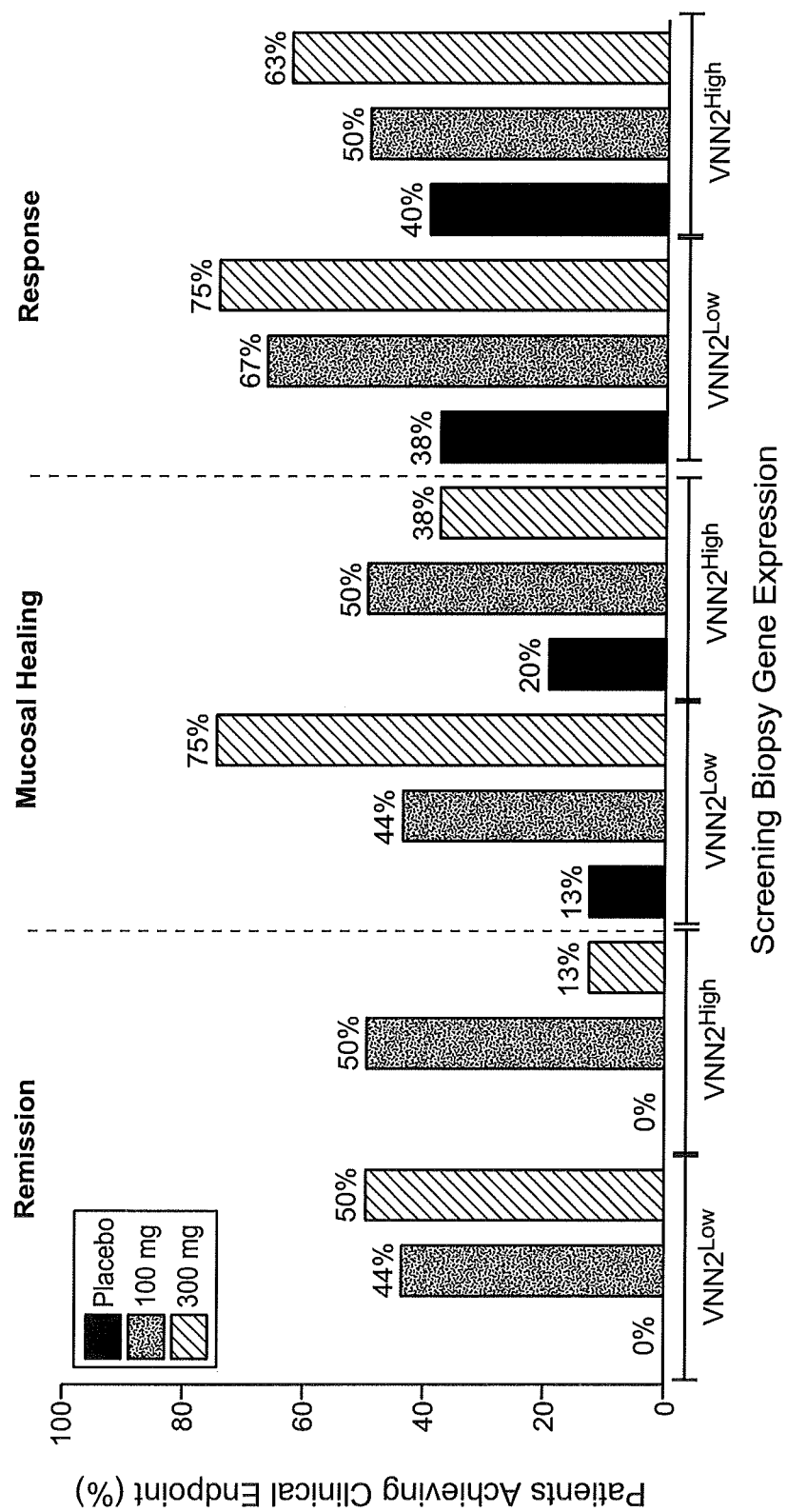
Figure 19B:
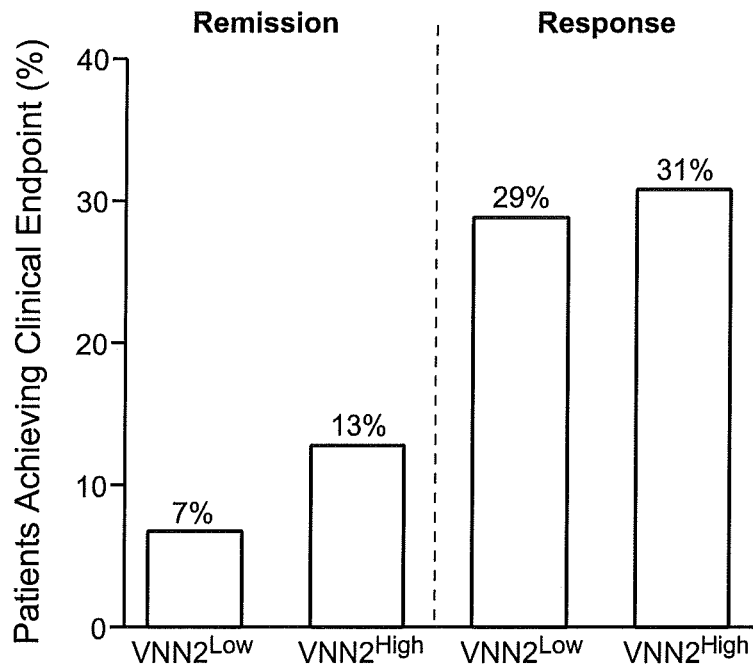
Figure 19C:
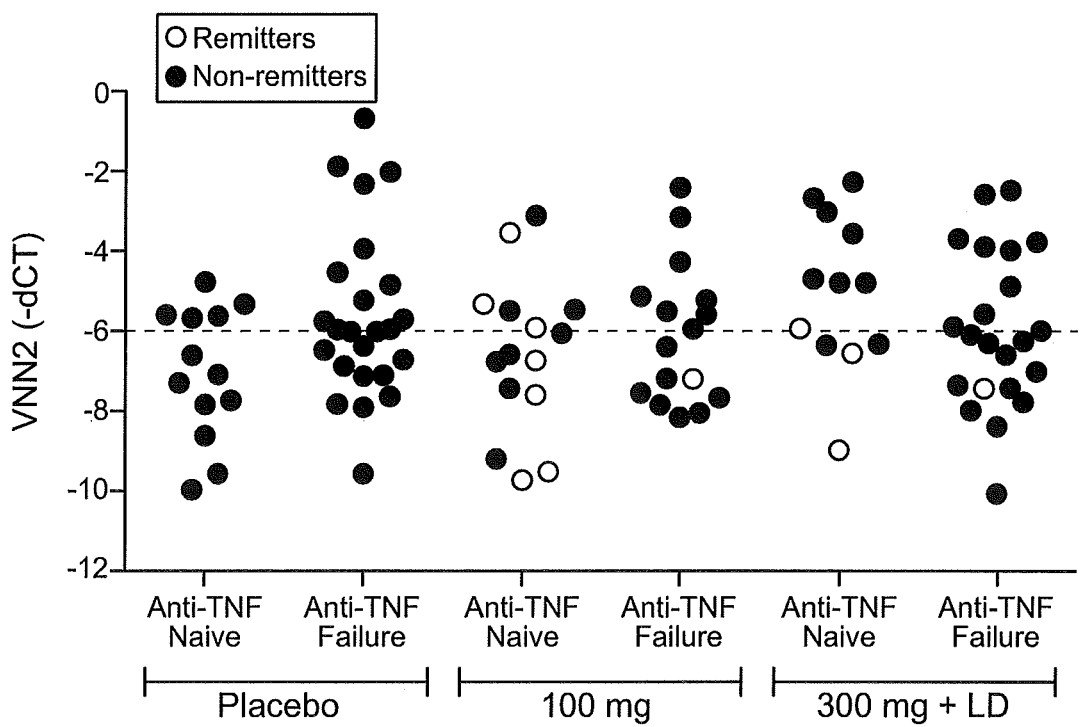
Figure 19D:
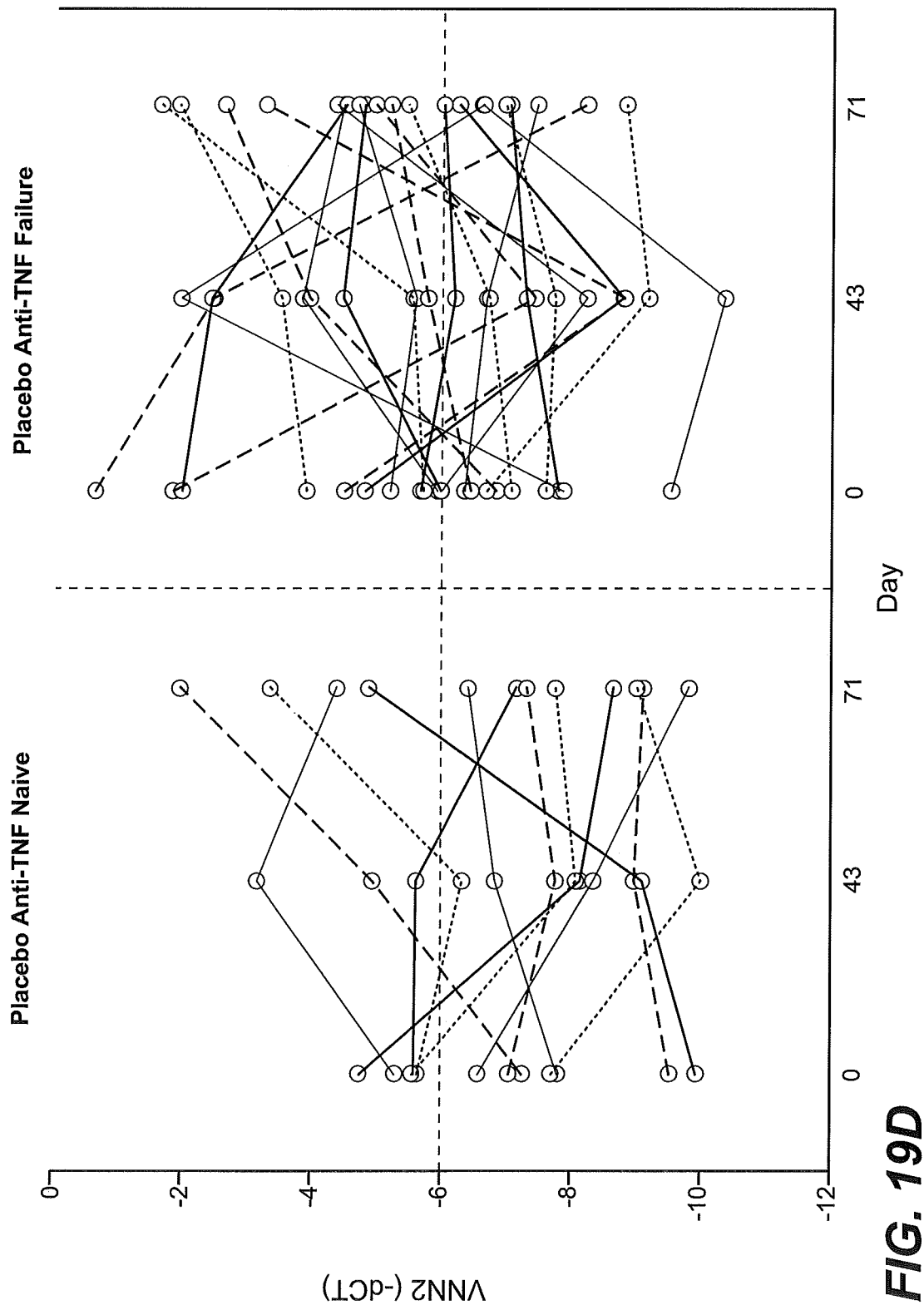
Figure 20A:
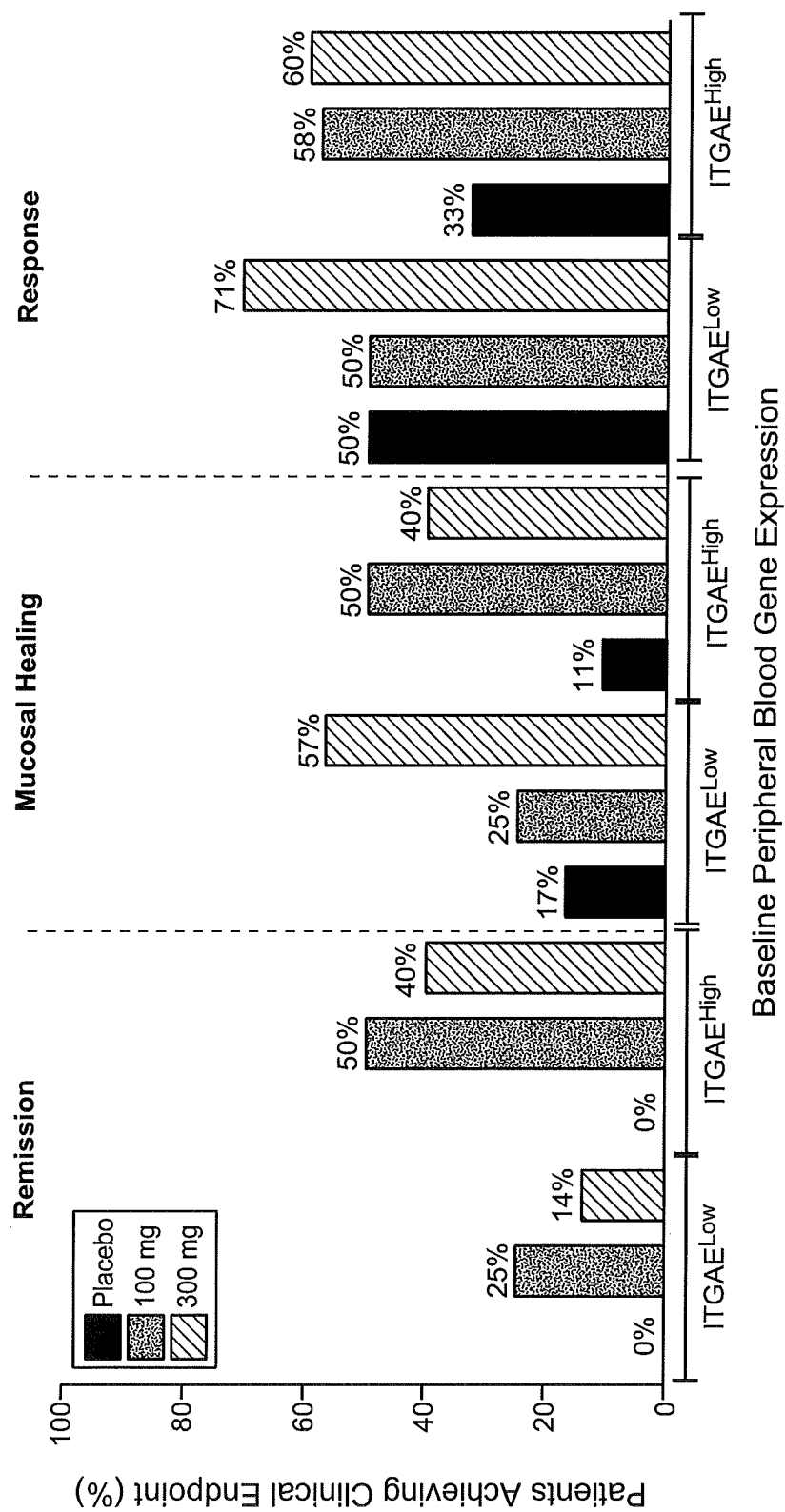
Figure 20B:
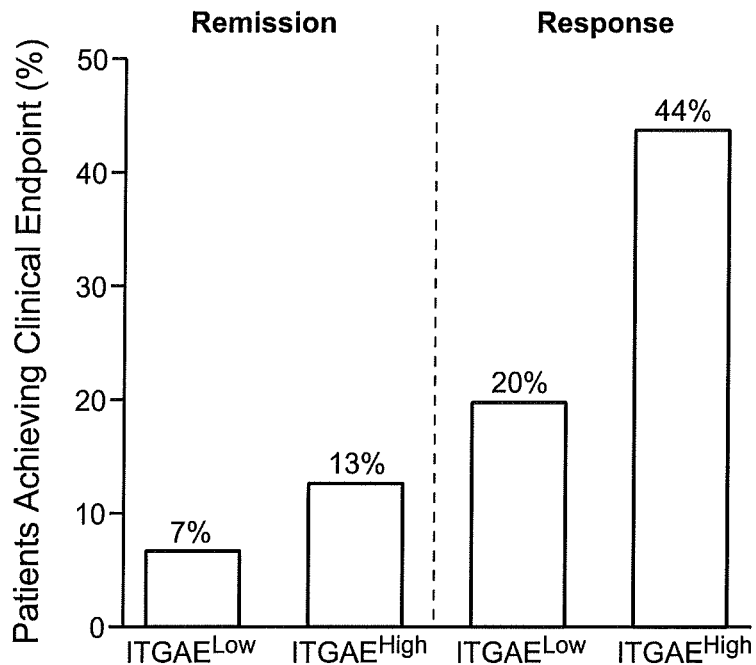
Figure 20C:
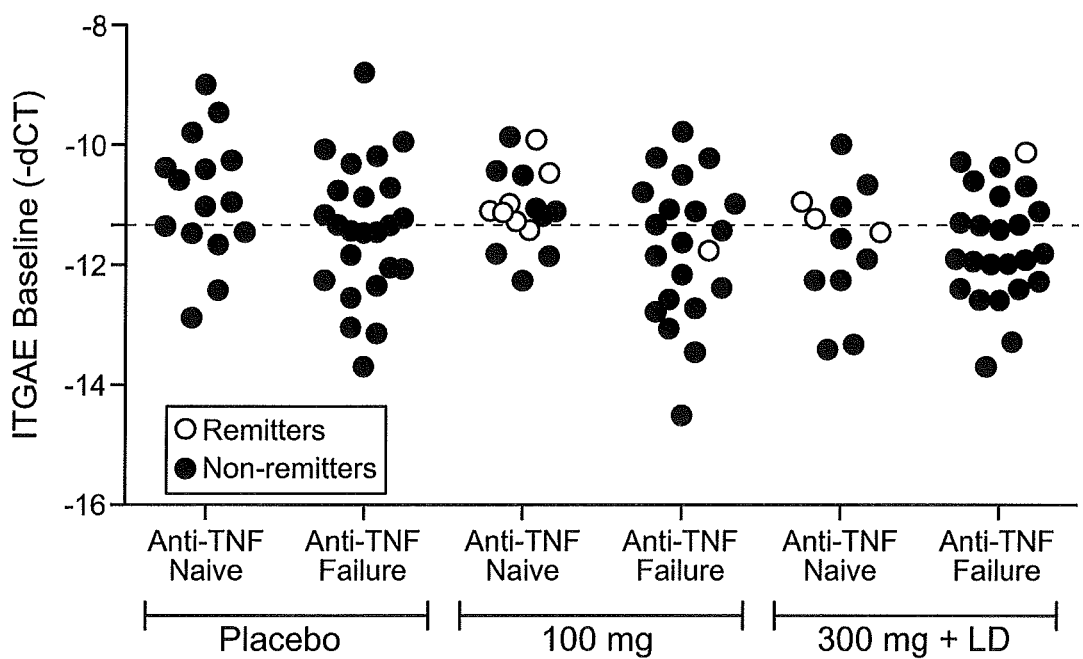
Figure 20D:
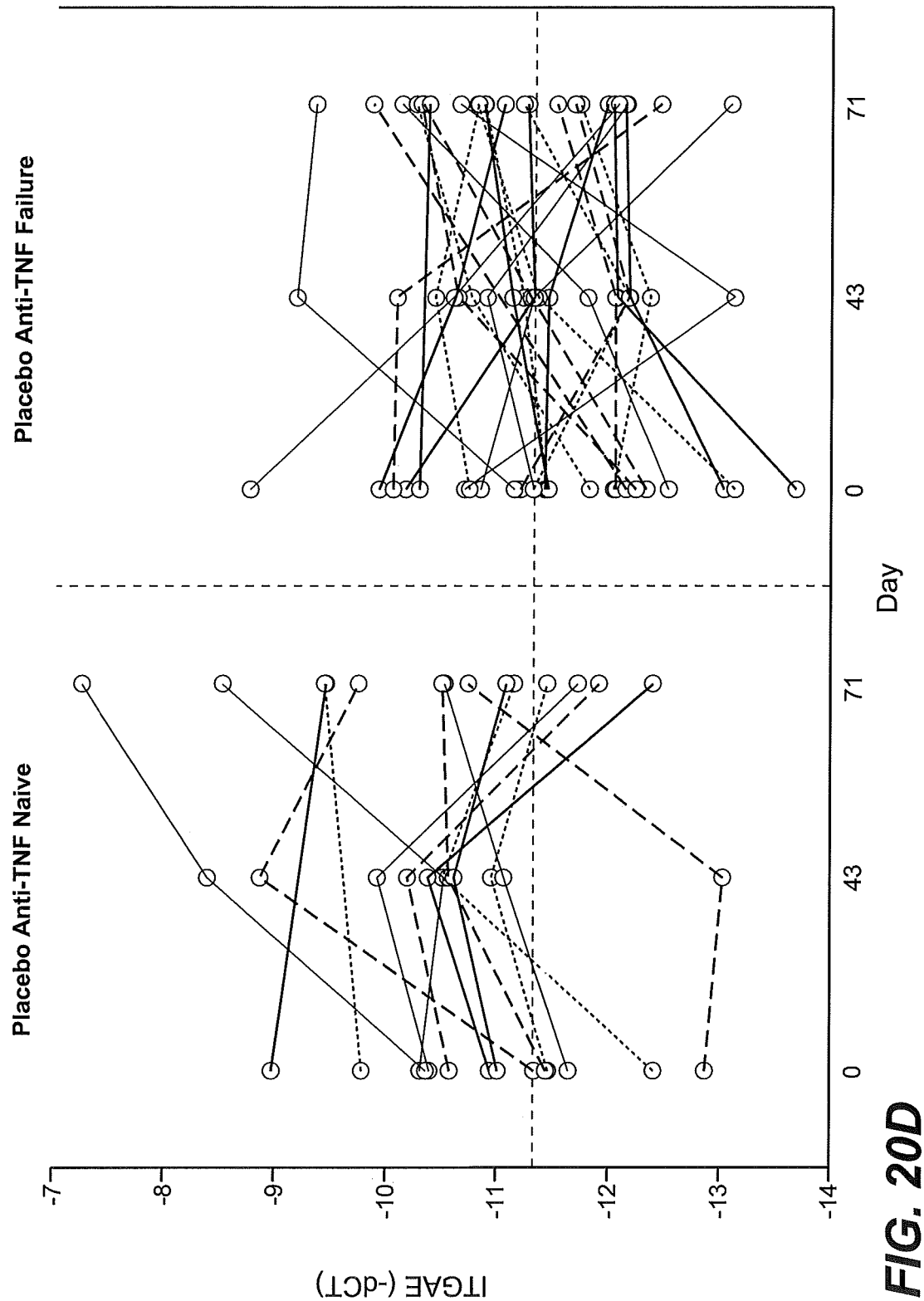
Figure 21A:
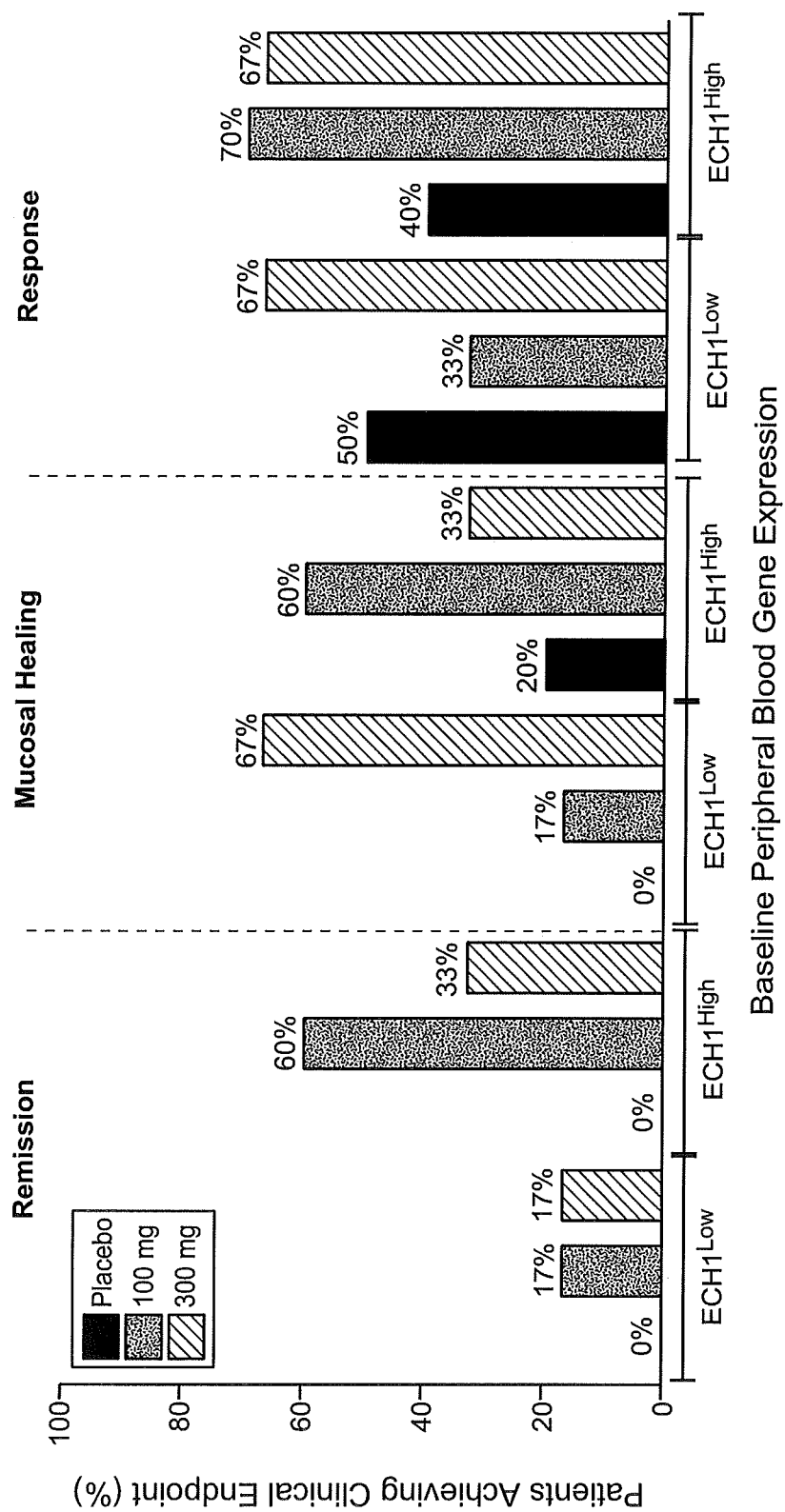
Figure 21B:
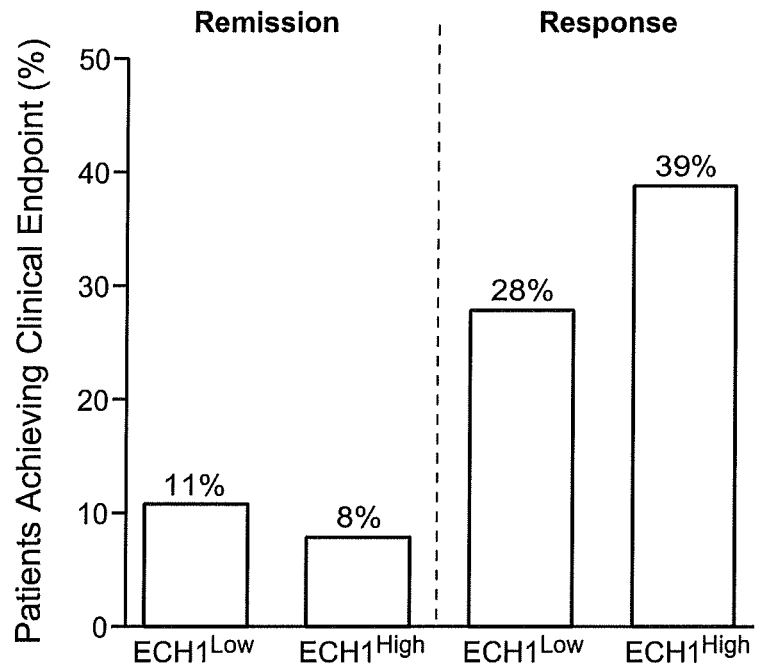
Figure 21C:
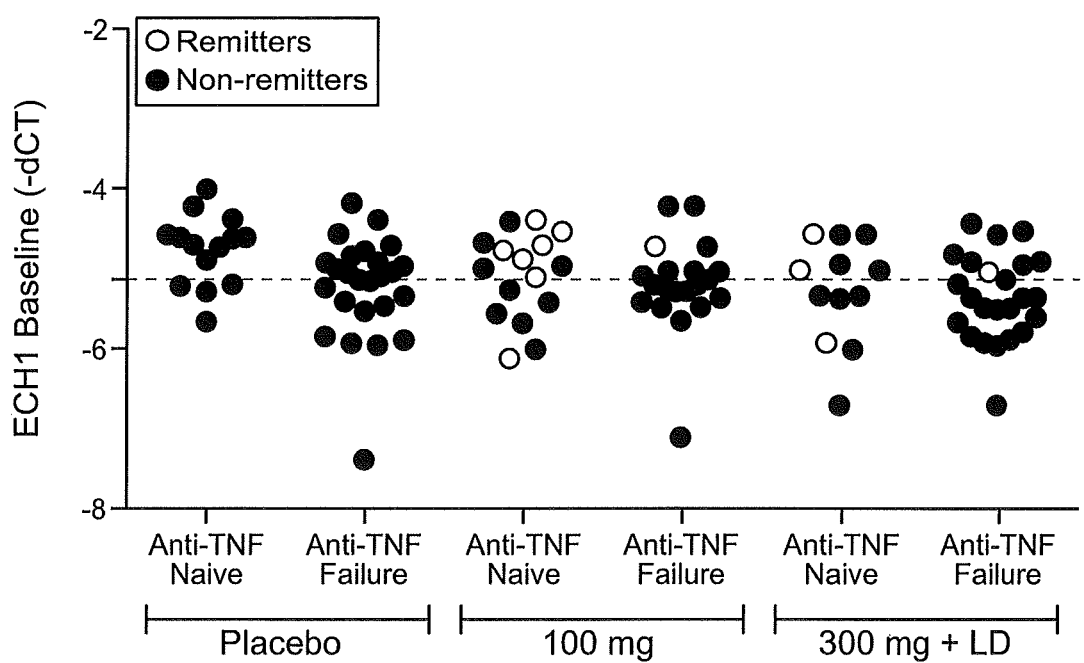
Figure 21D:
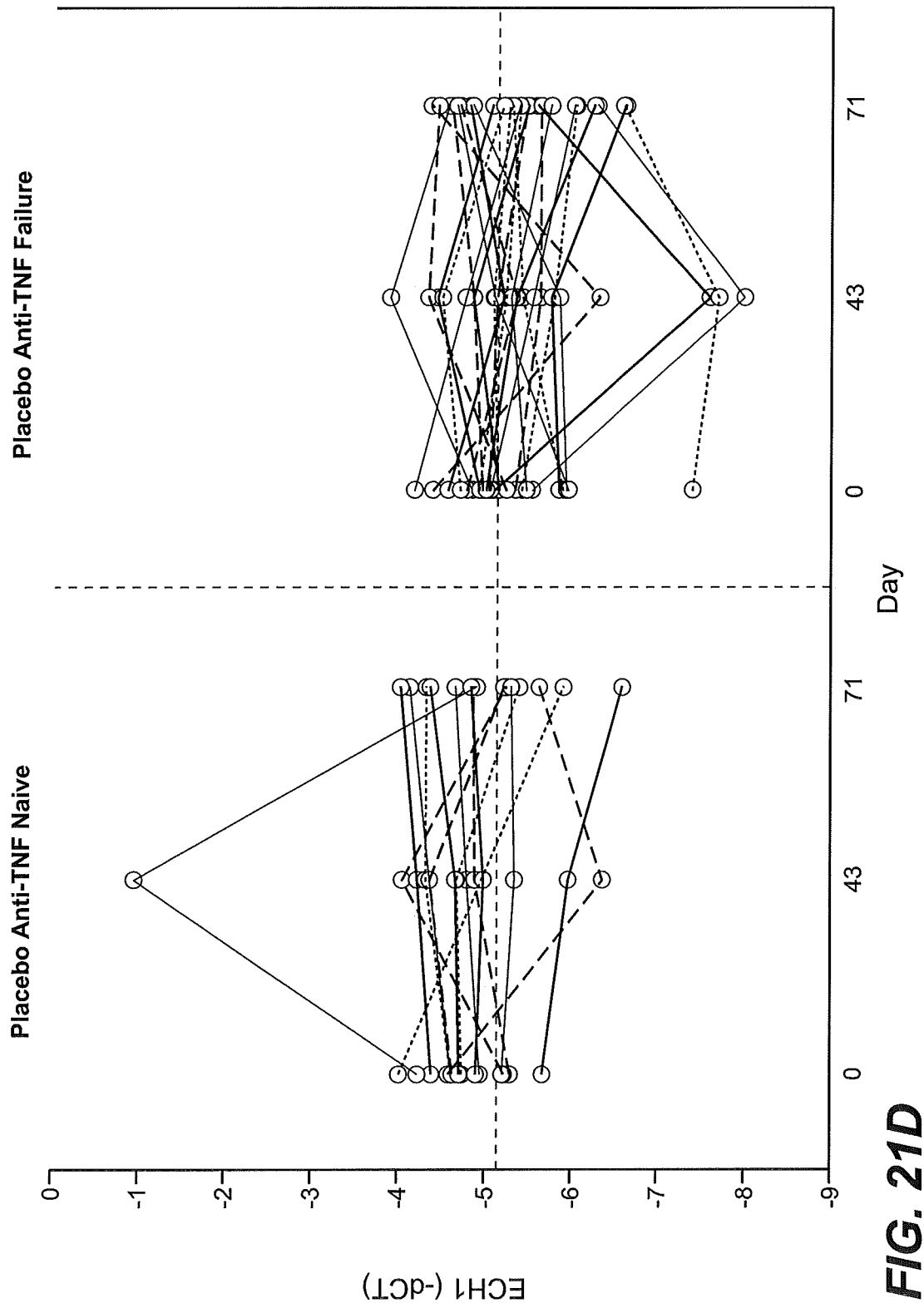
Figure 22A:
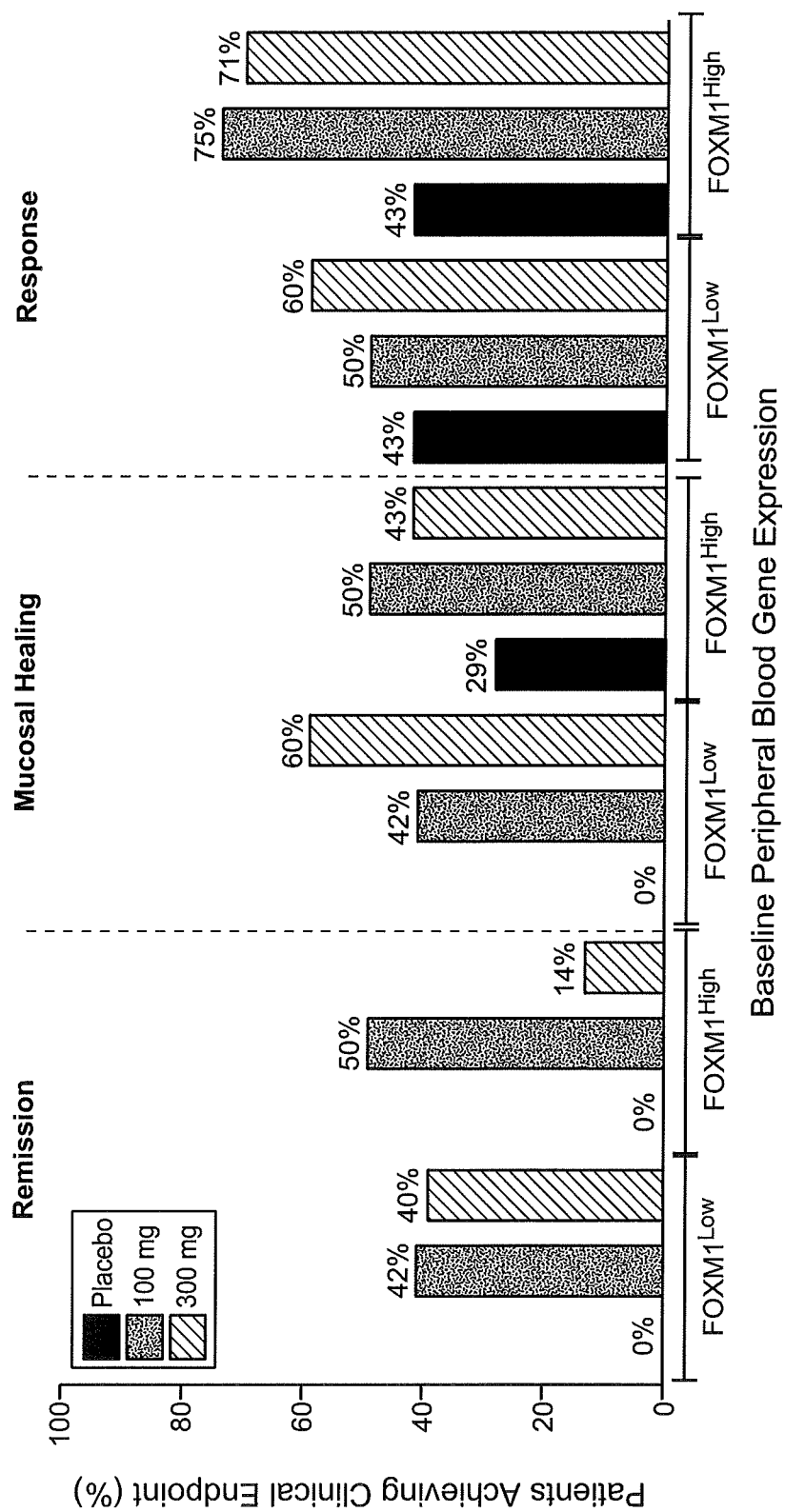
Figure 22B:
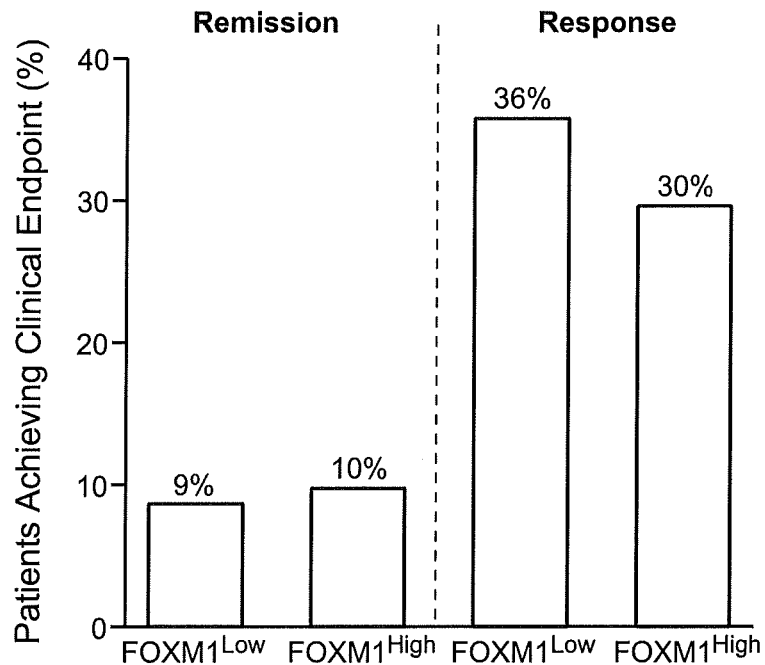
Figure 22C:
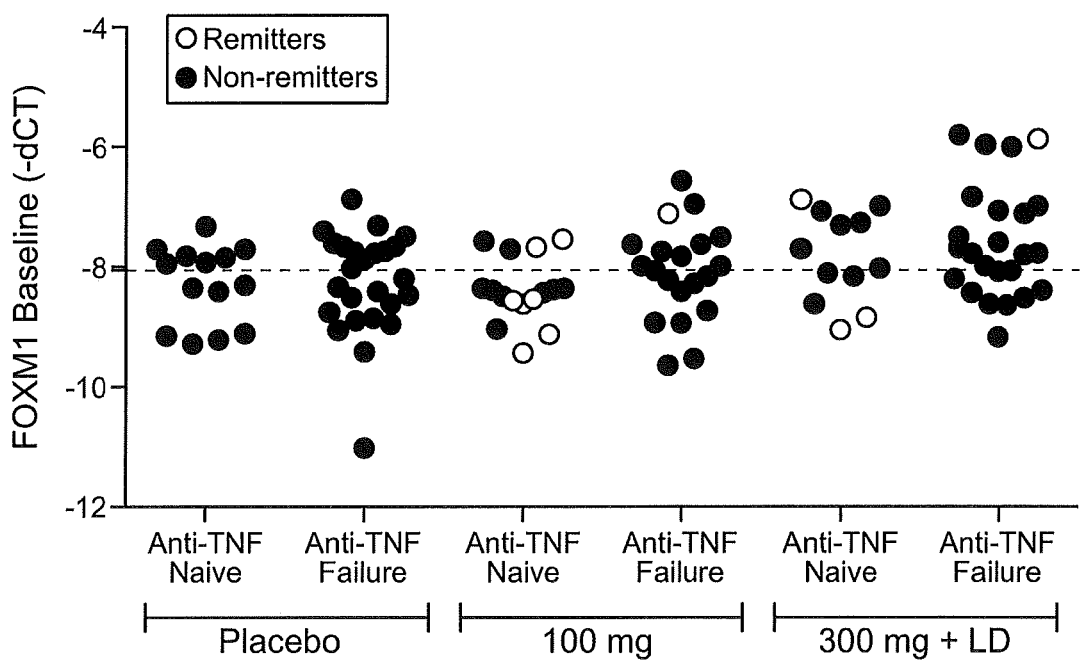
Figure 22D:
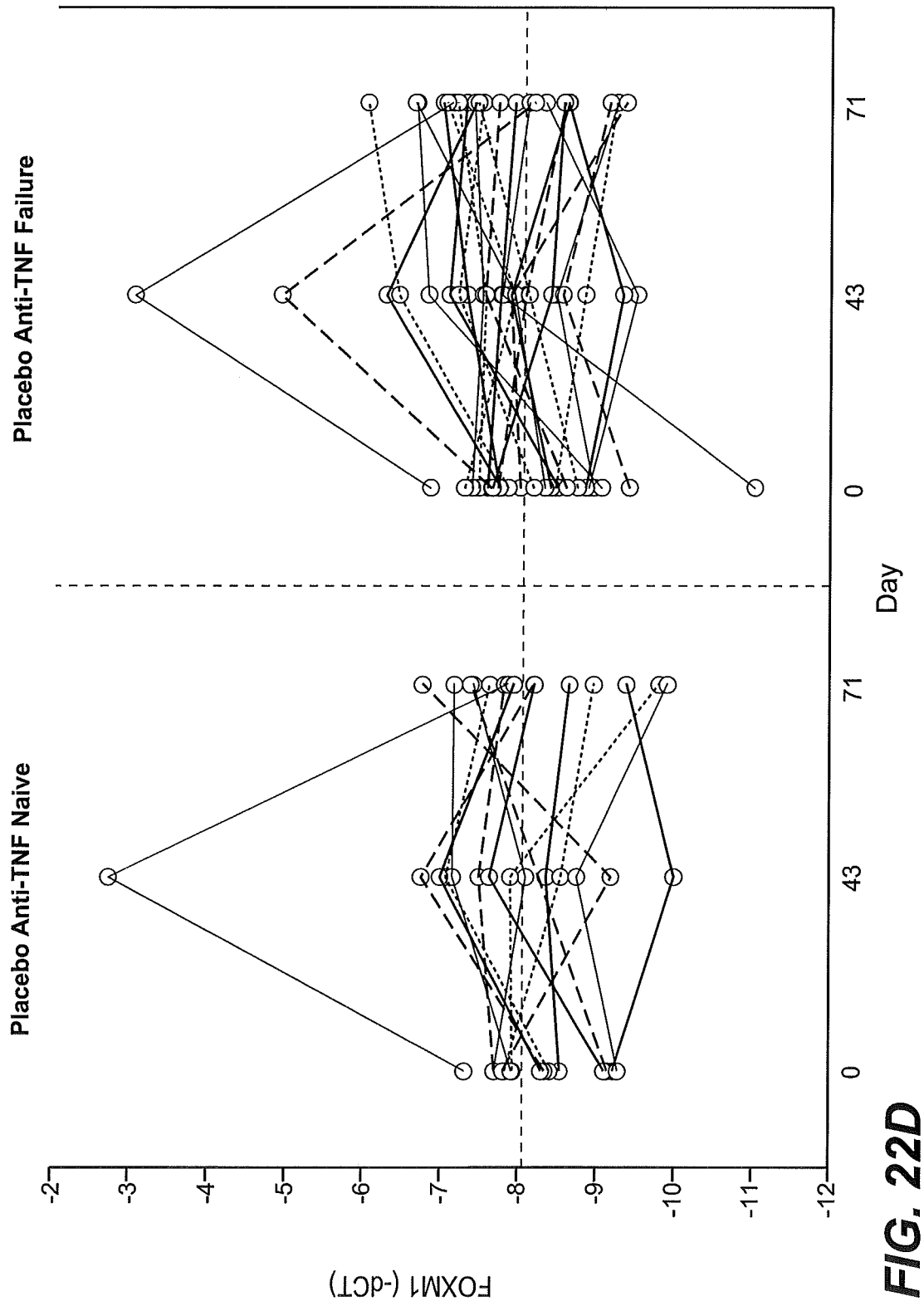
Figure 23A:
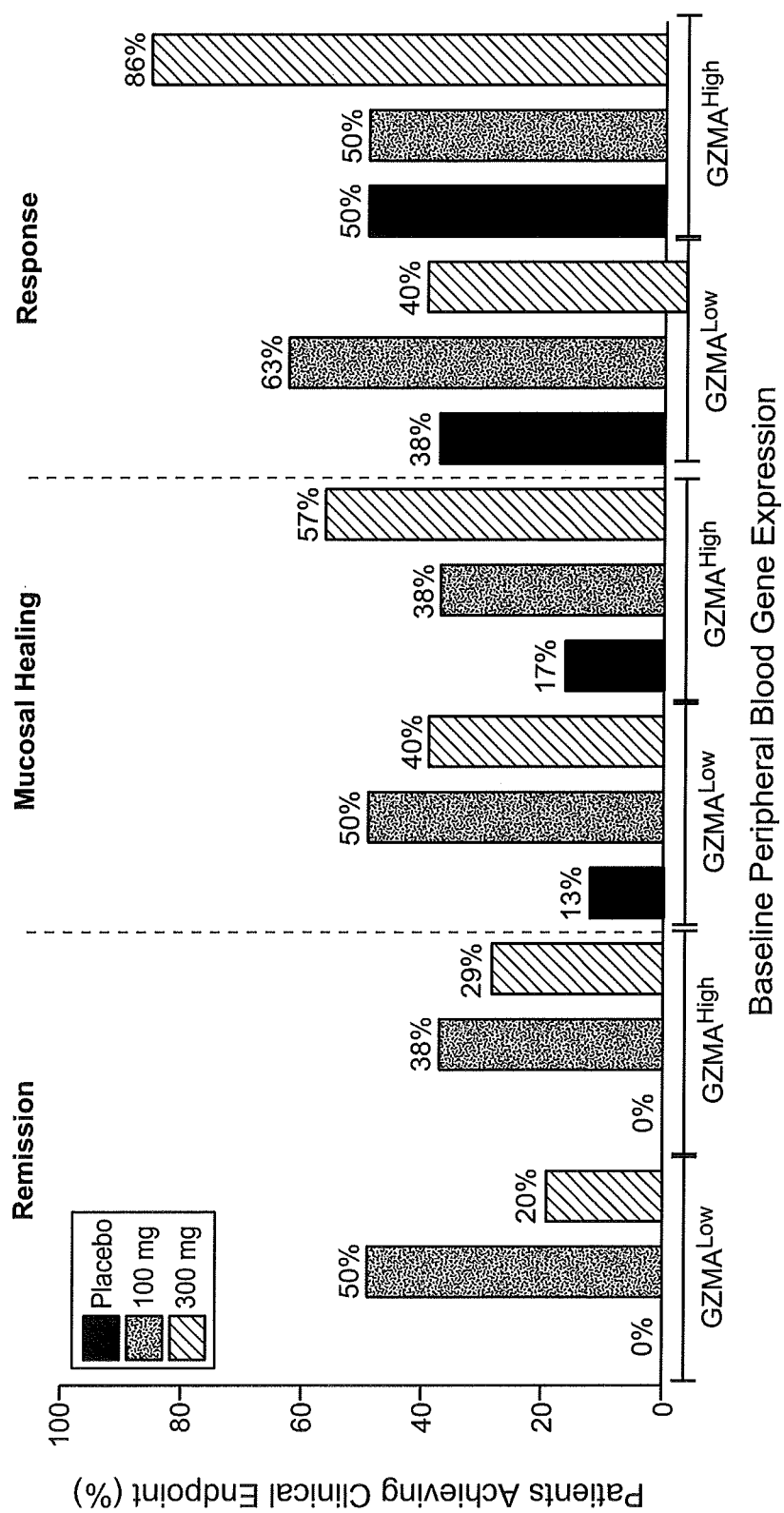
Figure 23B:
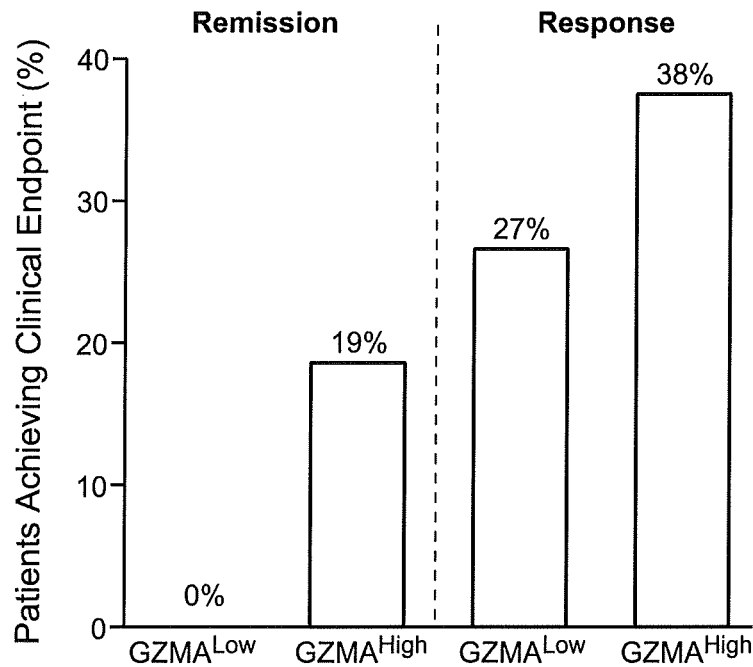
Figure 23C:
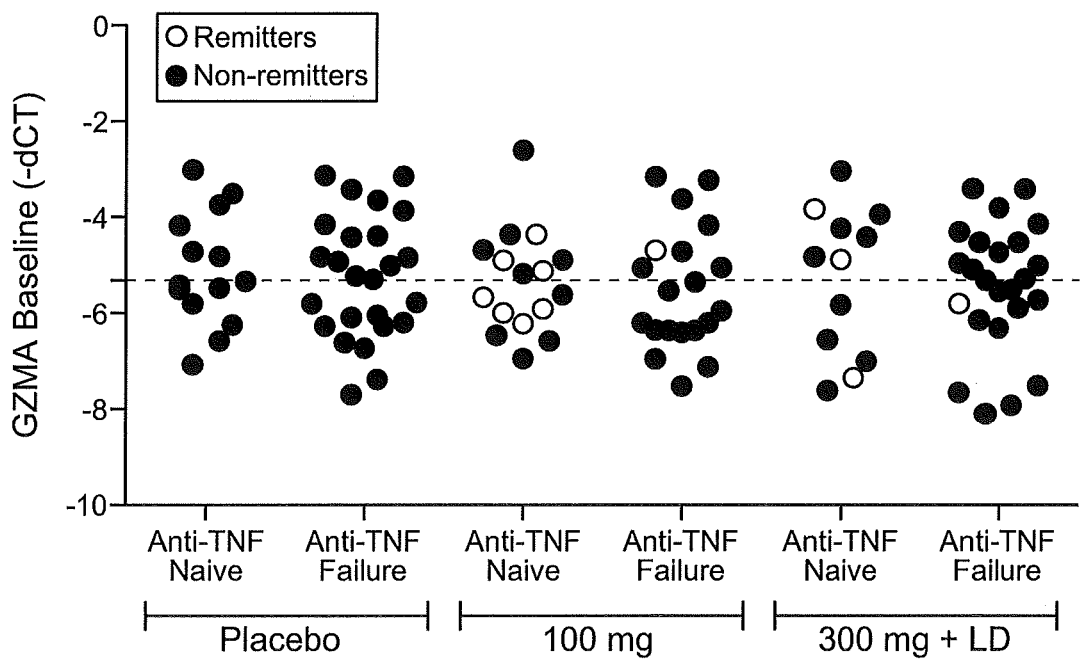
Figure 23D:
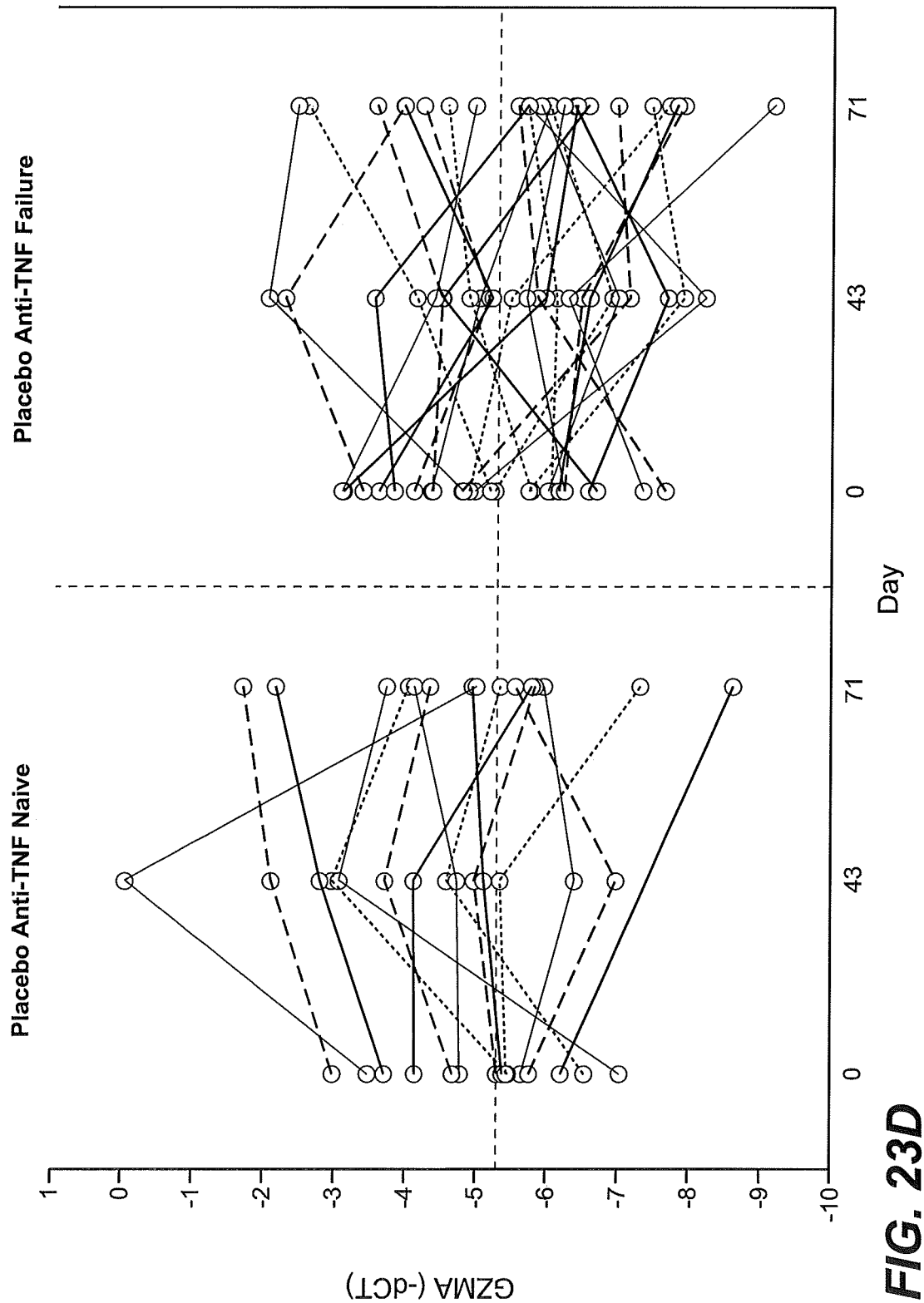
Figure 24A:
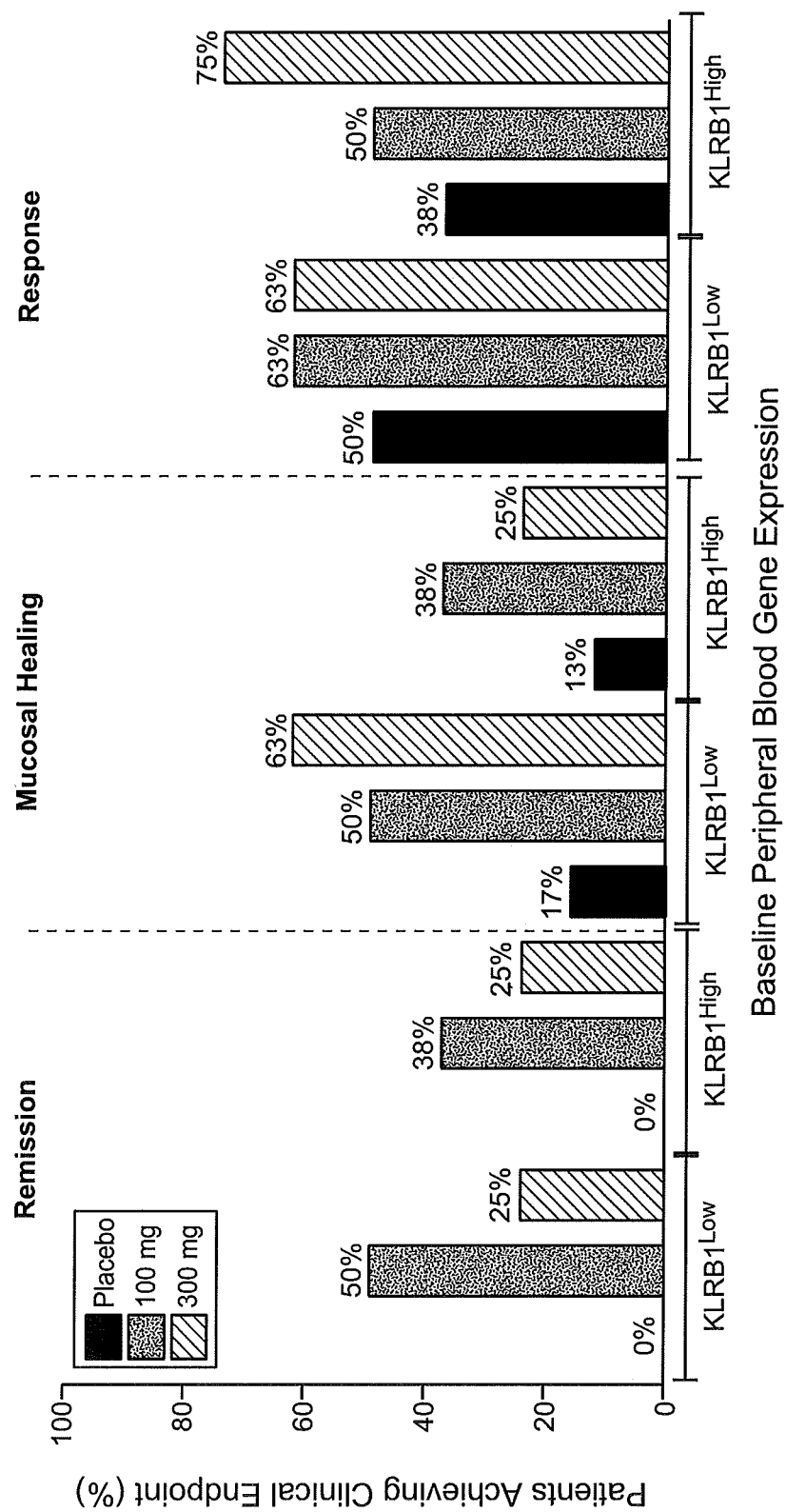
Figure 24B:
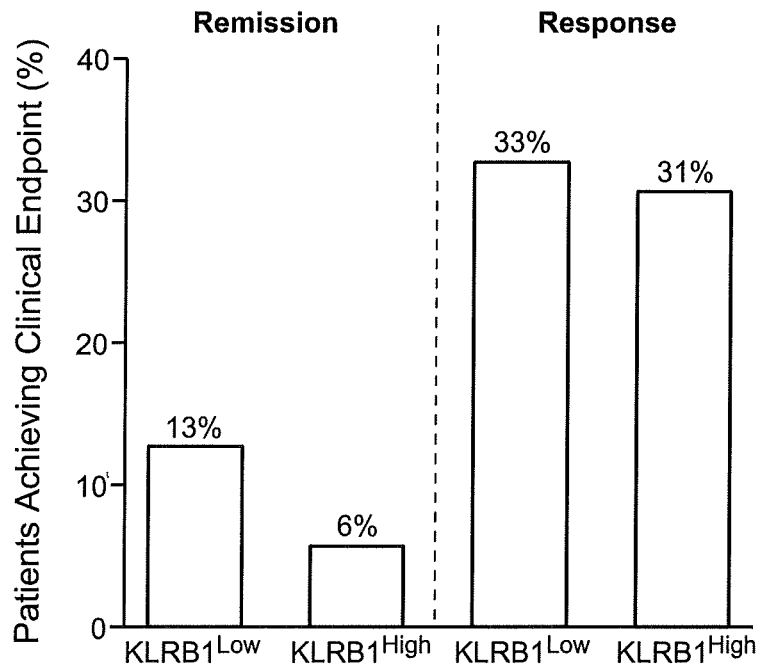
Figure 24C:
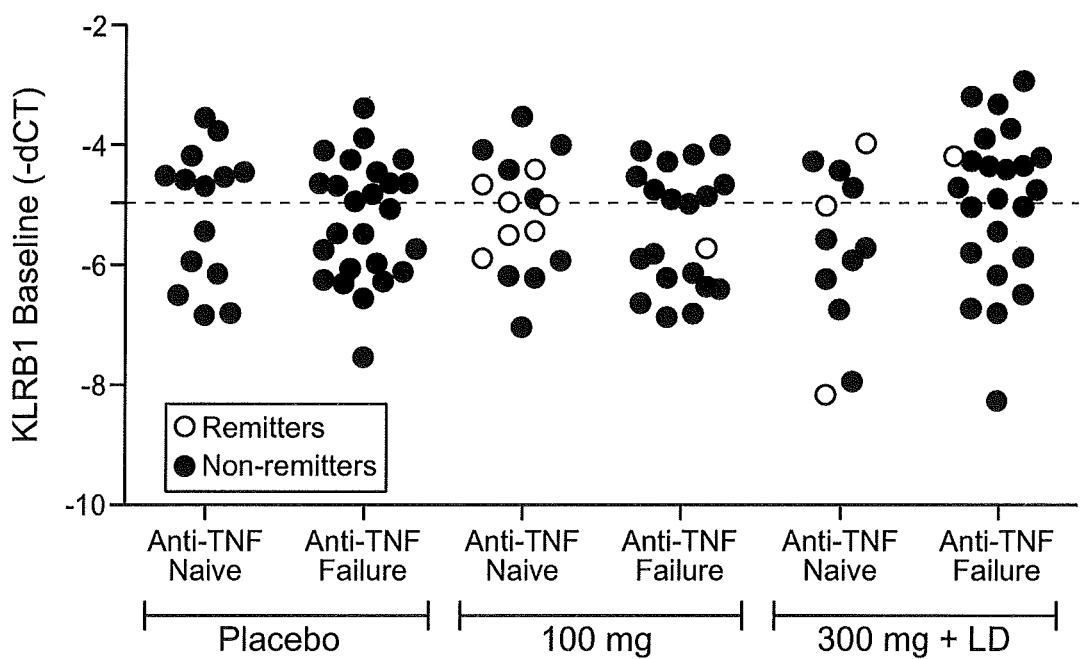
Figure 24D:
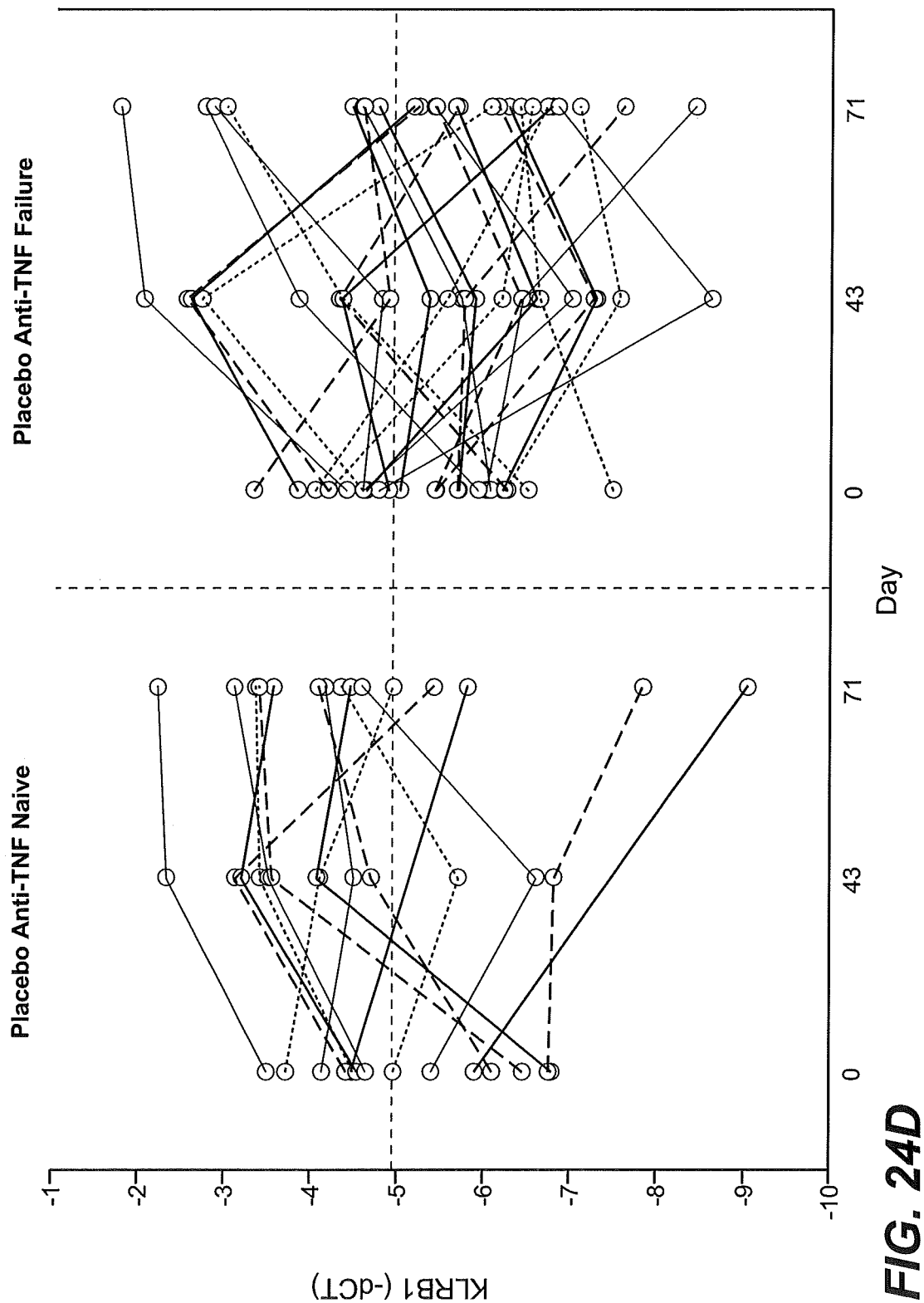
Figure 25A:
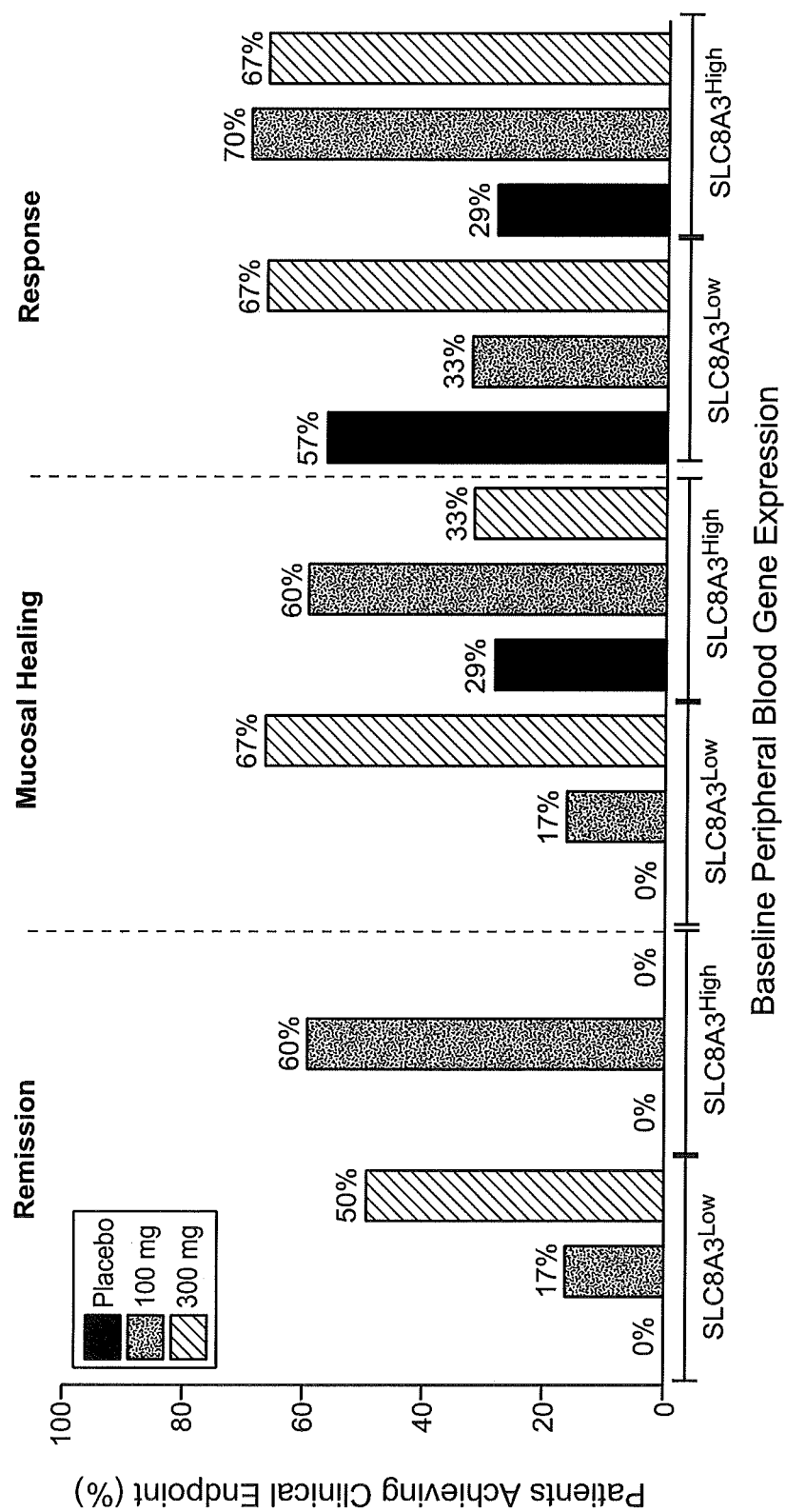
Figure 25B:
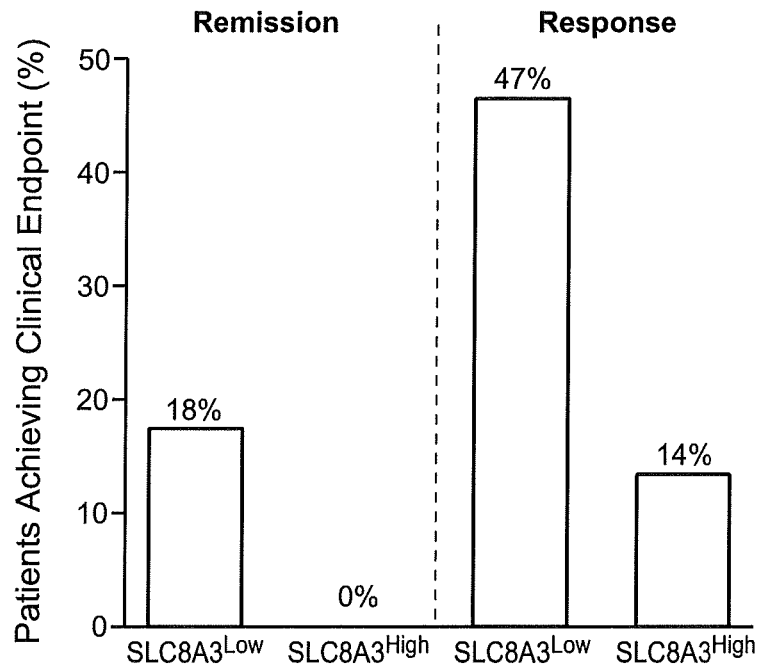
Figure 25C:
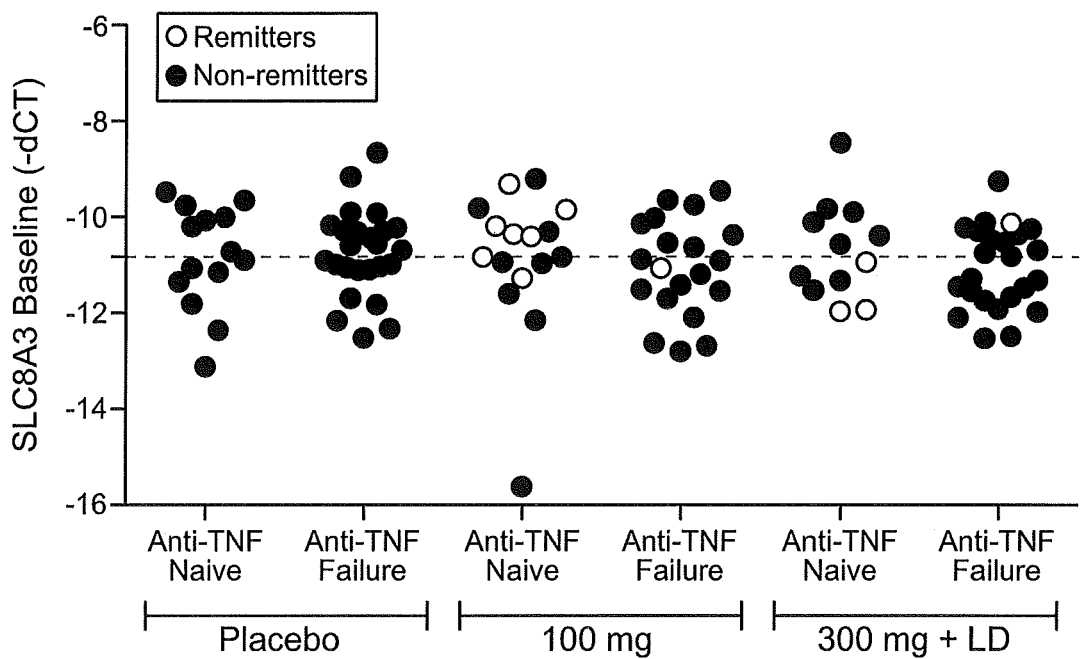
Figure 25D:
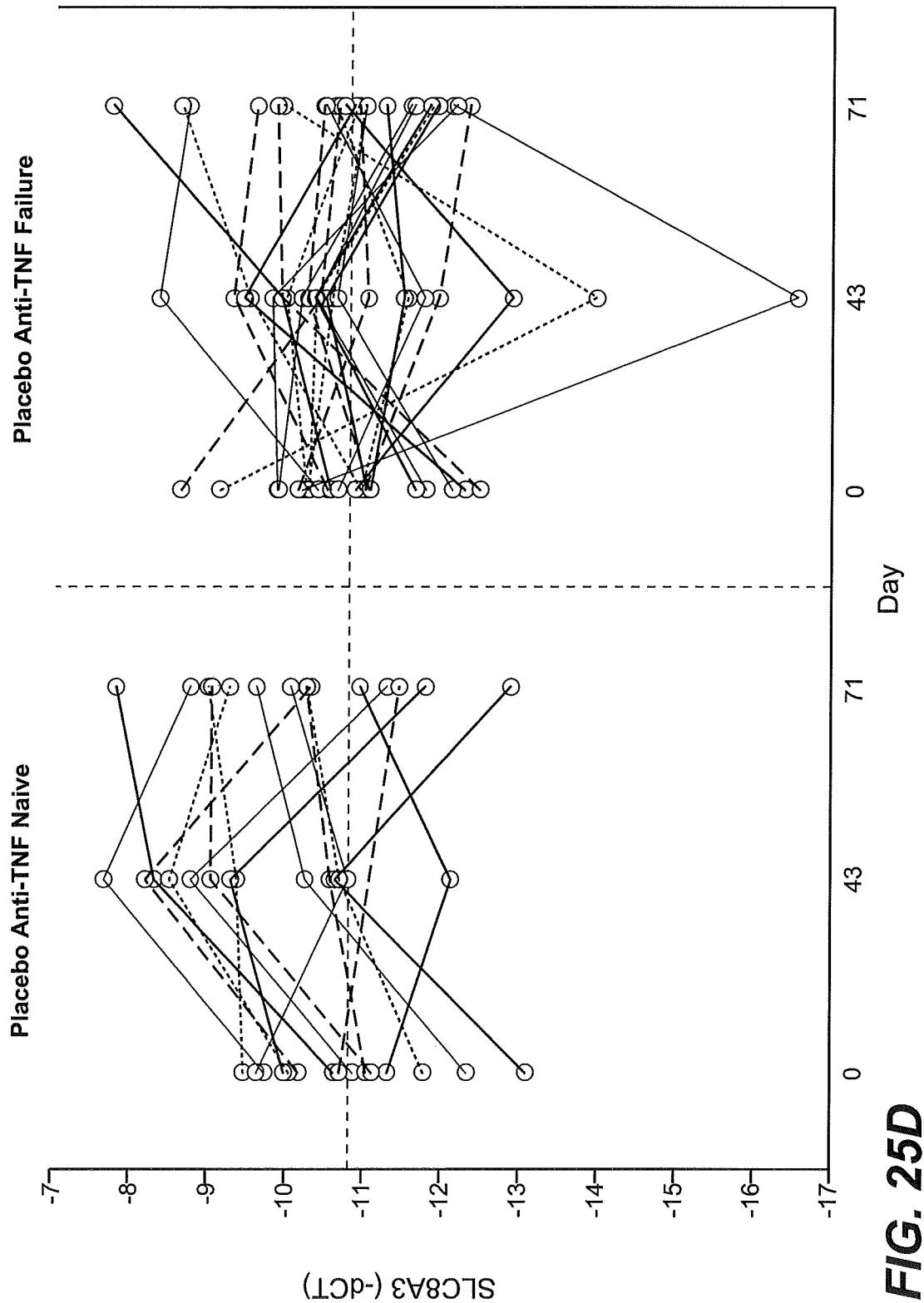
Figure 26A:
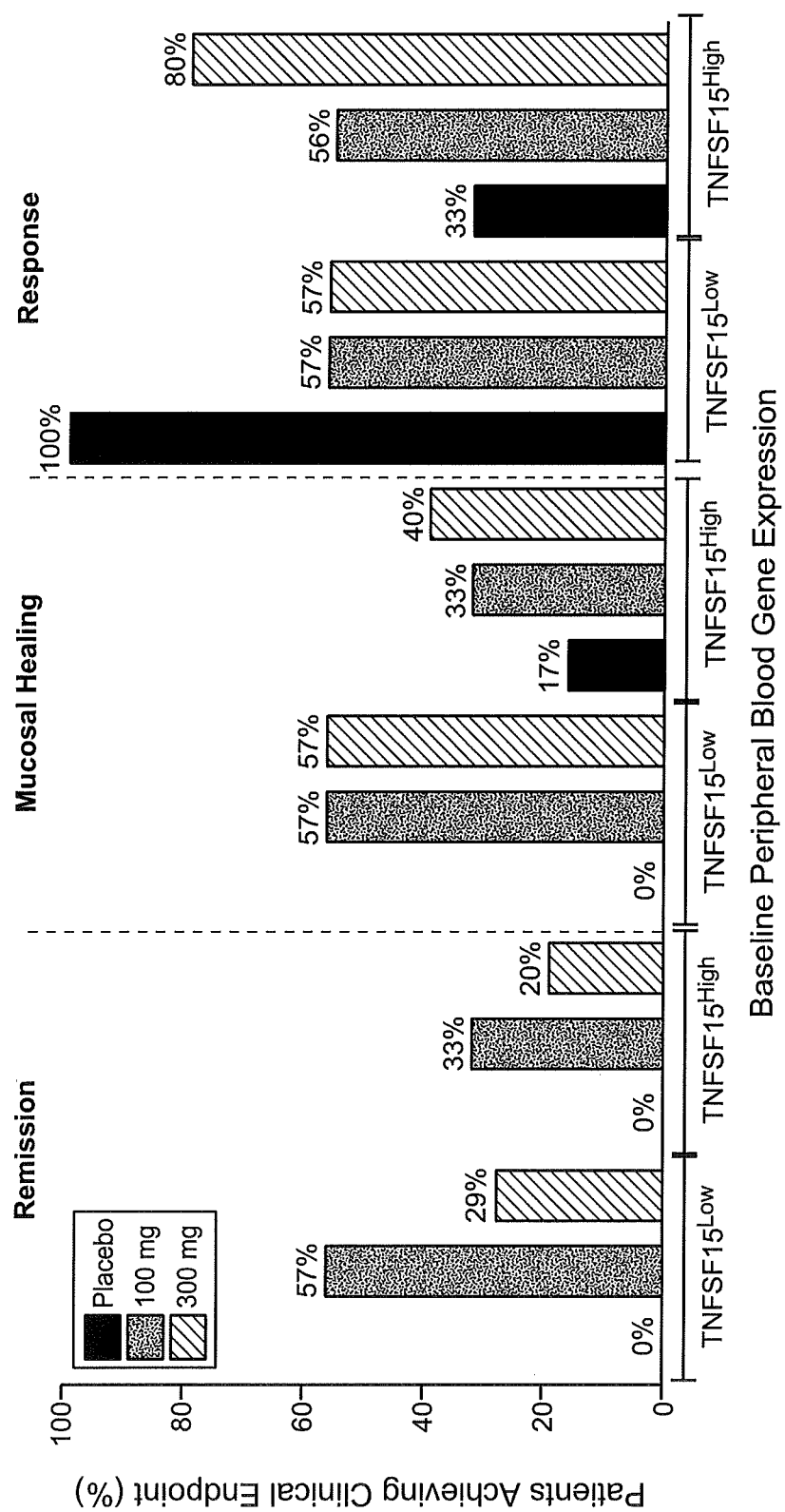
Figure 26B:
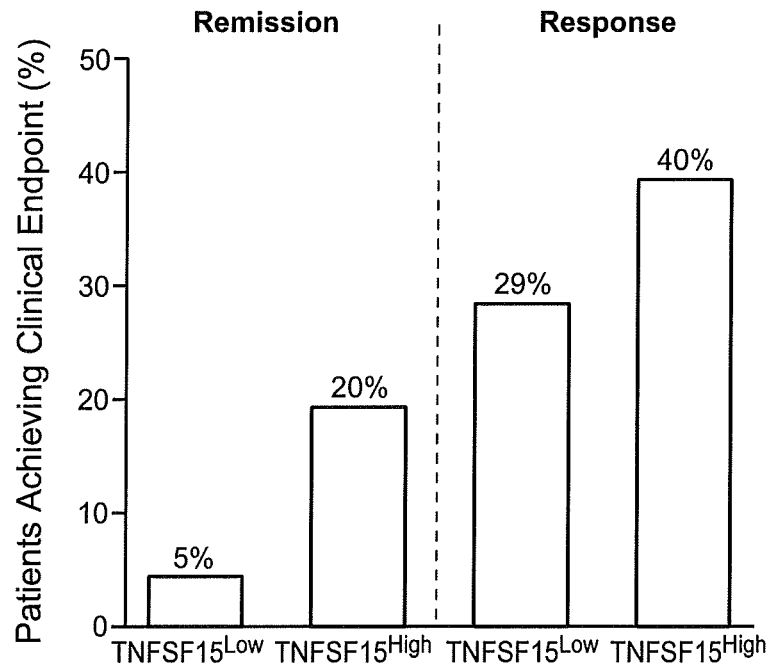
Figure 26C:
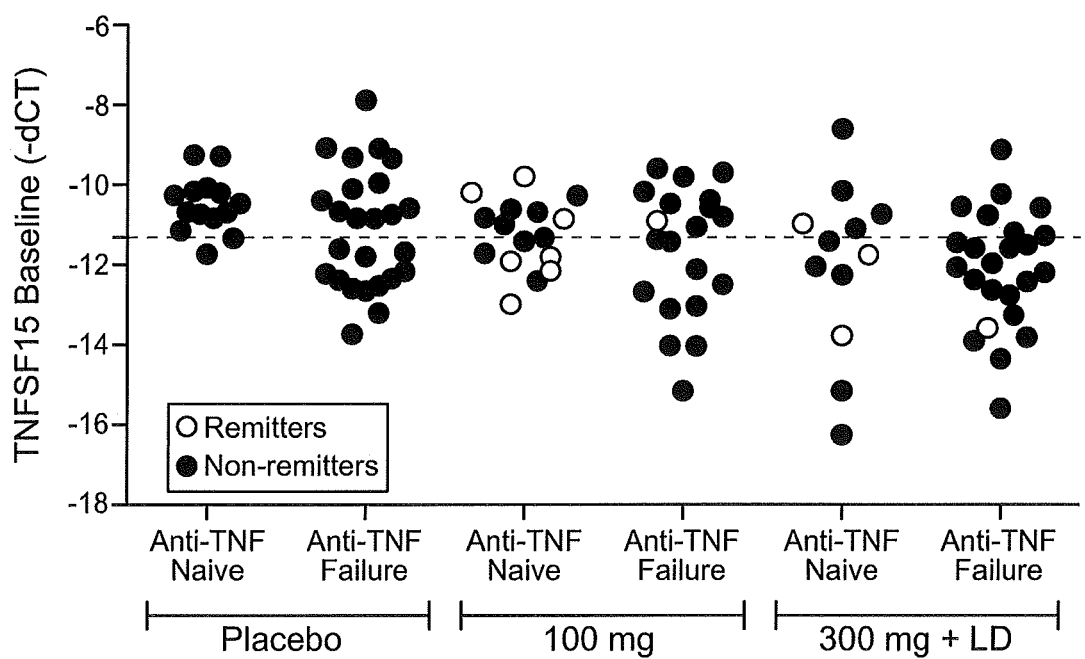
Figure 26D:
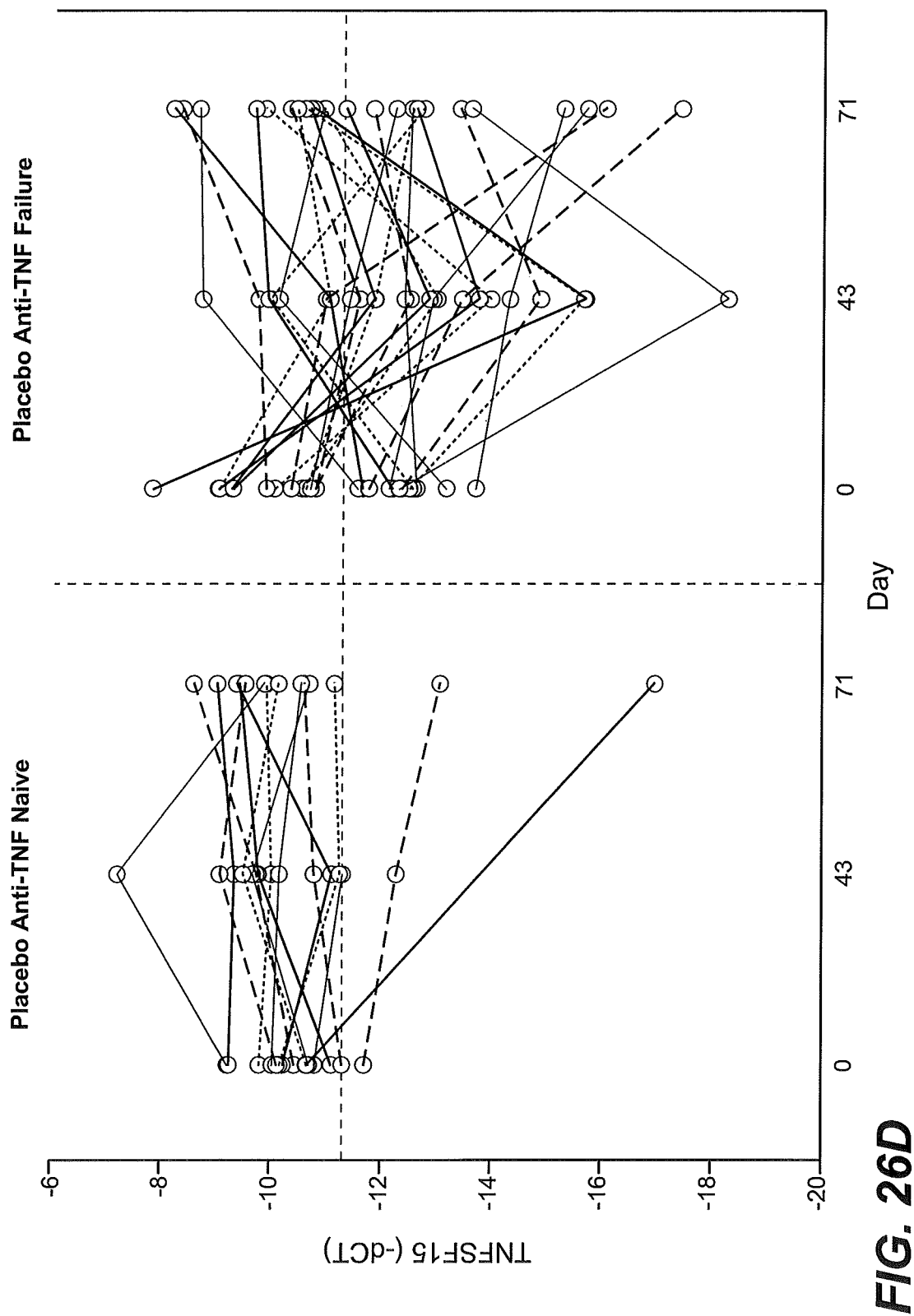
Figure 27A:
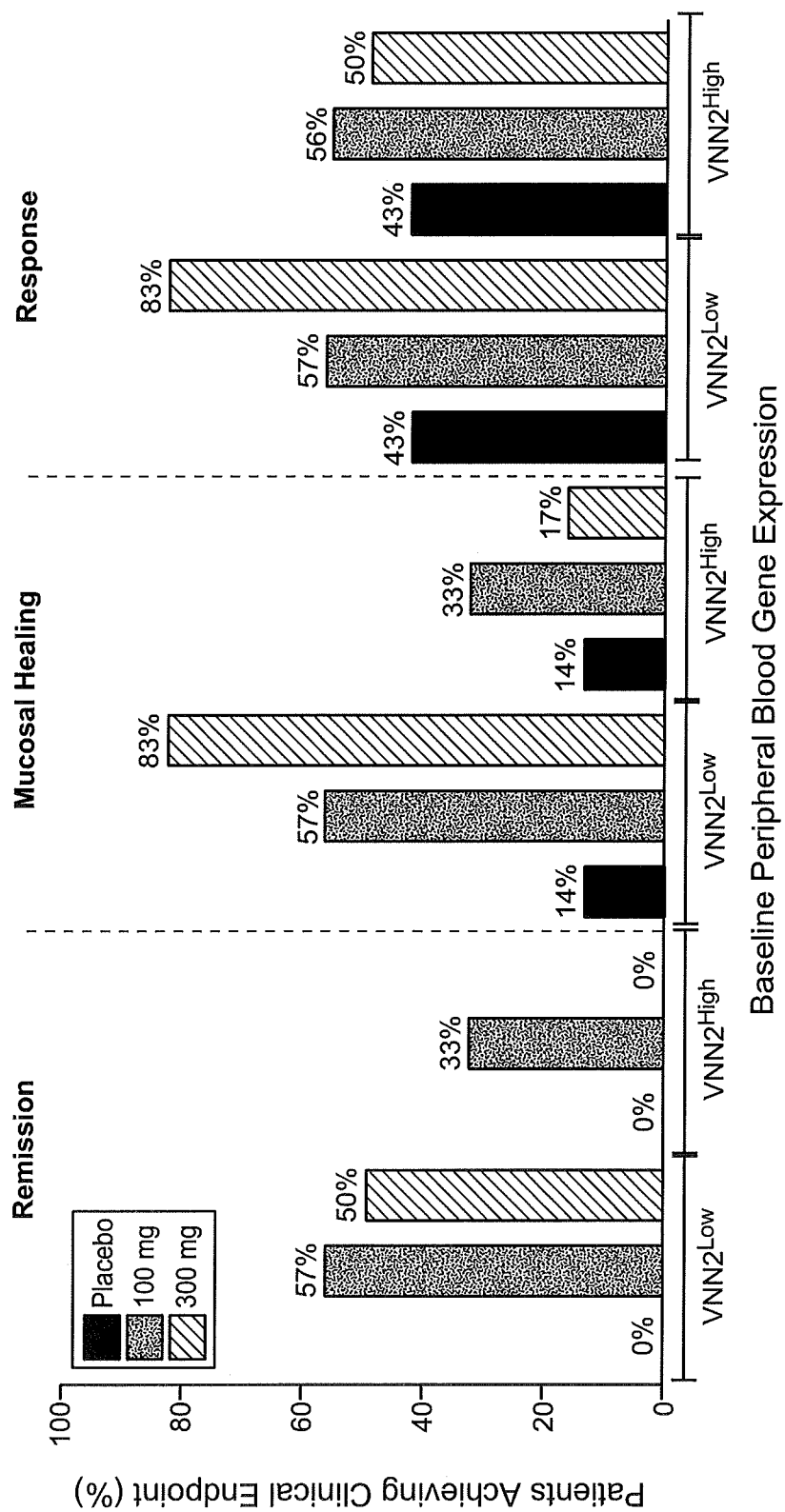
Figure 27B:
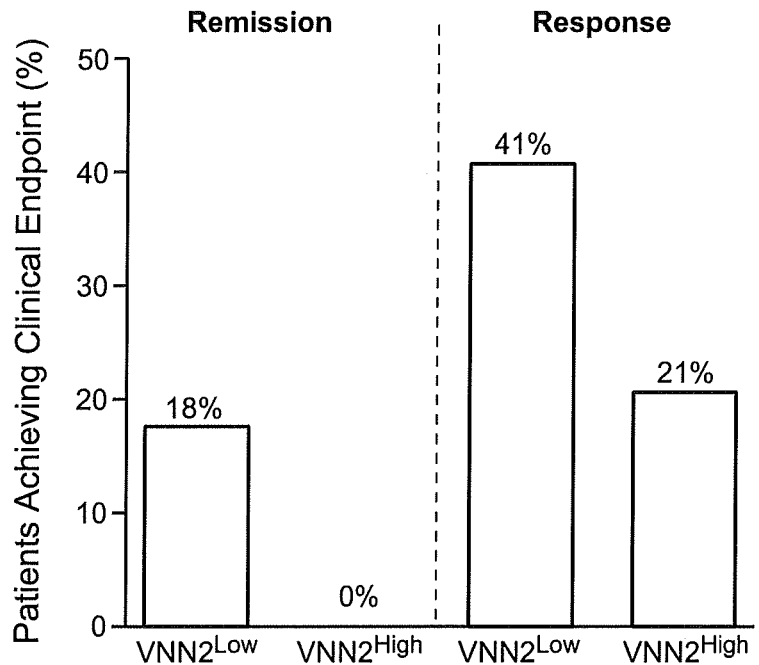
Figure 27C:
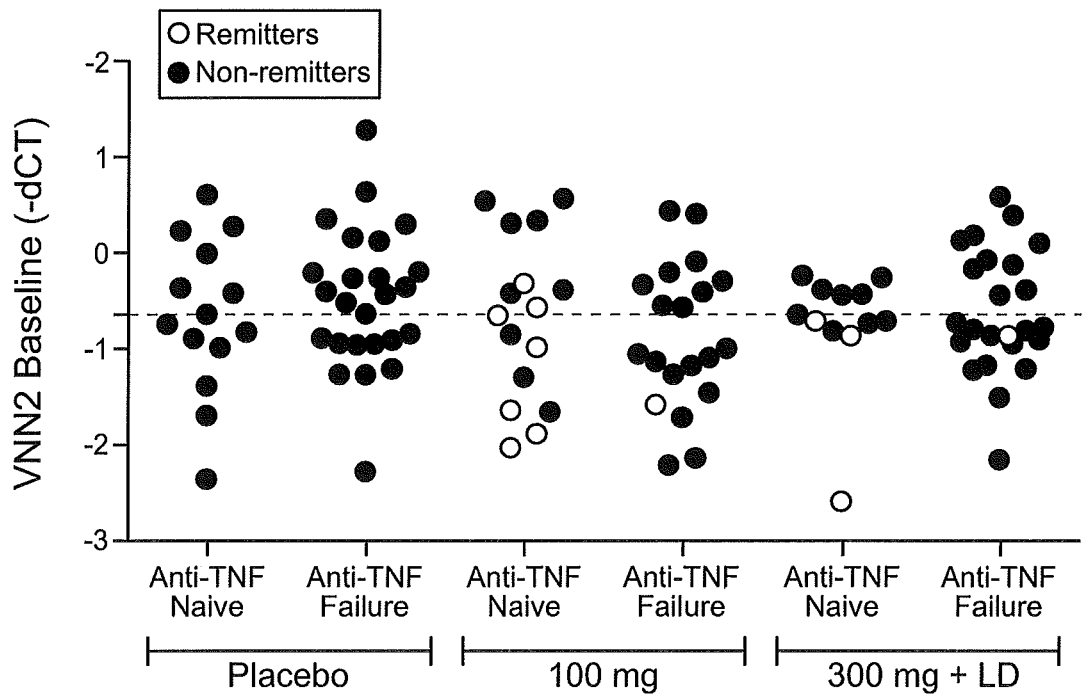
Figure 27D:
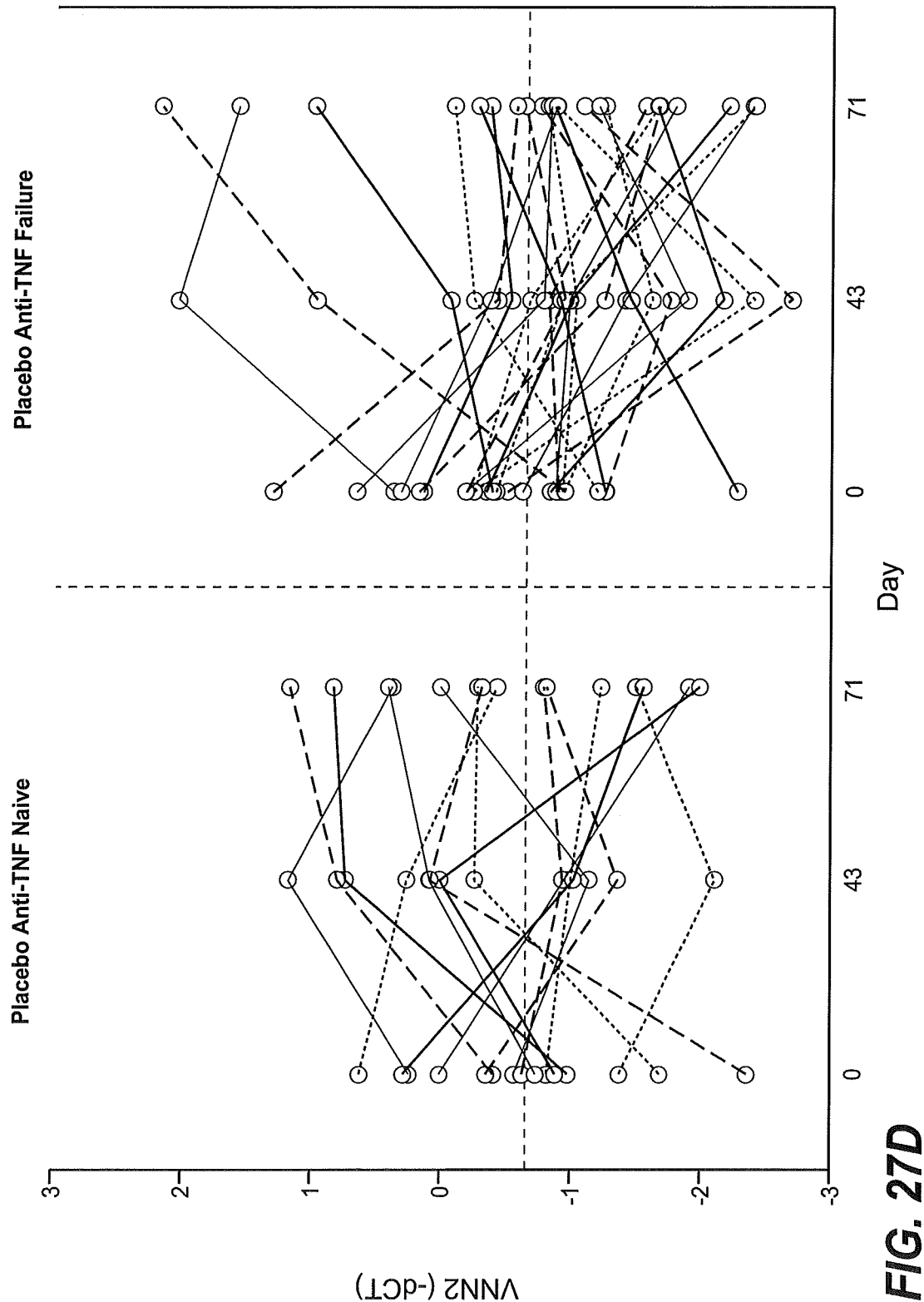

We also observed that below the median levels of baseline gene expression in screening biopsies of certain genes enriched for patient responsiveness to etrolizumab treatment. As shown in FIGS. 13A-13D, lower than median levels of gene expression in all patients (left half of each graph) and in anti-TNF naïve patients (right half of graph) of the indicated genes enriched for remission in patients treated with etrolizumab. The genes whose low expression enriched for remission as shown in FIGS. 13A-13D are SLC8A3 (FIG. 13A), TNFSF15 (FIG. 13B), CCL2 (FIG. 13C), and BEST2 (FIG. 13D). For the results shown in FIGS. 13A-13D, we also assessed qualitatively (i.e., gene expression higher than median, at median, or lower than median) the longitudinal stability of the gene expression levels in samples from the placebo arm of the study by measuring the gene expression levels of each of SLC8A3, TNFSF15, CCL2, and BEST2 in biopsies obtained from individual patients at screen, day 43 and day 71. These samples were compared pairwise for concordance and the mean concordance was calculated. The mean concordance in placebo samples for SLC8A3 was 66%, for TNFSF15, the mean concordance was 75%, for CCL2, the mean concordance was 70% and for BEST2, the mean concordance was 63%. As discussed above, and without being bound by theory, it is believed that genes with higher mean concordance reflect more stable aspects of the underlying biology than genes with lower mean concordance and thus such concordant genes may ultimately prove more robust for use as biomarkers for enriching anti-integrin beta7 antagonist responsiveness.

Additional results for each of SLC8A3 (FIGS. 14A-14D), TNFSF15 (FIGS. 15A-15D), CCL2 (FIGS. 16A-16D), and BEST2 (FIGS. 17A-17D) are shown. As shown in each of FIGS. 14A-14D, FIGS. 15A-15D, FIGS. 16A-16D, FIGS. 17A-17D, and consistent with the results presented above, low baseline expression of each of the identified genes enriched for etrolizumab responsiveness as assessed by remission. Furthermore, the data in FIGS. 14A-14D, FIGS. 15A-15D, FIGS. 16A-16D, FIGS. 17A-17D show that low baseline expression of each of SLC8A3, TNFSF15, CCL2, and BEST2 enriched for etrolizumab responsiveness as assessed by mucosal healing and clinical response, although the enrichment was less pronounced. Data for an additional gene, VNN2, examining baseline expression in screening biopsies and assessing etrolizumab responsiveness by remission, mucosal healing, and clinical response is shown in FIGS. 19A-19D.

In summary, we have shown that by investigating differential gene expression patterns between etrolizumab-treated patients who did not respond to the drug as assessed by the clinical endpoints of remission, mucosal healing, or clinical response and those who did respond to the drug using the same clinical endpoints, we were able to identify a number of genes expressed at higher than median levels that were associated with either etrolizumab response or non-response. Further analyses led us to identify a number of genes with high baseline expression or with low baseline expression that enriched for etrolizumab responsiveness. In particular, we determined that high baseline expression of granzyme A, KLRB1, and FOXM1 enriched for etrolizumab responsiveness as assessed by remission, mucosal healing and clinical response. Each of these genes demonstrated approximately 70% concordance in three longitudinal biopsies from patients in the placebo arm of the trial. The results reported here confirm and extend our previously-reported findings showing that high alphaE expression at baseline and certain additional genes with high baseline expression enriched for etrolizumab responsiveness (see, e.g., WO 2014/055824).

In the studies reported here, we also determined, in particular, that low baseline expression of SL8A3 (in tissue biopsy) and TNFSF15 enriched for etrolizumab responsiveness as assessed by remission, mucosal healing and clinical response. Each of these genes also demonstrated approximately 70% concordance in three longitudinal biopsies from patients in the placebo arm of the trial.

Peripheral Blood Gene Expression Analyses
Untreated Patient Sample Cohorts

Cohort 1: Ileal and colonic biopsy samples were taken during ileocolonoscopy from patients with UC (n=30), CD (n=67) and non-IBD healthy controls (n=14). Biopsies were taken from areas judged to be inflamed or uninflamed by the endoscopist. RNA was isolated from biopsy samples as detailed above. Cohort 2: Peripheral blood samples were collected in PAXgene RNA tubes from patients undergoing intestinal resection for UC (n=31) or CD (n=32). Additional PAXgene samples were collected from normal healthy controls (n=10). Cohort 3: Colonic biopsies were taken from both inflamed and uninflamed areas of the colon of both UC patients (n=13) and healthy controls (n=8) and placed into RNAlater and then isolated for RNA as detailed above, formalin, or processed immediately for cell sorting as detailed below. Collection and Processing of Peripheral Blood RNA In the etrolizumab phase 2 study samples, total RNA was isolated from frozen PAXgene blood tubes by automated isolation on a KingFisher™ (Thermo Scientific) magnetic particle separator. Briefly, tubes were allowed to thaw for 16 hours at room temperature. After centrifugation and washing to collect white blood cell pellets, cells were lysed in guanidinium-containing buffer. Organic extraction was performed prior to adding binding buffer and magnetic beads in preparation for the KingFisher™ run. The procedure was optimized for retention of microRNAs and included a DNAse treatment step and cleanup prior to elution from the magnetic beads. The purity and quantity of total RNA samples were determined by absorbance readings at 260 and 280 nm using a NanoDrop ND-1000 UV spectrophotometer. The integrity of total RNA was qualified by Agilent Bioanalyzer 2100 microfluidic electrophoresis, using the Nano Assay and the Caliper LabChip system. In peripheral blood samples from untreated patient samples, cohort 2 (described above), RNA was isolated using the PAXgene Blood RNA Kit IVD (Qiagen) according to the manufacturer's instructions. RNA was quantified using a Nanodrop spectrophotometer and RNA integrity was assessed on an Agilent 2100 Bioanalyzer using the RNA 6000 Pico Kit (Agilent Technologies).

Cell Isolation from Colonic Biopsies

Colonic biopsies collected from untreated patient samples, cohort 3 (described above) of mild to severely active UC patients were processed to a single cell suspension using previously published methods. Briefly, mononuclear cells were extracted by incubation with 5 mM 1,4-dithiothreitol followed by digestion with 1.5 mg/ml collagenase VIII and 0.05 mg/ml DNase I (all reagents from Sigma, St Louis, Mo., USA). The cell suspension was stained with Live/Dead® stain (Life Technologies Corporation, Carlsbad, Calif., USA), CD45 PeCy5, TCRαβPeCy7, CD8a APC Cy7, αE integrin (CD103) FITC, β7 integrin APC (all from Biolegend, London, UK) and CD8β PE (Beckman Coulter, Brea, Calif., USA). TCRαβ+, CD4+ or CD8+ T cells were sorted based on their expression of αE and β7 integrin directly into RLT buffer (Qiagen, Hilden, Germany) containing β-mercaptoethanol from which RNA was isolated using PicoPure RNA isolation kit according to manufacturer's protocol (Life Technologies Corporation, Carlsbad, Calif., USA). Purity of the sorted populations was assessed to ensure samples had ≥85% purity.

Gene Expression Analysis by Quantitative Polymerase Chain Reaction

RNA isolated from PAXgene tubes and sorted cells as described above was reverse transcribed into complementary deoxyribonucleic acid using the High-Capacity cDNA Reverse Transcription Kit (Life Technologies Corporation, Carlsbad, Calif., USA). Gene expression levels were assessed by real-time polymerase chain reaction, also referred to as quantitative polymerase chain reaction. Real-time polymerase chain reactions were run on the BioMark™

HD System (Fluidigm Corporation, South San Francisco, Calif., USA) with TaqMan PreAmp Master Mix (Life Technologies Corporation, Carlsbad, Calif., USA) and reagents (Fluidigm) using Taqman Gene Expression assays of respective genes (all from Life Technologies Corporation, Carlsbad, Calif., USA) according to manufacturer's instructions. Target gene expression was normalized to GAPDH expression using the ΔCt method.

Immunohistochemistry and Cell Quantification

Formalin-fixed tissue samples from the etrolizumab phase II study were embedded in paraffin blocks and cut into 4 μM sections for staining. Staining was performed on a Benchmark XT (Ventana Medical Systems, Inc., Tucson, Ariz., USA) autostainer with anti-integrin αE antibody (EPR4166; Abcam plc, Cambridge, Mass., USA), developed with 3,3'-diaminobenzidine and counterstained with haematoxylin. Whole slide images were acquired by the Olympus Nanozoomer automated slide scanning platform (Hamamatsu Photonics K.K., Bridgewater, N.J., USA) at 200× final magnification. Scanned slides were analysed in the MAT-LAB® software package (version R2012a; The MathWorks, Inc., Natick, Mass., USA) as 24-bit RGB images. Total cells, αE$^+$ cells, and αE$^+$ cells associated with crypt epithelium were counted. Crypt epithelial areas were identified using a combination of support vector machines and genetic programming, within which individual cell nuclei were segmented, and then scored immunohistochemistry positive if ≥25% of their total area colocalised with 3,3'-diaminobenzidine.

Dual immunofluorescence studies in untreated patient samples, cohort 3 (described above), were performed in formalin fixed paraffin embedded tissue samples using both anti-integrin αE antibody as detailed above and anti-granzyme A polyclonal goat IgG (R&D Systems, Minneapolis, Minn., USA) incubated for 60 min at 37° C. Anti-goat Omnimap-HRP was used as detection and DAPI and hematoxylin-II were used to counterstain the sections (Ventana Medical Systems, Inc., Tucson, Ariz., USA).

Statistical Analysis

Statistical testing was performed using the Wilcoxon rank-sum test or the Fisher exact test as appropriate. No adjustments for multiple comparisons were performed. Subgroup analyses using the sample median cutoff were performed for selected genes. The longitudinal stability of gene expression was evaluated in patients randomized to the placebo arm of the study.

Results

Following the methods and analyses described above, baseline gene expression in peripheral blood RNA samples was evaluated for prediction of response to etrolizumab. We analyzed baseline and day 1 peripheral blood samples from all patients (n=107). Gene expression was quantitated by quantitative polymerase chain reaction (qPCR) and enrichment was evaluated using a median cut-off approach. The two different etrolizumab dose groups described in Example 1 were combined for these analyses.

We analyzed the percentage of patients achieving remission, mucosal healing and response in patients stratified by baseline peripheral blood gene expression levels (low, below the median vs. high, at or above the median). FIGS. 20A-20D shows that at and higher than median levels of ITGAE gene expression in all patients enriched for remission in patients treated with etrolizumab. We also observed enrichment in remission in patients with high (at or above median) baseline peripheral blood ECH1 expression as shown in FIGS. 21A-21D. Peripheral blood gene expression was also evaluated for FOXM1 (FIGS. 22A-22D), GZMA (FIGS. 23A-23D) and KLRB1 (FIGS. 24A-24D). As shown in FIGS. 25A-25D, patients with high levels of SLC8A3 peripheral blood gene expression had increased remission in response to etrolizumab treatment, in contrast to the results observed with screening biopsy gene expression (FIGS. 14A-D).

The SLC8A3 gene encodes a sodium/calcium exchanger protein, NCX3, which functions as a membrane transporter for bidirectional switching of sodium and calcium to maintain calcium homeostasis in cells. NCX3 is expressed on human macrophages and myofibroblasts. While the relationship between tissue cells and circulating cells of the monocyte/macrophage lineage is not completely understood, and without being bound by theory, it may be that low monocyte/macrophage cell numbers in biopsy tissue is indicative of higher levels of circulating monocytes/macrophages. In that case, patients with low tissue monocyte/macrophage content as indicated by low SLC8A3 gene expression may largely overlap with patients with high circulating monocyte/macrophage content as indicated by high SLC8A3 gene expression. Accordingly, low levels of SLC8A3 gene expression in tissue and high levels of SLC8A3 gene expression in peripheral blood are related and that relationship explains how low level expression in tissue (FIGS. 14A-14D) and high level expression in peripheral blood (FIGS. 25A-25D) can each be predictive of responsiveness to etrolizumab treatment.

We also observed that below the median levels of baseline peripheral blood gene expression of certain genes enriched for patient responsiveness to etrolizumab treatment. As shown in FIGS. 26A-26D, lower than median levels of TNFSF15 gene expression enriched for remission in patients treated with etrolizumab. We also found that lower than median levels of VNN2 gene expression enriched for remission in response to etrolizumab as shown in FIGS. 27A-27D.

Figure 28A:
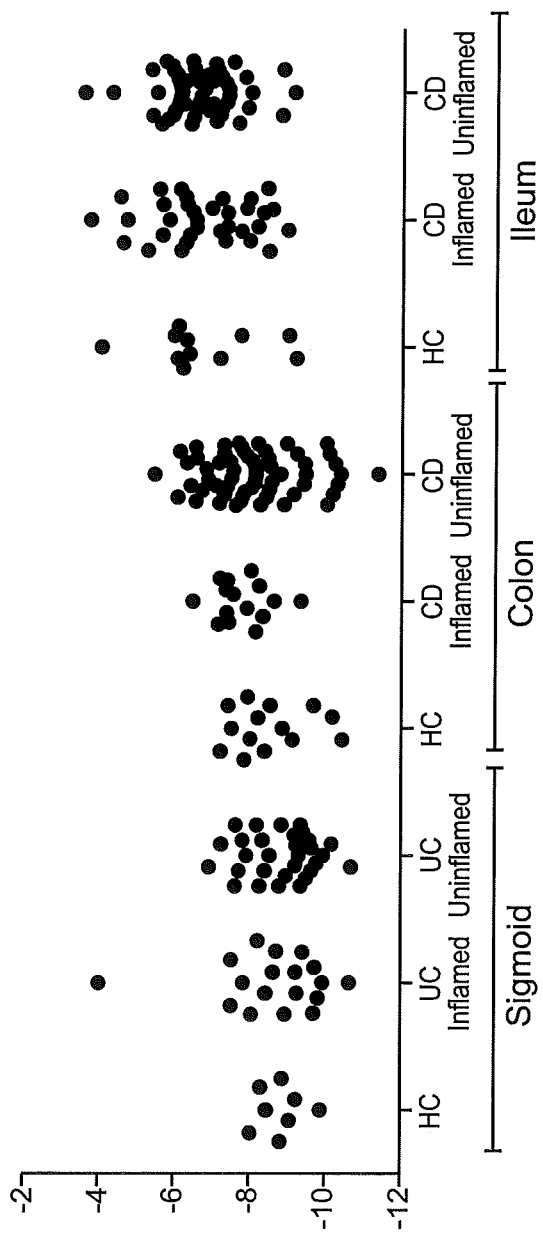
Figure 28B:
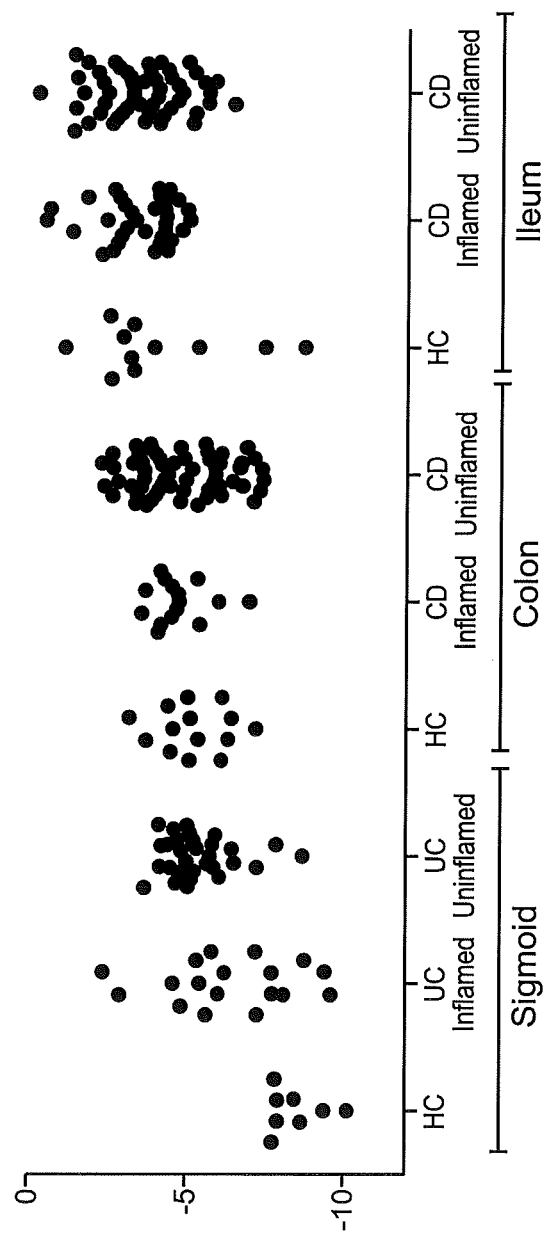
Figure 28C:
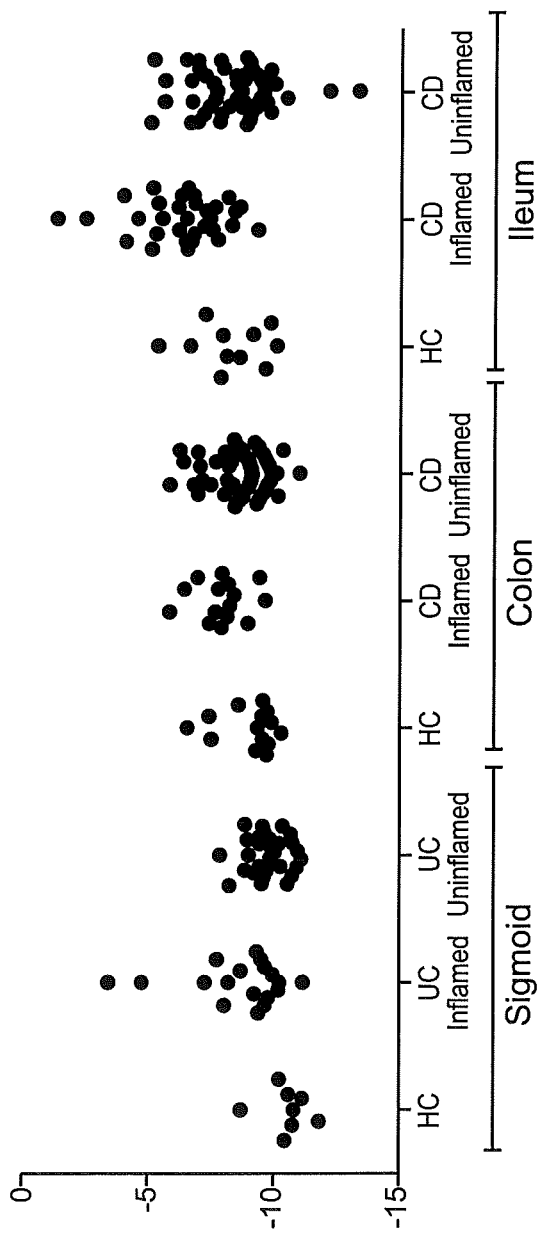
Figure 28D:
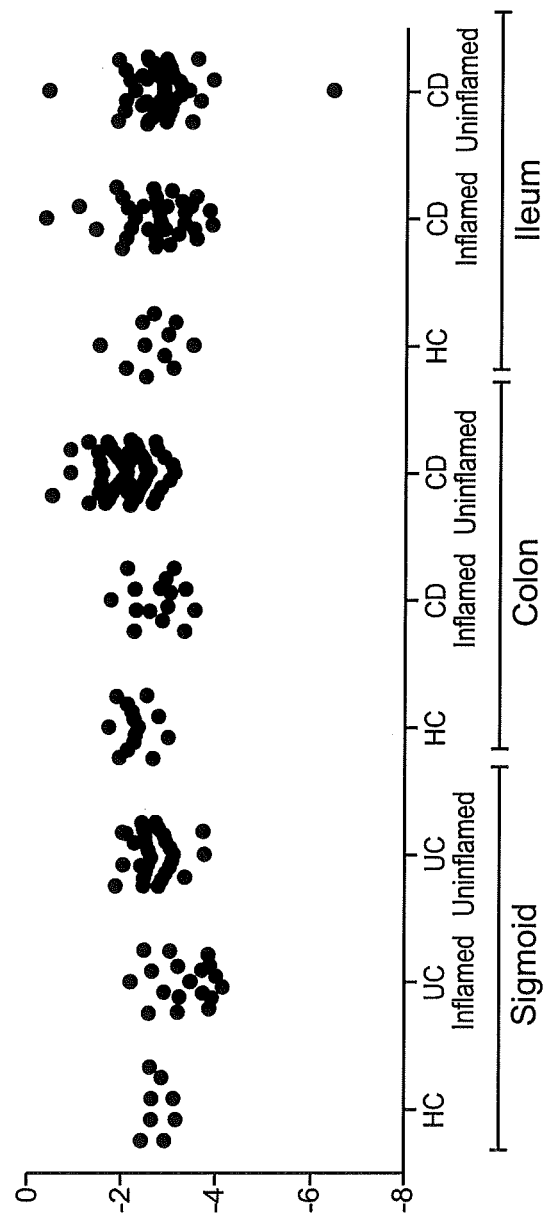
Figure 28E:
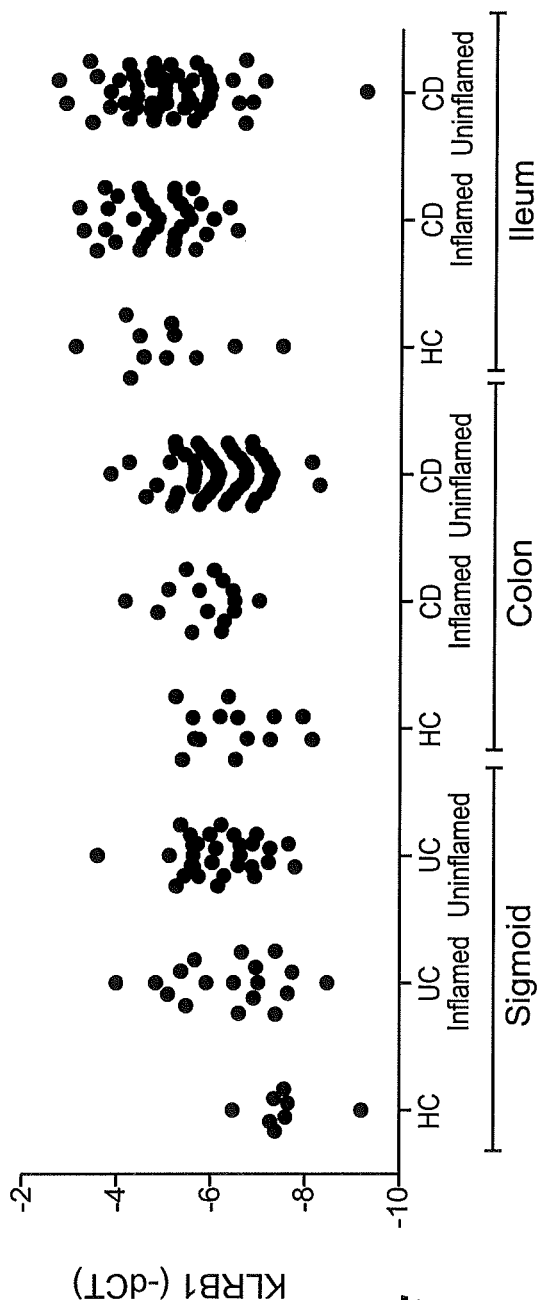
Figure 28F:
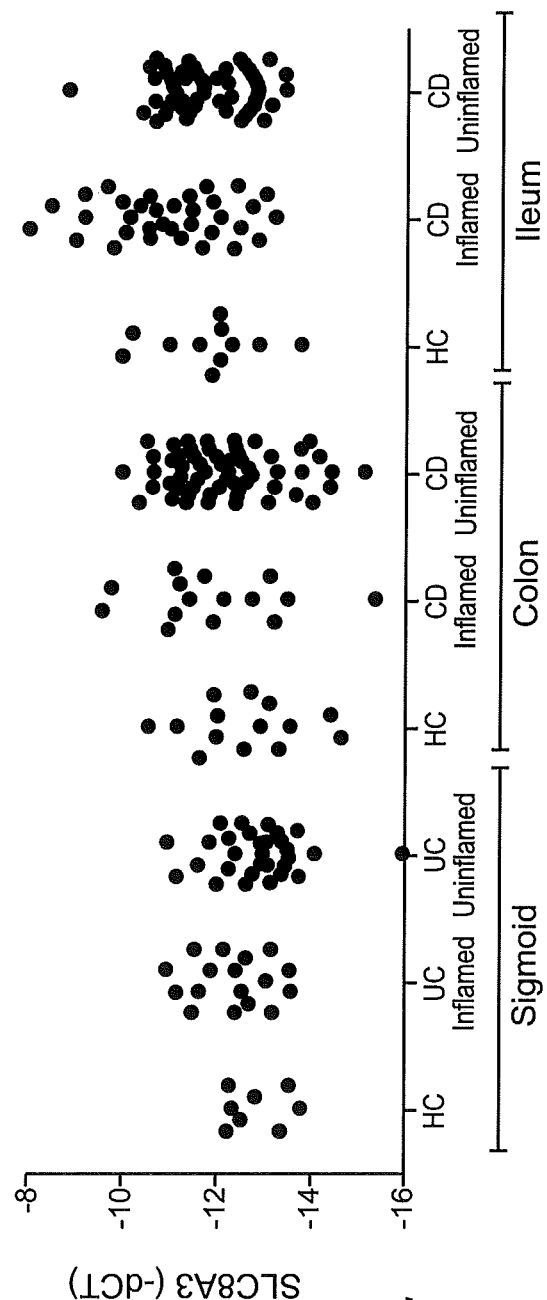
Figure 28G:
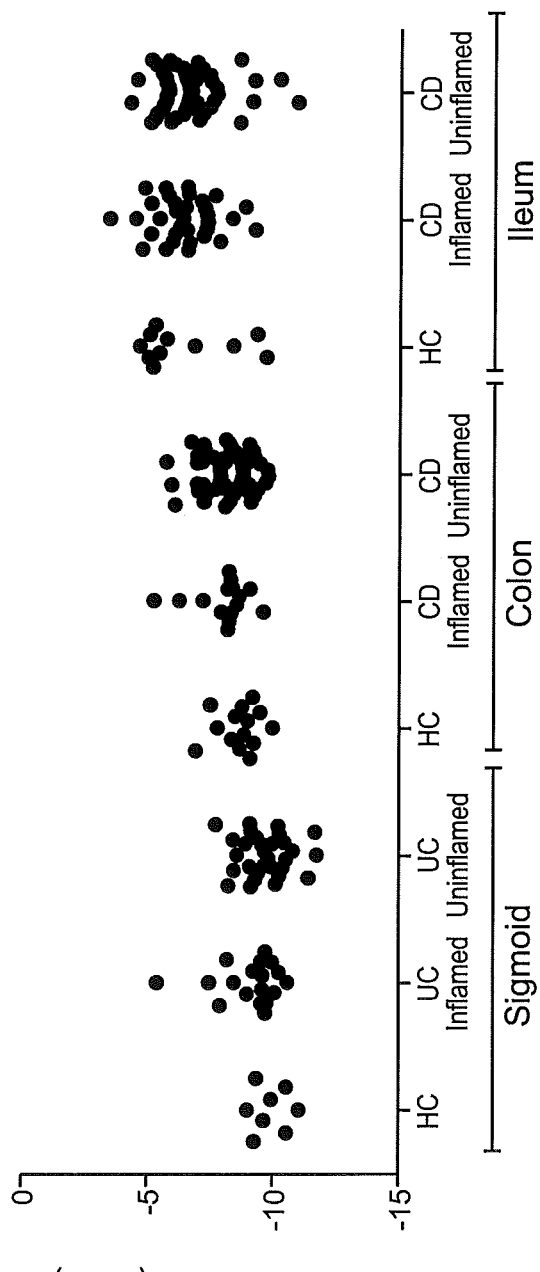
Figure 28H:
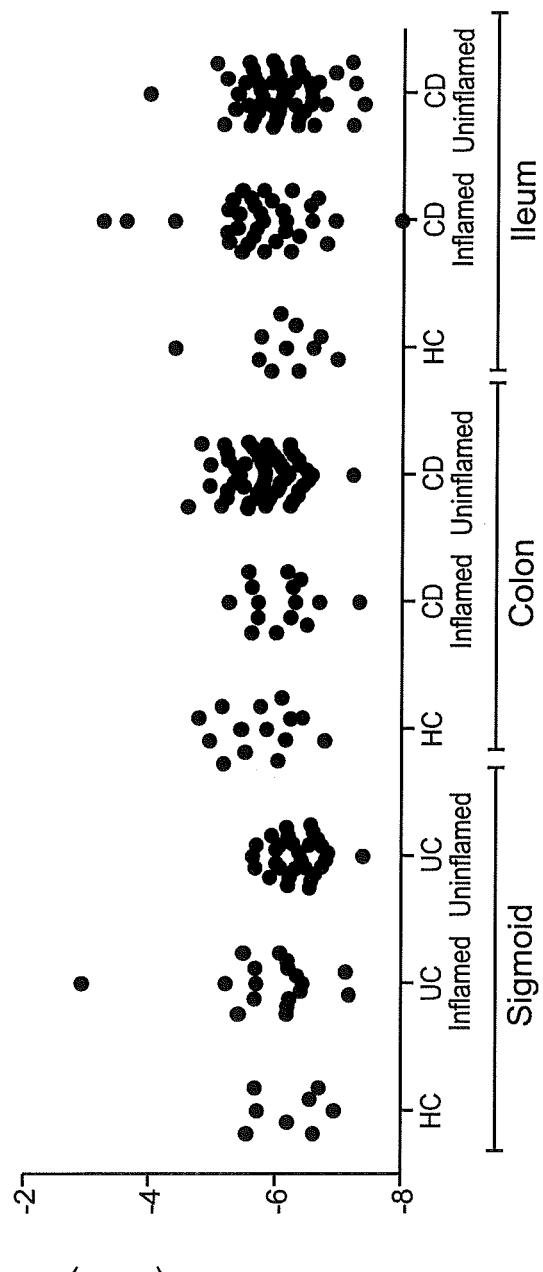

Next we evaluated the effect of inflammation on gene expression in mucosa] biopsies obtained from untreated patients as described above. Ileal and colonic biopsy samples were collected from patients with CD, UC or non-IBD healthy control subjects. Biopsies were taken from the sigmoid colon of non-IBD controls and UC patients and from the colon and ileum of non-IBD controls and CD patients. Uninflamed biopsies were taken from normal mucosa as judged by the endoscopist; if inflammatory disease was evident, additional biopsies were taken from an inflamed area. As shown in FIG. 28A, ITGAE gene expression is higher in ileal biopsies in comparison to colonic biopsies in both non-IBD and IBD patients. However, there was no significant difference between inflamed and uninflamed colonic biopsies or inflamed and uninflamed ileal biopsies in patients with IBD. Similarly, GZMA (FIG. 28B), KLRB1 (FIG. 28E), and TNFSF15 (FIG. 28G) had higher expression in ileal biopsies in comparison to colonic biopsies and were not different between inflamed and uninflamed colonic or ileal biopsies. VNN2 (FIG. 28C) was higher in the ileum than the colon and was also increased in the inflamed ileum in comparison to the uninflamed ileum of CD patients. Finally, ECH1 (FIG. 28D) was lower in the inflamed colon in comparison to uninflamed colon biopsies from CD patients.

Figure 29A:
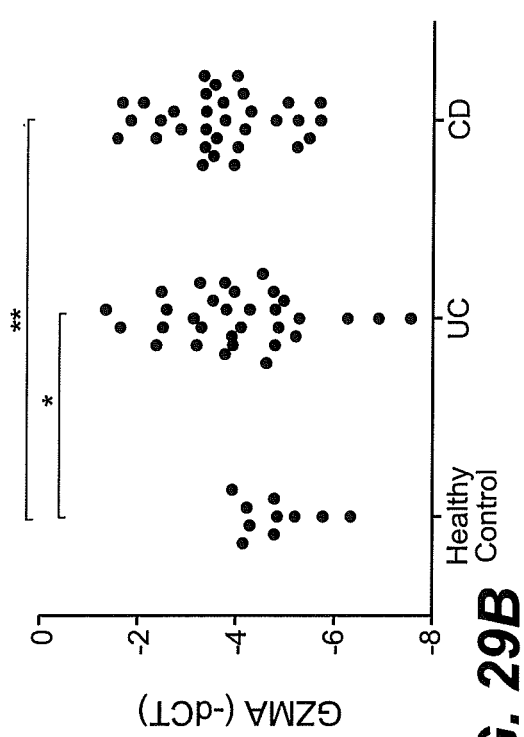
Figure 29B:
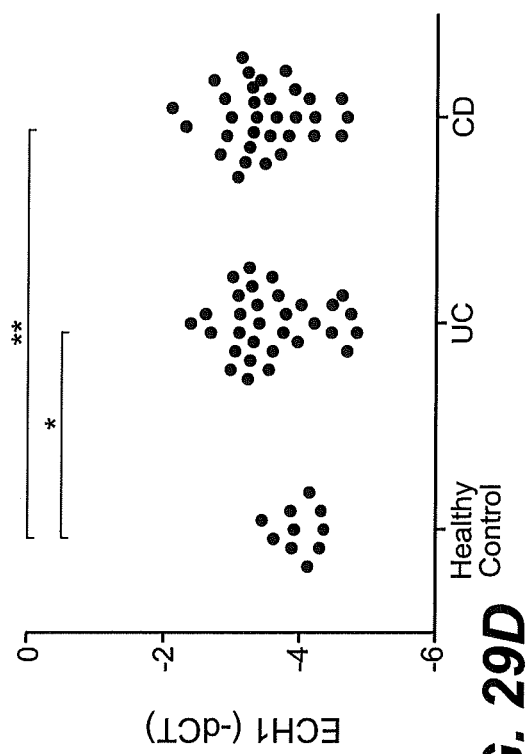
Figure 29C:
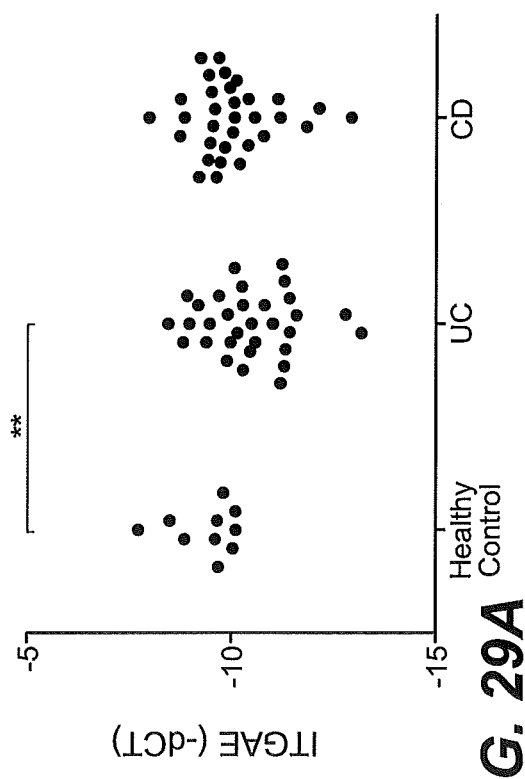
Figure 29D:
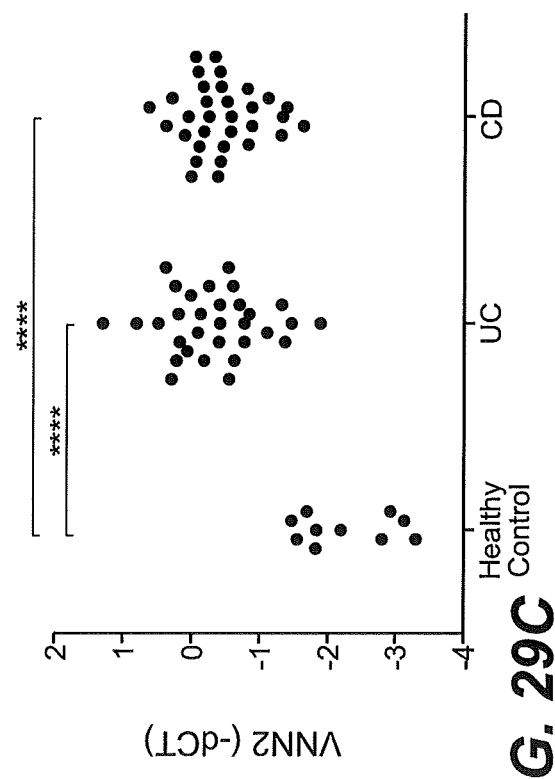
Figure 29E:
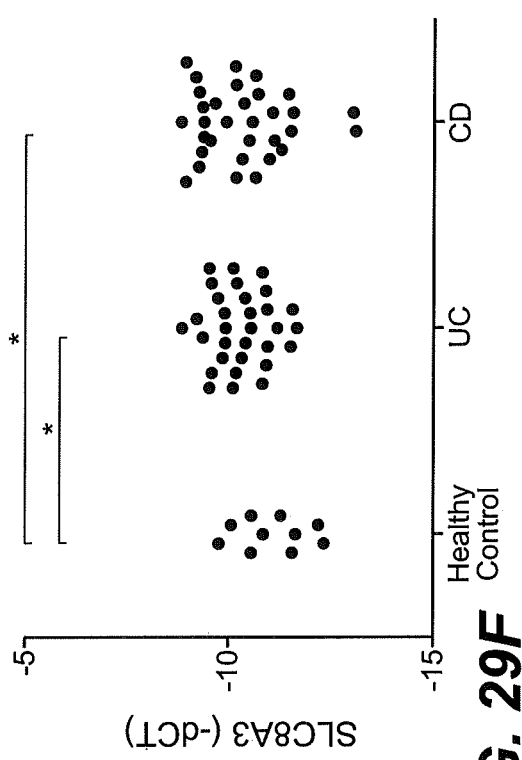
Figure 29F:
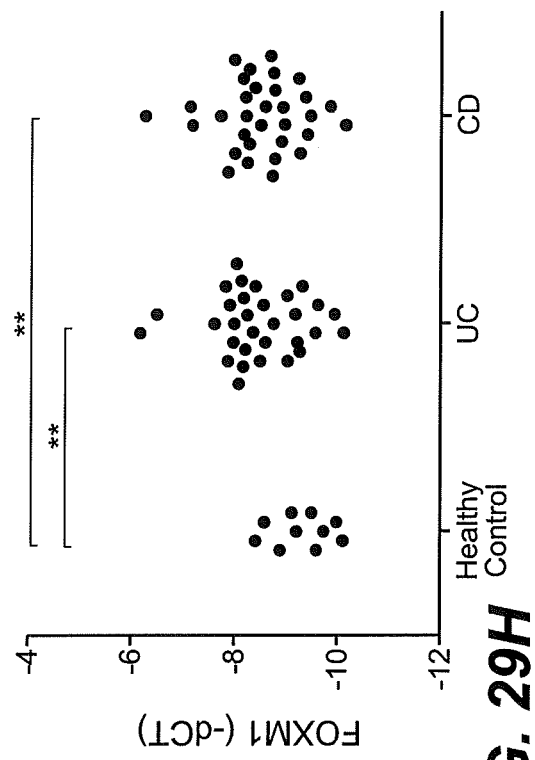
Figure 29G:
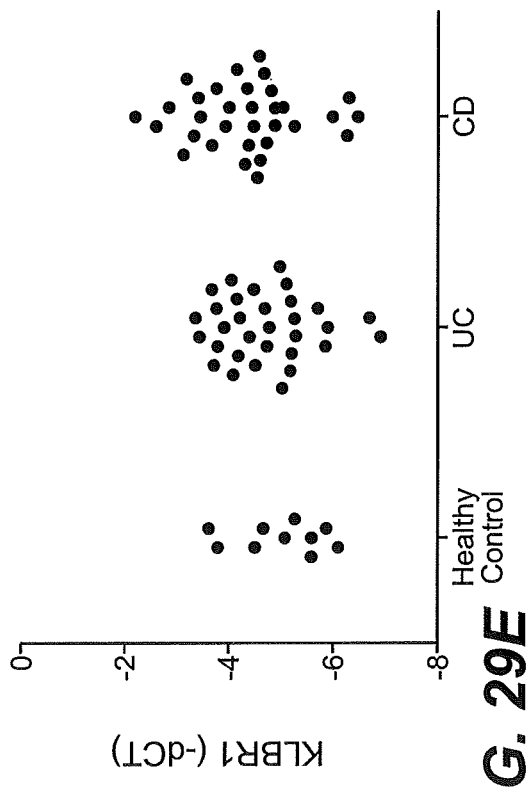
Figure 29H:
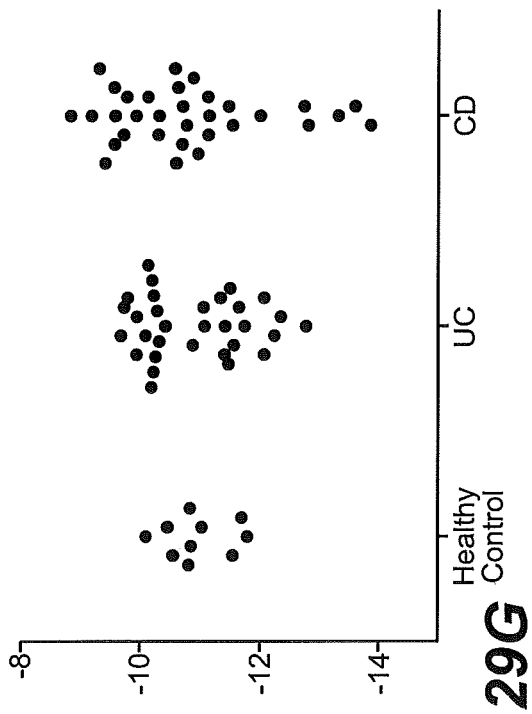

Peripheral blood gene expression was evaluated in untreated patient samples cohort 2. As shown in FIG. 29A, lower levels of ITGAE peripheral blood gene expression was observed in UC patients in comparison to healthy control subjects. Higher levels of GZMA (FIG. 29B) and ECH1 (FIG. 29D) peripheral blood gene expression were found in CD patients in comparison to healthy control subjects. VNN2 (FIG. 29C) and FOXM1 (FIG. 29H) gene expression levels were higher in both UC and CD patients in comparison to healthy control subjects.

Figure 30B:
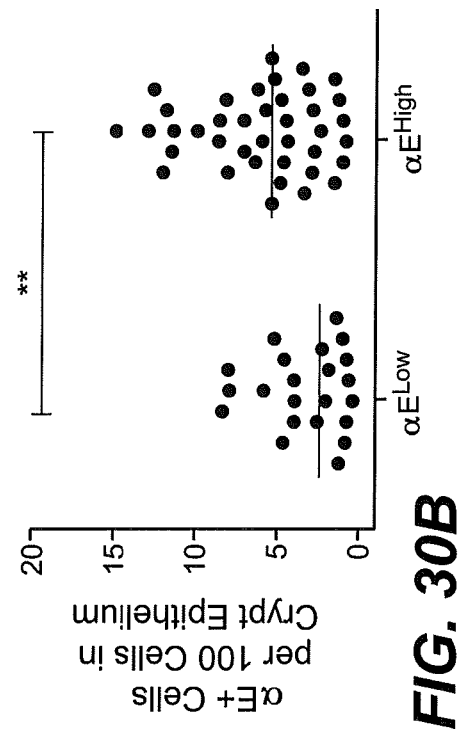
Figure 30A:
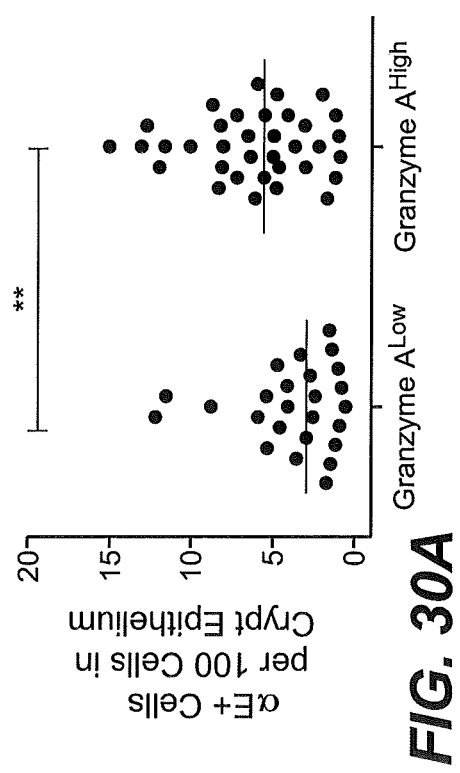
Figure 30D:
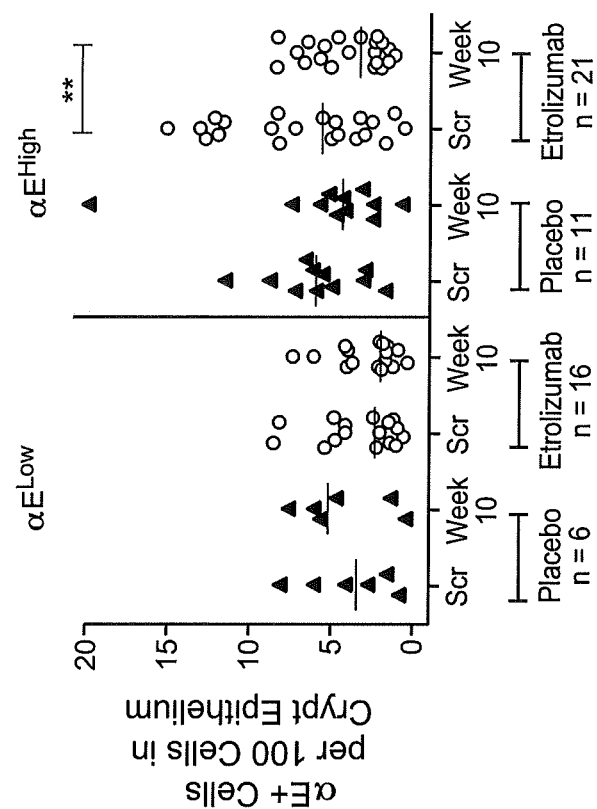
Figure 30C:
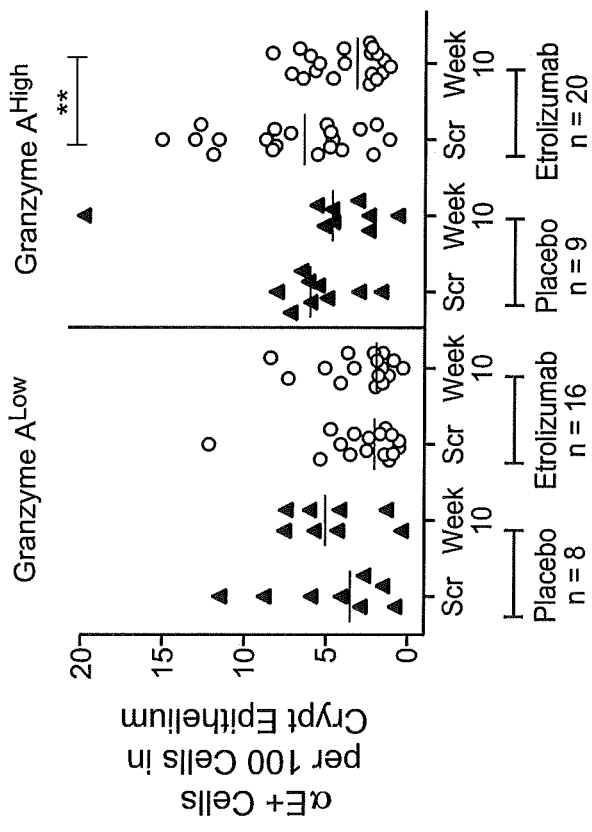

At baseline, the number of αE+ cells in crypt epithelium was significantly higher in both granzyme $A^{high}$ and $αE^{high}$ patients in comparison to granzyme $A^{low}$ and $αE^{low}$ patients (FIGS. 30A-30B, respectively). Etrolizumab treatment significantly reduced the number of αE+ cells in crypt epithelium at week 10 in granzyme $A^{high}$ and $αE^{high}$ patients, while there was no significant reduction in αE+ cells in crypt epithelium in granzyme $A^{low}$ and $αE^{low}$ patients after etrolizumab treatment as shown, respectively, in FIGS. 30C-30D.

Figure 31E:
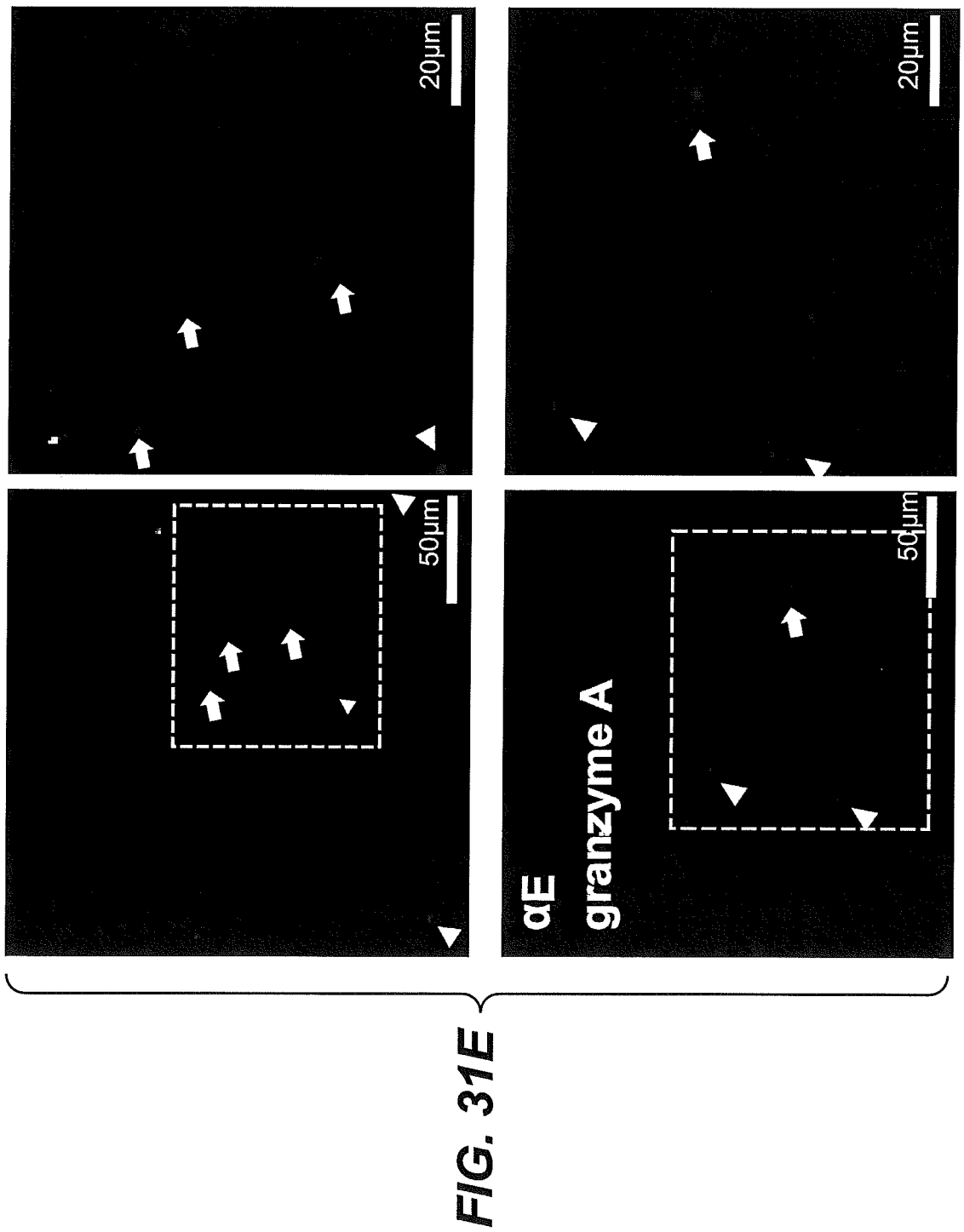

In flow cytometry-sorted CD4+αE+ T cells isolated from colonic biopsies from untreated UC patients in cohort 3, granzyme A gene expression was significantly upregulated in comparison to CD4+αE− T cells; the level of granzyme A in CD4+αE+ cells was also significantly higher in UC patients compared to non-IBD controls (FIG. 31A). Granzyme A gene expression was positively correlated with αE expression in sorted CD4+αE+ cells, but not CD8+αE+ cells, from UC patients (FIG. 31B). Consistent with data from untreated patient samples cohort 3, gene expression of granzyme A and αE was significantly positively correlated in baseline colonic biopsies from the etrolizumab phase II study population (FIG. 31C). In line with these observations, colonic biopsy gene expression of granzyme A was significantly correlated with the number of αE+ cells in the crypt epithelium and lamina propria in colonic biopsies from patients enrolled in the etrolizumab phase II study (FIG. 31D). Dual immunofluorescence analysis showed that granzyme A staining was limited to a subset of αE+ cells in colonic tissue (FIG. 31E). These data suggest that αE+ cells may be a source of granzyme A in the colon in UC patients.

To summarize, we have shown that high baseline peripheral blood expression of ITGAE, ECH1, and SLC8A3 enriched for etrolizumab responsiveness as assessed by remission, mucosal healing and clinical response. The results reported here confirm and extend our previously-reported findings showing that high alphaE expression at baseline and certain additional genes with high baseline expression enriched for etrolizumab responsiveness. We also determined, in particular, that low baseline peripheral blood expression of VNN2 and TNF SF15 enriched for etrolizumab responsiveness as assessed by remission, mucosal healing and clinical response. We evaluated peripheral blood gene expression of these genes in an independent cohort and found them to be overlapping with healthy controls with some changes in samples from patients with IBD.

We also evaluated biopsy gene expression of the genes described herein in untreated patient cohorts and found gene expression to be elevated in the ileum in some cases (ITGAE, GZMA, KLRB1, TNF SF15) but not different in inflamed samples from patients with either CD or UC. VNN2 had elevated gene expression in the ileum and was also increased in inflamed vs. uninflamed biopsies. ECH1 was lower in the inflamed colon in comparison to uninflamed colon. Further work on overlap of ITGAE and GZMA showed that ITGAE and GZMA were correlated in biopsies, that GZMA expression was higher in sorted αE+CD4+ T cells in comparison to αE-CD4+ T cells and that a subset of αE+ cells co-expressed granzyme A by immunofluorescence.

In summary, the expression levels of the genes described herein, individually or in combination, thus show potential for use as predictive biomarkers to identify IBD patients, such as UC and Crohn's disease patients, most likely to benefit from treatment with therapeutic agents that target the beta7 integrin subunit, including etrolizumab. The biomarkers can be measured by a number of methods, e.g., by qPCR, and various tissue samples may be used for measurement, e.g., intestinal biopsies or peripheral blood.

What is claimed is:

1. A method of treating a subject having a gastrointestinal inflammatory disorder, the method comprising: (a) measuring the mRNA expression level of ECH1 in a biological sample of the subject; (b) comparing the mRNA expression level of ECH1 measured in (a) to a reference mRNA expression level of ECH1; (c) identifying the subject as likely to respond to a therapy comprising an integrin beta7 antagonist when the mRNA expression level of ECH1 measured in (a) is above the reference mRNA expression level of ECH1; and (d) administering the therapy to the subject identified in (c).

2. The method of claim 1, wherein 105 mg of the integrin beta7 antagonist is administered subcutaneously once every four weeks.

3. The method of claim 1, wherein an initial dose of 210 mg of the integrin beta7 antagonist is administered subcutaneously followed by a first subsequent dose of 210 mg of the integrin beta7 antagonist administered subcutaneously two weeks after the initial dose, a second subsequent dose of 210 mg of the integrin beta7 antagonist administered subcutaneously four weeks after the initial dose, a third subsequent dose of 210 mg of the integrin beta7 antagonist administered subcutaneously eight weeks after the initial dose, and a fourth subsequent dose of 210 mg of the integrin beta7 antagonist administered subcutaneously twelve weeks after the initial dose.

4. The method of claim 1, wherein the gastrointestinal inflammatory disorder is an inflammatory bowel disease.

5. The method of claim 4, wherein the inflammatory bowel disease is ulcerative colitis or Crohn's disease.

6. The method of claim 5, wherein the inflammatory bowel disease is ulcerative colitis and the response is selected from the group consisting of clinical response, mucosal healing, and remission.

7. The method of claim 1, wherein the biological sample is selected from the group consisting of intestinal tissue and peripheral whole blood.

8. The method of claim 1, wherein the mRNA expression level is measured by an RNA sequencing method, microarray, or a PCR method.

9. The method of claim 8, wherein the PCR method comprises qPCR.

10. The method of claim 1, wherein measuring the mRNA expression level of ECH1 comprises amplifying the mRNA of ECH1, and detecting the amplified ECH1 mRNA.

11. The method of claim 1, wherein each of the reference mRNA expression level is a median mRNA expression value.

12. The method of claim 1, wherein the subject is not previously treated with an anti-TNF therapeutic agent.

13. The method of claim 6, wherein administration of the integrin beta7 antagonist results in one or more of the following: (1) a 3-point decrease and 30% reduction from baseline in MCS and ≥1-point decrease in rectal bleeding subscore or absolute rectal bleeding score of 0 or 1, (2) an endoscopic subscore of 0 or 1, and (3) MCS ≤2 with no individual subscore >1.

14. The method of claim 1, wherein the integrin beta7 antagonist is a monoclonal anti-beta7 antibody or an antigen-binding fragment thereof.

15. The method of claim 14, wherein the anti-beta7 antibody is selected from the group consisting of a chimeric antibody, a human antibody, and a humanized antibody.

16. The method of claim 14, wherein the anti-beta7 antibody or antigen-binding fragment thereof comprises three heavy chain hypervariable region (HVR-H1-H3) sequences and three light chain hypervariable region (HVR-L1-L3) sequences, wherein: (i) the HVR-L1 comprises the amino acid sequence set forth in SEQ ID NO:9; (ii) the HVR-L2 comprises the amino acid sequence set forth in SEQ ID NO:2; (iii) the HVR-L3 comprises the amino acid sequence set forth in SEQ ID NO:3; (iv) the HVR-H1 comprises the amino acid sequence set forth in SEQ ID NO:4; (v) the HVR-H2 comprises the amino acid sequence set forth in SEQ ID NO:5; and (vi) the HVR-H3 comprises the amino acid sequence set forth in SEQ ID NO:19.

17. The method of claim 16, wherein the anti-beta7 antibody or antigen-binding fragment thereof comprises a variable light chain comprising the amino acid sequence set forth in SEQ ID NO:31 and a variable heavy chain comprising the amino acid sequence set forth in SEQ ID NO:32.

18. The method of claim 17, wherein the anti-beta7 antibody is etrolizumab.

19. The method of claim 1, further comprising:
(i) measuring the mRNA expression level of at least one High Expression Predictive Gene ("HEPG") selected from the group consisting of GZMA, KLRB1, FOXM1, CCDC90A, CCL4, CPA2, CXCR6, DDO, FAM125B, FASLG, FGF9, GPR15, GZMB, KCNMA1, PHF14, TIFAB, TMEM200A, TMIGD2, and SLC8A3 in the biological sample;
(ii) comparing the mRNA expression level of the at least one HEPG measured in (i) to a reference mRNA expression level of the at least one HEPG; and
(iii) predicting that the subject will likely respond to the therapy when the mRNA expression level of ECH1 measured in (a) is above the reference mRNA expression level of ECH1, and the mRNA expression level of the at least one HEPG measured in (i) is above the reference mRNA expression level of the at least one HEPG.

20. The method of claim 1, further comprising:
(aa) measuring the mRNA expression level of at least one Low Expression Predictive Gene ("LEPG") selected from the group consisting of SLC8A3, TNFSF15, BEST2, CCL2, CCL3, CCL3L1/3, CPA3, FGF7, HAMP, ILIA, IL18RAP, INHBA, LIF, LMO4, LRRC4, MLK7.AS1, MT1M, MUCL1, MX1, PMCH, REM2, SSTR2, TM4SF4, TMEM154, UROS, VNN2, and VNN3 in the biological sample;
(ab) comparing the mRNA expression level detected (aa) to a reference mRNA expression level of the at least one LEPG; and
(ac) predicting that the subject will likely respond to the therapy when the mRNA expression level of ECH1 measured in (a) is above the reference level of ECH1, and the mRNA expression level of the at least one LEPG measured in (aa) is below the reference mRNA expression level of the at least one LEPG.

21. The method of claim 20, wherein the reference mRNA expression level of the at least one LEPG is a median mRNA expression value of the at least one LEPG.

22. The method of claim 19, wherein measuring the mRNA expression level of the at least one HEPG comprises amplifying the mRNA of the at least one HEPG, and detecting the amplified mRNA.

23. The method of claim 20, wherein the at least one LEPG is selected from the group consisting of SLC8A3, TNFSF15, BEST2, VNN2, and CCL2.

24. The method of claim 20, wherein the at least one LEPG is selected from the group consisting of SLC8A3, VNN2, and TNFSF15.

25. The method of claim 19, wherein the at least one HEPG is selected from the group consisting of GZMA, KLRB1, FOXM1, SLC8A3, and ECH1.

26. The method of claim 20, wherein measuring the mRNA expression level of the at least one LEPG comprises amplifying the mRNA of the at least one LEPG, and detecting the amplified mRNA.

27. The method of claim 19, wherein the reference mRNA expression level of the at least one HEPG is a median mRNA expression value of the at least one HEPG.

* * * * *